United States Patent
Yang et al.

(10) Patent No.: US 11,639,343 B2
(45) Date of Patent: May 2, 2023

(54) COMPOUNDS TARGETING AND DEGRADING BCR-ABL PROTEIN AND ITS ANTITUMOR APPLICATION

(71) Applicant: ShanghaiTech University, Shanghai (CN)

(72) Inventors: Xiaobao Yang, Shanghai (CN); Biao Jiang, Shanghai (CN); Qianqian Yin, Shanghai (CN); Jinju Chen, Shanghai (CN); Quanju Zhao, Shanghai (CN); Chaowei Ren, Shanghai (CN); Renhong Sun, Shanghai (CN); Ning Sun, Shanghai (CN); Xing Qiu, Shanghai (CN); Ying Kong, Shanghai (CN); Yan Li, Shanghai (CN); Linyi Liu, Shanghai (CN)

(73) Assignee: ShanghaiTech University, Shanghai (CN)

( * ) Notice: Subject to any disclaimer, the term of this patent is extended or adjusted under 35 U.S.C. 154(b) by 0 days.

(21) Appl. No.: 17/015,319

(22) Filed: Sep. 9, 2020

(65) Prior Publication Data
US 2020/0407342 A1    Dec. 31, 2020

Related U.S. Application Data

(63) Continuation of application No. PCT/CN2019/077535, filed on Mar. 8, 2019.

(51) Int. Cl.
| C07D 401/14 | (2006.01) |
| C07D 417/14 | (2006.01) |
| A61P 35/02  | (2006.01) |
| A61K 45/06  | (2006.01) |

(52) U.S. Cl.
CPC ............ C07D 401/14 (2013.01); A61P 35/02 (2018.01); C07D 417/14 (2013.01); A61K 45/06 (2013.01)

(58) Field of Classification Search
CPC ...... C07D 401/14; C07D 417/14; A61P 35/02
See application file for complete search history.

(56) References Cited

U.S. PATENT DOCUMENTS

| 10,730,862 B2 | 8/2020 | Crews et al. |
| 2015/0291562 A1 | 10/2015 | Crew et al. |

FOREIGN PATENT DOCUMENTS

| CN | 104736569 A | 6/2015 |
| CN | 106458993 A | 2/2017 |
| WO | 2016149668 A1 | 9/2016 |
| WO | 2017079267 A1 | 5/2017 |
| WO | 2017117474 A1 | 7/2017 |
| WO | 2018098288 A1 | 5/2018 |

OTHER PUBLICATIONS

Datta et al. Crystal structures of drugs: Advances in determination, prediction, and engineering; 2004, Nature Reviews, vol. 3, pp. 42-57.*

Golub et al., Science, vol. 286, Oct. 15, 1999, pp. 531-537.*

International Search Report with English translation issued in corresponding International Application No. PCT/CN2019/077535, dated Jun. 14, 2019 (11 pages).

Written Opinion with English translation issued in corresponding International Application No. PCT/CN2019/0//535, dated Jun. 14, 2019 (15 pages).

Lai, Ashton C. et al., "Modular PROTAC Design for the Degradation of Oncogenic BCR-ABL", Angewandte Chemie International Edition, Wiley Online Library, Wiley-VCH Verlag GmbH & Co. KGaA, vol. 55, 2016, pp. 807-810 (4 pages).

Quintas-Cardama, Alfonso et al., "Dasatinib (BMS-354825) is active in Philadelphia chromosome-positive chronic myelogenous leukemia after imatinib and nilotinib (AMN107) therapy failure", Clinical Trials and Observations, Blood, The American Society of Hematology, vol. 109, No. 2, Jan. 2007, pp. 497-499 (4 pages).

Kantarjian, Hagop M. et al., "Nilotinib (formerly AMN107), a highly selective BCR-ABL tyrosine kinase inhibitor, is effective in patients with Philadelphia chromosome-positive chronic myelogenous leukemia in chronic phase following imatinib resistance and intolerance", Clinical Trials and Observations, Blood, The American Society of Hematology, vol. 110, No. 10, Nov. 2007, pp. 3540-3546 (8 pages).

(Continued)

*Primary Examiner* — Samira J Jean-Louis

(74) *Attorney, Agent, or Firm* — Osha Bergman Watanabe & Burton LLP

(57) ABSTRACT

The present disclosure provides a compound of formula (I) targeting and degrading BCR-ABL protein and its use in the field of antitumor. The compound of formula (I) shows degradation and inhibitory effects on BCR-ABL target protein, which is mainly comprised of four moieties, wherein the first moiety (BCR-ABL-TKIs) is compound moiety with BCR-ABL tyrosine kinase inhibited activity; the second moiety (the LIN) is link units; the third moiety (the ULM) is a small molecule ligand for VHL or CRBN proteases with ubiquitination; and the four moiety (the group A) is carbonyl group that covalently binds to BCR-ABL-TKIs and LIN, and the LIN is further covalently bonded to ULM. A series of compounds designed and synthesized by the present disclosure shows extensive pharmacological effective, which function to degrade BCR-ABL protein and inhibit BCR-ABL effective, and can be utilized for treating relevant tumor.

Formula (I)

29 Claims, 7 Drawing Sheets

(56) References Cited

OTHER PUBLICATIONS

Cortes, Jorge, "Bosutinib in the Treatment of Chronic Myelogenous Leukemia", Advances in LLM: Current Developments in the Management of Leukemia, Lymphoma, and Myeloma, Ed. Susan O'Brien, Clinical Advances in Hematology & Oncology, vol. 10, Issue 11, Nov. 2012, pp. 736-737 (2 pages).

Li, Shaoguang, "Src-family kinases in the development and therapy of Philadelphia chromosome-positive chronic myeloid leukemia and acute lymphoblastic leukemia", Leukemia & Lymphoma, Informa UK Ltd., vol. 49, No. 1, Jan. 2008, pp. 19-26 (8 pages).

Araujo, John and Christopher Logothetis, "Dasatinib: A potent SRC inhibitor in clinical development for the treatment of solid tumors", Cancer Treatment Reviews, ScienceDirect, Elsevier Ltd., vol. 36, 2010, pp. 492-500 (9 pages).

Daud, Adil I. et al., "Phase I Study of Bosutinib, a Src/Abl Tyrosine Kinase Inhibitor, Administered to Patients with Advanced Solid Tumors", Cancer Therapy: Clinical, Clinical Cancer Research, American Association for Cancer Research, vol. 18, No. 4, Feb. 2012, pp. 1092-1100 (9 pages).

Martell, Marc Poch et al., "Ponatinib in the therapy of Chronic Myeloid Leukemia", Expert Review of Hematology, Taylor & Francis, Sep. 2016 (39 pages).

Konig, H et al., "Enhanced BCR-ABL kinase inhibition does not result in increased inhibition of downstream signaling pathways or increased growth suppression in CML progenitors", Leukemia, Nature Publishing Group, vol. 22, Feb. 2008, pp. 748-755 (8 pages).

Ichim, Christine Victoria, "Kinase-Independent Mechanisms of Resistance of Leukemia Stem Cells to Tyrosine Kinase Inhibitors", Stems Cells Translational Medicine, AlphaMed Press, vol. 3, Mar. 2014, pp. 405-415 (11 pages).

Komander, David and Michael Rape, "The Ubiquitin Code", Annual Review of Biochemistry, Annual Reviews, vol. 81, Apr. 2012, pp. 203-229 (27 pages).

Sakamoto, Kathleen, "Protacs for Treatment of Cancer", Pediatric Research, International Pediatric Research Foundation, Inc, vol. 67, No. 5, 2010, pp. 505-508 (4 pages).

Nowell, Peter C., "Übersicht: The minute Chromosome (PH1) in chronic granulocytic Leukemia", Blut: Zeitschrift für Blutforschung, Eds. G. Blumenthal et al., vol. 8, No. 2, Apr. 1962, pp. 65-66 (2 pages).

Lu, Jing et al., "Hijacking the E3 Ubiquitin Ligase Cereblon to Efficiently Target BRD4", Chemisty & Biology, CellPress, Elsevier Ltd, vol. 22, Jun. 2015, pp. 1-9 (10 pages).

Bondeson, Daniel P. et al., "Catalytic in vivo protein knockdown by small-molecule PROTACs", Nature Chemical Biology, Nature America, Inc., Jun. 2015 (9 pages).

Itoh, Yukihiro et al., "Development of target protein-selective degradation inducer for protein knockdown", Bioorganic & Medicinal Chemistry, ScienceDirect, Elsevier Ltd., vol. 19, Mar. 2011, pp. 3229-3241 (13 pages).

Rowly, Janet D., "A New Consistent Chromosomal Abnormality in Chronic Myelogenous Leukaemia identified by Quinacrine Fluorescence and Giemsa Staining", Nature, Nature Publishing Group, vol. 243, Jun. 1973, pp. 290-293 (4 pages).

Kurzrock, Razelle et al., "Philadelphia Chromosome-Positive Leukemias: From Basic Mechanisms to Molecular Therapeutics", Annals of Internal Medicine, American College of Physicians, vol. 138, No. 10, May 2003, pp. 819-E831 (13 pages).

"Corrections", The New England Journal of Medicine, vol. 346, No. 24, Jun. 2002, pp. 1923 (1 page).

Mauro, Michael J. and Brian J. Druker, "STI571: Targeting BCR-ABL as Therapy for CML", The Oncologist, AlphaMed Press, vol. 6, 2001, pp. 233-238 (6 pages).

Leoni, Veronica and Andrea Biondi, "Tyrosine kinase inhibitors in BCR-ABL positive acute lymphoblastic leukemia", Editorials, Haematologica, vol. 100, No. 3, 2015, pp. 295-299 (5 pages).

Buchdunger, Elisabeth et al., "Bcr-Abl inhibition as a modality of CML therapeutics", Biochimica et Biophysica Acta, Elsevier Science B.V., vol. 1551, 2001, pp. M11-M18 (8 pages).

O'Hare, Thomas et al., "Bcr-Abl kinase domain mutations, drug resistance, and the road to a cure for chronic myeloid leukemia", Blood, The American Society of Hematology, vol. 110, No. 7, Oct. 2007, pp. 2242-2249 (8 pages).

* cited by examiner

COMPOUNDS TARGETING AND DEGRADING BCR-ABL PROTEIN AND ITS ANTITUMOR APPLICATION

TECHNICAL FIELD

The present disclosure relates to the compounds targeting and degrading BCR-ABL fusion protein and their use in antitumor.

BACKGROUND

T(9;22)(q34;q11) Chromosomal heterotopy, also known as the Philadelphia chromosome translocation or the Philadelphia chromosome (PH), is manifested as the translocation between the long arm of chromosome 9 and the length of chromosome 22, so that the Abelson leukemia virus 1 gene located on chromosome 9 is translocated to the fracture on chromosome 22 from the clustered gene, forming the BCR-ABL fusion gene. This characteristic chromosomal heterotopia exists in most chronic myeloid leukemia (CML), some acute lymphoblastic leukemia (all) and a few acute myeloid leukemia (AML). Under normal conditions, the activity of tyrosine-protein kinase is strictly regulated. Compared with normal tyrosine-protein kinase, BCR-ABL fusion protein has a sustained activation of tyrosine kinase activity (TK), which can activate downstream signaling pathways, including RAS, Janus kinase (JAK)/signal transcriber and activators of transcription (STAT) and phosphatidylinositol-3-kinase (PI-3K) can promote cell proliferation, reduce the dependence of growth factor, and inhibit apoptosis, which can lead to malignant transformation of cells. It is the root cause of $Ph^+$ leukemia (Philadelphia chromosome-positive leukemia).

In the past, the traditional treatment based on interferon or chemotherapy had a poor response and side effects, and could not fundamentally eliminate the pathogenic BCR-ABL gene. Therefore, it is impossible for patients to get relief in genetics or molecular biology. Allogeneic hematopoietic stem cell transplantation is limited by age and appropriate donor, and the incidence of transplantation-related complications is high, the risk of death is high, so only a small number of patients can be treated with this method. At present, tyrosine kinase inhibitors (TKIs) have made a great breakthrough in the treatment of $Ph^+$ leukemia, which has become the first-line treatment method of CML [4,5]; at the same time, adding TKI inhibitors in induction chemotherapy has become the gold standard of induction chemotherapy for $Ph^+$ ALL patients [6], which improves the disease-free survival rate (DFS) and total survival rate (OS) as a whole. With the further study of TKI, the first-generation drugs (imatinib) and the second-generation drugs (such as Dasatinib and Bosutinib) have been used in the clinical treatment of $Ph^+$ leukemia.

Gleevec is the first molecular targeted drug for the treatment of cancer, which was approved for marketing in the United States in 2001. As the first TKI inhibitor for BCR-ABL protein, Gleevec has become the first-line drug for the treatment of CML [7]. The mechanism of function is to replace ATP in BCR-ABL fusion protein structure. Gleevec makes tyrosine kinase catalytic center site unable to combine with ATP, and competitively inhibits BCR-ABL phosphorylation and substrate phosphorylation. Finally, Gleevec inhibits the proliferation of BCR-ABL positive leukemia cells and promotes their apoptosis. As a first-line drug, it can induce the majority of CML patients to obtain long-term and sustained clinical remission, which has better efficacy and safety. However, the long-term effect is weak for the patients in the acceleration stage and the emergency stage. And once the treatment is stopped, the disease often relapses, so patients need to take long-term medication. The secondary drug resistance and the economic burden of patients are serious problems that cannot be avoided. With the in-depth study of the mechanism of drug resistance, the increase of tyrosine kinase activity caused by point mutation or increased gene expression in BCR ABL kinase region is the main cause of drug resistance [8]. At present, there are more and more point mutations, which can occur in the ATP binding ring (P-ring), imatinib binding site—the activation ring (A-ring) or the catalytic region (C-ring). These point mutations interfere with the binding of drugs to BCR-ABL protein, resulting in the reduction of patients' sensitivity to treatment. To overcome the drug resistance of imatinib, the second generation of TKI inhibitors of BCR-ABL came into being, including Dasatinib (Sprycel) [9] [10] and Bosutinib (Bosulif) [11], which can inhibit imatinib resistance caused by most BCR-ABL mutations except T315I.

Dasatinib is a dual kinase inhibitor of BCR-ABL tyrosine kinase and Src family kinase. Previous research shown that the occurrence of $Ph^+$ leukemia depends on the dual activation of Src kinase and BCR-ABL kinase [12]. Dasatinib can inhibit both tyrosine kinase and Src kinase and can penetrate the blood-brain barrier. It was used to treat CML and $Ph^+$ all by the US FDA on Jun. 28, 2006. Different from imatinib, the inhibitory effect of Dasatinib does not depend on conformation. It can combine with activated and non-activated BCR ABL kinases, so it can overcome the resistance caused by many point mutations in ABL kinase region (Except T315I mutation). Besides, Dasatinib can also inhibit the spontaneous phosphorylation of Src kinase protein in a variety of human tumor cells, which is also effective for some solid tumors [13].

Bosudinib, a powerful dual inhibitor of protein kinase SRC-ABL, can effectively inhibit wild-type BCR-ABL and most imatinib-resistant BCR-ABL mutations (Except for V299L and T315I). On Sep. 4, 2012, the FDA approved Bosudinib mainly for the treatment of CML patients with intolerance or resistance to imatinib in the chronic, accelerated or cataclysmic phase, and clinical studies showed that it is also effective for some solid tumors [14].

Although the new generation of TKIs can overcome the problem of drug resistance, it is impossible to clear CML leukemic stem cells by TKI alone [16], which is the root of disease recurrence, so CML patients need to take drugs for a long time. A theoretical hypothesis that TKI can not clear CML leukemia stem cells is that although TKI can inhibit the kinase activity of BCR-ABL in leukemia stem cells, BCR-ABL can play a role of non-kinase activity, as a scaffold protein "protein scaffold" to start compensatory signal pathway and help leukemia stem cells survive [17]. Therefore, the treatment strategy of BCR-ABL degradation may be able to effectively remove CML leukemic stem cells, which solves the problem of patients requiring long-term medication and the secondary drug resistance caused by this problem.

Malignant tumor is a great threat to human health. For the target protein, we can achieve the purpose of treating tumors by degrading protein expression. Ubiquitin mediated protein degradation pathway controls the selective degradation of most proteins in eukaryotic cells. In this pathway, proteins are first labeled by ubiquitin and then recognized and degraded by the proteasome. Ubiquitin protein ligase (E3) binds directly to protein, which determines the specificity of degradation [18]. It is a new model of drug development to design protein degrading targeting drug (PROTAD) by using the ubiquitination process in vivo. PROTAD small-molecule drugs use the ubiquitin-proteasome system inherent in cells to regulate target protein degradation [19]. PROTAD can be combined with the target protein and E3 ubiquitin ligase at the same time, making the target protein that could not be combined with E3 ubiquitin, and then recognized and degraded by the proteasome. Different from traditional small molecules for protein kinase active sites, PROTAD can target proteins without obvious active sites, such as transcription factors and scaffolds, which are often difficult to design small molecular inhibitors by traditional methods [20]. Therefore, PROTAD has a very broad application prospect. At present, there have been successful reports on the application of PROTAD technology, including estrogen-related receptor α (ER-α) [21], cell retinoid-binding protein (CRABP-II) [22] and BRD4 [20].

So far, there has not been any report on the PROTAD compounds that can degrade BCR-ABL protein by recruiting Von Hippel Lindau (VHL) E3 ubiquitin ligase. A series of PROTAD compounds which were designed and synthesized for the first time in the present disclosure can effectively degrade BCR-ABL and c-ABL proteins by recruiting VHL E3 ligase; In addition, although some PROTAD compounds with the recruitment of Cereblon (CRBN) E3 ligase to degrade BCR-ABL protein [23] have been reported to degrade bcr-abl protein [23], the newly designed PROTAD compounds show better effect on BCR-ABL protein degradation than the reported literature[23].

SUMMARY OF INVENTION

The present disclosure provides a compound of formula (I):

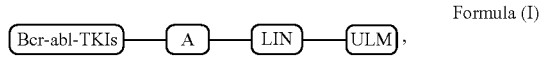
Formula (I)

or a salt, enantiomer, stereoisomer, solvate, or polymorph thereof, wherein BCR-ABL-TKIs, LIN, ULM, the moiety A and all substituents arevas defined in the detailed description of the present invention.

The present disclosure also provides a pharmaceutical composition, containing the compound of formula (I) as described herein or a pharmaceutically acceptable salt thereof, and at least one pharmaceutically acceptable carrier.

The present disclosure also provides the compound of formula (I), or a pharmaceutically acceptable salt thereof for use as a medicament:

Formula (I)

The present disclosure also provides the compound of formula (I), or a pharmaceutically acceptable salt thereof for use in the prevention and/or treatment of a cancer.

The present disclosure also provides the use of the compound of formula (I) or a pharmaceutically acceptable salt thereof for the preparation of a medicament for preventing and/or treating a cancer.

The present disclosure also provides a method of treating or preventing a cancer, comprising administering to a subject in need a therapeutically effective amount of a compound of formula (I), or a pharmaceutically acceptable salt thereof, or a pharmaceutical composition according to the present invention.

DETAILED DESCRIPTION OF THE INVENTION

Figure 1:
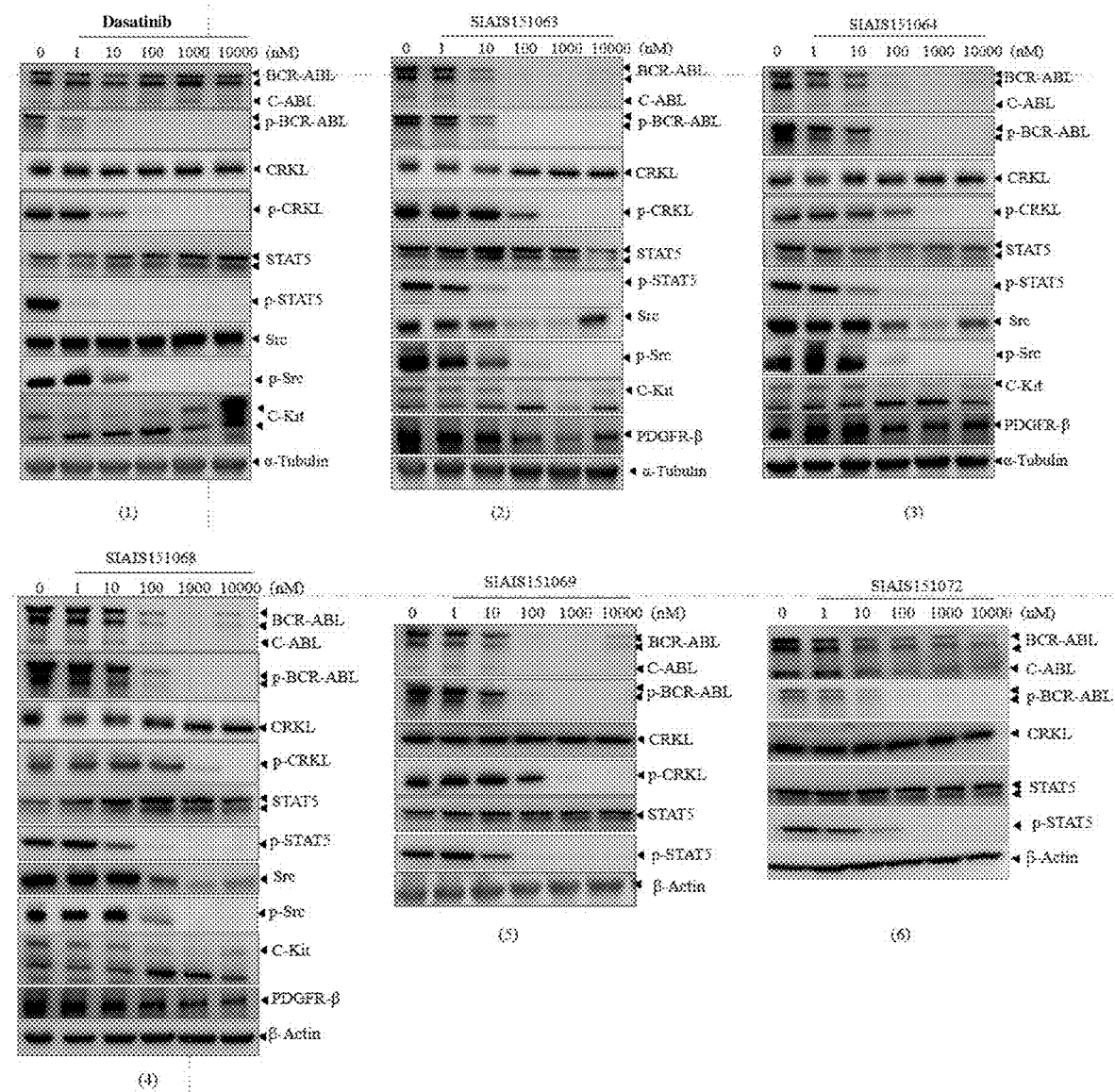
FIG. 1 shows the results of the degradation activity of a series of PROTAD compounds according to embodiments of the present disclosure (the (1)-(27) and (30)-(35) in FIG. 1) on BCR-ABL and c-ABL proteins compared with the comparative examples (the (28) and (29) in FIG. 1), as detected by the Western-blot method.
Figure 1:
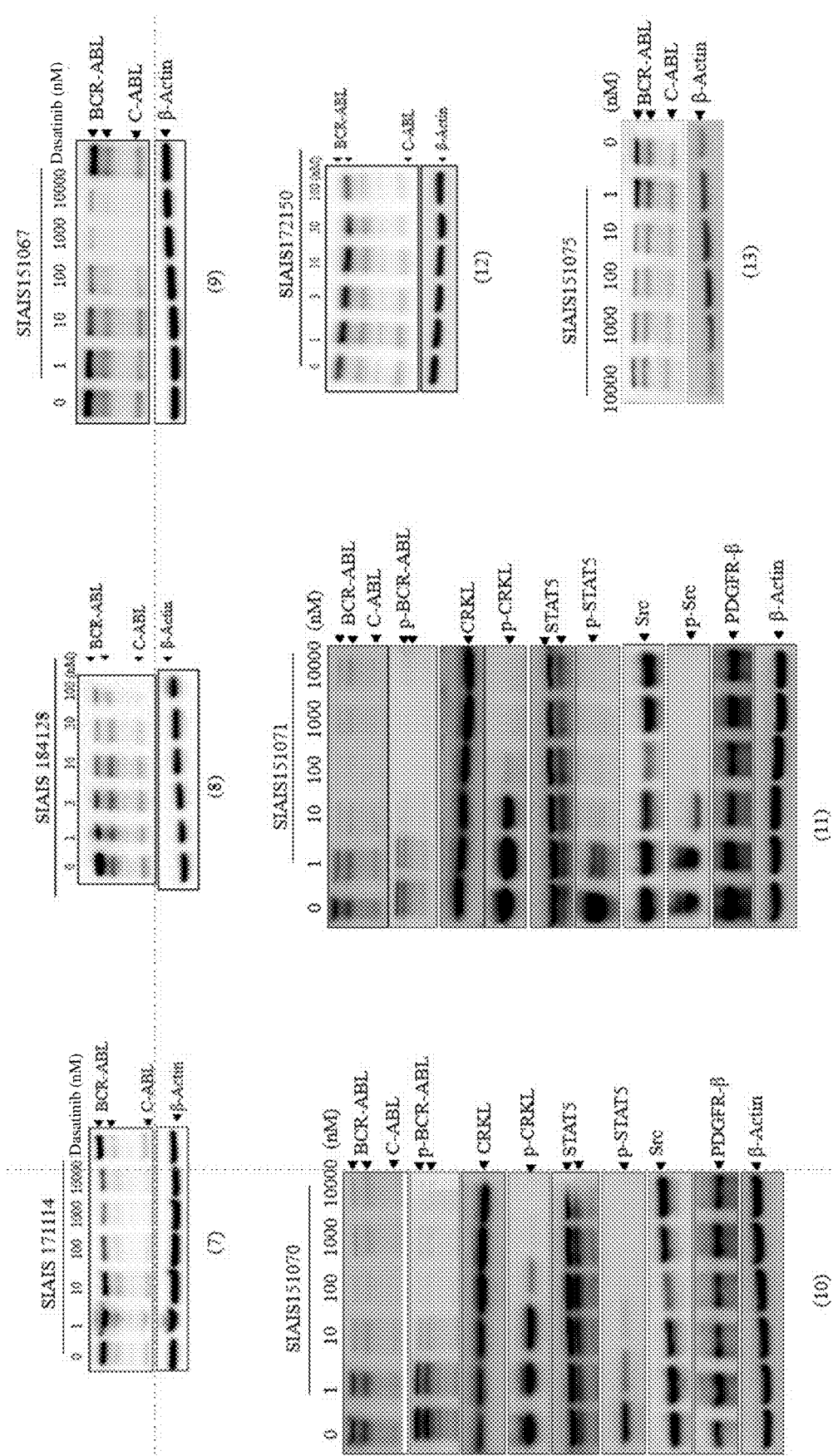
Figure 1:
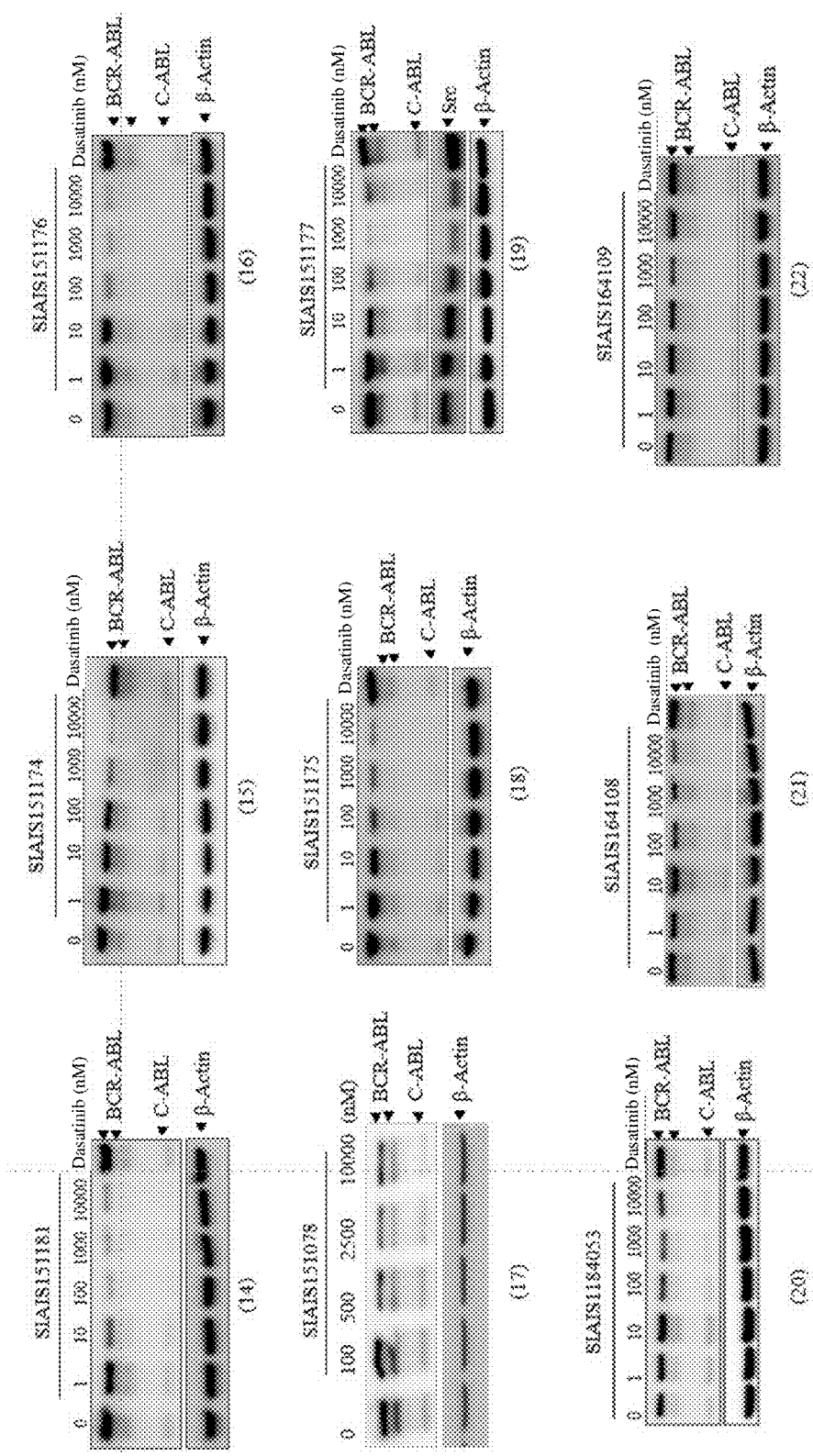
Figure 1:
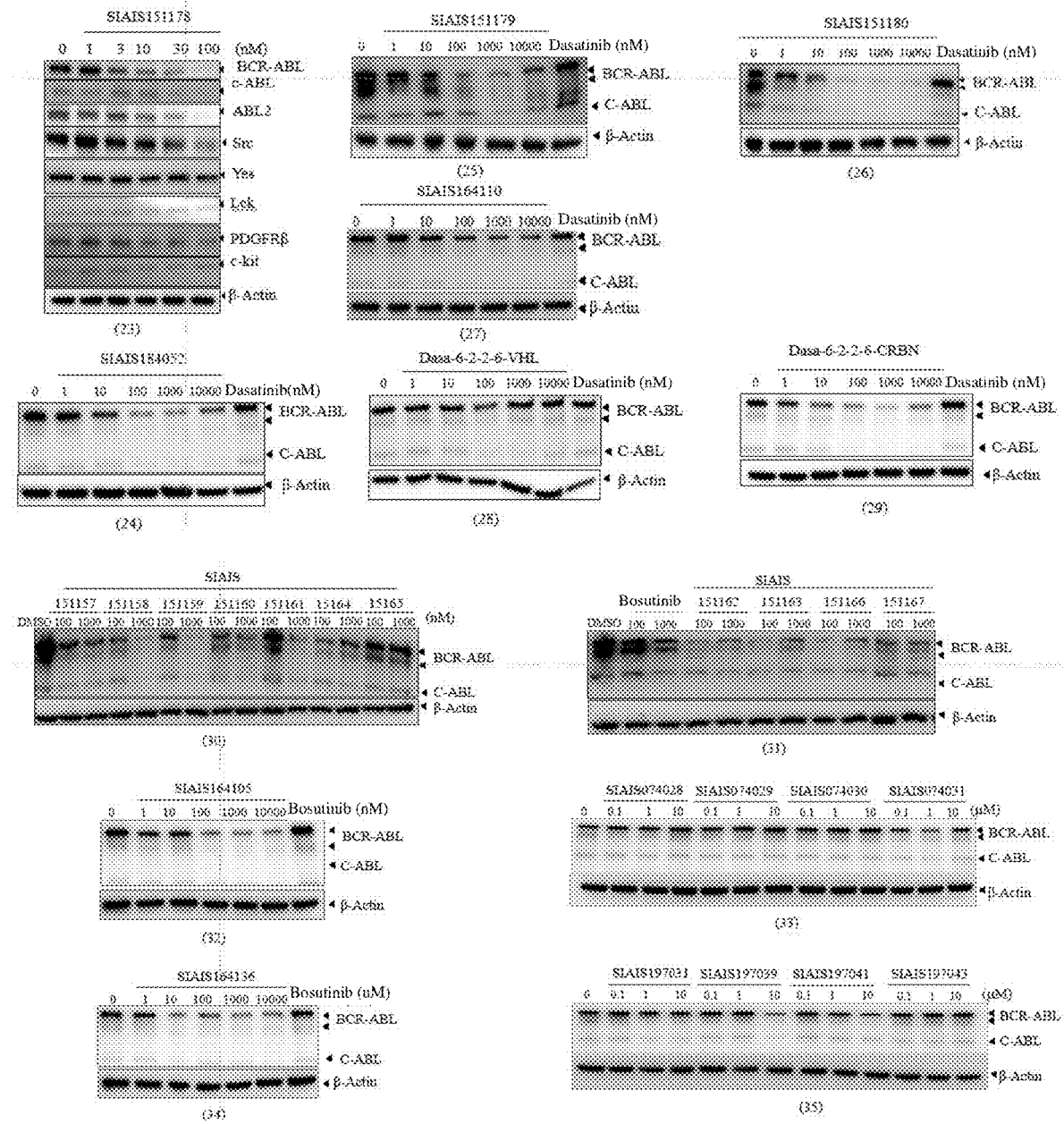

So far, there are no reports on the PROTAD compounds that can degrade BCR-ABL protein by recruiting Von Hippel Lindau (VHL) E3 ubiquitin ligase. A series of PROTAD compounds which were designed and synthesized for the first time in the present disclosure can effectively degrade BCR-ABL and c-ABL proteins by recruiting VHL E3 ligase. In addition, another series of PROTAD compounds which were designed and synthesized for the first time in the present disclosure can effectively degrade BCR-ABL proteins by recruiting Cereblon (CRBN) E3 ligase. Although some PROTAD compounds utilizing Cereblon (CRBN) E3 ligase have been reported [23], a series of novel PROTAD compounds in the present disclosure have better effects on BCR-ABL protein degradation than the available literature [23].

Therefore, in one aspect, the present disclosure provides the compound of formula (I):

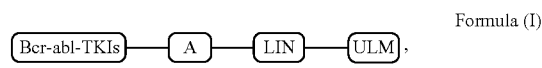
Formula (I)

or a salt, enantiomer, stereoisomer, solvate, or polymorph thereof, in which the Bcr-abl-TKIs is covalently bonded to the group LIN via group A, and ULM covalently binds to the group LIN;

wherein the Bcr-abl-TKIs is a Bcr-abl tyrosine kinase inhibitor or their analogs with the same function;

LIN is a linker, which is a linear or branched alkylene chain, wherein the linear or branched alkylene chain is optionally interrupted one or more times (e.g., 1-20, 1-15, 1-10, 1-9, 1-8, 1-7,1-6, 1-5, 1-4, 1-3, or 1-2 times, or 1 time) by one or more selected from the group consisting of —O—, —CONH—, —NHCO—, —NH—, alkynylene, alkenylene, cycloalkylene, arylene, heterocyclylene or heteroarylene or any combination thereof, wherein the linear or branched alkylene chain is optionally substituted with one or more substituents;

ULM is a small molecule ligand with ubiquitination function on VHL or CRBN protease; and the group A is —CO—.

In one embodiment of the present disclosure, the Bcr-abl-TKIs represents the compound moiety represented by the following general formula:

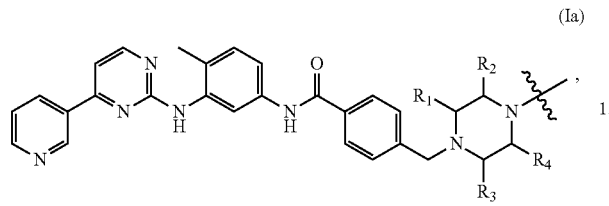

(Ia)

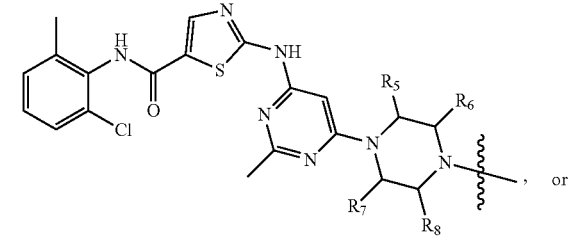

(Ib)

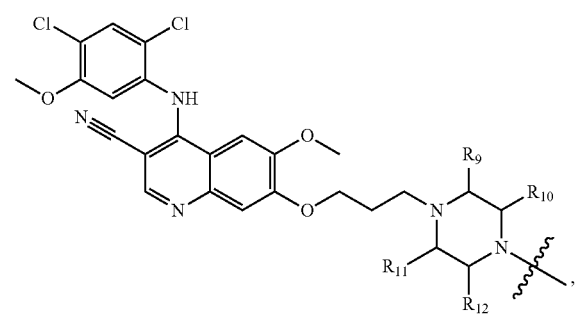

(Ic)

wherein $R_1$, $R_2$, $R_3$, $R_4$, $R_5$, $R_6$, $R_7$, $R_8$, $R_9$, $R_{10}$, $R_{11}$, and $R_{12}$ each independently represent alkyl or H.

In one embodiment of the present disclosure, $R_1$, $R_2$, $R_3$, $R_4$, $R_5$, $R_6$, $R_7$, $R_8$, $R_9$, $R_{10}$, $R_{11}$, and $R_{12}$ each independently represent linear or branched chain $C_{1-10}$ alkyl or H. In a sub-embodiment of the present disclosure, the $C_{1-10}$ alkyl is preferably $C_{1-9}$ alkyl, more preferably $C_{1-8}$ alkyl, still more preferably $C_{2-8}$ alkyl, more preferably $C_{1-7}$ alkyl, even more preferably $C_{1-6}$ alkyl, $C_{1-5}$ alkyl, $C_{1-4}$ alkyl, or $C_{1-3}$ alkyl. Representative examples include, but are not limited to, methyl, ethyl, n-propyl, isopropyl, n-butyl, isobutyl, sec-butyl, tert-butyl, n-pentyl, isopentyl, neopentyl and tert-pentyl.

In one embodiment of the present disclosure, the ULM represents the structure of formula (II):

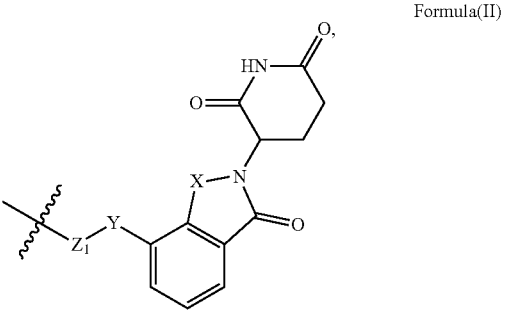

Formula(II)

wherein X is —$CH_2$— or —CO—, Y is —$CH_2$—, —NH— or —O—, and $Z_1$ is carbonyl or $Z_1$ is absent.

In one embodiment of the present disclosure, the ULM represents the structure of formula (III):

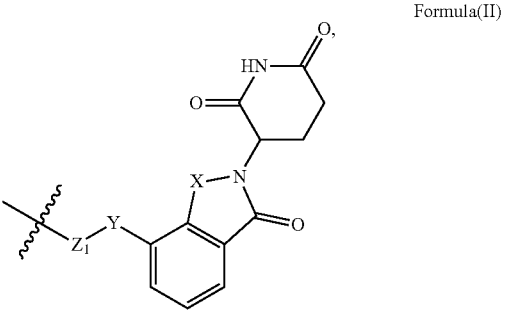

Formula(III)

wherein $Z_2$ is carbonyl or $Z_2$ is absent.

In one embodiment of the present disclosure, the LIN is methylene or linear or branched $C_2$-$C_{30}$ alkylene chain (preferably $C_2$-$C_{29}$ alkylene chain, $C_2$-$C_{28}$ alkylene chain, $C_2$-$C_{27}$ alkylene chain, $C_2$-$C_{26}$ alkylene chain, $C_2$-$C_{25}$ alkylene chain, $C_2$-$C_{24}$ alkylene chain, $C_2$-$C_{23}$ alkylene chain, $C_2$-$C_{22}$ alkylene chain, $C_2$-$C_{21}$ alkylene chain, $C_2$-$C_2$ alkylene chain, $C_2$-$C_{19}$ alkylene chain, $C_2$-$C_{18}$ alkylene chain, $C_2$-$C_{17}$ alkylene chain, $C_2$-$C_{16}$ alkylene chain, $C_2$-$C_{15}$ alkylene chain, $C_2$-$C_{14}$ alkylene chain, $C_2$-$C_{13}$ alkylene chain, $C_2$-$C_{12}$ alkylene chain, $C_2$-$C_{11}$ alkylene chain, $C_2$-$C_{10}$ alkylene chain, $C_2$-$C_9$ alkylene chain, $C_2$-$C_8$ alkylene chain, $C_2$-$C_7$ alkylene chain, $C_2$-$C_6$ alkylene chain, $C_2$-$C_5$ alkylene chain, $C_2$-$C_4$ alkylene chain, $C_2$-$C_3$ alkylene chain), wherein the LIN is optionally substituted by one or more substituents; when the LIN is a linear or branched $C_2$-$C_{30}$ alkylene chain, the linear or branched $C_2$-$C_{30}$ alkylene chain is optionally interrupted one or more times (e.g., 1-20, 1-15, 1-10, 1-9, 1-8, 1-7, 1-6, 1-5, 1-4, 1-3, or 1-2 times, or 1 time) by one or more selected from the group consisting of —O—, —CONH—, —NHCO—, —NH—, alkynylene, alkenylene, cycloalkylene, arylene, heterocyclylene or heteroarylene or any combination thereof.

In one embodiment of the present disclosure, the LIN represents:

a linear or branched $C_1$-$C_{20}$ alkylene chain, —$(CH_2)_{n1}$—$(O(CH_2)_{n2})_{m1}$—, —$(CH_2)_{n1}$—$(O(CH_2)_{n2})_{m1}$—O—$(CH_2)_{n3}$—, —$(CR_{13}R_{14})_{n1}$—$(O(CR_{15}R_{16})_{n2})_{m1}$—, —$(CR_{17}R_{18})_{n1}$—$(O(CR_{19}R_{20})_{n2})_{m1}$—O—$(CR_{21}R_{22})_{n3}$—, —$(CH_2)_{n1}$—$(CONH$—$(CH_2)_{n2})_{m1}$—, —$(CH_2)_{n1}$—$(CONH$—$(CH_2)_{n2})_{m1}$—O—$(CH_2)_{n3}$—, —$(CH_2)_{n1}$—$(O(CH_2)_{n2})_{m1}$—O—$(CH_2)_{n3}$—CONH—$(CH_2)_{n4}$—$(O(CH_2)_{n5})_{m2}$—O—$(CH_2)_{n6}$—, —$(CR_{23}R_{24})_{n1}$—$(O(CR_{25}R_{26})_{n2})_{m1}$—O—$(CR_{27}R_{28})_{n3}$—CONH—$(CR_{29}R_{30})_{n4}$—$(O(CR_{31}R_{32})_{n5})_{m2}$—O—$(CR_{33}R_{34})_{n6}$—, —$(CR_{35}R_{36})_{n1}$—CONH—$(O(CR_{37}R_{38})_{n2})_{m1}$—, —$(CH_2)_{n1}$—NHCO—$(CH_2)_{n2}$—, —$(CH_2)_{n1}$—(NHCO—$(CH_2)_{n2})_{m1}$—, —$(CH_2)_{n1}$—(NHCO—$(CH_2)_{n2})_{m1}$—O—$(CH_2)_{n3}$—, a linear or branched alkylene group interrupted one or more times (e.g., 1-20, 1-15, 1-10, 1-9, 1-8, 1-7, 1-6, 1-5, 1-4, 1-3, or 1-2 times, or 1 time) by one or more selected from the group consisting of alkynylene, alkenylene, cycloalkylene, arylene, heterocyclylene, heteroarylene groups, or any combination thereof, or —$(CH_2)_{n1}$—$(O(CH_2)_{n2})_{m1}$— in which carbon chain is interrupted one or more times (e.g., 1-20, 1-15, 1-10, 1-9, 1-8, 1-7, 1-6, 1-5, 1-4, 1-3, or 1-2 times, or 1 time) by one or more selected from the group consisting of arylene, heteroarylene, heterocyclylene, heteroarylene, or any combination thereof;

$R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{33}$, $R_{34}$, $R_{35}$, $R_{36}$, $R_{37}$, and $R_{38}$ each independently represent H, a linear or branched $C_1$-$C_{10}$ alkyl or $C_3$-$C_{10}$ cycloalkyl, wherein in the same group LIN, $R_{13}$, $R_{14}$, $R_{15}$, and $R_{16}$ are not H at the same time, $R_{17}$, $R_{18}$, $R_{19}$, $R_{20}$, $R_{21}$, and $R_{22}$ are not H at the same time, $R_{23}$, $R_{24}$, $R_{25}$, $R_{26}$, $R_{27}$, $R_{28}$, $R_{29}$, $R_{30}$, $R_{31}$, $R_{32}$, $R_{33}$, and $R_{34}$ are not H at the same time, or $R_{35}$, $R_{36}$, $R_{37}$, and $R_{38}$ are not H at the same time;

n1, n2, n3, n4, n5, n6, m1, and m2 are each independently an integer of 1, 2, 3, 4, 5, 6, 7, 8, 9, 10, 11, 12, 13, 14, 15, 16, 17, 18, 19, or 20.

In one embodiment of the present disclosure, the LIN represents —$(CH_2)_{n1}$—$(O(CH_2)_{n2})_{m1}$—, or —$(CH_2)_{n1}$—$(O(CH_2)_{n2})_{m1}$—O—$(CH_2)_{n3}$—, wherein n1, n2, n3, and m1 each independently represent an integer of 1, 2, 3, 4, 5, 6, 7, 8, 9, 10, 11, 12, 13, 14, 15, 16, 17, 18, 19 or 20; wherein the LIN is optionally substituted by one or more substituents, the substituents are selected from the group consisting of hydroxyl, amino, mercapto and halogen. In one embodiment of the present disclosure, the LIN represents:

—$CH_2O(CH_2)_2OCH_2$—; —$CH_2O(CH_2)_2O(CH_2)_2$—; —$(CH_2)_3O(CH_2)_2$—;
—$(CH_2)_3O(CH_2)_2O(CH_2)_2$—; —$(CH_2)_3O(CH_2)_3$—; —$(CH_2)_2O(CH_2)_2$—;
—$(CH_2)_2O(CH_2)_2OCH_2$—; —$(CH_2)_2O(CH_2)_2O(CH_2)_2$—; —$(CH_2)_2O(CH_2)_2O(CH_2)_3$—;
—$(CH_2)_2O(CH_2)_2O(CH_2)_2O(CH_2)_2$—; —$(CH_2)_2O(CH_2)_2O(CH_2)_2O(CH_2)_3$—;
—$(CH_2)_5O(CH_2)_2O(CH_2)_2O(CH_2)_5$—; —$(CH_2)_5O(CH_2)_2O(CH_2)_2O(CH_2)_6$—;
—$(CH_2)_2O(CH_2)_2O(CH_2)_2O(CH_2)_2O(CH_2)_2$—;
—$(CH_2)_2O(CH_2)_2O(CH_2)_2O(CH_2)_2O(CH_2)_3$—;
—$(CH_2)_2O(CH_2)_2O(CH_2)_2O(CH_2)_2O(CH_2)_2O(CH_2)_2$—;
—$(CH_2)_3O(CH_2)_2O(CH_2)_2O(CH_2)_2O(CH_2)_2O(CH_2)_2$—; or
—$(CH_2)_3O(CH_2)_2O(CH_2)_2O(CH_2)_2O(CH_2)_2O(CH_2)_3$—.

In one embodiment of the present disclosure, the LIN represents a linear or branched $C_1$-$C_{20}$ alkylene chain optionally substituted by one or more substituents, wherein the substituents are selected from the group consisting of hydroxyl, amino, mercapto and halogen. In one embodiment of the present disclosure, the LIN represents:

—$CH_2$—; —$(CH_2)_2$—; —$(CH_2)_3$—; —$(CH_2)_4$—;
—$(CH_2)_5$—; —$(CH_2)_6$—; —$(CH_2)_7$—; —$(CH_2)_8$—;
—$(CH_2)_9$—; —$(CH_2)_{10}$—; —$(CH_2)_{11}$—; —$(CH_2)_{12}$—;
—$(CH_2)_{13}$—; —$(CH_2)_{14}$—; —$(CH_2)_{15}$—; —$(CH_2)_{16}$—;
—$(CH_2)_{17}$—; —$(CH_2)_{18}$—; —$(CH_2)_{19}$—; or —$(CH_2)_{20}$—.

In one embodiment of the present disclosure, the LIN represents a linear or branched alkylene chain optionally substituted one or more times (e.g., 1-20, 1-15, 1-10, 1-9, 1-8, 1-7, 1-6, 1-5, 1-4, 1-3, or 1-2 times, or 1 time) by one or more substituents selected from the group consisting of hydroxyl, amino, mercapto and halogen.

In one embodiment of the present disclosure, the LIN is a linear or branched $C_1$-$C_3$ alkylene chain (preferably $C_1$-$C_{29}$ alkylene chain, $C_1$-$C_{28}$ alkylene chain, $C_1$-$C_{27}$ alkylene chain, $C_1$-$C_{26}$ alkylene chain, $C_1$-$C_{25}$ alkylene chain, $C_1$-$C_{24}$ alkylene chain, $C_1$-$C_{23}$ alkylene chain, $C_1$-$C_{22}$alkylene chain, $C_1$-$C_{21}$ alkylene chain, $C_1$-$C_{20}$ alkylene chain, $C_1$-$C_{19}$ alkylene chain, $C_1$-$C_{18}$ alkylene chain, $C_1$-$C_{17}$ alkylene chain, $C_1$-$C_{16}$ alkylene chain, $C_1$-$C_{15}$ alkylene chain, $C_1$-$C_{14}$ alkylene chain, $C_1$-$C_{13}$ alkylene chain, $C_1$-$C_{12}$ alkylene chain, $C_1$-$C_{11}$ alkylene chain, $C_1$-$C_{10}$ alkylene chain, $C_1$-$C_9$ alkylene chain, $C_1$-$C_8$ alkylene chain, $C_1$-$C_7$ alkylene chain, $C_1$-$C_6$ alkylene chain, $C_1$-$C_5$ alkylene chain, $C_1$-$C_4$ alkylene chain, $C_1$-$C_3$ alkylene chain, or $C_1$-$C_2$ alkylene chain) optionally substituted by one or more substituents selected from hydroxyl, amino, mercapto, halogen, or any combination thereof. In a sub-embodiment of the present disclosure, the number of the substituents may be, such as, 1-30, 1-25, 1-20, or 1-15, 1-10, 1-9, 1-8, 1-7, 1-6, 1-5, 1-4, 1-3, or 1-2, or 20, 19, 18, 17, 16, 15, 14, 13, 12, 11, 10, 9, 8, 7, 6, 5, 4, 3, 2, or 1.

In one embodiment of the present disclosure, the LIN represents a linear or branched alkylene chain interrupted one or more times (e.g., 1-20, 1-15, 1-10, 1-9, 1-8, 1-7, 1-6, 1-5, 1-4, 1-3, or 1-2 times, or 1 time) by one or more substituents selected from the group consisting of heterocyclylene, heteroarylene groups, or any combination thereof, or —$(CH_2)_{n1}$—$(O(CH_2)_{n2})_{m1}$— in which carbon chain is interrupted one or more times (e.g., 1-20, 1-15, 1-10, 1-9, 1-8, 1-7, 1-6, 1-5, 1-4, 1-3, or 1-2 times, or 1 time) by one or more selected from the group consisting of arylene, heterocyclylene, heteroarylene, or any combination thereof, wherein n1, n2, and m1 each independently represent an integer of 1, 2, 3, 4, 5, 6, 7, 8, 9, 10, 11, 12, 13, 14, 15, 16, 17, 18, 19 or 20; wherein the LIN is optionally substituted by one or more substituents selected from the group consisting of hydroxyl, amino, mercapto and halogen. In one embodiment of the present disclosure, the LIN represents:

—$(CH_2)_{n1}$-triazolylene-$(CH_2)_{n2}$—, —$(CH_2)_{n1}$—$(O(CH_2)_{n2})_{m1}$—O—$(CH_2)_{n3}$— triazolylene-$(CH_2)_{n4}$—$(O(CH_2)_{n5})_{m2}$—O—$(CH_2)_{n6}$—, —$(CH_2)_{n1}$-triazolylene-$(CH_2)_{n2}$—$(O(CH_2)_{n3})_{m1}$—O—$(CH_2)_{n4}$—, or —$(CH_2)_{n1}$—$(O(CH_2)_{n2})_{m1}$—O—$(CH_2)_{n3}$— triazolylene-$(CH_2)_{n4}$—; and wherein n1, n2, n3, n4, n5, n6, m1, and m2 each independently represent an integer of 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30.

In one embodiment of the present disclosure, the LIN represents:

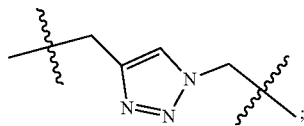

-continued

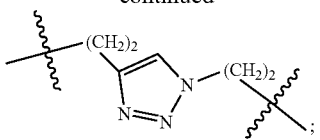

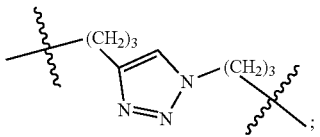

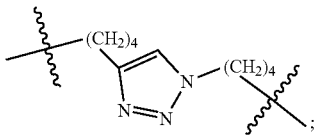

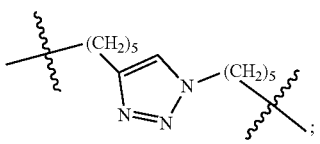

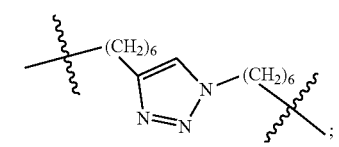

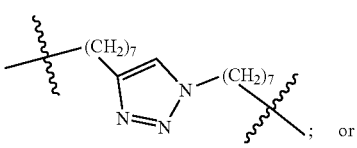

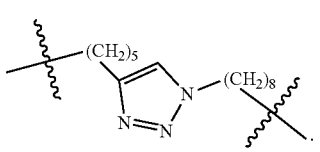

In one embodiment of the present disclosure, the LIN represents —$(CH_2)_{n1}$—$(CONH$—$(CH_2)_{n2})_{m1}$—, —$(CH_2)_{n1}$—$(CONH$—$(CH_2)_{n2})_{m1}$—O—$(CH_2)_{n3}$—, or —$(CH_2)_{n1}$—$(O(CH_2)_{n2})_{m1}$—O—$(CH_2)_{n3}$—CONH —$(CH_2)_{n4}$—$(O(CH_2)_{n5})_{m2}$—O—$(CH_2)_{n6}$—; wherein n1, n2, n3, n4, n5, n6, m1, and m2 each independently represent an integer of 1, 2, 3, 4, 5, 6, 7, 8, 9, 10, 11, 12, 13, 14, 15, 16, 17, 18, 19 or 20; wherein the LIN is optionally substituted by one or more substituents selected from the group consisting of hydroxyl, amino, mercapto and halogen. In one embodiments of the present disclosure, the LIN represents:
—$CH_2CONHCH_2$—; —$(CH_2)_2CONH(CH_2)_2$—;
—$(CH_2)_3CONH(CH_2)_3$—; —$(CH_2)_4CONH(CH_2)_4$—;
—$(CH_2)_3CONH(CH_2)_4$—; —$(CH_2)_5CONH(CH_2)_5$—;
—$(CH_2)_6CONH(CH_2)_7$—; —$(CH_2)_6CONH(CH_2)_6$—;
—$(CH_2)_7CONH(CH_2)_7$—; —$(CH_2)_8CONH(CH_2)_8$—;
—$(CH_2)_9CONH(CH_2)_9$—; —$(CH_2)_{10}CONH(CH_2)_{10}$—; or —$(CH_2)_2CONH(CH_2)_2$—O—$(CH_2)_2$—.

In one embodiment of the present disclosure, the LIN represents —$(CH_2)_{n1}$—NHCO—$(CH_2)_{n2}$—, wherein n1 and n2 are each independently the integer of 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30; wherein the LIN is optionally substituted by one or more substituents selected from the group consisting of hydroxyl, amino, mercapto and halogen. In one embodiment of the present disclosure, the LIN is —$(CH_2)_{n1}$—NHCO—$(CH_2)_{n2}$—, wherein n1 and n2 are each independently the integer of 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30.

In one embodiment of the present disclosure, the LIN is
—$CH_2NHCOCH_2$—, —$(CH_2)_2NHCO(CH_2)_2$—,
—$(CH_2)_3NHCO(CH_2)_3$—, —$(CH_2)_4NHCO(CH_2)_4$—,
—$(CH_2)_5NHCO(CH_2)_5$—, —$(CH_2)_6NHCO(CH_2)_6$—,
—$(CH_2)_6NHCO(CH_2)_6$—, —$(CH_2NHCO(CH_2)_7$—,
—$(CH_2)_8NHCO(CH_2)_8$—, —$(CH_2)_9NHCO(CH_2)_9$—,
—$(CH_2)_{10}NHCO(CH_2)_{10}$—, —$(CH_2)_{11}NHCO(CH_2)_{11}$—,
—$(CH_2)_{12}NHCO(CH_2)_{12}$—, or —$(CH_2)_4NHCO(CH_2)_8$—.

In one embodiment of the present disclosure, the LIN is a linear or branched alkylene chain interrupted one or more times (e.g., 1-20, 1-15, 1-10, 1-9, 1-8, 1-7, 1-6, 1-5, 1-4, 1-3, or 1-2 times, or 1 time) by one or more alkenylene groups; wherein the LIN is optionally substituted by one or more substituents selected from the group consisting of hydroxyl, amino, mercapto and halogen. In one embodiment of the present disclosure, the LIN is —$(CH_2)_{n1}$—CH=CH—$(CH_2)_{n2}$—, wherein n1 and n2 are each independently the integer of 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30.

In one embodiment of the present disclosure, the LIN is a linear or branched alkylene chain interrupted one or more times (e.g., 1-20, 1-15, 1-10, 1-9, 1-8, 1-7, 1-6, 1-5, 1-4, 1-3, or 1-2 times, or 1 time) by one or more alkynylene groups; wherein the LIN is optionally substituted by one or more substituents selected from the group consisting of hydroxyl, amino, mercapto and halogen. In one embodiment, the LIN is —$(CH_2)_{n1}$—C≡C—$(CH_2)_{n2}$— or —$(CH_2)_{n1}$—C≡C—C≡C—$(CH_2)_{n2}$—, wherein n1 and n2 are each independently the integer of 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30.

In one embodiment of the present disclosure, the compound of formula (I) may be also a compound of formula (IV):

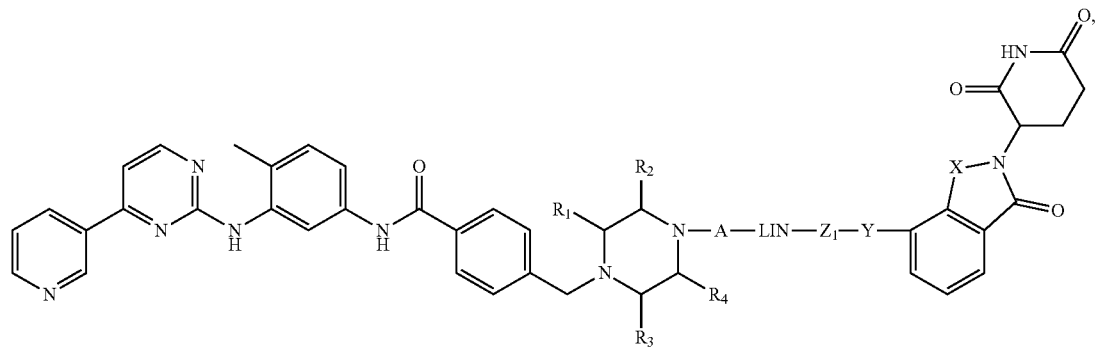

Formula (IV)

wherein the group A, LIN, X, Y, $Z_1$, $R_1$, $R_2$, $R_3$, and $R_4$ are as defined above, including the definitions in all embodiments thereof.

In one embodiment of the present disclosure, the compound of formula (I) may be also a compound of formula (V):

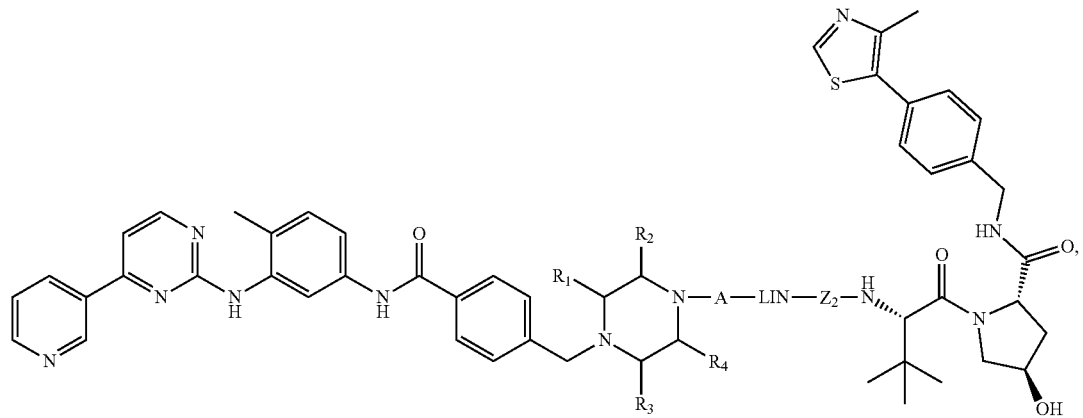

Formula (V)

wherein the group A, LIN, $Z_2$, $R_1$, $R_2$, $R_3$, and $R_4$ are as defined above, including the definitions in all embodiments thereof.

In one embodiment of the present disclosure, the compound of formula (I) may be also a compound of formula (VI):

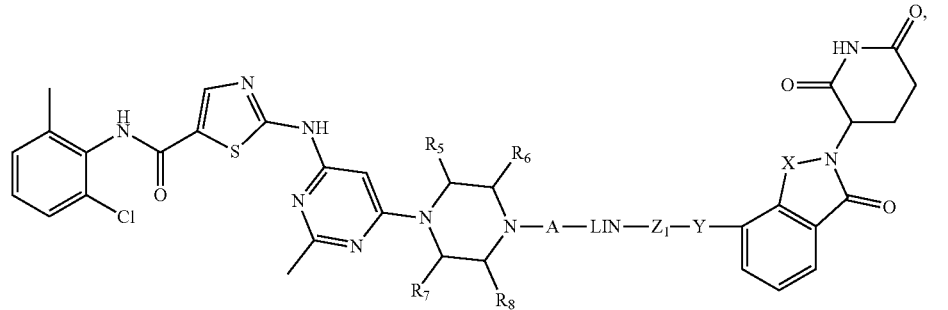

Formula (VI)

wherein the group A, LIN, X, Y, $Z_1$, $R_5$, $R_6$, $R_7$, and $R_8$ are as defined above, including the definitions in all embodiments thereof.

In one embodiment of the present disclosure, the compound of formula (I) may be also a compound of formula (VII):

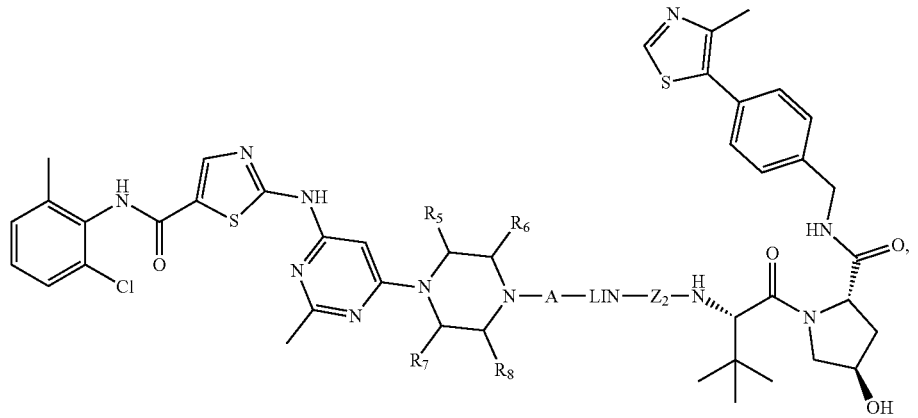

Formula (VII)

wherein the group A, LIN, $Z_2$, $R_5$, $R_6$, $R_7$, and $R_8$ are as defined above, including the definitions in all embodiments thereof.

In one embodiment of the present disclosure, the compound of formula (I) may be also a compound of formula (VIII):

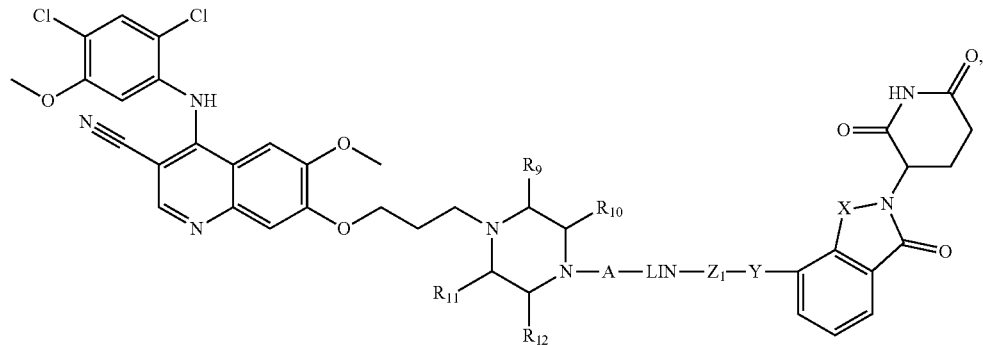

Formula (VIII)

wherein the group A, LIN, X, Y, $Z_1$, $R_9$, $R_{10}$, $R_{11}$, and $R_{12}$ are as defined above, including the definitions in all embodiments thereof.

In one embodiment of the present disclosure, the compound of formula (I) may be also a compound of formula (IX)

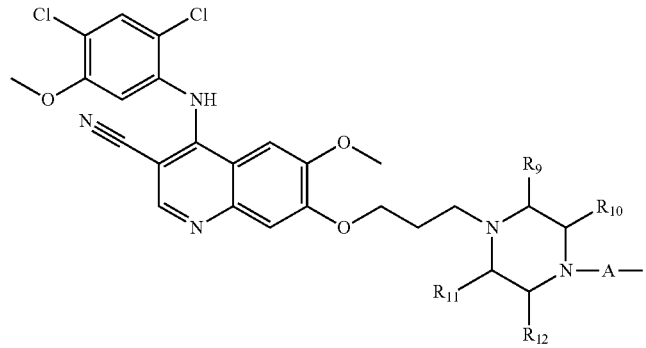 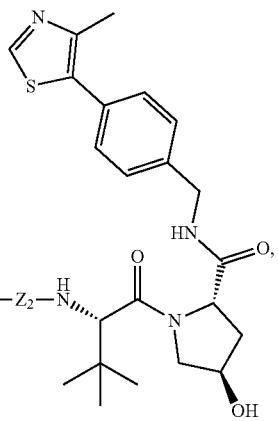
Formula (IX)
wherein the group A, LIN, $Z_2$, $R_9$, $R_{10}$, $R_{11}$, and $R_{12}$ are as defined above, including the definitions in all embodiments thereof.
Particularly preferred are the following compounds of formula (I) and salts thereof (especially pharmaceutically acceptable salts) in Table 1 of the present disclosure:

TABLE 1

The structure of compounds and its name

| Compound No. | Structure of compound | Name of the compound |
|---|---|---|
| SIAIS171114 | | N-(2-chloro-6-methylphenyl)-2-((6-(4-(6-(2-(2-((6-((2-(2,6-dioxopiperidin-3-yl)-1,3-dioxoisoindolin-4-yl)amino)-6-oxohexyl)oxy)ethoxy)ethoxy)hexanoyl)piperazin-1-yl)-2-methylpyrimidin-4-yl)amino)thiazole-5-carboxamide |

TABLE 1-continued

The structure of compounds and its name

| Compound No. | Structure of compound | Name of the compound |
|---|---|---|
|  |  | N-(2-chloro-6-methylphenyl)-2-((6-(4-(6-(2-(2-(6-((2-(2,6-dioxopiperidin-3-yl)-1,3-dioxoisoindolin-4-yl)amino)hexyl)oxy)ethoxy)ethoxy)hexanoyl)piperazin-1-yl)-2-methylpyrimidin-4-yl)amino)thiazole-5-carboxamide |

TABLE 1-continued

The structure of compounds and its name

| Compound No. | Structure of compound | Name of the compound |
|---|---|---|
| SIAIS151 063 | 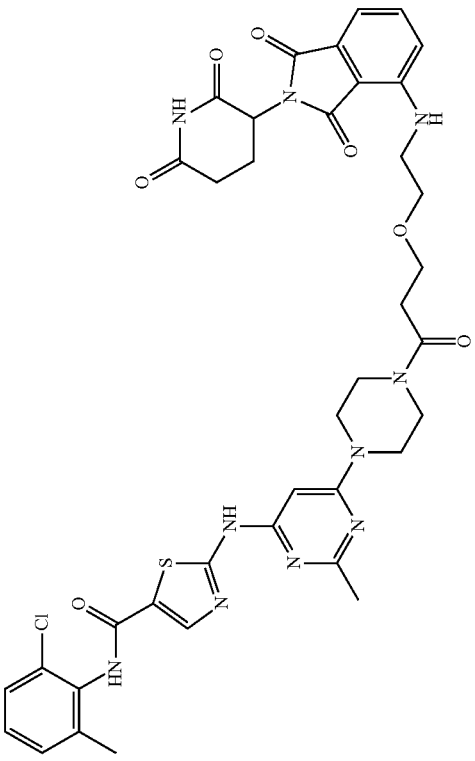 | N-(2-chloro-6-methylphenyl)-2-((6-(4-(3-(2-((2-(2,6-dioxopiperidin-3-yl)-1,3-dioxoisoindolin-4-yl)amino)ethoxy)propanoyl)piperazin-1-yl)-2-methylpyrimidin-4-yl)amino)thiazole-5-carboxamide |
| | | N-(2-chloro-6-methylphenyl)-2-((6-(4-(3-(2-(2,6-dioxopiperidin-3-yl)-1,3-dioxoisoindolin-4-yl)propoxy)propanoyl)piperazin-1-yl)-2-methylpyrimidin-4-yl)amino)thiazole-5-carboxamide |

TABLE 1-continued

The structure of compounds and its name

| Compound No. | Structure of compound | Name of the compound |
|---|---|---|
| | 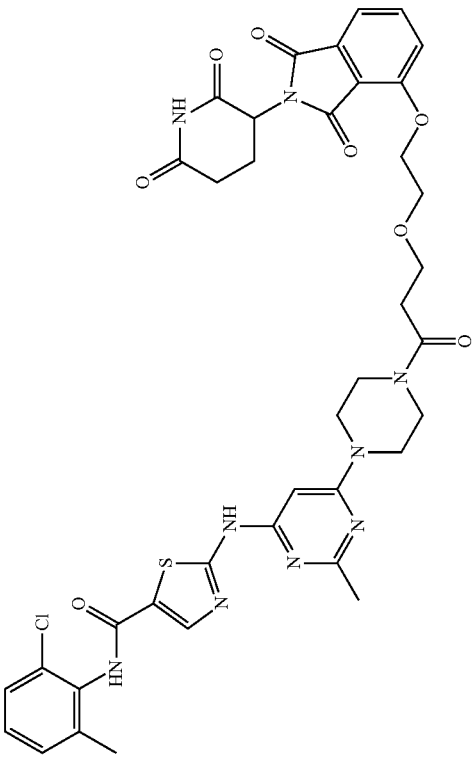 | N-(2-chloro-6-methylphenyl)-2-((6-(4-(3-(2-((2-(2,6-dioxopiperidin-3-yl)-1,3-dioxoisoindolin-4-yl)oxy)ethoxy)propanoyl)piperazin-1-yl)-2-methylpyrimidin-4-yl)amino)thiazole-5-carboxamide |
| SIAIS151064 | 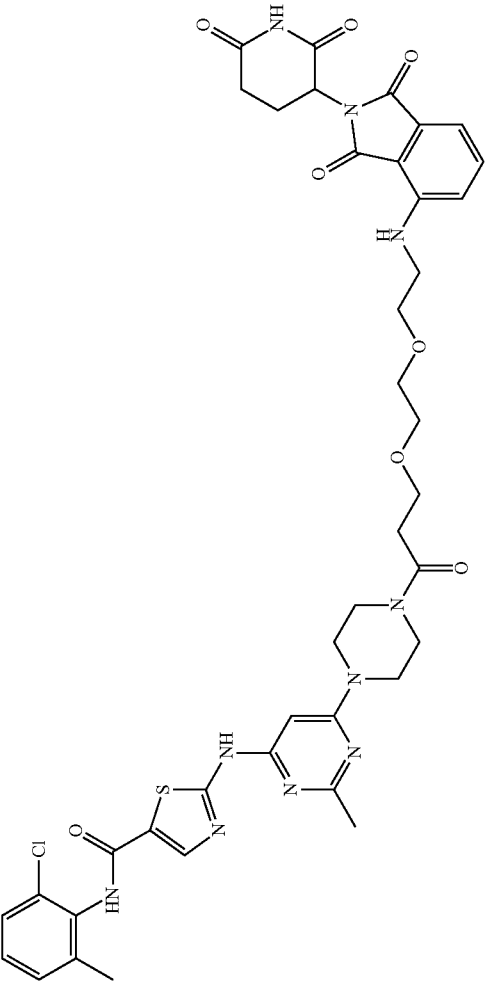 | N-(2-chloro-6-methylphenyl)-2-((6-(4-(3-(2-(2-((2-(2,6-dioxopiperidin-3-yl)-1,3-dioxoisoindolin-4-yl)amino)ethoxy)ethoxy)propanoyl)piperazin-1-yl)-2-methylpyrimidin-4-yl)amino)thiazole-5-carboxamide |

TABLE 1-continued

The structure of compounds and its name

| Compound No. | Structure of compound | Name of the compound |
|---|---|---|
| | | N-(2-chloro-6-methylphenyl)-2-((6-(4-(3-(2-(3-(2-(2,6-dioxopiperidin-3-yl)-1,3-dioxoisoindolin-4-yl)propoxy)ethoxy)propanoyl)piperazin-1-yl)-2-methylpyrimidin-4-yl)amino)thiazole-5-carboxamide |
| | | N-(2-chloro-6-methylphenyl)-2-((6-(4-(3-(2-(2-((2-(2,6-dioxopiperidin-3-yl)-1,3-dioxoisoindolin-4-yl)oxy)ethoxy)ethoxy)propanoyl)piperazin-1-yl)-2-methylpyrimidin-4-yl)amino)thiazole-5-carboxamide |

TABLE 1-continued

The structure of compounds and its name

| Compound No. | Structure of compound | Name of the compound |
|---|---|---|
| SIAIS151 067 | | N-(2-chloro-6-methylphenyl)-2-((6-(4-(3-(2-(2-(2-((2-(2,6-dioxopiperidin-3-yl)-1,3-dioxoisoindolin-4-yl)amino)ethoxy)ethoxy)ethoxy)propanoyl)piperazin-1-yl)-2-methylpyrimidin-4-yl)amino)thiazole-5-carboxamide |
| SIAIS151 068 | | N-(2-chloro-6-methylphenyl)-2-((6-(4-(1-((2-(2,6-dioxopiperidin-3-yl)-1,3-dioxoisoindolin-4-yl)amino)-3,6,9,12-tetraoxapentadecan-15-oyl)piperazin-1-yl)-2-methylpyrimidin-4-yl)amino)thiazole-5-carboxamide |

TABLE 1-continued

The structure of compounds and its name

| Compound No. | Structure of compound | Name of the compound |
|---|---|---|
| | 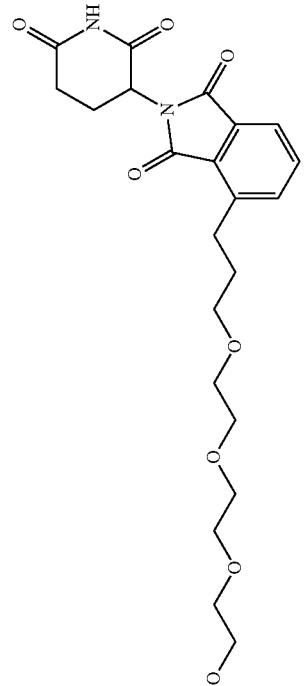 | N-(2-chloro-6-methylphenyl)-2-((6-(4-(16-(2-(2,6-dioxopiperidin-3-yl)-1,3-dioxoisoindolin-4-yl)-4,7,10,13-tetraoxahexadecanoyl)piperazin-1-yl)-2-methylpyrimidin-4-yl)amino)thiazole-5-carboxamide |
| | | N-(2-chloro-6-methylphenyl)-2-((6-(4-(1-((2-(2,6-dioxopiperidin-3-yl)-1,3-dioxoisoindolin-4-yl)oxy)-3,6,9,12-tetraoxapentadecan-15-oyl)piperazin-1-yl)-2-methylpyrimidin-4-yl)amino)thiazole-5-carboxamide |

TABLE 1-continued

The structure of compounds and its name

| Compound No. | Structure of compound | Name of the compound |
|---|---|---|
| SIAIS151 069 | | N-(2-chloro-6-methylphenyl)-2-((6-(4-(1-((2-(2,6-dioxopiperidin-3-yl)-1,3-dioxoisoindolin-4-yl)amino)-3,6,9,12,15-pentaoxaoctadecan-18-oyl)piperazin-1-yl)-2-methylpyrimidin-4-yl)amino)thiazole-5-carboxamide |
| SIAIS151 072 | | N-(2-chloro-6-methylphenyl)-2-((6-(4-(2-(2,6-dioxopiperidin-3-yl)-1,3-dioxoisoindolin-4-yl)glycyl)piperazin-1-yl)-2-methylpyrimidin-4-yl)amino)thiazole-5-carboxamide |

TABLE 1-continued

The structure of compounds and its name

| Compound No. | Structure of compound | Name of the compound |
|---|---|---|
| SIAIS172 150 | | N-(2-chloro-6-methylphenyl)-2-(6-(4-(3-(2-(2,6-dioxopiperidin-3-yl)-1,3-dioxoisoindolin-4-yl)propanoyl)piperazin-1-yl)-2-methylpyrimidin-4-yl)aminothiazole-5-carboxamide |
| SIAIS184 128 | | N-(2-chloro-6-methylphenyl)-2-((6-(4-(2-((2-(2,6-dioxopiperidin-3-yl)-1,3-dioxoisoindolin-4-yl)oxy)acetyl)piperazin-1-yl)-2-methylpyrimidin-4-yl)aminothiazole-5-carboxamide |

TABLE 1-continued

The structure of compounds and its name

| Compound No. | Structure of compound | Name of the compound |
|---|---|---|
| SIAIS151074 | | N-(2-chloro-6-methylphenyl)-2-((6-(4-(3-((2-(2,6-dioxopiperidin-3-yl)-1,3-dioxoisoindolin-4-yl)amino)propanoyl)piperazin-1-yl)-2-methylpyrimidin-4-yl)amino)thiazole-5-carboxamide |
| SIAIS151070 | | N-(2-chloro-6-methylphenyl)-2-((6-(4-(4-((2-(2,6-dioxopiperidin-3-yl)-1,3-dioxoisoindolin-4-yl)amino)butanoyl)piperazin-1-yl)-2-methylpyrimidin-4-yl)amino)thiazole-5-carboxamide |

TABLE 1-continued

The structure of compounds and its name

| Compound No. | Structure of compound | Name of the compound |
|---|---|---|
| | 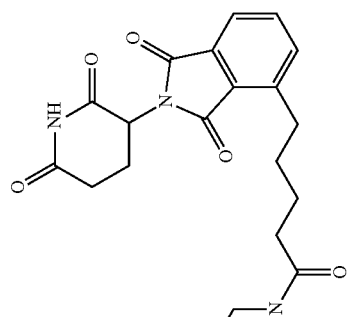 | N-(2-chloro-6-methylphenyl)-2-((6-(4-(5-(2-(2,6-dioxopiperidin-3-yl)-1,3-dioxoisoindolin-4-yl)pentanoyl)piperazin-1-yl)-2-methylpyrimidin-4-yl)amino)thiazole-5-carboxamide |
| | 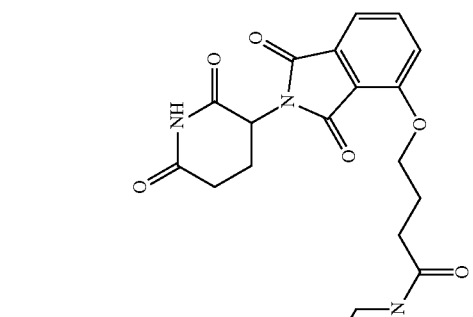 | N-(2-chloro-6-methylphenyl)-2-((6-(4-((2-(2,6-dioxopiperidin-3-yl)-1,3-dioxoisoindolin-4-yl)oxy)butanoyl)piperazin-1-yl)-2-methylpyrimidin-4-yl)amino)thiazole-5-carboxamide |

TABLE 1-continued

The structure of compounds and its name

| Compound No. | Structure of compound | Name of the compound |
|---|---|---|
| SIAIS151071 | | N-(2-chloro-6-methylphenyl)-2-((6-(4-(5-((2-(2,6-dioxopiperidin-3-yl)-1,3-dioxoisoindolin-4-yl)amino)pentanoyl)piperazin-1-yl)-2-methylpyrimidin-4-yl)amino)thiazole-5-carboxamide |
| SIAIS151075 | | N-(2-chloro-6-methylphenyl)-2-((6-(4-(6-((2-(2,6-dioxopiperidin-3-yl)-1,3-dioxoisoindolin-4-yl)amino)hexanoyl)piperazin-1-yl)-2-methylpyrimidin-4-yl)amino)thiazole-5-carboxamide |

TABLE 1-continued

The structure of compounds and its name

| Compound No. | Structure of compound | Name of the compound |
|---|---|---|
| | 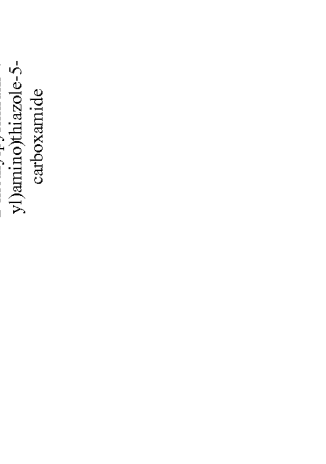 | N-(2-chloro-6-methylphenyl)-2-((6-(4-(7-(2-(2,6-dioxopiperidin-3-yl)-1,3-dioxoisoindolin-4-yl)heptanoyl)piperazin-1-yl)-2-methylpyrimidin-4-yl)amino)thiazole-5-carboxamide |
| | 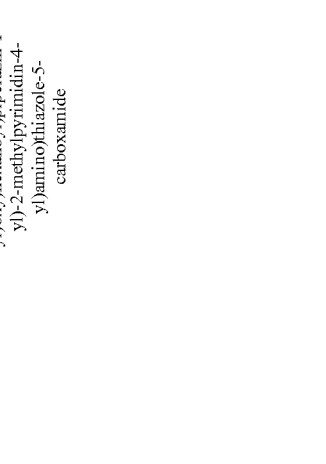 | N-(2-chloro-6-methylphenyl)-2-((6-(4-((2-(2,6-dioxopiperidin-3-yl)-1,3-dioxoisoindolin-4-yl)oxy)hexanoyl)piperazin-1-yl)-2-methylpyrimidin-4-yl)amino)thiazole-5-carboxamide |

TABLE 1-continued

The structure of compounds and its name

| Compound No. | Structure of compound | Name of the compound |
|---|---|---|
| SIAIS151 181 | 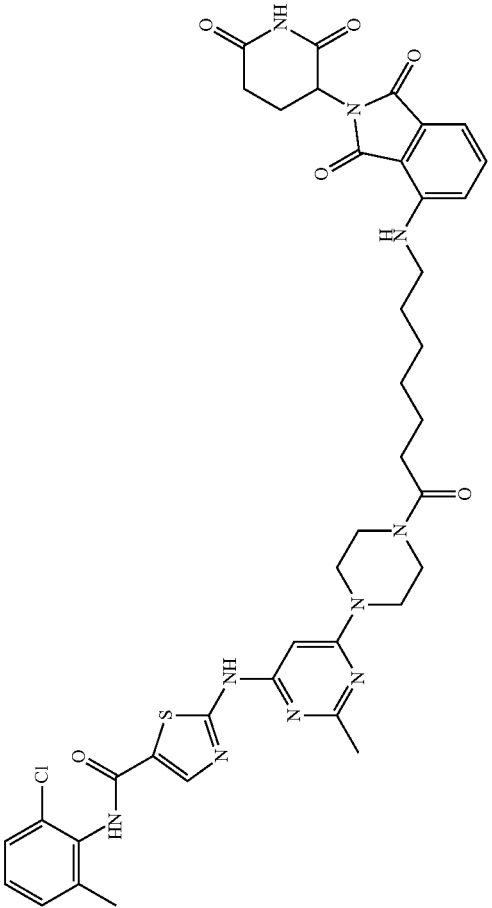 | N-(2-chloro-6-methylphenyl)-2-((6-(4-(7-((2-(2,6-dioxopiperidin-3-yl)-1,3-dioxoisoindolin-4-yl)amino)heptanoyl)piperazin-1-yl)-2-methylpyrimidin-4-yl)amino)thiazole-5-carboxamide |
| | | N-(2-chloro-6-methylphenyl)-2-((6-(4-(8-((2-(2,6-dioxopiperidin-3-yl)-1,3-dioxoisoindolin-4-yl)amino)octanoyl)piperazin-1-yl)-2-methylpyrimidin-4-yl)amino)thiazole-5-carboxamide |

TABLE 1-continued

The structure of compounds and its name

| Compound No. | Structure of compound | Name of the compound |
|---|---|---|
| | 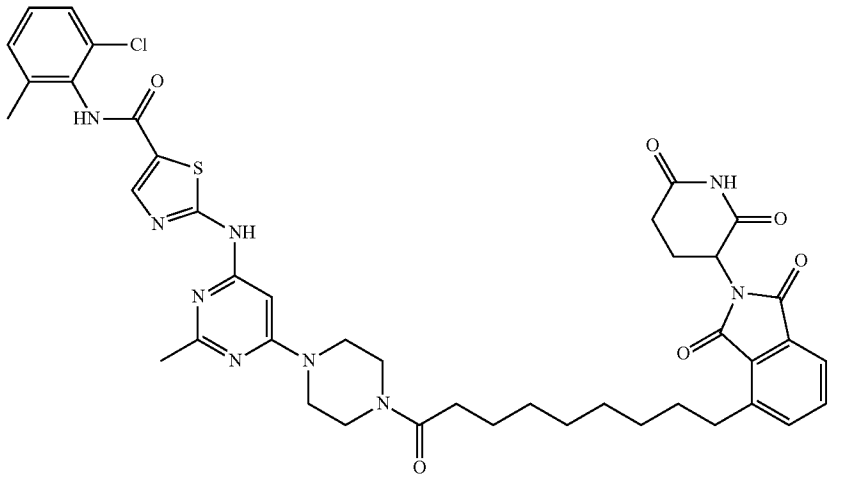 | N-(2-chloro-6-methylphenyl)-2-(2-(6-(4-(9-(2-(2,6-dioxopiperidin-3-yl)-1,3-dioxoisoindolin-4-yl)nonanoyl)piperazin-1-yl)-2-methylpyrimidin-4-yl)aminothiazole-5-carboxamide |
| | 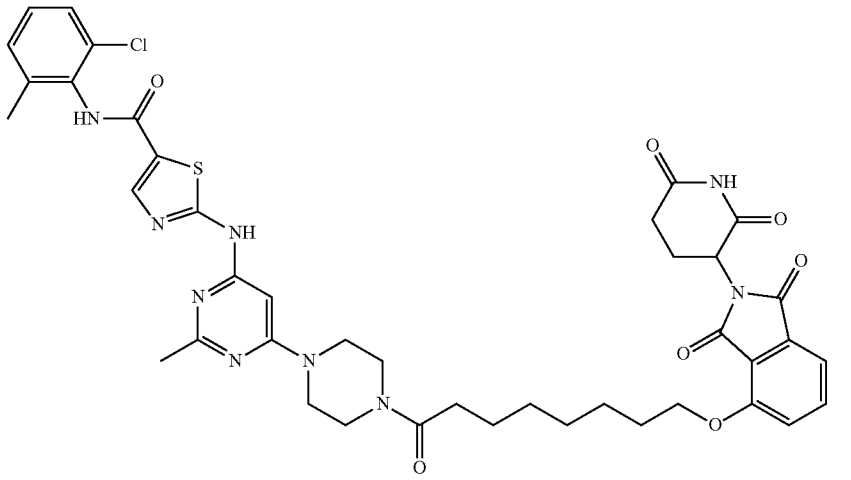 [SMILES: Cc1nc(Nc2ncc(C(=O)Nc3c(C)cccc3Cl)s2)cc(N2CCN(C(=O)CCCCCCCCc3cccc4c3C(=O)N(C3CCC(=O)NC3=O)C4=O)CC2)n1] | N-(2-chloro-6-methylphenyl)-2-(2-(6-(4-(8-((2-(2,6-dioxopiperidin-3-yl)-1,3-dioxoisoindolin-4-yl)oxy)octanoyl)piperazin-1-yl)-2-methylpyrimidin-4-yl)aminothiazole-5-carboxamide |

TABLE 1-continued

The structure of compounds and its name

| Compound No. | Structure of compound | Name of the compound |
|---|---|---|
| SIAIS184 053 | 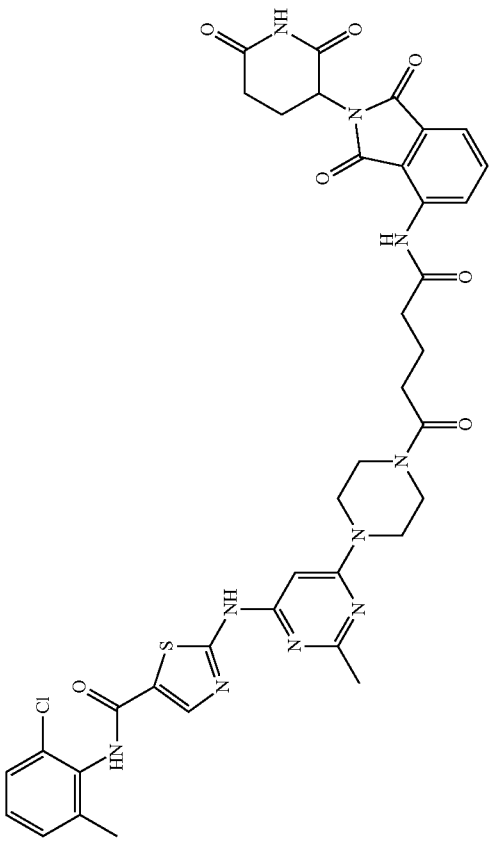 | N-(2-chloro-6-methylphenyl)-2-((6-(4-(5-((2-(2,6-dioxopiperidin-3-yl)-1,3-dioxoisoindolin-4-yl)amino)-5-oxopentanoyl)piperazin-1-yl)-2-methylpyrimidin-4-yl)amino)thiazole-5-carboxamide |
| | | N-(2-chloro-6-methylphenyl)-2-((6-(4-(6-((2-(2,6-dioxopiperidin-3-yl)-1,3-dioxoisoindolin-4-yl)amino)-6-oxohexanoyl)piperazin-1-yl)-2-methylpyrimidin-4-yl)amino)thiazole-5-carboxamide |

TABLE 1-continued

The structure of compounds and its name

| Compound No. | Structure of compound | Name of the compound |
|---|---|---|
| | 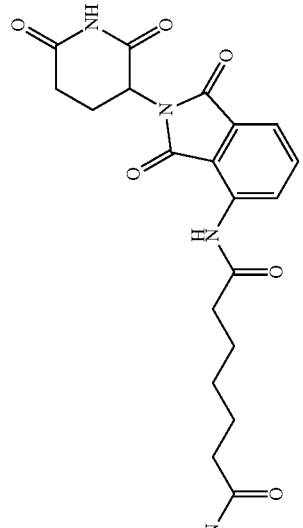 | N-(2-chloro-6-methylphenyl)-2-((6-(4-(7-((2-(2,6-dioxopiperidin-3-yl)-1,3-dioxoisoindolin-4-yl)amino)-7-oxoheptanoyl)piperazin-1-yl)-2-methylpyrimidin-4-yl)amino)thiazole-5-carboxamide |
| | | N-(2-chloro-6-methylphenyl)-2-((6-(4-(8-((2-(2,6-dioxopiperidin-3-yl)-1,3-dioxoisoindolin-4-yl)amino)-8-oxooctanoyl)piperazin-1-yl)-2-methylpyrimidin-4-yl)amino)thiazole-5-carboxamide |

TABLE 1-continued

The structure of compounds and its name

| Compound No. | Structure of compound | Name of the compound |
|---|---|---|
| SIAIS164 133 | | N-(2-chloro-6-methylphenyl)-2-((6-(4-(4-((2-(2-(2,6-dioxopiperidin-3-yl)-1,3-dioxoisoindolin-4-yl)amino)ethyl)amino)-4-oxobutanoyl)piperazin-1-yl)-2-methylpyrimidin-4-yl)amino)thiazole-5-carboxamide |
| SIAIS164 132 | | N-(2-chloro-6-methylphenyl)-2-((6-(4-(4-((2-(2-(2-(2,6-dioxopiperidin-3-yl)-1,3-dioxoisoindolin-4-yl)amino)ethoxy)ethyl)amino)-4-oxobutanoyl)piperazin-1-yl)-2-methylpyrimidin-4-yl)amino)thiazole-5-carboxamide |

TABLE 1-continued

The structure of compounds and its name

| Compound No. | Structure of compound | Name of the compound |
|---|---|---|
| SIAIS164 108 | | N-(2-chloro-6-methylphenyl)-2-((6-(4-(3-((2-(2,6-dioxopiperidin-3-yl)-1-oxoisoindolin-4-yl)amino)-3-oxopropanoyl)piperazin-1-yl)-2-methylpyrimidin-4-yl)amino)thiazole-5-carboxamide |
| SIAIS164 109 | | N-(2-chloro-6-methylphenyl)-2-((6-(4-(4-((2-(2,6-dioxopiperidin-3-yl)-1-oxoisoindolin-4-yl)amino)-4-oxobutanoyl)piperazin-1-yl)-2-methylpyrimidin-4-yl)amino)thiazole-5-carboxamide |

TABLE 1-continued

The structure of compounds and its name

| Compound No. | Structure of compound | Name of the compound |
|---|---|---|
| SIAIS164 110 | | N-(2-chloro-6-methylphenyl)-2-((6-(4-(5-((2-(2,6-dioxopiperidin-3-yl)-1-oxoisoindolin-4-yl)amino)-5-oxopentanoyl)piperazin-1-yl)-2-methylpyrimidin-4-yl)amino)thiazole-5-carboxamide |
| SIAIS164 181 | | N-(2-chloro-6-methylphenyl)-2-((6-(4-(6-((2-(2,6-dioxopiperidin-3-yl)-1-oxoisoindolin-4-yl)amino)-6-oxohexanoyl)piperazin-1-yl)-2-methylpyrimidin-4-yl)amino)thiazole-5-carboxamide |

TABLE 1-continued

The structure of compounds and its name

| Compound No. | Structure of compound | Name of the compound |
|---|---|---|
| SIAIS164 | 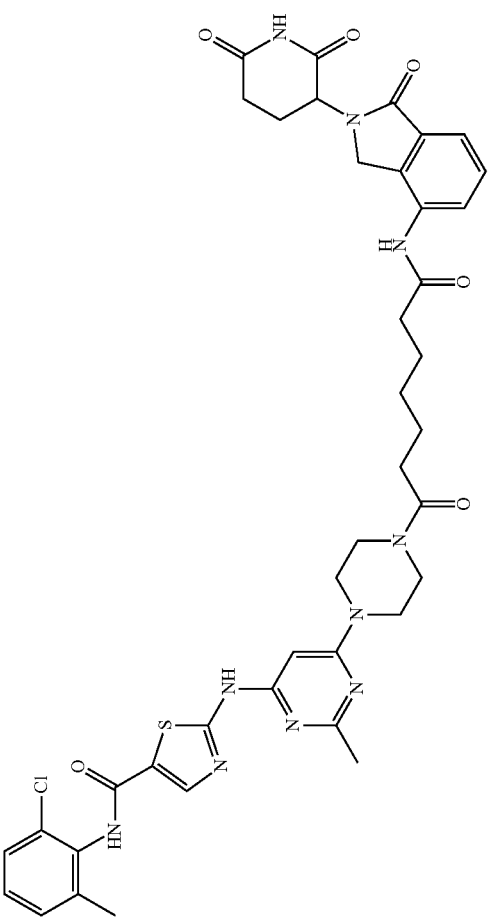 | N-(2-chloro-6-methylphenyl)-2-((6-(4-(7-((2-(2,6-dioxopiperidin-3-yl)-1-oxoisoindolin-4-yl)amino)-7-oxoheptanoyl)piperazin-1-yl)-2-methylpyrimidin-4-yl)amino)thiazole-5-carboxamide |
| 182 | | N-(2-chloro-6-methylphenyl)-2-((6-(4-(8-((2-(2,6-dioxopiperidin-3-yl)-1-oxoisoindolin-4-yl)amino)-8-oxooctanoyl)piperazin-1-yl)-2-methylpyrimidin-4-yl)amino)thiazole-5-carboxamide |

TABLE 1-continued

The structure of compounds and its name

| Compound No. | Structure of compound | Name of the compound |
|---|---|---|
| | 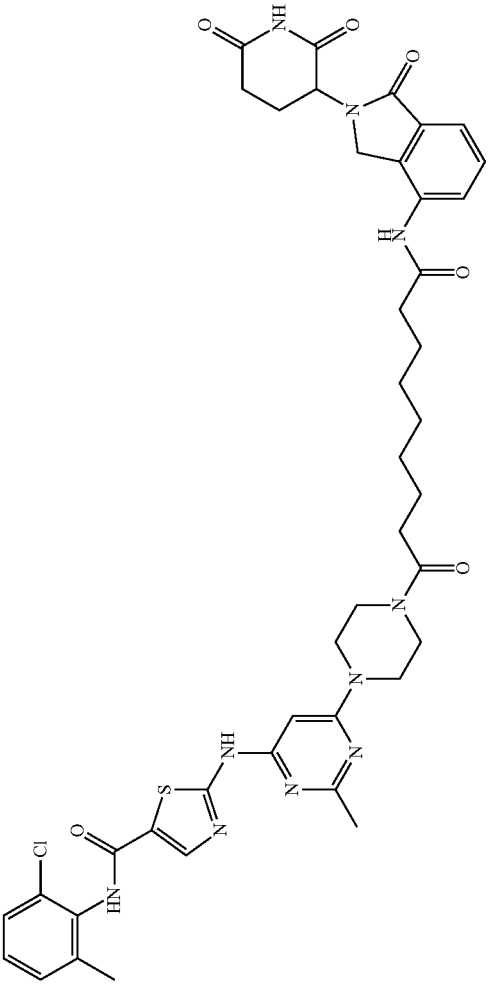 | N-(2-chloro-6-methylphenyl)-2-((6-(4-(9-((2-(2,6-dioxopiperidin-3-yl)-1-oxoisoindolin-4-yl)amino)-9-oxononanoyl)piperazin-1-yl)-2-methylpyrimidin-4-yl)amino)thiazole-5-carboxamide |
| | | N-(2-chloro-6-methylphenyl)-2-((6-(4-(10-((2-(2,6-dioxopiperidin-3-yl)-1-oxoisoindolin-4-yl)amino)-10-oxodecanoyl)piperazin-1-yl)-2-methylpyrimidin-4-yl)amino)thiazole-5-carboxamide |

TABLE 1-continued

The structure of compounds and its name

| Compound No. | Structure of compound | Name of the compound |
|---|---|---|
| | 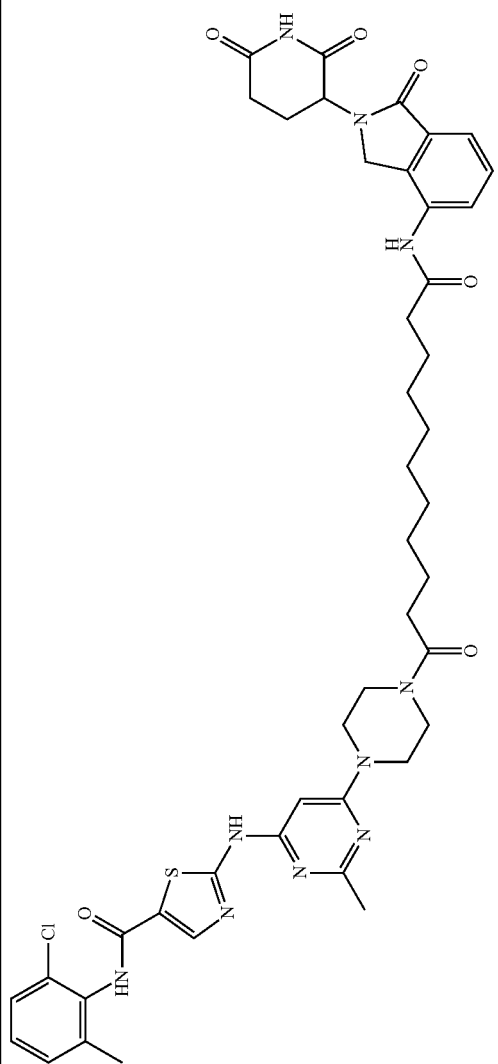 | N-(2-chloro-6-methylphenyl)-2-((6-(4-(11-((2-(2,6-dioxopiperidin-3-yl)-1-oxoisoindolin-4-yl)amino)-11-oxoundecanoyl)piperazin-1-yl)-2-methylpyrimidin-4-yl)amino)thiazole-5-carboxamide |
| | | N-(2-chloro-6-methylphenyl)-2-((6-(4-(3-((2-(2,6-dioxopiperidin-3-yl)-1-oxoisoindolin-4-yl)amino)propanoyl)piperazin-1-yl)-2-methylpyrimidin-4-yl)amino)thiazole-5-carboxamide |

TABLE 1-continued

The structure of compounds and its name

| Compound No. | Structure of compound | Name of the compound |
|---|---|---|
| | 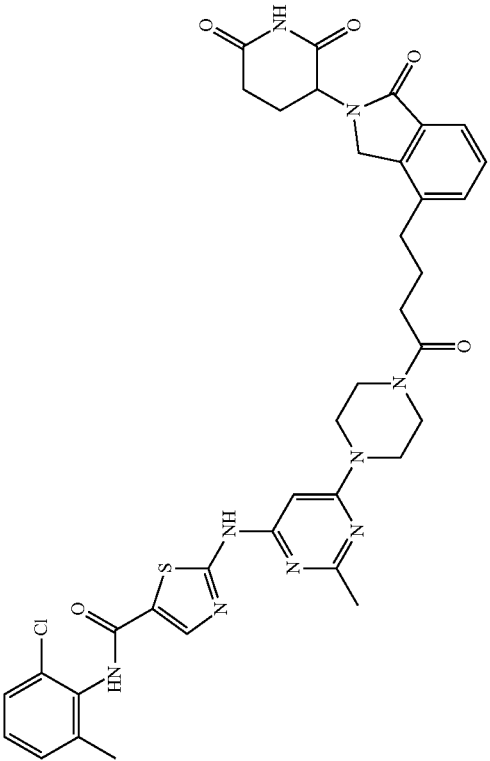 | N-(2-chloro-6-methylphenyl)-2-(4-(4-(2-(2,6-dioxopiperidin-3-yl)-1-oxoisoindolin-4-yl)butanoyl)piperazin-1-yl)-2-methylpyrimidin-4-yl)amino)thiazole-5-carboxamide |
| | | N-(2-chloro-6-methylphenyl)-2-((6-(4-(3-((2-(2,6-dioxopiperidin-3-yl)-1-oxoisoindolin-4-yl)oxy)propanoyl)piperazin-1-yl)-2-methylpyrimidin-4-yl)amino)thiazole-5-carboxamide |

TABLE 1-continued

The structure of compounds and its name

| Compound No. | Structure of compound | Name of the compound |
|---|---|---|
| | 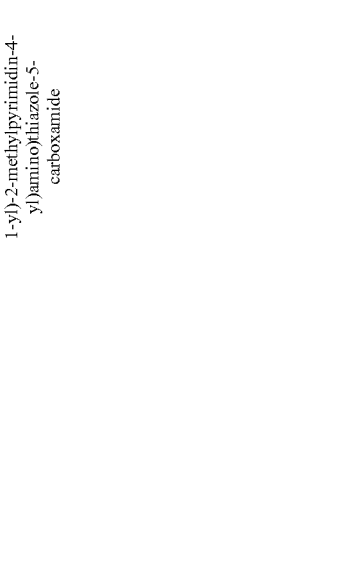 | N-(2-chloro-6-methylphenyl)-2-((6-(4-(4-((2-(2,6-dioxopiperidin-3-yl)-1-oxoisoindolin-4-yl)amino)butanoyl)piperazin-1-yl)-2-methylpyrimidin-4-yl)amino)thiazole-5-carboxamide |
| |  | N-(2-chloro-6-methylphenyl)-2-((6-(4-(5-(2-(2,6-dioxopiperidin-3-yl)-1-oxoisoindolin-4-yl)pentanoyl)piperazin-1-yl)-2-methylpyrimidin-4-yl)amino)thiazole-5-carboxamide |

TABLE 1-continued

The structure of compounds and its name

| Compound No. | Structure of compound | Name of the compound |
|---|---|---|
|  | 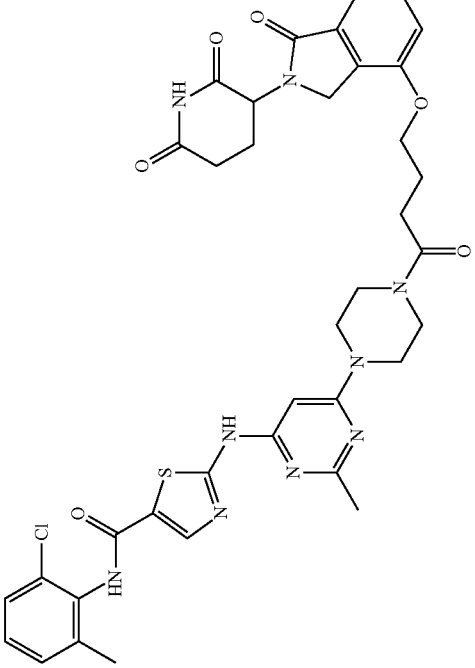 | N-(2-chloro-6-methylphenyl)-2-((6-(4-(4-((2-(2,6-dioxopiperidin-3-yl)-1-oxoisoindolin-4-yl)oxy)butanoyl)piperazin-1-yl)-2-methylpyrimidin-4-yl)amino)thiazole-5-carboxamide |
| SIAIS184052 |  | N-(2-chloro-6-methylphenyl)-2-((6-(4-(5-((2-(2,6-dioxopiperidin-3-yl)-1-oxoisoindolin-4-yl)amino)pentanoyl)piperazin-1-yl)-2-methylpyrimidin-4-yl)amino)thiazole-5-carboxamide |

TABLE 1-continued

The structure of compounds and its name

| Compound No. | Structure of compound | Name of the compound |
|---|---|---|
| | 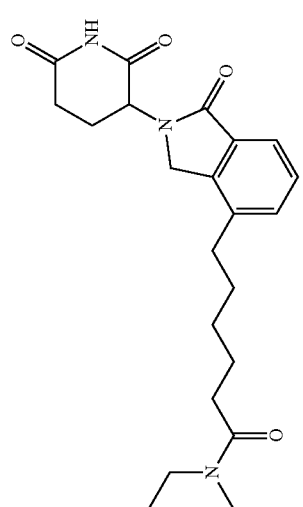 | N-(2-chloro-6-methylphenyl)-2-((6-(4-(6-(2-(2,6-dioxopiperidin-3-yl)-1-oxoisoindolin-4-yl)hexanoyl)piperazin-1-yl)-2-methylpyrimidin-4-yl)amino)thiazole-5-carboxamide |
| | 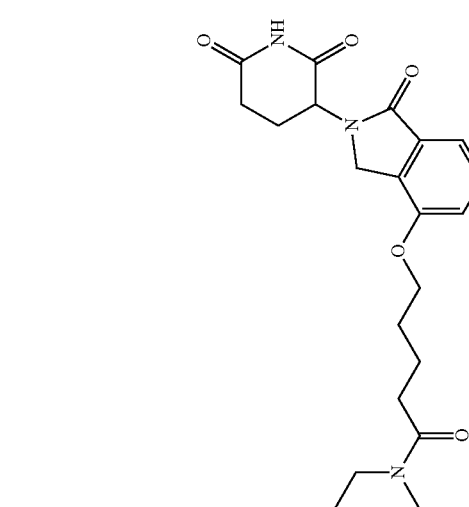 | N-(2-chloro-6-methylphenyl)-2-((6-(4-(5-((2-(2,6-dioxopiperidin-3-yl)-1-oxoisoindolin-4-yl)oxy)pentanoyl)piperazin-1-yl)-2-methylpyrimidin-4-yl)amino)thiazole-5-carboxamide |

TABLE 1-continued

The structure of compounds and its name

| Compound No. | Structure of compound | Name of the compound |
|---|---|---|
| | 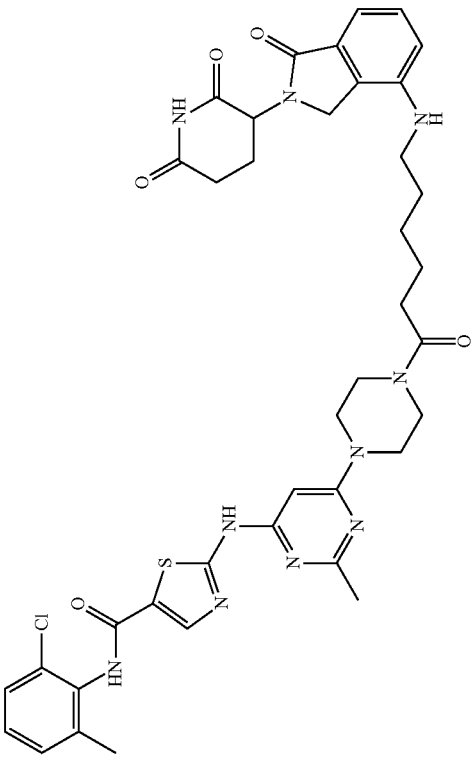 | N-(2-chloro-6-methylphenyl)-2-((6-(4-(6-((2-(2,6-dioxopiperidin-3-yl)-1-oxoisoindolin-4-yl)amino)hexanoyl)piperazin-1-yl)-2-methylpyrimidin-4-yl)amino)thiazole-5-carboxamide |
| | | N-(2-chloro-6-methylphenyl)-2-((6-(4-(7-((2-(2,6-dioxopiperidin-3-yl)-1-oxoisoindolin-4-yl)amino)heptanoyl)piperazin-1-yl)-2-methylpyrimidin-4-yl)amino)thiazole-5-carboxamide |

TABLE 1-continued

The structure of compounds and its name

| Compound No. | Structure of compound | Name of the compound |
|---|---|---|
|  | 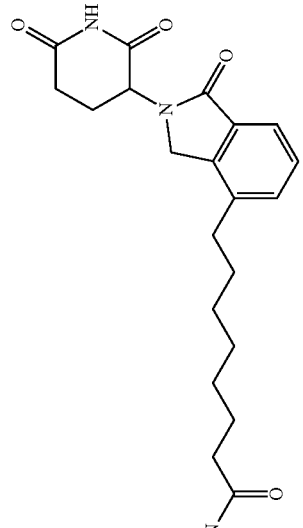 | N-(2-chloro-6-methylphenyl)-2-((6-(4-(8-(2-(2,6-dioxopiperidin-3-yl)-1-oxoisoindolin-4-yl)octanoyl)piperazin-1-yl)-2-methylpyrimidin-4-yl)amino)thiazole-5-carboxamide |
|  | 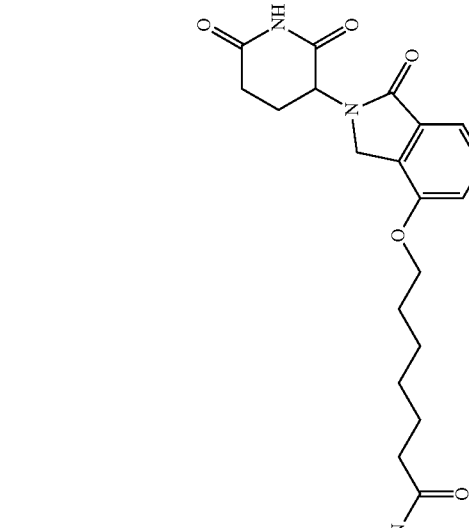 | N-(2-chloro-6-methylphenyl)-2-((6-(4-(7-((2-(2,6-dioxopiperidin-3-yl)-1-oxoisoindolin-4-yl)oxy)heptanoyl)piperazin-1-yl)-2-methylpyrimidin-4-yl)amino)thiazole-5-carboxamide |

TABLE 1-continued

The structure of compounds and its name

| Compound No. | Structure of compound | Name of the compound |
|---|---|---|
| SIAIS180147 | | N-(2-chloro-6-methylphenyl)-2-((6-(4-((S)-3-((2S,4R)-4-hydroxy-2-((4-(4-methylthiazol-5-yl)benzyl)carbamoyl)pyrrolidine-1-carbonyl)-2,2-dimethyl-5-oxo-11,14,17-trioxa-4-azatricosan-23-oyl)piperazin-1-yl)-2-methylpyrimidin-4-yl)amino)thiazole-5-carboxamide |

TABLE 1-continued
The structure of compounds and its name
| Compound No. | Structure of compound | Name of the compound |
|---|---|---|
| | 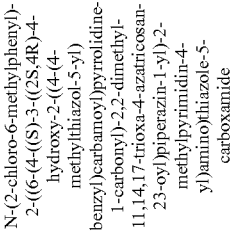 | N-(2-chloro-6-methylphenyl)-2-((6-(4-((S)-3-((2S,4R)-4-hydroxy-2-((4-(4-methylthiazol-5-yl)benzyl)carbamoyl)pyrrolidine-1-carbonyl)-2,2-dimethyl-11,14,17-trioxa-4-azatricosan-23-oyl)piperazin-1-yl)-2-methylpyrimidin-4-yl)amino)thiazole-5-carboxamide |

TABLE 1-continued

The structure of compounds and its name

| Compound No. | Structure of compound | Name of the compound |
|---|---|---|
| SIAIS151 080 | | N-(2-chloro-6-methylphenyl)-2-((6-(4-(2-(2-(2-(((S)-1-((2S,4R)-4-hydroxy-2-((4-(4-methylthiazol-5-yl)benzyl)carbamoyl)pyrrolidine-1-yl)-3,3-dimethyl-1-oxobutan-2-yl)amino)-2-oxoethoxy)ethoxy)acetyl)piperazin-1-yl)-2-methylpyrimidin-4-yl)amino)thiazole-5-carboxamide |
| SIAIS151 076 | | N-(2-chloro-6-methylphenyl)-2-((6-(4-(2-(2-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)ethoxy)acetyl)piperazin-1-yl)-2-methylpyrimidin-4-yl)amino)thiazole-5-carboxamide |

TABLE 1-continued
The structure of compounds and its name
| Compound No. | Structure of compound | Name of the compound |
|---|---|---|
| SIAIS151 077 | 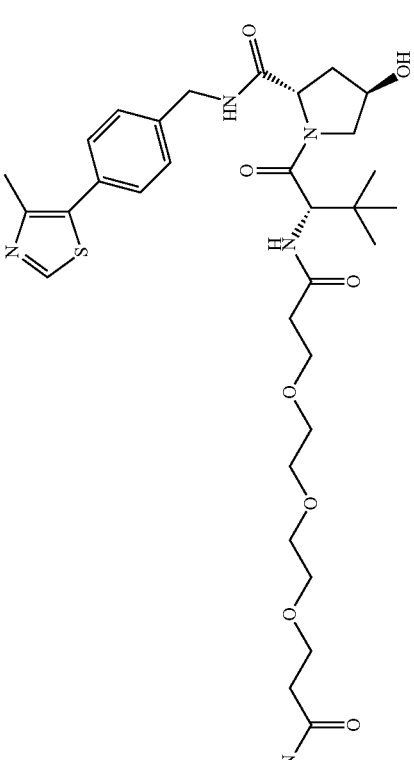 | N-(2-chloro-6-methylphenyl)-2-((6-(4-((S)-15-((2S,4R)-4-hydroxy-2-((4-(4-methylthiazol-5-yl)benzyl)carbamoyl)pyrrolidine-1-carbonyl)-16,16-dimethyl-13-oxo-4,7,10-trioxa-14-azaheptadecanoyl)piperazin-1-yl)-2-methylpyrimidin-4-yl)amino)thiazole-5-carboxamide |

TABLE 1-continued
The structure of compounds and its name
| Compound No. | Structure of compound | Name of the compound |
|---|---|---|
| SIAIS151 078 | 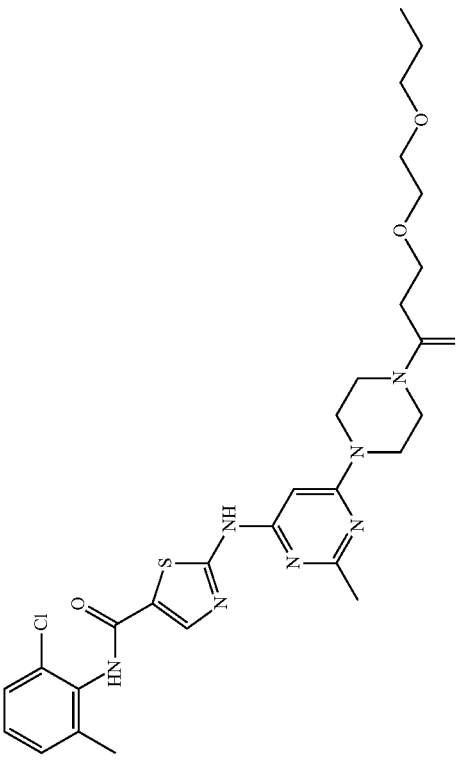 | N-(2-chloro-6-methylphenyl)-2-((6-(4-((S)-18-((2S,4R)-4-hydroxy-2-((4-(4-methylthiazol-5-yl)benzyl)carbamoyl)pyrrolidine-1-carbonyl)-19,19-dimethyl-16-oxo-4,7,10,13-tetraoxa-17-azaicosanoyl)piperazin-1-yl)-2-methylpyrimidin-4-yl)amino)thiazole-5-carboxamide |

TABLE 1-continued

The structure of compounds and its name

| Compound No. | Structure of compound | Name of the compound |
|---|---|---|
| SIAIS151 079 | | N-(2-chloro-6-methylphenyl)-2-((6-(4-((S)-21-((2S,4R)-4-hydroxy-2-((4-(4-methylthiazol-5-yl)benzyl)carbamoyl)pyrrolidine-1-carbonyl)-22,22-dimethyl-19-oxo-4,7,10,13,16-pentaoxa-20-azatricosanoyl)piperazin-1-yl)-2-methylpyrimidin-4-yl)amino)thiazole-5-carboxamide |

TABLE 1-continued

The structure of compounds and its name

| Compound No. | Structure of compound | Name of the compound |
|---|---|---|
| | 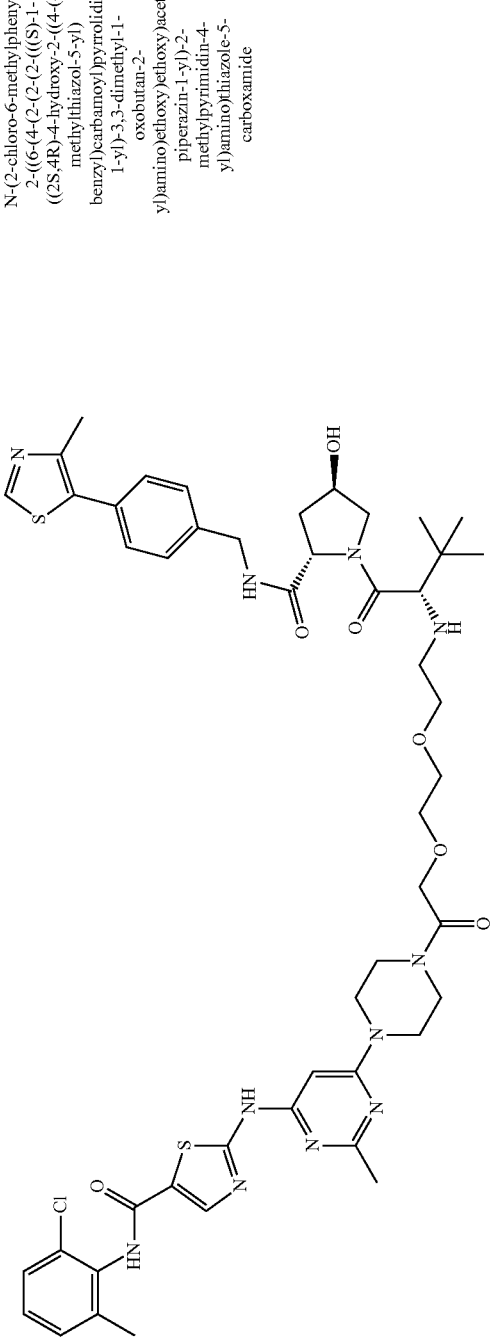 | N-(2-chloro-6-methylphenyl)-2-((6-(4-(2-(2-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)ethoxy)ethoxy)acetyl)piperazin-1-yl)-2-methylpyrimidin-4-yl)amino)thiazole-5-carboxamide |
| | | N-(2-chloro-6-methylphenyl)-2-((6-(4-(3-(2-(3-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)propoxy)ethoxy)propanoyl)piperazin-1-yl)-2-methylpyrimidin-4-yl)amino)thiazole-5-carboxamide |

TABLE 1-continued
The structure of compounds and its name
| Compound No. | Structure of compound | Name of the compound |
|---|---|---|
| | 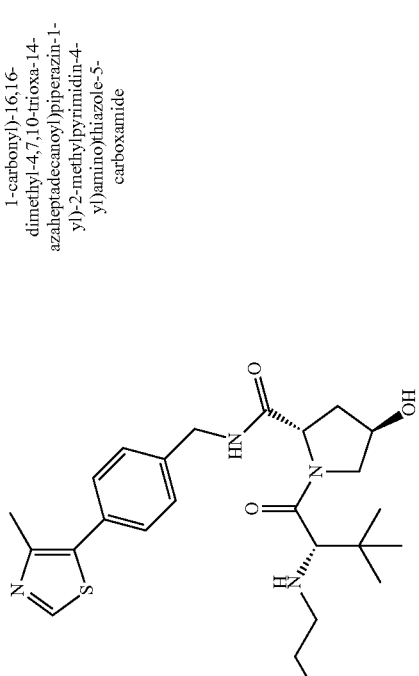 | N-(2-chloro-6-methylphenyl)-2-((6-(4-((S)-15-((2S,4R)-4-hydroxy-2-((4-(4-methylthiazol-5-yl)benzyl)carbamoyl)pyrrolidine-1-carbonyl)-16,16-dimethyl-4,7,10-trioxa-14-azaheptadecanoyl)piperazin-1-yl)-2-methylpyrimidin-4-yl)amino)thiazole-5-carboxamide |

TABLE 1-continued
The structure of compounds and its name
| Compound No. | Structure of compound | Name of the compound |
|---|---|---|
| | 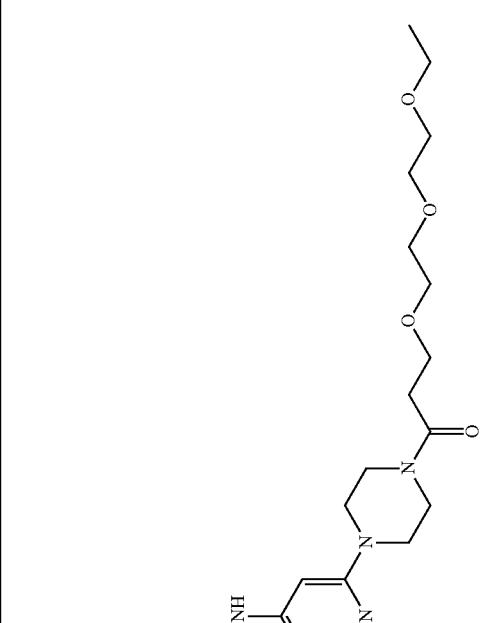 | N-(2-chloro-6-methylphenyl)-2-((6-(4-((S)-18-((2S,4R)-4-hydroxy-2-((4-(4-methylthiazol-5-yl)benzyl)carbamoyl)pyrrolidine-1-carbonyl)-19,19-dimethyl-4,7,10,13-tetraoxa-17-azaicosanoyl)piperazin-1-yl)-2-methylpyrimidin-4-yl)amino)thiazole-5-carboxamide |

TABLE 1-continued
The structure of compounds and its name
| Compound No. | Structure of compound | Name of the compound |
|---|---|---|
| SIAIS151 174 |  | N-(2-chloro-6-methylphenyl)-2-((6-(4-(4-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-4-oxobutanoyl)piperazin-1-yl)-2-methylpyrimidin-4-yl)amino)thiazole-5-carboxamide |

TABLE 1-continued
The structure of compounds and its name
| Compound No. | Structure of compound | Name of the compound |
|---|---|---|
| SIAIS151175 | 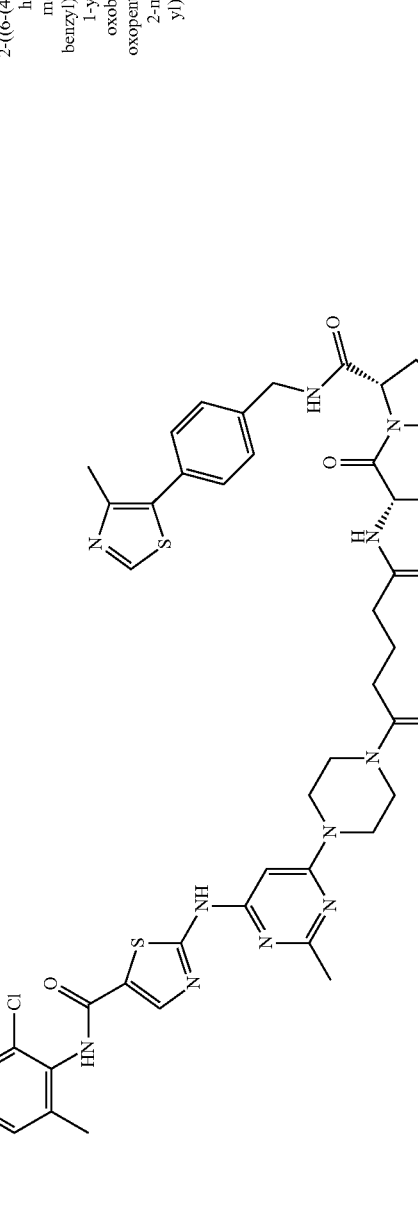 | N-(2-chloro-6-methylphenyl)-2-((6-(4-(5-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-5-oxopentanoyl)piperazin-1-yl)-2-methylpyrimidin-4-yl)amino)thiazole-5-carboxamide |

TABLE 1-continued

The structure of compounds and its name

| Compound No. | Structure of compound | Name of the compound |
|---|---|---|
| SIAIS151 176 | 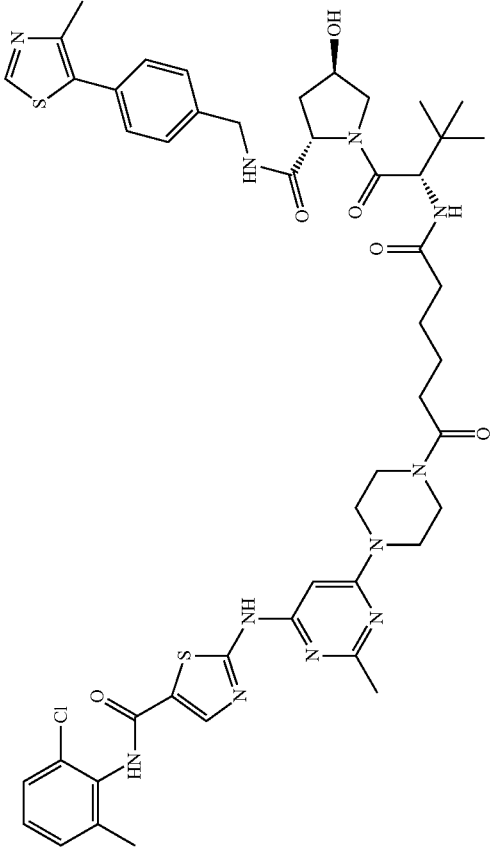 | N-(2-chloro-6-methylphenyl)-2-((6-(4-(6-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-6-oxohexanoyl)piperazin-1-yl)-2-methylpyrimidin-4-yl)amino)thiazole-5-carboxamide |
| | | N-(2-chloro-6-methylphenyl)-2-((6-(4-(6-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)hexanoyl)piperazin-1-yl)-2-methylpyrimidin-4-yl)amino)thiazole-5-carboxamide |

TABLE 1-continued
The structure of compounds and its name
| Compound No. | Structure of compound | Name of the compound |
|---|---|---|
| SIAIS151 177 | 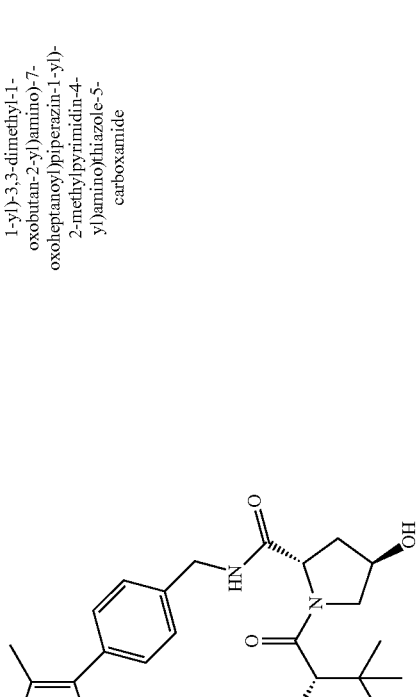 | N-(2-chloro-6-methylphenyl)-2-((6-(4-(7-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-7-oxoheptanoyl)piperazin-1-yl)-2-methylpyrimidin-4-yl)amino)thiazole-5-carboxamide |

TABLE 1-continued
The structure of compounds and its name
| Compound No. | Structure of compound | Name of the compound |
|---|---|---|
| | 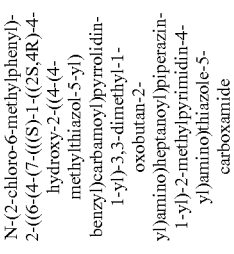 | N-(2-chloro-6-methylphenyl)-2-((6-(4-(7-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)heptanoyl)piperazin-1-yl)-2-methylpyrimidin-4-yl)amino)thiazole-5-carboxamide |

TABLE 1-continued

The structure of compounds and its name

| Compound No. | Structure of compound | Name of the compound |
|---|---|---|
| SIAIS151 178 | 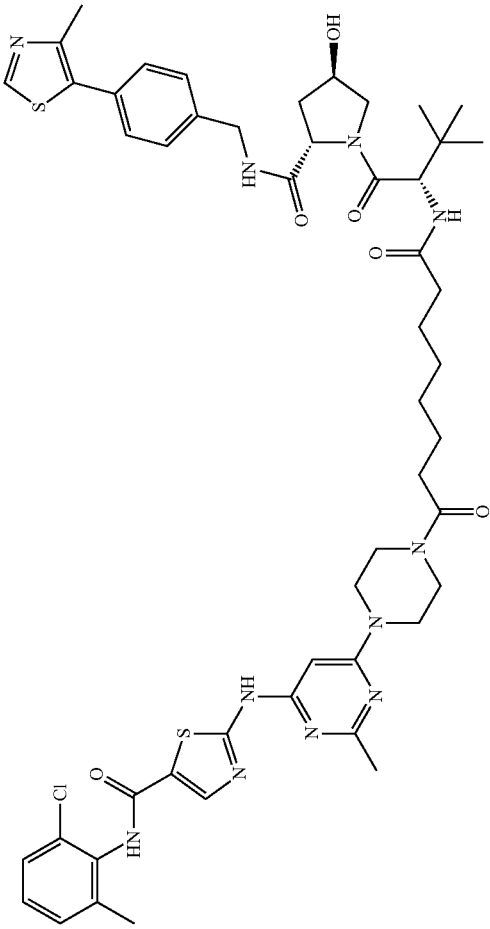 | N-(2-chloro-6-methylphenyl)-2-((6-(4-(8-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-8-oxooctanoyl)piperazin-1-yl)-2-methylpyrimidin-4-yl)amino)thiazole-5-carboxamide |
|  |  | N-(2-chloro-6-methylphenyl)-2-((6-(4-(8-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)octanoyl)piperazin-1-yl)-2-methylpyrimidin-4-yl)amino)thiazole-5-carboxamide |

TABLE 1-continued

The structure of compounds and its name

| Compound No. | Structure of compound | Name of the compound |
|---|---|---|
| SIAIS151 179 | | N-(2-chloro-6-methylphenyl)-2-((6-(4-(9-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-9-oxononanoyl)piperazin-1-yl)-2-methylpyrimidin-4-yl)amino)thiazole-5-carboxamide |

TABLE 1-continued
The structure of compounds and its name
| Compound No. | Structure of compound | Name of the compound |
|---|---|---|
| | 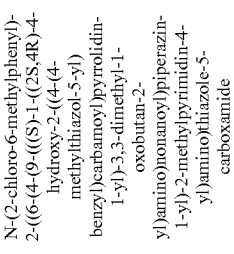 | N-(2-chloro-6-methylphenyl)-2-((6-(4-(9-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)nonanoyl)piperazin-1-yl)-2-methylpyrimidin-4-yl)amino)thiazole-5-carboxamide |

TABLE 1-continued
The structure of compounds and its name
| Compound No. | Structure of compound | Name of the compound |
|---|---|---|
| SIAIS151 180 | 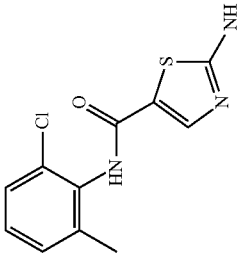 | N-(2-chloro-6-methylphenyl)-2-((6-(4-(10-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-10-oxodecanoyl)piperazin-1-yl)-2-methylpyrimidin-4-yl)amino)thiazole-5-carboxamide |

TABLE 1-continued
The structure of compounds and its name
| Compound No. | Structure of compound | Name of the compound |
|---|---|---|
| | 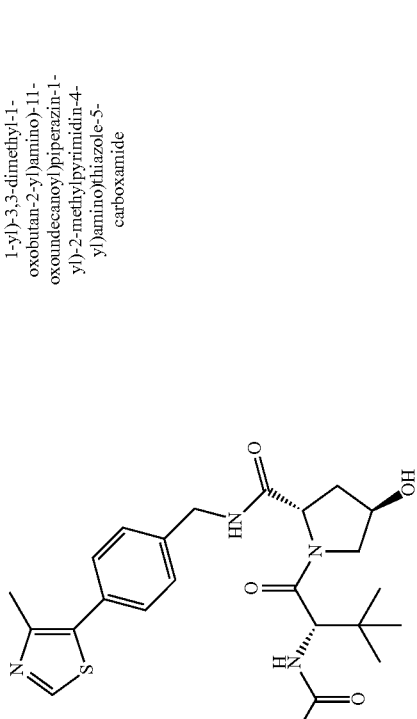 | N-(2-chloro-6-methylphenyl)-2-((6-(4-(11-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-11-oxoundecanoyl)piperazin-1-yl)-2-methylpyrimidin-4-yl)amino)thiazole-5-carboxamide |

TABLE 1-continued

The structure of compounds and its name

| Compound No. | Structure of compound | Name of the compound |
|---|---|---|
| | | N-(2-chloro-6-methylphenyl)-2-((6-(4-(12-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-12-oxododecanoyl)piperazin-1-yl)-2-methylpyrimidin-4-yl)amino)thiazole-5-carboxamide |

TABLE 1-continued
The structure of compounds and its name
| Compound No. | Structure of compound | Name of the compound |
|---|---|---|
| | 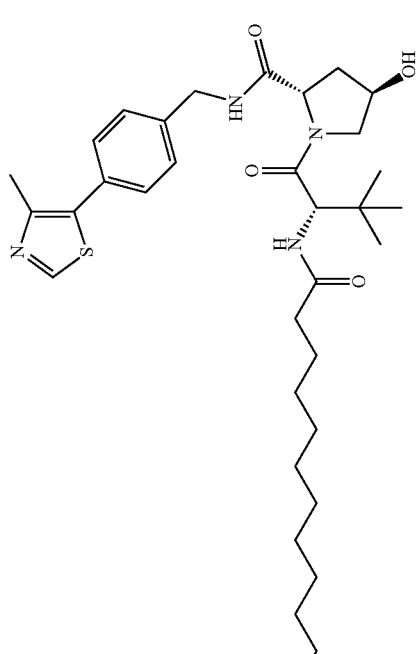 | N-(2-chloro-6-methylphenyl)-2-((6-(4-(13-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-13-oxotridecanoyl)piperazin-1-yl)-2-methylpyrimidin-4-yl)amino)thiazole-5-carboxamide |

TABLE 1-continued
The structure of compounds and its name
| Compound No. | Structure of compound | Name of the compound |
|---|---|---|
| SIAIS164 193 | 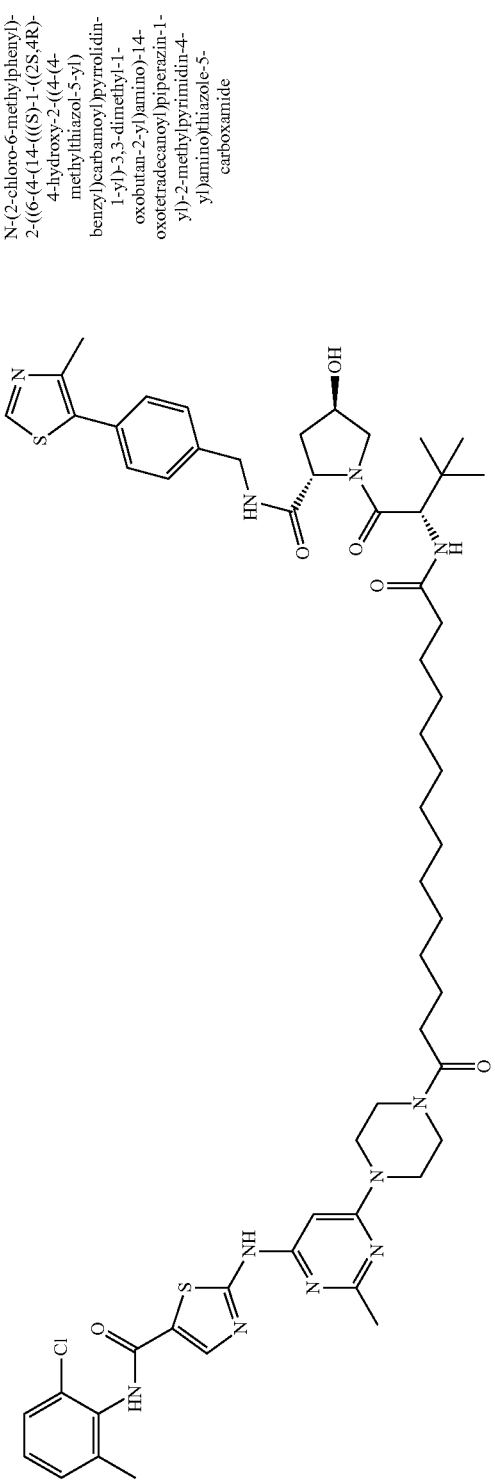 | N-(2-chloro-6-methylphenyl)-2-((6-(4-(14-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-14-oxotetradecanoyl)piperazin-1-yl)-2-methylpyrimidin-4-yl)amino)thiazole-5-carboxamide |

TABLE 1-continued
The structure of compounds and its name
| Compound No. | Structure of compound | Name of the compound |
|---|---|---|
| | 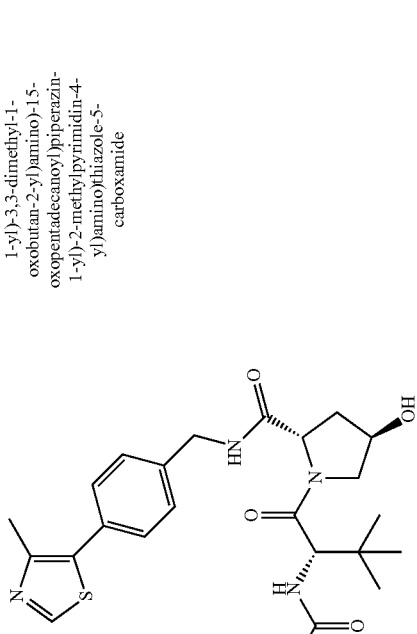 | N-(2-chloro-6-methylphenyl)-2-((6-(4-(15-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-15-oxopentadecanoyl)piperazin-1-yl)-2-methylpyrimidin-4-yl)amino)thiazole-5-carboxamide |

TABLE 1-continued
The structure of compounds and its name
| Compound No. | Structure of compound | Name of the compound |
|---|---|---|
| | 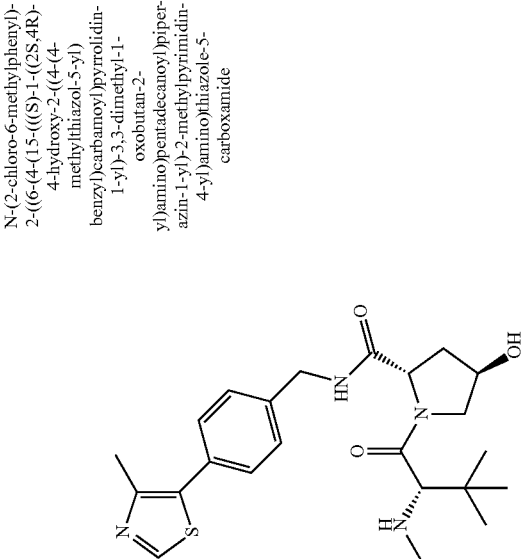 | N-(2-chloro-6-methylphenyl)-2-((6-(4-(15-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)pentadecanoyl)piperazin-1-yl)-2-methylpyrimidin-4-yl)amino)thiazole-5-carboxamide |

TABLE 1-continued
The structure of compounds and its name
| Compound No. | Structure of compound | Name of the compound |
|---|---|---|
| SIAIS164 194 | 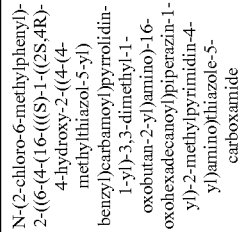 | N-(2-chloro-6-methylphenyl)-2-((6-(4-(16-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-16-oxohexadecanoyl)piperazin-1-yl)-2-methylpyrimidin-4-yl)amino)thiazole-5-carboxamide |

TABLE 1-continued

The structure of compounds and its name

| Compound No. | Structure of compound | Name of the compound |
|---|---|---|
| SIAIS184 032 | | N1-(5-(4-(6-((5-((2-chloro-6-methylphenyl)carbamoyl)thiazol-2-yl)amino)-2-methylpyrimidin-4-yl)piperazin-1-yl)-5-oxopentyl)-N10-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)decanediamide |

TABLE 1-continued
The structure of compounds and its name
| Compound No. | Structure of compound | Name of the compound |
|---|---|---|
| SIAIS164 134 | 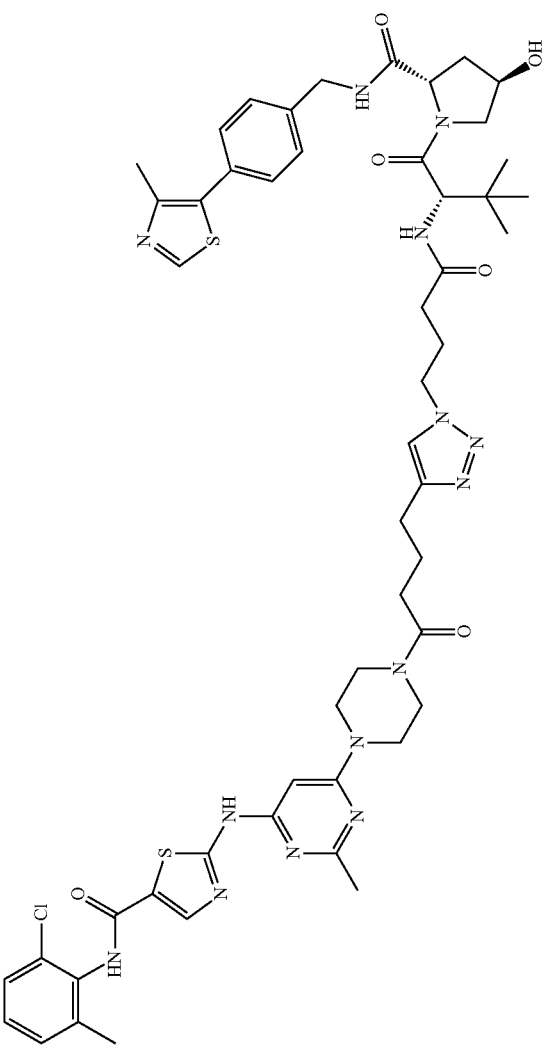 | N-(2-chloro-6-methylphenyl)-2-((6-(4-(4-(1-(4-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-4-oxobutyl)-1H-1,2,3-triazol-4-yl)butanoyl)piperazin-1-yl)-2-methylpyrimidin-4-yl)amino)thiazole-5-carboxamide |

TABLE 1-continued
The structure of compounds and its name
| Compound No. | Structure of compound | Name of the compound |
|---|---|---|
|  | 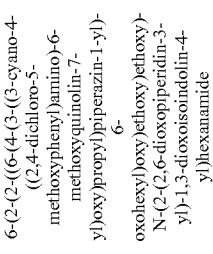 | 6-(2-(2-(((6-(4-(3-((3-cyano-4-((2,4-dichloro-5-methoxyphenyl)amino)-6-methoxyquinolin-7-yl)oxy)propyl)piperazin-1-yl)-6-oxohexyl)oxy)ethoxy)ethoxy)-N-(2-(2,6-dioxopiperidin-3-yl)-1,3-dioxoisoindolin-4-yl)hexanamide |

TABLE 1-continued

The structure of compounds and its name

| Compound No. | Structure of compound | Name of the compound |
|---|---|---|
| | 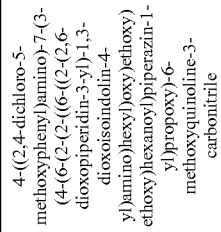 | 4-((2,4-dichloro-5-methoxyphenyl)amino)-7-(3-(4-(6-(2-(2-((6-((2-(2,6-dioxopiperidin-3-yl)-1,3-dioxoisoindolin-4-yl)amino)hexyl)oxy)ethoxy)ethoxy)hexanoyl)piperazin-1-yl)propoxy)-6-methoxyquinoline-3-carbonitrile |
| SIAIS151 157 | 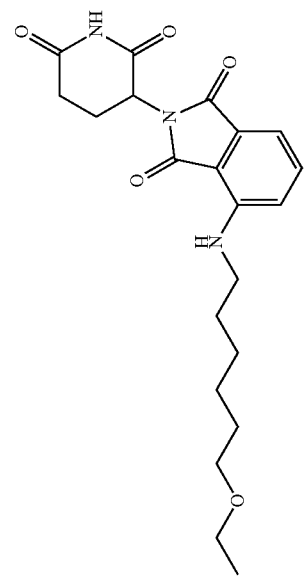 | 4-((2,4-dichloro-5-methoxyphenyl)amino)-7-(3-(4-(3-(2-((2-(2,6-dioxopiperidin-3-yl)-1,3-dioxoisoindolin-4-yl)amino)ethoxy)propanoyl)piperazin-1-yl)propoxy)-6-methoxyquinoline-3-carbonitrile |

TABLE 1-continued

The structure of compounds and its name

| Compound No. | Structure of compound | Name of the compound |
|---|---|---|
| | 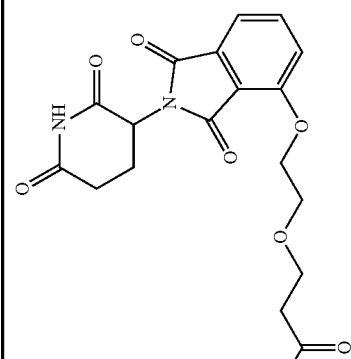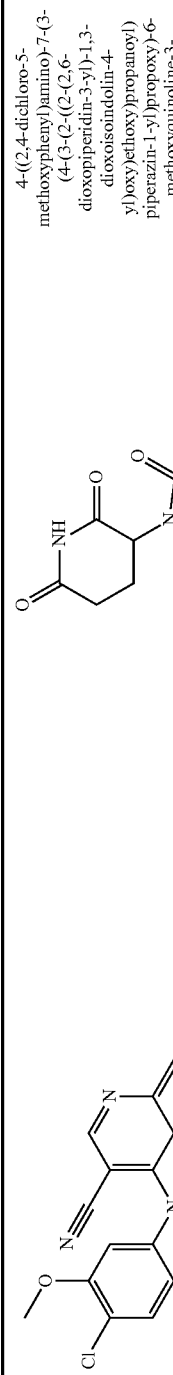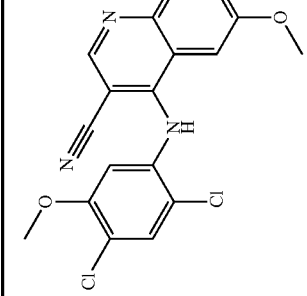 | 4-((2,4-dichloro-5-methoxyphenyl)amino)-7-(3-(4-(3-(2-(2-(2,6-dioxopiperidin-3-yl)-1,3-dioxoisoindolin-4-yl)oxy)ethoxy)propanoyl)piperazin-1-yl)propoxy)-6-methoxyquinoline-3-carbonitrile |
| | 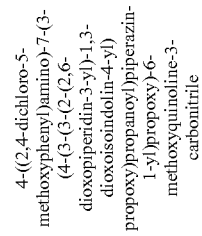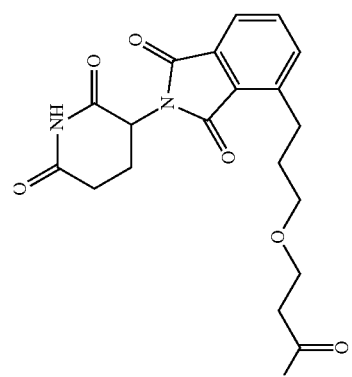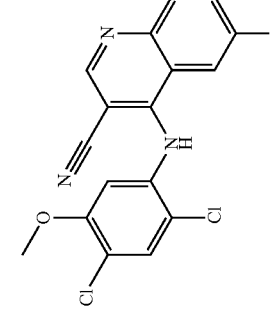 | 4-((2,4-dichloro-5-methoxyphenyl)amino)-7-(3-(4-(3-(2-(2,6-dioxopiperidin-3-yl)-1,3-dioxoisoindolin-4-yl)propoxy)propanoyl)piperazin-1-yl)propoxy)-6-methoxyquinoline-3-carbonitrile |

TABLE 1-continued

The structure of compounds and its name

| Compound No. | Structure of compound | Name of the compound |
|---|---|---|
| SIAIS151 158 | 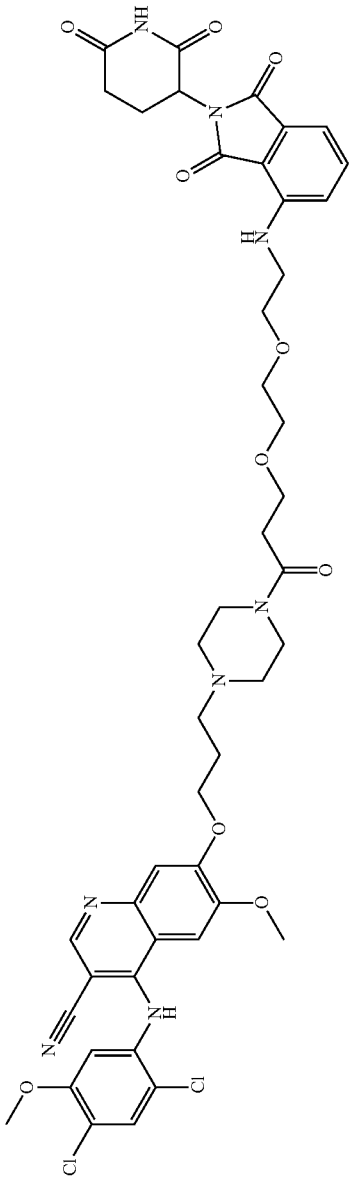 | 4-((2,4-dichloro-5-methoxyphenyl)amino)-7-(3-(4-(3-(2-(2-((2-(2,6-dioxopiperidin-3-yl)-1,3-dioxoisoindolin-4-yl)amino)ethoxy)ethoxy)propanoyl)piperazin-1-yl)propoxy)-6-methoxyquinoline-3-carbonitrile |
|  | 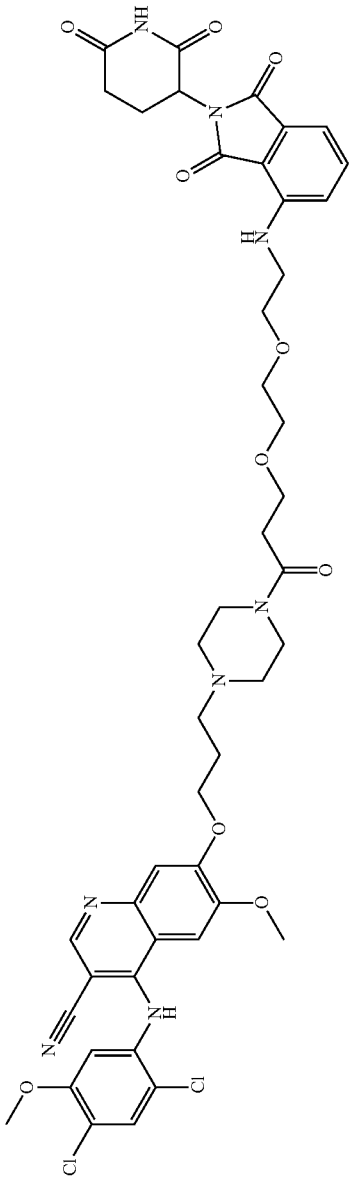 | 4-((2,4-dichloro-5-methoxyphenyl)amino)-7-(3-(4-(3-(2-(3-(2-(2,6-dioxopiperidin-3-yl)-1,3-dioxoisoindolin-4-yl)propoxy)ethoxy)propanoyl)piperazin-1-yl)propoxy)-6-methoxyquinoline-3-carbonitrile |

TABLE 1-continued

The structure of compounds and its name

| Compound No. | Structure of compound | Name of the compound |
|---|---|---|
| SIAIS151 | 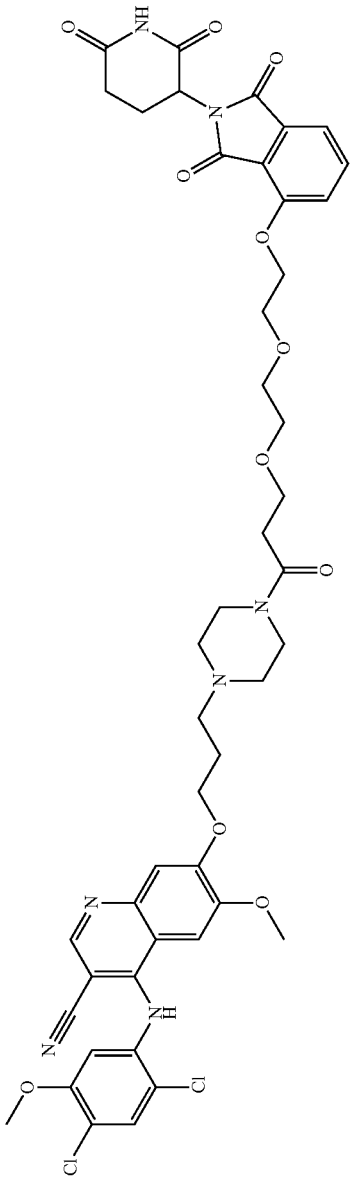 | 4-((2,4-dichloro-5-methoxyphenyl)amino)-7-(3-(4-(3-(2-(2-(2-(2,6-dioxopiperidin-3-yl)-1,3-dioxoisoindolin-4-yl)oxy)ethoxy)ethoxy)propanoyl)piperazin-1-yl)propoxy)-6-methoxyquinoline-3-carbonitrile |
| SIAIS159 | | 4-((2,4-dichloro-5-methoxyphenyl)amino)-7-(3-(4-(3-(2-(2-(2-(2,6-dioxopiperidin-3-yl)-1,3-dioxoisoindolin-4-yl)amino)ethoxy)ethoxy)propanoyl)piperazin-1-yl)propoxy)-6-methoxyquinoline-3-carbonitrile |

| Compound No. | Structure of compound | Name of the compound |
|---|---|---|
|  |  | 4-((2,4-dichloro-5-methoxyphenyl)amino)-7-(3-(4-(3-(2-(2-(3-(2-(2-(2,6-dioxopiperidin-3-yl)-1,3-dioxoisoindolin-4-yl)propoxy)ethoxy)ethoxy)propanoyl)piperazin-1-yl)propoxy)-6-methoxyquinoline-3-carbonitrile |
|  |  | 4-((2,4-dichloro-5-methoxyphenyl)amino)-7-(3-(4-(3-(2-(2-(2-(2,6-dioxopiperidin-3-yl)-1,3-dioxoisoindolin-4-yl)oxy)ethoxy)ethoxy)propanoyl)piperazin-1-yl)propoxy)-6-methoxyquinoline-3-carbonitrile |

TABLE 1-continued

The structure of compounds and its name

| Compound No. | Structure of compound | Name of the compound |
|---|---|---|
| SIAIS151160 | | 4-((2,4-dichloro-5-methoxyphenyl)amino)-7-(3-(4-(1-((2-(2,6-dioxopiperidin-3-yl)-1,3-dioxoisoindolin-4-yl)amino)-3,6,9,12-tetraoxapentadecan-15-oyl)piperazin-1-yl)propoxy)-6-methoxyquinoline-3-carbonitrile |

TABLE 1-continued
The structure of compounds and its name
| Compound No. | Structure of compound | Name of the compound |
|---|---|---|
| | 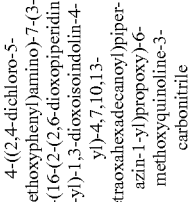 | 4-((2,4-dichloro-5-methoxyphenyl)amino)-7-(3-(4-(16-(2-(2,6-dioxopiperidin-3-yl)-1,3-dioxoisoindolin-4-yl)-4,7,10,13-tetraoxahexadecanoyl)piperazin-1-yl)propoxy)-6-methoxyquinoline-3-carbonitrile |

TABLE 1-continued
The structure of compounds and its name
| Compound No. | Structure of compound | Name of the compound |
|---|---|---|
| |  | 4-((2,4-dichloro-5-methoxyphenyl)amino)-7-(3-(4-(1-((2-(2,6-dioxopiperidin-3-yl)-1,3-dioxoisoindolin-4-yl)oxy)-3,6,9,12-tetraoxapentadecan-15-oyl)piperazin-1-yl)propoxy)-6-methoxyquinoline-3-carbonitrile |

TABLE 1-continued

The structure of compounds and its name

| Compound No. | Structure of compound | Name of the compound |
|---|---|---|
| SIAIS151 161 | 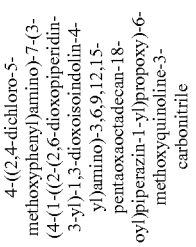 | 4-((2,4-dichloro-5-methoxyphenyl)amino)-7-(3-(4-(1-((2-(2,6-dioxopiperidin-3-yl)-1,3-dioxoisoindolin-4-yl)amino)-3,6,9,12,15-pentaoxaoctadecan-18-oyl)piperazin-1-yl)propoxy)-6-methoxyquinoline-3-carbonitrile |
| SIAIS151 164 | 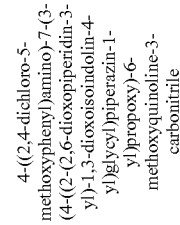 | 4-((2,4-dichloro-5-methoxyphenyl)amino)-7-(3-(4-((2-(2,6-dioxopiperidin-3-yl)-1,3-dioxoisoindolin-4-yl)glycyl)piperazin-1-yl)propoxy)-6-methoxyquinoline-3-carbonitrile |

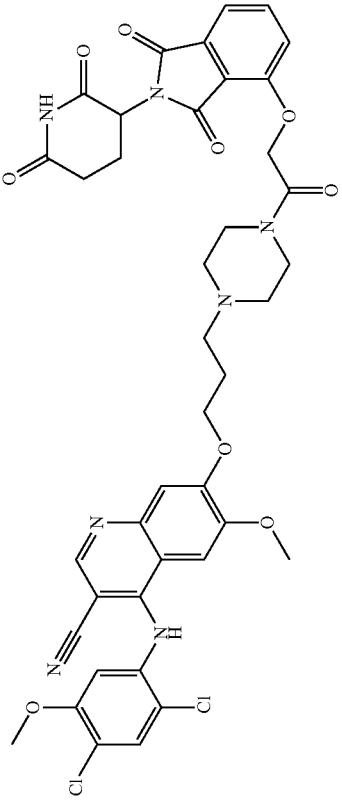
| Compound No. | Structure of compound | Name of the compound |
|---|---|---|
| 149 | | 4-((2,4-dichloro-5-methoxyphenyl)amino)-7-(3-(4-(2-((2-(2,6-dioxopiperidin-3-yl)-1,3-dioxoisoindolin-4-yl)oxy)acetyl)piperazin-1-yl)propoxy)-6-methoxyquinoline-3-carbonitrile |
| 150 | | 4-((2,4-dichloro-5-methoxyphenyl)amino)-7-(3-(4-(3-(2-(2,6-dioxopiperidin-3-yl)-1,3-dioxoisoindolin-4-yl)propanoyl)piperazin-1-yl)propoxy)-6-methoxyquinoline-3-carbonitrile |

TABLE 1-continued

The structure of compounds and its name

| Compound No. | Structure of compound | Name of the compound |
|---|---|---|
| SIAIS151 165 | | 4-((2,4-dichloro-5-methoxyphenyl)amino)-7-(3-(4-(3-((2-(2,6-dioxopiperidin-3-yl)-1,3-dioxoisoindolin-4-yl)amino)propanoyl)piperazin-1-yl)propoxy)-6-methoxyquinoline-3-carbonitrile |
| SIAIS151 162 | | 4-((2,4-dichloro-5-methoxyphenyl)amino)-7-(3-(4-(4-((2-(2,6-dioxopiperidin-3-yl)-1,3-dioxoisoindolin-4-yl)amino)butanoyl)piperazin-1-yl)propoxy)-6-methoxyquinoline-3-carbonitrile |

TABLE 1-continued

The structure of compounds and its name

| Compound No. | Structure of compound | Name of the compound |
|---|---|---|
| | 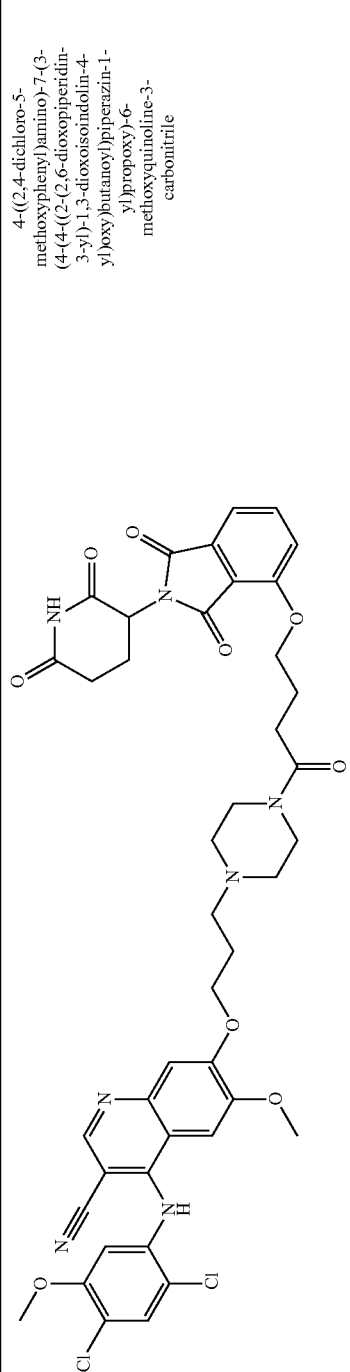 | 4-((2,4-dichloro-5-methoxyphenyl)amino)-7-(3-(4-(4-((2-(2,6-dioxopiperidin-3-yl)-1,3-dioxoisoindolin-4-yl)oxy)butanoyl)piperazin-1-yl)propoxy)-6-methoxyquinoline-3-carbonitrile |
| | 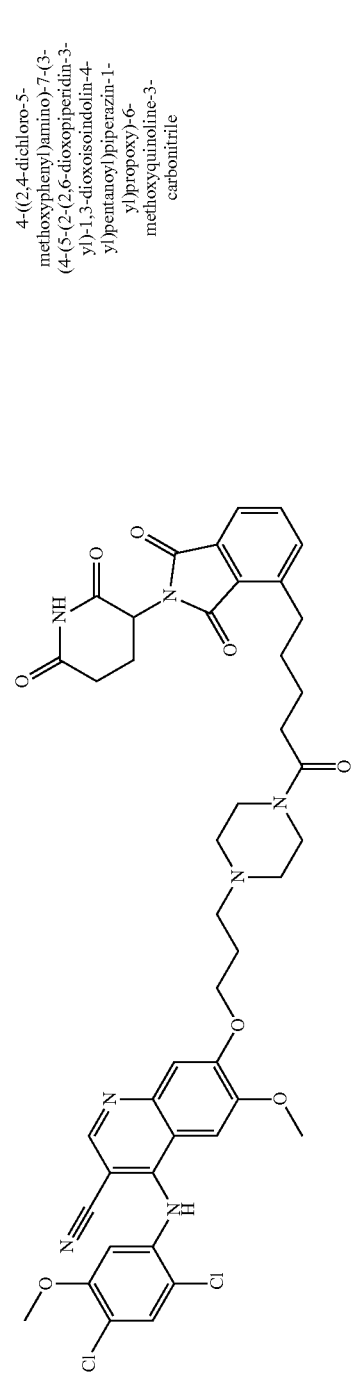 | 4-((2,4-dichloro-5-methoxyphenyl)amino)-7-(3-(4-(5-(2-(2,6-dioxopiperidin-3-yl)-1,3-dioxoisoindolin-4-yl)pentanoyl)piperazin-1-yl)propoxy)-6-methoxyquinoline-3-carbonitrile |

TABLE 1-continued

The structure of compounds and its name

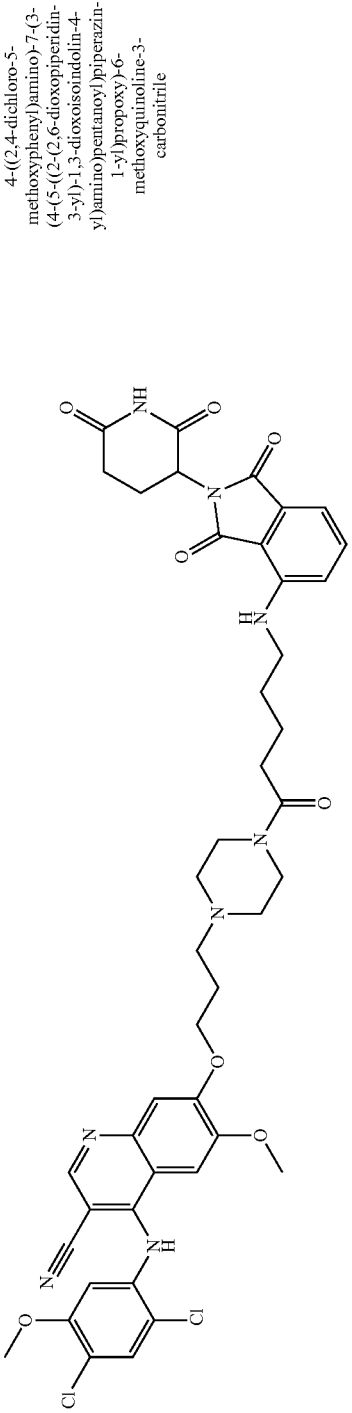

| Compound No. | Structure of compound | Name of the compound |
|---|---|---|
| SIAIS151 | | 4-((2,4-dichloro-5-methoxyphenyl)amino)-7-(3-(4-(5-((2-(2,6-dioxopiperidin-3-yl)-1,3-dioxoisoindolin-4-yl)amino)pentanoyl)piperazin-1-yl)propoxy)-6-methoxyquinoline-3-carbonitrile |
| 163 | | 4-((2,4-dichloro-5-methoxyphenyl)amino)-7-(3-(4-(5-((2-(2,6-dioxopiperidin-3-yl)-1,3-dioxoisoindolin-4-yl)oxy)pentanoyl)piperazin-1-yl)propoxy)-6-methoxyquinoline-3-carbonitrile |

TABLE 1-continued

The structure of compounds and its name

| Compound No. | Structure of compound | Name of the compound |
|---|---|---|
| | 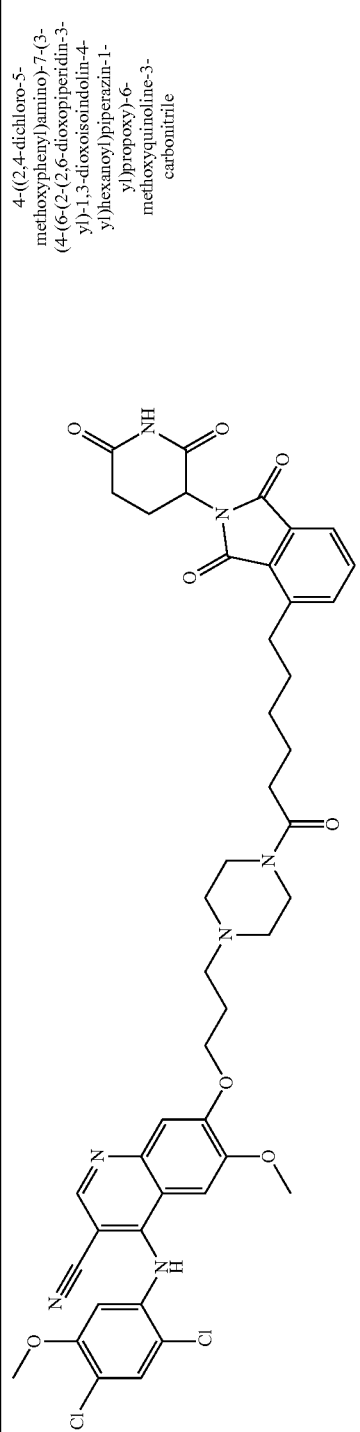 | 4-((2,4-dichloro-5-methoxyphenyl)amino)-7-(3-(4-(6-(2-(2,6-dioxopiperidin-3-yl)-1,3-dioxoisoindolin-4-yl)hexanoyl)piperazin-1-yl)propoxy)-6-methoxyquinoline-3-carbonitrile |
| SIAIS151 166 | 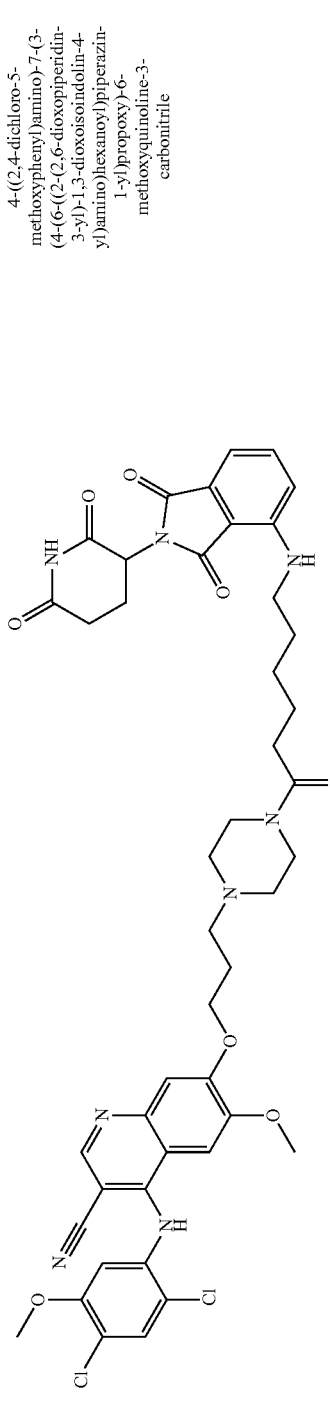 | 4-((2,4-dichloro-5-methoxyphenyl)amino)-7-(3-(4-(6-((2-(2,6-dioxopiperidin-3-yl)-1,3-dioxoisoindolin-4-yl)amino)hexanoyl)piperazin-1-yl)propoxy)-6-methoxyquinoline-3-carbonitrile |

TABLE 1-continued

The structure of compounds and its name

| Compound No. | Structure of compound | Name of the compound |
|---|---|---|
| SIAIS151 167 | 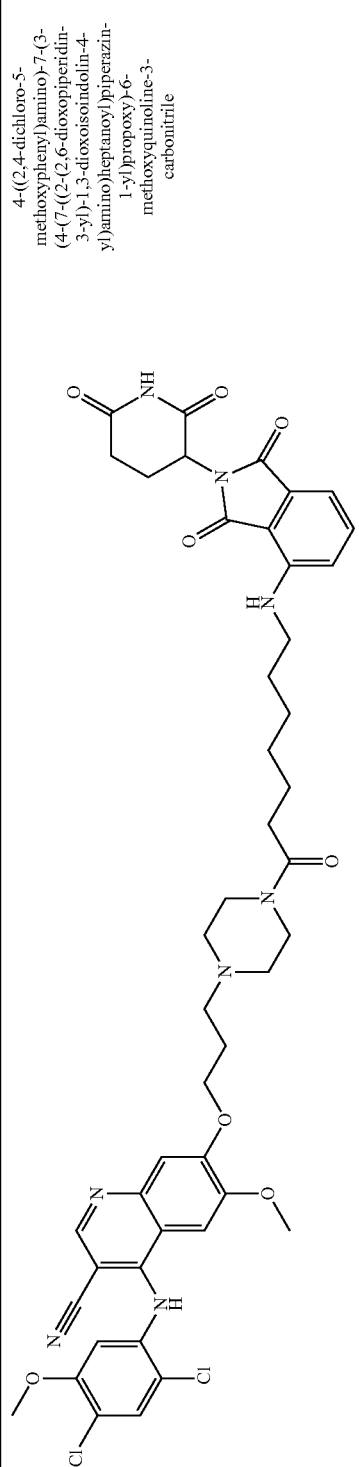 | 4-((2,4-dichloro-5-methoxyphenyl)amino)-7-(3-(4-(7-((2-(2,6-dioxopiperidin-3-yl)-1,3-dioxoisoindolin-4-yl)amino)heptanoyl)piperazin-1-yl)propoxy)-6-methoxyquinoline-3-carbonitrile |
| | | 4-((2,4-dichlorophenyl)amino)-7-(3-(4-(8-((2-(2,6-dioxopiperidin-3-yl)-1,3-dioxoisoindolin-4-yl)amino)octanoyl)piperazin-1-yl)propoxy)-6-methoxyquinoline-3-carbonitrile |

TABLE 1-continued

The structure of compounds and its name

| Compound No. | Structure of compound | Name of the compound |
|---|---|---|
| 161 | 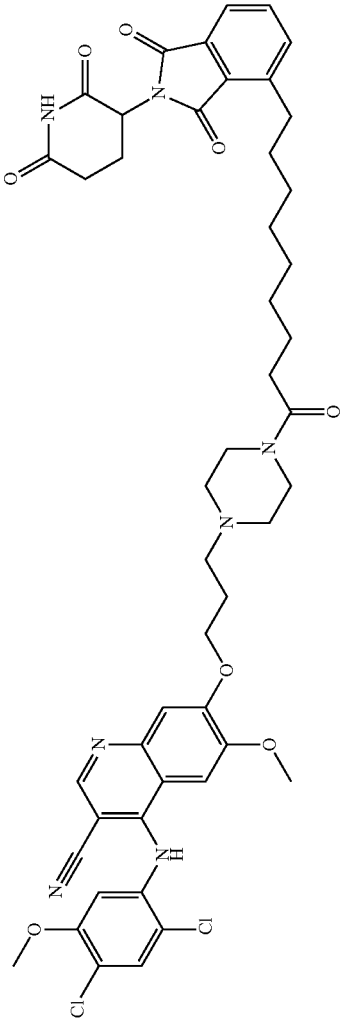 | 4-((2,4-dichloro-5-methoxyphenyl)amino)-7-(3-(4-(9-(2-(2,6-dioxopiperidin-3-yl)-1,3-dioxoisoindolin-4-yl)nonanoyl)piperazin-1-yl)propoxy)-6-methoxyquinoline-3-carbonitrile |
| 162 | 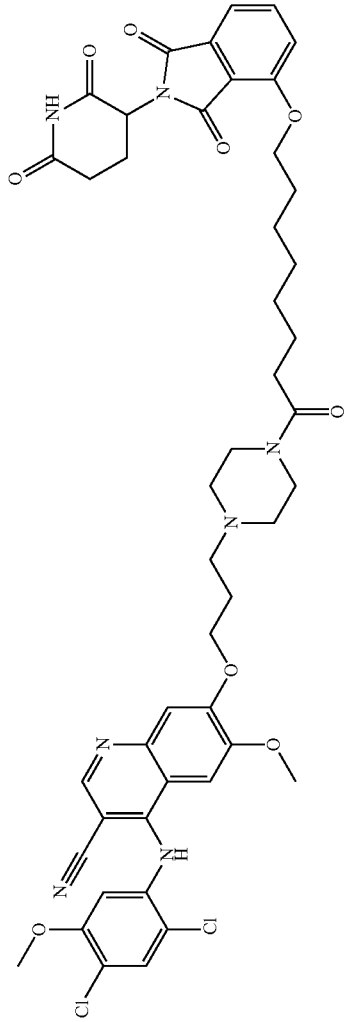 | 4-((2,4-dichloro-5-methoxyphenyl)amino)-7-(3-(4-(8-((2-(2,6-dioxopiperidin-3-yl)-1,3-dioxoisoindolin-4-yl)oxy)octanoyl)piperazin-1-yl)propoxy)-6-methoxyquinoline-3-carbonitrile |

TABLE 1-continued

The structure of compounds and its name

| Compound No. | Structure of compound | Name of the compound |
|---|---|---|
| SIAIS164 136 | | 4-(4-(3-((3-cyano-4-((2,4-dichloro-5-methoxyphenyl)amino)-6-methoxyquinolin-7-yl)oxy)propyl)piperazin-1-yl)-N-(2-((2-(2,6-dioxopiperidin-3-yl)-1,3-dioxoisoindolin-4-yl)amino)ethyl)-4-oxobutanamide |
| SIAIS164 104 | | 3-(4-(3-((3-cyano-4-((2,4-dichloro-5-methoxyphenyl)amino)-6-methoxyquinolin-7-yl)oxy)propyl)piperazin-1-yl)-N-(2-(2,6-dioxopiperidin-3-yl)-1-oxoisoindolin-4-yl)-3-oxopropanamide |

TABLE 1-continued

The structure of compounds and its name

| Compound No. | Structure of compound | Name of the compound |
|---|---|---|
| SIAIS164 105 | | 4-(4-(3-((3-cyano-4-((2,4-dichloro-5-methoxyphenyl)amino)-6-methoxyquinolin-7-yl)oxy)propyl)piperazin-1-yl)-N-(2-(2,6-dioxopiperidin-3-yl)-1-oxoisoindolin-4-yl)-4-oxobutanamide |
| SIAIS164 106 | | 5-(4-(3-((3-cyano-4-((2,4-dichloro-5-methoxyphenyl)amino)-6-methoxyquinolin-7-yl)oxy)propyl)piperazin-1-yl)-N-(2-(2,6-dioxopiperidin-3-yl)-1-oxoisoindolin-4-yl)-5-oxopentanamide |

TABLE 1-continued

The structure of compounds and its name

| Compound No. | Structure of compound | Name of the compound |
|---|---|---|
| | 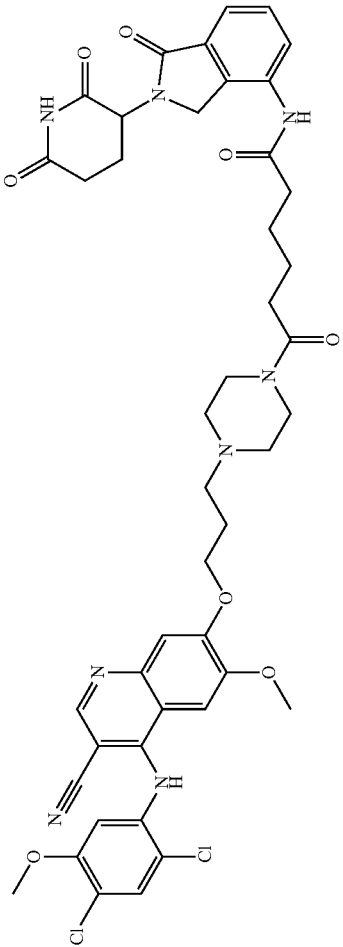 | 6-(4-(3-((3-cyano-4-((2,4-dichloro-5-methoxyphenyl)amino)-6-methoxyquinolin-7-yl)oxy)propyl)piperazin-1-yl)-N-(2-(2,6-dioxopiperidin-3-yl)-1-oxoisoindolin-4-yl)-6-oxohexanamide |
| | | 7-(4-(3-((3-cyano-4-((2,4-dichloro-5-methoxyphenyl)amino)-6-methoxyquinolin-7-yl)oxy)propyl)piperazin-1-yl)-N-(2-(2,6-dioxopiperidin-3-yl)-1-oxoisoindolin-4-yl)-7-oxoheptanamide |

TABLE 1-continued

The structure of compounds and its name

| Compound No. | Structure of compound | Name of the compound |
|---|---|---|
| | 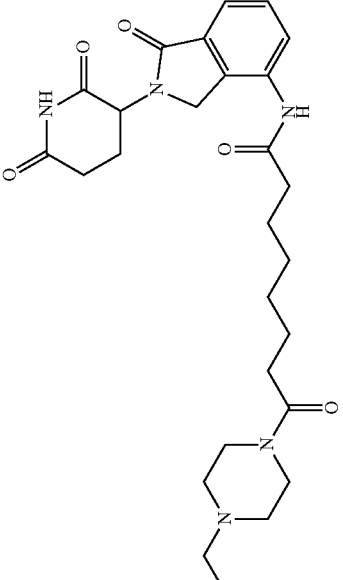 | 8-(4-(3-((3-cyano-4-((2,4-dichloro-5-methoxyphenyl)amino)-6-methoxyquinolin-7-yl)oxy)propyl)piperazin-1-yl)-N-(2-(2,6-dioxopiperidin-3-yl)-1-oxoisoindolin-4-yl)-8-oxooctanamide |
| | | 9-(4-(3-((3-cyano-4-((2,4-dichloro-5-methoxyphenyl)amino)-6-methoxyquinolin-7-yl)oxy)propyl)piperazin-1-yl)-N-(2-(2,6-dioxopiperidin-3-yl)-1-oxoisoindolin-4-yl)-9-oxononanamide |

TABLE 1-continued

The structure of compounds and its name

| Compound No. | Structure of compound | Name of the compound |
|---|---|---|
| | | 10-(4-(3-((3-cyano-4-((2,4-dichloro-5-methoxyphenyl)amino)-6-methoxyquinolin-7-yl)oxy)propyl)piperazin-1-yl)-N-(2-(2,6-dioxopiperidin-3-yl)-1-oxoisoindolin-4-yl)-10-oxodecanamide |
| | | 11-(4-(3-((3-cyano-4-((2,4-dichloro-5-methoxyphenyl)amino)-6-methoxyquinolin-7-yl)oxy)propyl)piperazin-1-yl)-N-(2-(2,6-dioxopiperidin-3-yl)-1-oxoisoindolin-4-yl)-11-oxoundecanamide |

TABLE 1-continued

The structure of compounds and its name

| Compound No. | Structure of compound | Name of the compound |
|---|---|---|
| | 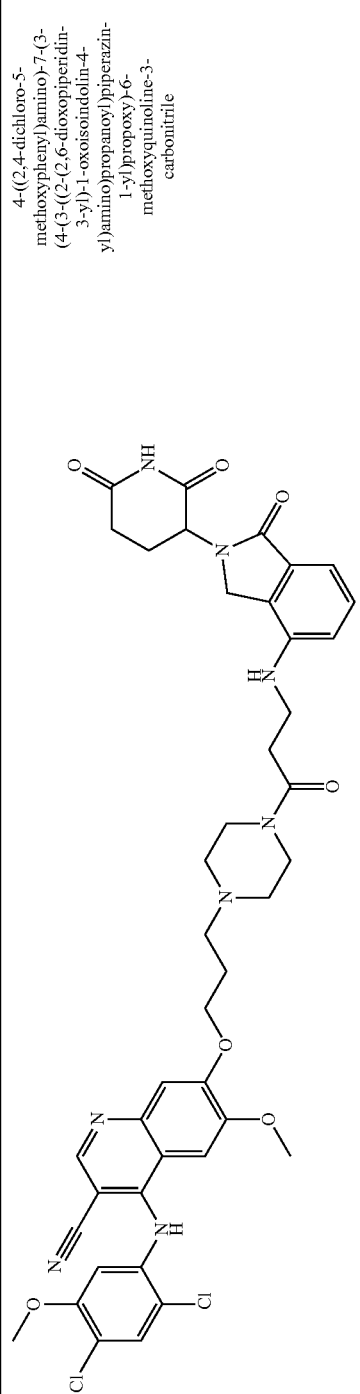 | 4-((2,4-dichloro-5-methoxyphenyl)amino)-7-(3-(4-(3-((2-(2,6-dioxopiperidin-3-yl)amino)propanoyl)piperazin-1-yl)propoxy)-6-methoxyquinoline-3-carbonitrile |
| | | 4-((2,4-dichloro-5-methoxyphenyl)amino)-7-(3-(4-(4-((2-(2,6-dioxopiperidin-3-yl)-1-oxoisoindolin-4-yl)amino)butanoyl)piperazin-1-yl)propoxy)-6-methoxyquinoline-3-carbonitrile |

TABLE 1-continued

The structure of compounds and its name

| Compound No. | Structure of compound | Name of the compound |
|---|---|---|
| | 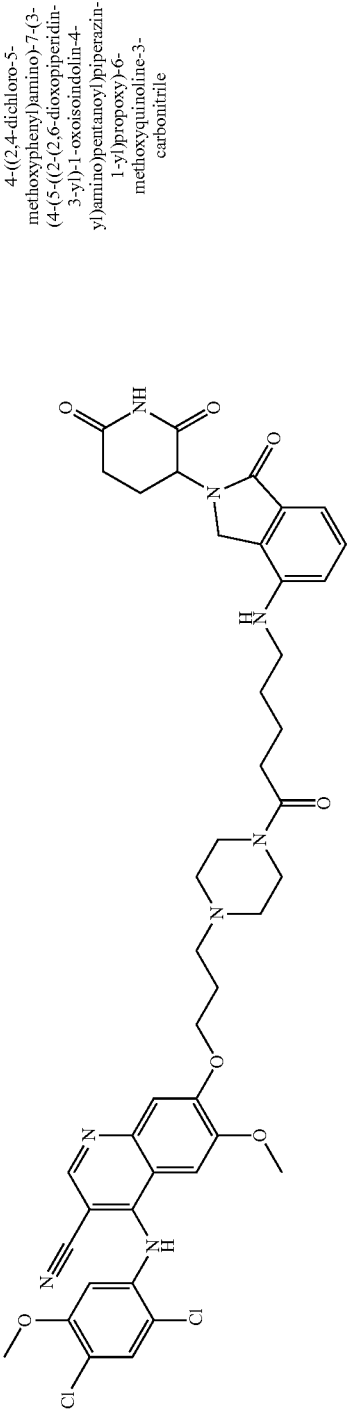 | 4-((2,4-dichloro-5-methoxyphenyl)amino)-7-(3-(4-(5-((2-(2,6-dioxopiperidin-3-yl)-1-oxoisoindolin-4-yl)amino)pentanoyl)piperazin-1-yl)propoxy)-6-methoxyquinoline-3-carbonitrile |
| | | 4-((2,4-dichloro-5-methoxyphenyl)amino)-7-(3-(4-(6-((2-(2,6-dioxopiperidin-3-yl)-1-oxoisoindolin-4-yl)amino)hexanoyl)piperazin-1-yl)propoxy)-6-methoxyquinoline-3-carbonitrile |

TABLE 1-continued

The structure of compounds and its name

| Compound No. | Structure of compound | Name of the compound |
|---|---|---|
| |  | 4-((2,4-dichloro-5-methoxyphenyl)amino)-7-(3-(4-(7-((2-(2,6-dioxopiperidin-3-yl)amino)heptanoyl)piperazin-1-yl)propoxy)-6-methoxyquinoline-3-carbonitrile |
| |  | 4-((2,4-dichloro-5-methoxyphenyl)amino)-7-(3-(4-(8-((2-(2,6-dioxopiperidin-3-yl)-1-oxoisoindolin-4-yl)amino)octanoyl)piperazin-1-yl)propoxy)-6-methoxyquinoline-3-carbonitrile |

TABLE 1-continued

The structure of compounds and its name

| Compound No. | Structure of compound | Name of the compound |
|---|---|---|
| | 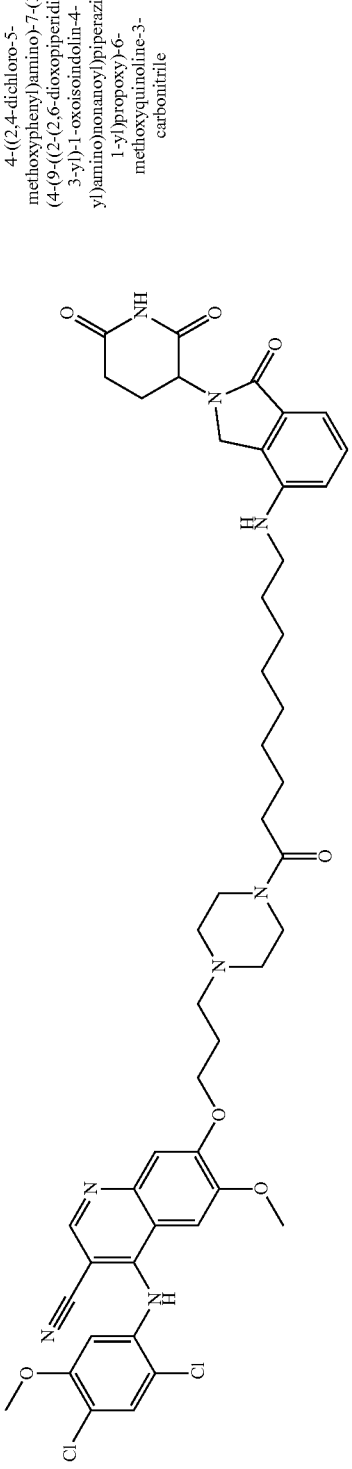 | 4-((2,4-dichloro-5-methoxyphenyl)amino)-7-(3-(4-(9-((2-(2,6-dioxopiperidin-3-yl)amino)nonanoyl)piperazin-1-yl)propoxy)-6-methoxyquinoline-3-carbonitrile |
| | | 4-((2,4-dichloro-5-methoxyphenyl)amino)-7-(3-(4-(3-((2-(2,6-dioxopiperidin-3-yl)-1-oxoisoindolin-4-yl)oxy)propanoyl)piperazin-1-yl)propoxy)-6-methoxyquinoline-3-carbonitrile |

TABLE 1-continued

The structure of compounds and its name

| Compound No. | Structure of compound | Name of the compound |
|---|---|---|
| | 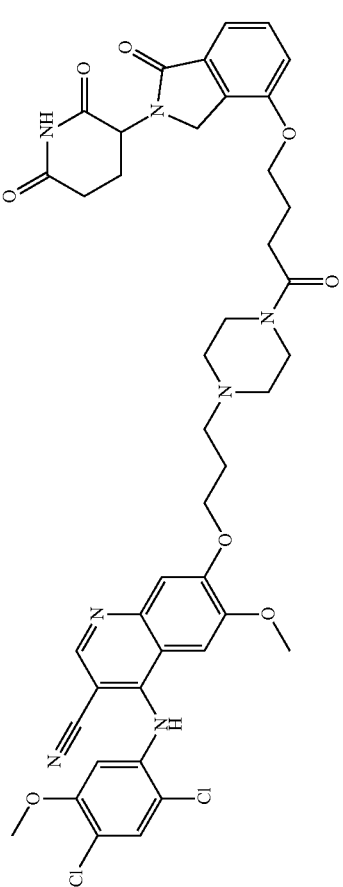 | 4-((2,4-dichloro-5-methoxyphenyl)amino)-7-(3-(4-(4-((2-(2,6-dioxopiperidin-3-yl)-1-oxoisoindolin-4-yl)oxy)butanoyl)piperazin-1-yl)propoxy)-6-methoxyquinoline-3-carbonitrile |
| | | 4-((2,4-dichloro-5-methoxyphenyl)amino)-7-(3-(4-(5-((2-(2,6-dioxopiperidin-3-yl)-1-oxoisoindolin-4-yl)oxy)pentanoyl)piperazin-1-yl)propoxy)-6-methoxyquinoline-3-carbonitrile |

TABLE 1-continued

The structure of compounds and its name

| Compound No. | Structure of compound | Name of the compound |
|---|---|---|
| | | 4-((2,4-dichloro-5-methoxyphenyl)amino)-7-(3-(4-(6-((2-(2,6-dioxopiperidin-3-yl)-1-oxoisoindolin-4-yl)oxy)hexanoyl)piperazin-1-yl)propoxy)-6-methoxyquinoline-3-carbonitrile |
| | | 4-((2,4-dichloro-5-methoxyphenyl)amino)-7-(3-(4-(7-((2-(2,6-dioxopiperidin-3-yl)-1-oxoisoindolin-4-yl)oxy)heptanoyl)piperazin-1-yl)propoxy)-6-methoxyquinoline-3-carbonitrile |

TABLE 1-continued

The structure of compounds and its name

| Compound No. | Structure of compound | Name of the compound |
|---|---|---|
| | 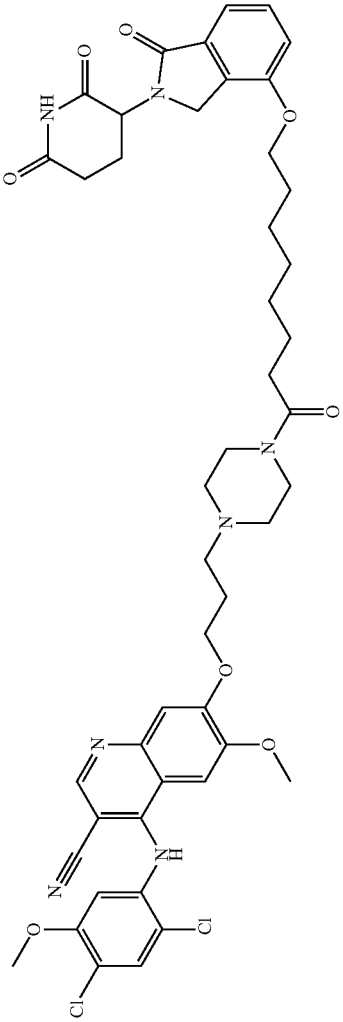 | 4-((2,4-dichloro-5-methoxyphenyl)amino)-7-(3-(4-(8-((2-(2,6-dioxopiperidin-3-yl)oxy)octanoyl)piperazin-1-yl)propoxy)-6-methoxyquinoline-3-carbonitrile |
| | | 4-((2,4-dichloro-5-methoxyphenyl)amino)-7-(3-(4-(9-((2-(2,6-dioxopiperidin-3-yl)-1-oxoisoindolin-4-yl)oxy)nonanoyl)piperazin-1-yl)propoxy)-6-methoxyquinoline-3-carbonitrile |

TABLE 1-continued

The structure of compounds and its name

| Compound No. | Structure of compound | Name of the compound |
|---|---|---|
| | 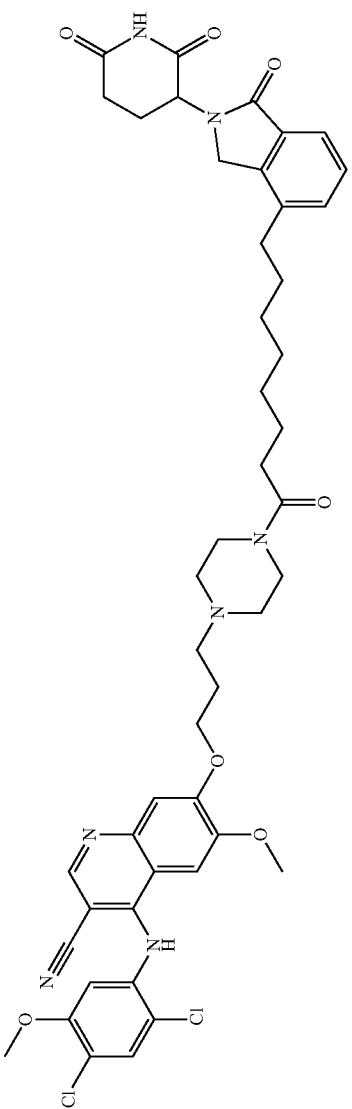 | 4-((2,4-dichloro-5-methoxyphenyl)amino)-7-(3-(4-(8-(2-(2,6-dioxopiperidin-3-yl)-1-oxoisoindolin-4-yl)octanoyl)piperazin-1-yl)propoxy)-6-methoxyquinoline-3-carbonitrile |
| | | 4-((2,4-dichloro-5-methoxyphenyl)amino)-7-(3-(4-(9-(2-(2,6-dioxopiperidin-3-yl)-1-oxoisoindolin-4-yl)nonanoyl)piperazin-1-yl)propoxy)-6-methoxyquinoline-3-carbonitrile |

TABLE 1-continued

The structure of compounds and its name

| Compound No. | Structure of compound | Name of the compound |
|---|---|---|
| | 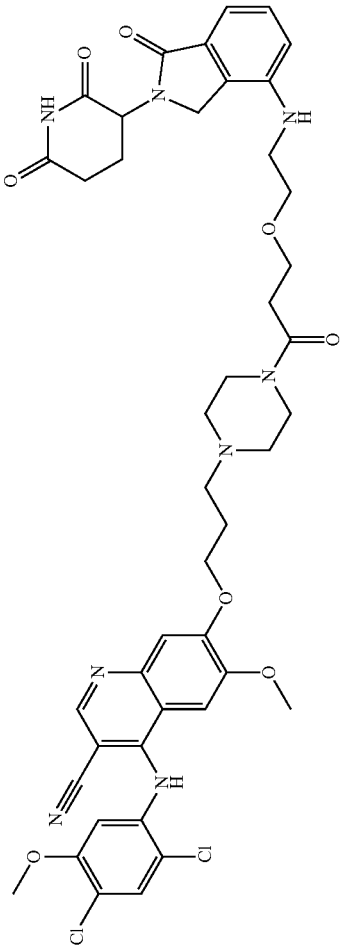 | 4-((2,4-dichloro-5-methoxyphenyl)amino)-7-(3-(4-(3-(2-((2-(2,6-dioxopiperidin-3-yl)-1-oxoisoindolin-4-yl)amino)ethoxy)propanoyl)piperazin-1-yl)propoxy)-6-methoxyquinoline-3-carbonitrile |
| | | 4-((2,4-dichloro-5-methoxyphenyl)amino)-7-(3-(4-(2-((2-(2,6-dioxopiperidin-3-yl)-1-oxoisoindolin-4-yl)amino)ethoxy)butanoyl)piperazin-1-yl)propoxy)-6-methoxyquinoline-3-carbonitrile |

TABLE 1-continued

The structure of compounds and its name

| Compound No. | Structure of compound | Name of the compound |
|---|---|---|
| 191 | 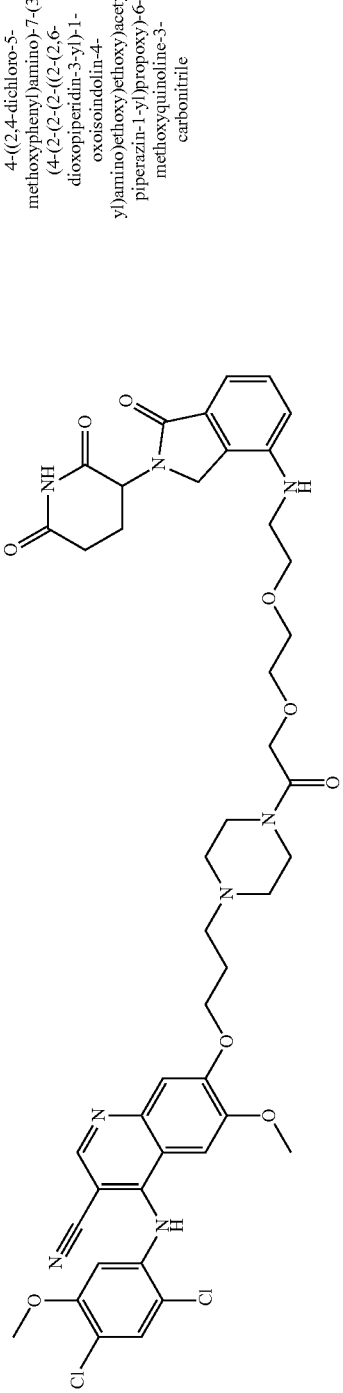 | 4-((2,4-dichloro-5-methoxyphenyl)amino)-7-(3-(4-(2-(2-(2-(2,6-dioxopiperidin-3-yl)-(4-(2-(2-(2-(2,6-yl)amino)ethoxy)ethoxy)acetyl)piperazin-1-yl)propoxy)-6-methoxyquinoline-3-carbonitrile |
| 192 | 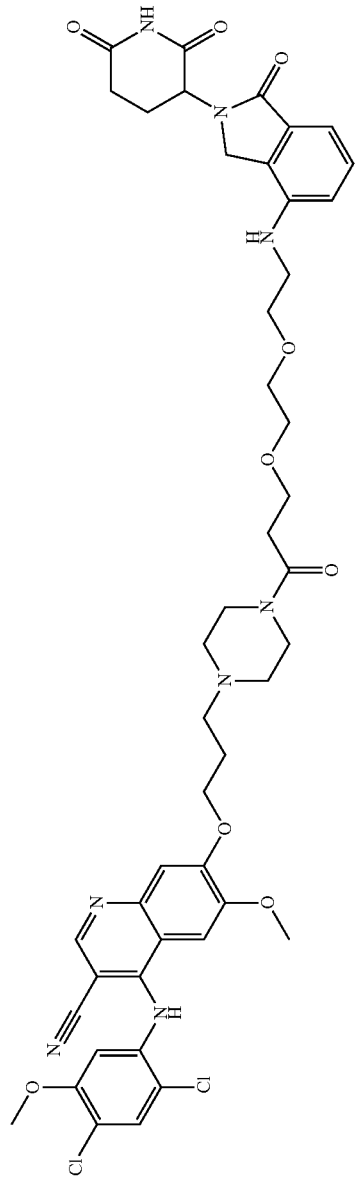 | 4-((2,4-dichloro-5-methoxyphenyl)amino)-7-(3-(4-(3-(2-(2-(2,6-dioxopiperidin-3-yl)-1-oxoisoindolin-4-yl)amino)ethoxy)ethoxy)propanoyl)piperazin-1-yl)propoxy)-6-methoxyquinoline-3-carbonitrile |

TABLE 1-continued

The structure of compounds and its name

| Compound No. | Structure of compound | Name of the compound |
|---|---|---|
| | 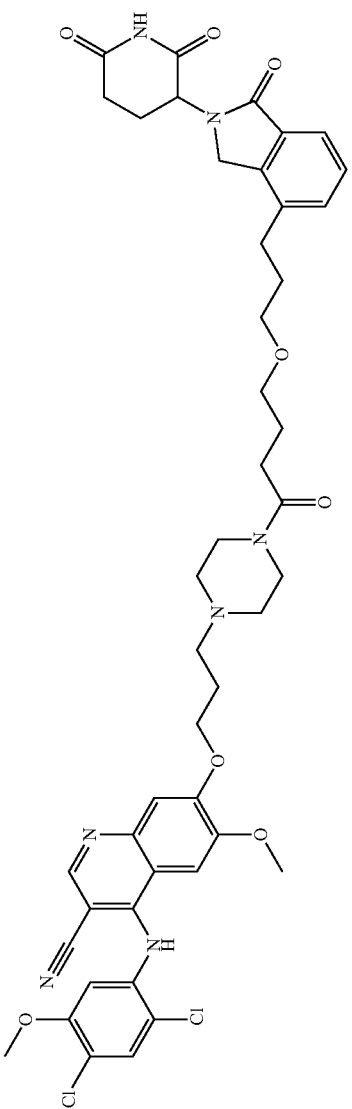 | 4-((2,4-dichloro-5-methoxyphenyl)amino)-7-(3-(4-(4-(3-(2-(2,6-dioxopiperidin-3-yl)-1-oxoisoindolin-4-yl)propoxy)butanoyl)piperazin-1-yl)propoxy)-6-methoxyquinoline-3-carbonitrile |
| | | 4-((2,4-dichloro-5-methoxyphenyl)amino)-7-(3-(4-(2-(3-(2-(2,6-dioxopiperidin-3-yl)-1-oxoisoindolin-4-yl)propoxy)ethoxy)acetyl)piperazin-1-yl)propoxy)-6-methoxyquinoline-3-carbonitrile |

TABLE 1-continued
The structure of compounds and its name
| Compound No. | Structure of compound | Name of the compound |
|---|---|---|
| | 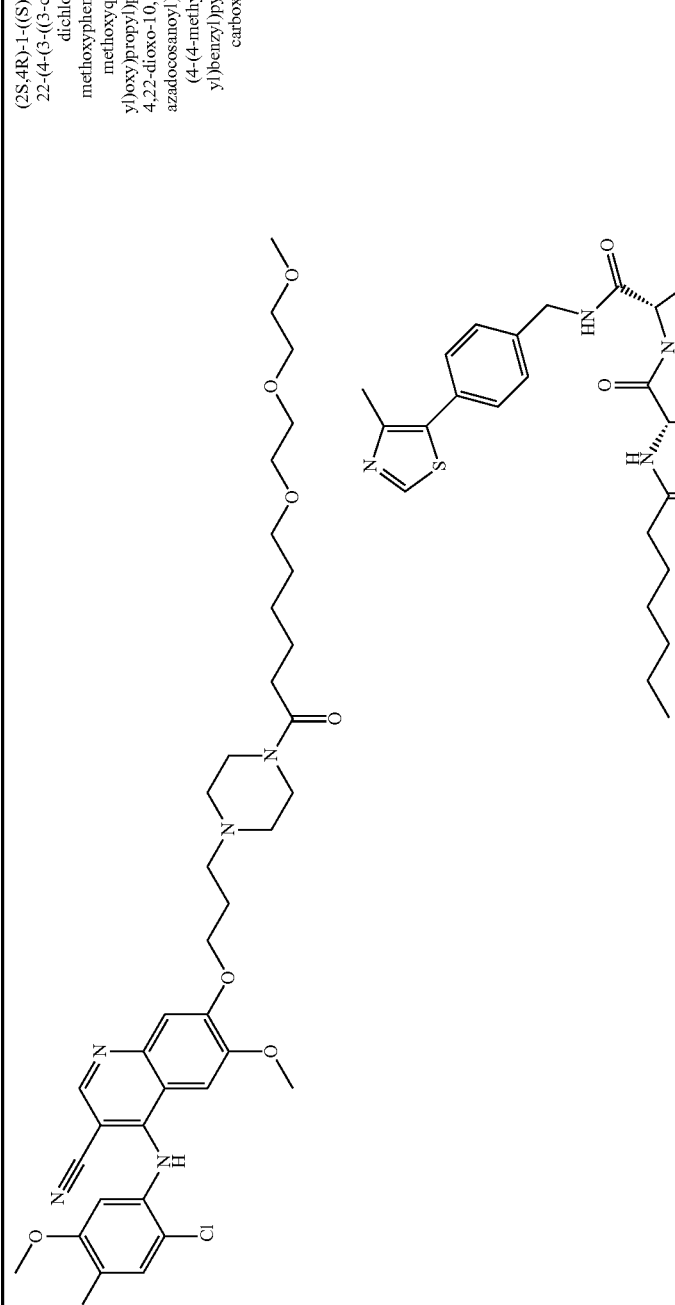 | (2S,4R)-1-((S)-2-(tert-butyl)-22-(4-(3-((3-cyano-4-((2,4-dichloro-5-methoxyphenyl)amino)-6-methoxyquinolin-7-yl)oxy)propyl)piperazin-1-yl)-4,22-dioxo-10,13,16-trioxa-3-azadocosanoyl)-4-hydroxy-N-(4-(4-methylthiazol-5-yl)benzyl)pyrrolidine-2-carboxamide |

TABLE 1-continued
The structure of compounds and its name
| Compound No. | Structure of compound | Name of the compound |
|---|---|---|
| | 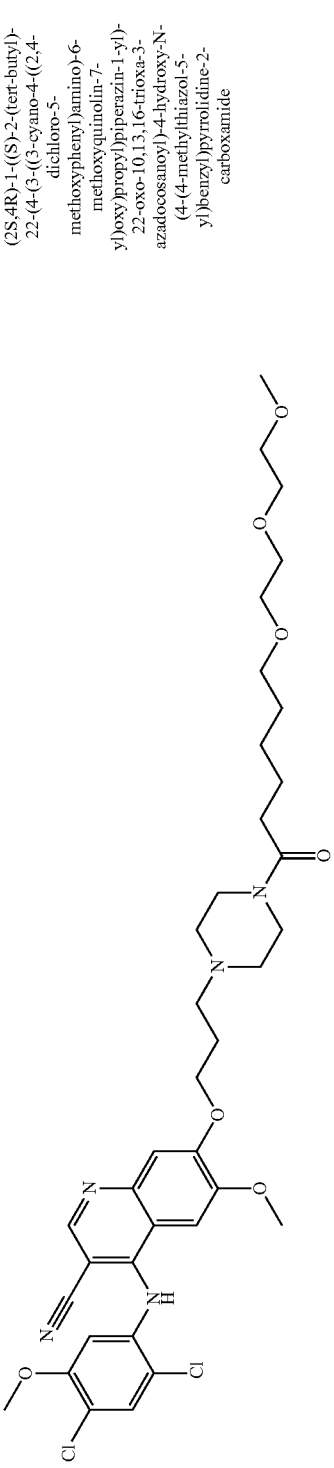 | (2S,4R)-1-((S)-2-(tert-butyl)-22-(4-(3-((3-cyano-4-((2,4-dichloro-5-methoxyphenyl)amino)-6-methoxyquinolin-7-yl)oxy)propyl)piperazin-1-yl)-22-oxo-10,13,16-trioxa-3-azadocosanoyl)-4-hydroxy-N-(4-(4-methylthiazol-5-yl)benzyl)pyrrolidine-2-carboxamide |

TABLE 1-continued

The structure of compounds and its name

| Compound No. | Structure of compound | Name of the compound |
|---|---|---|
| | 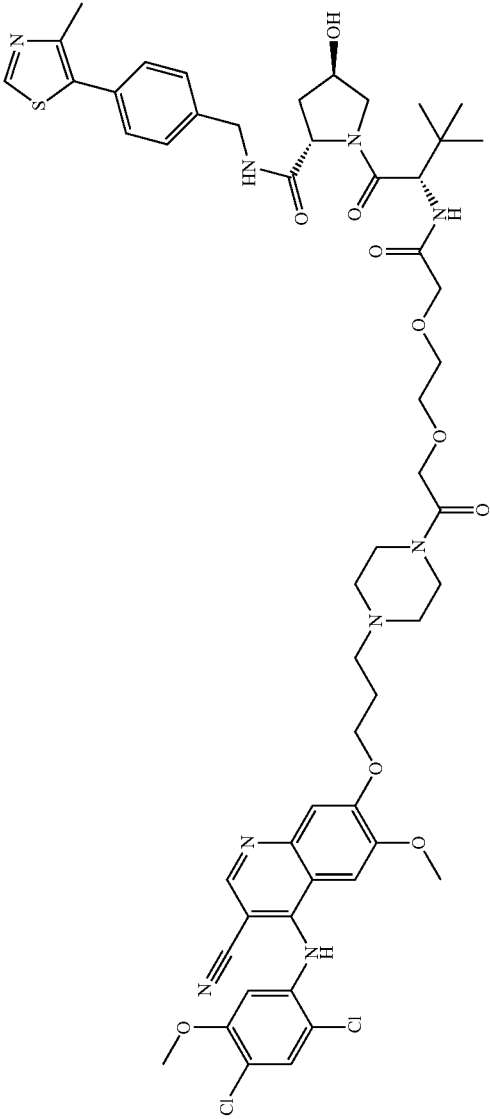 | (2S,4R)-1-((S)-2-(2-(2-(2-(4-(3-((3-cyano-4-((2,4-dichloro-5-methoxyphenyl)amino)-6-methoxyquinolin-7-yl)oxy)propyl)piperazin-1-yl)-2-oxoethoxy)ethoxy)acetamido)-3,3-dimethylbutanoyl)-4-hydroxy-N-(4-(4-methylthiazol-5-yl)benzyl)pyrrolidine-2-carboxamide |
| | 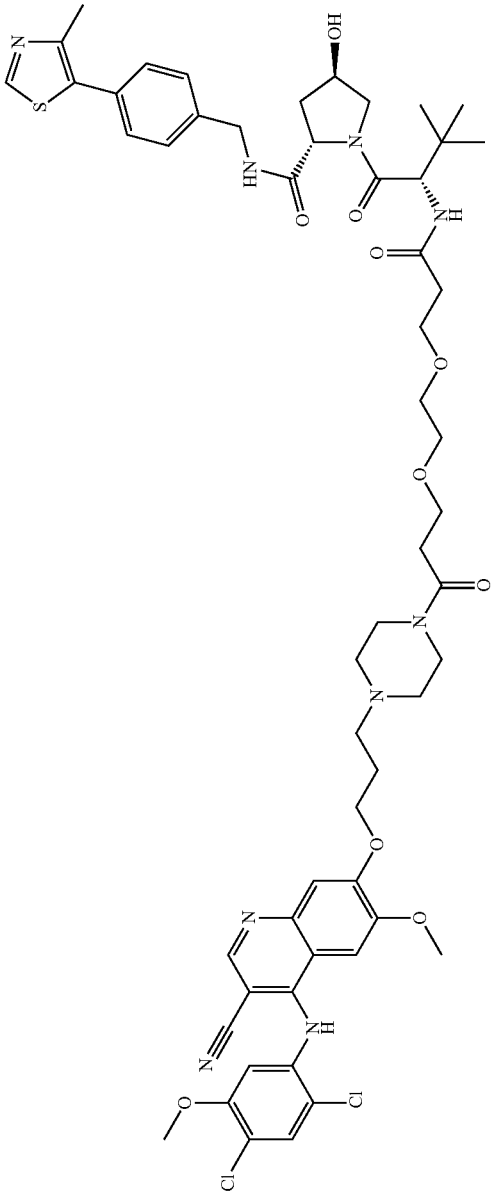 | (2S,4R)-1-((S)-2-(3-(2-(3-(4-(3-((3-cyano-4-((2,4-dichloro-5-methoxyphenyl)amino)-6-methoxyquinolin-7-yl)oxy)propyl)piperazin-1-yl)-3-oxopropoxy)ethoxy)propanamido)-3,3-dimethylbutanoyl)-4-hydroxy-N-(4-(4-methylthiazol-5-yl)benzyl)pyrrolidine-2-carboxamide |

TABLE 1-continued

The structure of compounds and its name

| Compound No. | Structure of compound | Name of the compound |
|---|---|---|
|  |  | (2S,4R)-1-((S)-2-((3-(2-(3-(4-(3-((3-cyano-4-((2,4-dichloro-5-methoxyphenyl)amino)-6-methoxyquinolin-7-yl)oxy)propyl)piperazin-1-yl)-3-oxopropoxy)ethoxy)propyl)amino)-3,3-dimethylbutanoyl)-4-hydroxy-N-(4-(4-methylthiazol-5-yl)benzyl)pyrrolidine-2-carboxamide |

TABLE 1-continued
The structure of compounds and its name
| Compound No. | Structure of compound | Name of the compound |
|---|---|---|
| SIAIS172082 | 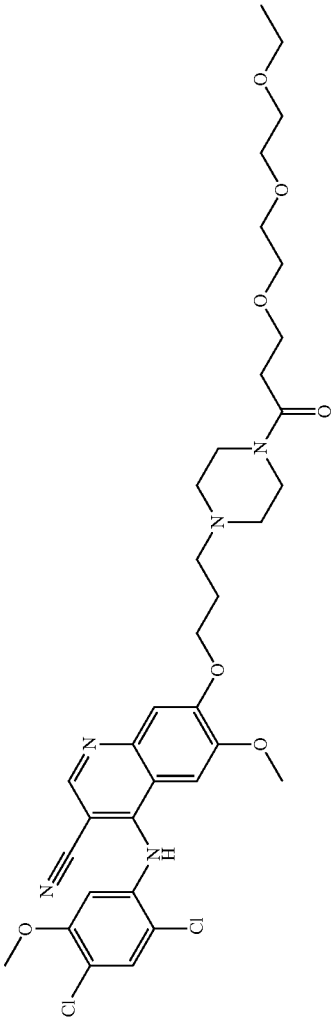 | (2S,4R)-1-((S)-2-(tert-butyl)-16-(4-(3-((3-ethoxypropyl)amino)-6-methoxy-5-methoxyphenyl)amino)-7-methoxyquinolin-7-yl)oxy)propyl)piperazin-1-yl)-4,16-dioxo-7,10,13-trioxa-3-azahexadecanoyl)-4-hydroxy-N-(4-(4-methylthiazol-5-yl)benzyl)pyrrolidine-2-carboxamide |

TABLE 1-continued
The structure of compounds and its name
| Compound No. | Structure of compound | Name of the compound |
|---|---|---|
| | 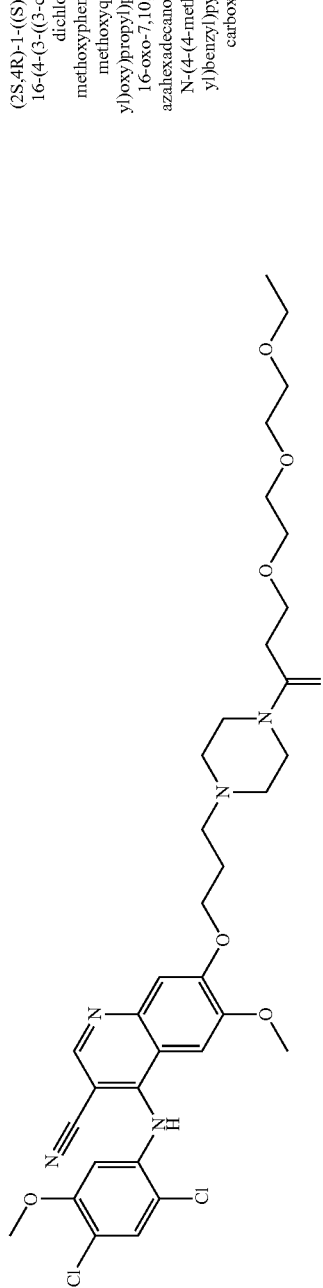 | (2S,4R)-1-((S)-2-(tert-butyl)-16-(4-(3-((3-cyano-4-((2,4-dichloro-5-methoxyphenyl)amino)-6-methoxyquinolin-7-yl)oxy)propyl)piperazin-1-yl)-16-oxo-7,10,13-trioxa-3-azahexadecanoyl)-4-hydroxy-N-(4-(4-methylthiazol-5-yl)benzyl)pyrrolidine-2-carboxamide |

TABLE 1-continued

The structure of compounds and its name

| Compound No. | Structure of compound | Name of the compound |
|---|---|---|
| SIAIS172 083 | | (2S,4R)-1-((S)-2-(tert-butyl)-19-(4-(3-((3-cyano-4-((2,4-dichloro-5-methoxyphenyl)amino)-6-methoxyquinolin-7-yl)oxy)propyl)piperazin-1-yl)-4,19-dioxo-7,10,13,16-tetraoxa-3-azanonadecanoyl)-4-hydroxy-N-(4-(4-methylthiazol-5-yl)benzyl)pyrrolidine-2-carboxamide |

TABLE 1-continued
The structure of compounds and its name
| Compound No. | Structure of compound | Name of the compound |
|---|---|---|
| SIAIS172 084 | 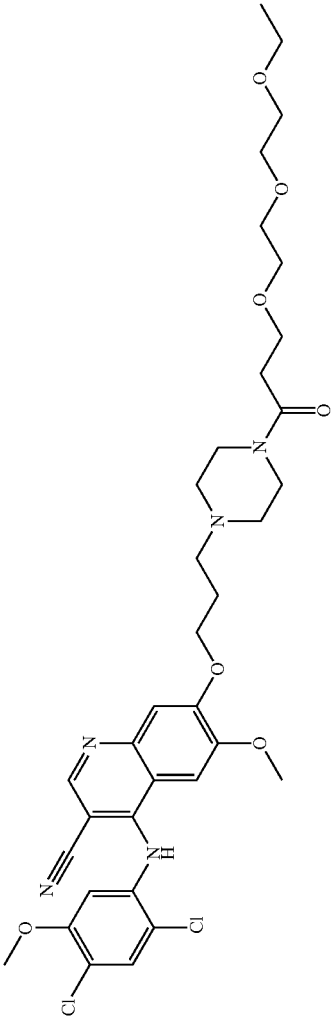 | (2S,4R)-1-((S)-2-(tert-butyl)-22-(4-(3-((3-cyano-4-((2,4-dichloro-5-methoxyphenyl)amino)-6-methoxyquinolin-7-yl)oxy)propyl)piperazin-1-yl)-4,22-dioxo-7,10,13,16,19-pentaoxa-3-azadocosanoyl)-4-hydroxy-N-(4-(4-methylthiazol-5-yl)benzyl)pyrrolidine-2-carboxamide |

TABLE 1-continued

The structure of compounds and its name

| Compound No. | Structure of compound | Name of the compound |
|---|---|---|
| SIAIS172 072 | | (2S,4R)-1-((S)-2-(4-(4-(3-((3-cyano-4-((2,4-dichloro-5-methoxyphenyl)amino)-6-methoxyquinolin-7-yl)oxy)propyl)piperazin-1-yl)-4-oxobutanamido)-3,3-dimethylbutanoyl)-4-hydroxy-N-(4-(4-methylthiazol-5-yl)benzyl)pyrrolidine-2-carboxamide |
| SIAIS172 073 | | (2S,4R)-1-((S)-2-(5-(4-(3-((3-cyano-4-((2,4-dichloro-5-methoxyphenyl)amino)-6-methoxyquinolin-7-yl)oxy)propyl)piperazin-1-yl)-5-oxopentanamido)-3,3-dimethylbutanoyl)-4-hydroxy-N-(4-(4-methylthiazol-5-yl)benzyl)pyrrolidine-2-carboxamide |

TABLE 1-continued

The structure of compounds and its name

| Compound No. | Structure of compound | Name of the compound |
|---|---|---|
| SIAIS172 074 | 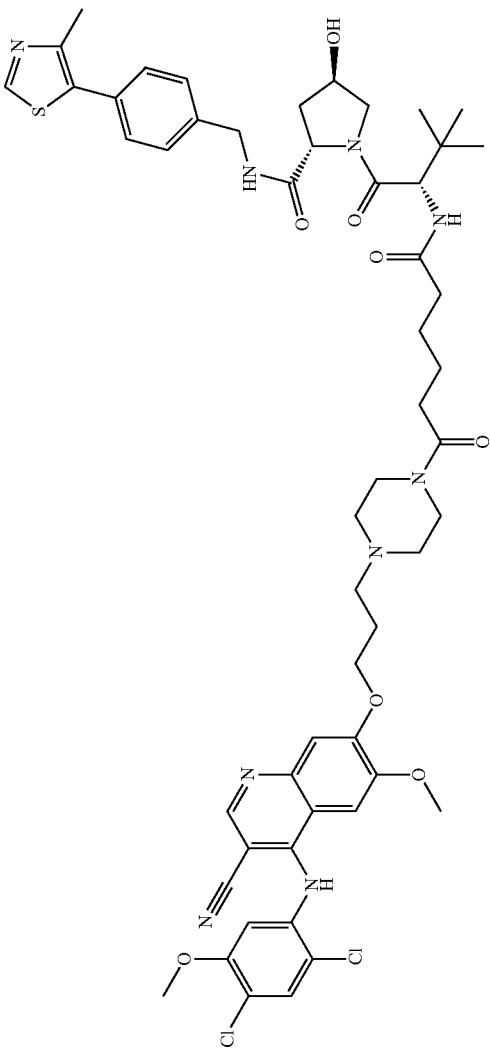 | (2S,4R)-1-((S)-2-(6-(4-(3-((3-cyano-4-((2,4-dichloro-5-methoxyphenyl)amino)-6-methoxyquinolin-7-yl)oxy)propyl)piperazin-1-yl)-6-oxohexanamido)-3,3-dimethylbutanoyl)-4-hydroxy-N-(4-(4-methylthiazol-5-yl)benzyl)pyrrolidine-2-carboxamide<br><br>(2S,4R)-1-((S)-2-(6-(4-(3-((3-cyano-4-((2,4-dichloro-5-methoxyphenyl)amino)-6-methoxyquinolin-7-yl)oxy)propyl)piperazin-1-yl)-6-oxohexyl)amino)-3,3-dimethylbutanoyl)-4-hydroxy-N-(4-(4-methylthiazol-5-yl)benzyl)pyrrolidine-2-carboxamide |

TABLE 1-continued

The structure of compounds and its name

| Compound No. | Structure of compound | Name of the compound |
|---|---|---|
| SIAIS172 075 | 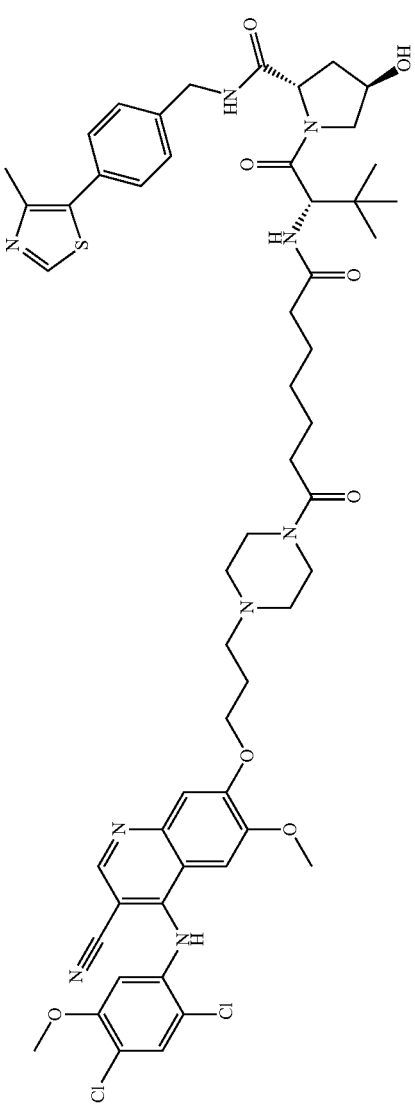 | (2S,4R)-1-((S)-2-(7-(4-(3-((3-cyano-4-((2,4-dichloro-5-methoxyphenyl)amino)-6-methoxyquinolin-7-yl)oxy)propyl)piperazin-1-yl)-7-oxoheptanamido)-3,3-dimethylbutanoyl)-4-hydroxy-N-(4-(4-methylthiazol-5-yl)benzyl)pyrrolidine-2-carboxamide |
| | | (2S,4R)-1-((S)-2-(7-(4-(3-((3-cyano-4-((2,4-dichloro-5-methoxyphenyl)amino)-6-methoxyquinolin-7-yl)oxy)propyl)piperazin-1-yl)-7-oxoheptyl)amino)-3,3-dimethylbutanoyl)-4-hydroxy-N-(4-(4-methylthiazol-5-yl)benzyl)pyrrolidine-2-carboxamide |

TABLE 1-continued

The structure of compounds and its name

| Compound No. | Structure of compound | Name of the compound |
|---|---|---|
| SIAIS172 076 | 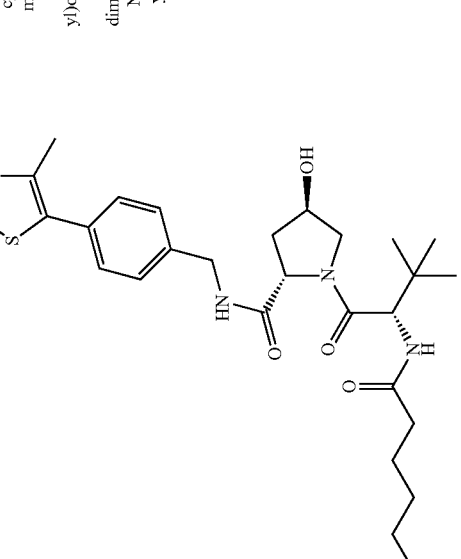 | (2S,4R)-1-((S)-2-(8-(4-(3-((3-cyano-4-((2,4-dichloro-5-methoxyphenyl)amino)-6-methoxyquinolin-7-yl)oxy)propyl)piperazin-1-yl)-8-oxooctanamido)-3,3-dimethylbutanoyl)-4-hydroxy-N-(4-(4-methylthiazol-5-yl)benzyl)pyrrolidine-2-carboxamide |
| | 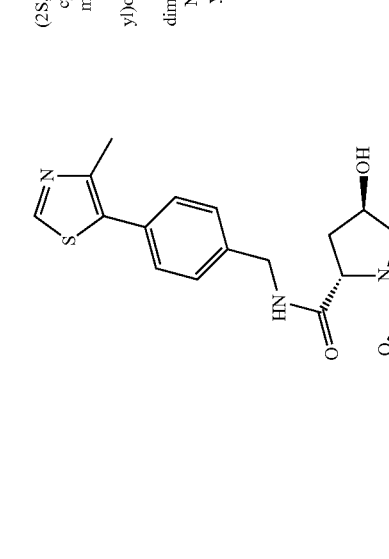 | (2S,4R)-1-((S)-2-(8-(4-(3-((3-cyano-4-((2,4-dichloro-5-methoxyphenyl)amino)-6-methoxyquinolin-7-yl)oxy)propyl)piperazin-1-yl)-8-oxooctyl)amino)-3,3-dimethylbutanoyl)-4-hydroxy-N-(4-(4-methylthiazol-5-yl)benzyl)pyrrolidine-2-carboxamide |

TABLE 1-continued

The structure of compounds and its name

| Compound No. | Structure of compound | Name of the compound |
|---|---|---|
| SIAIS172 077 | | (2S,4R)-1-((S)-2-(9-(4-(3-((3-cyano-4-((2,4-dichloro-5-methoxyphenyl)amino)-6-methoxyquinolin-7-yl)oxy)propyl)piperazin-1-yl)-9-oxononanamido)-3,3-dimethylbutanoyl)-4-hydroxy-N-(4-(4-methylthiazol-5-yl)benzyl)pyrrolidine-2-carboxamide |
| SIAIS172 078 | | (2S,4R)-1-((S)-2-(10-(4-(3-((3-cyano-4-((2,4-dichloro-5-methoxyphenyl)amino)-6-methoxyquinolin-7-yl)oxy)propyl)piperazin-1-yl)-10-oxodecanamido)-3,3-dimethylbutanoyl)-4-hydroxy-N-(4-(4-methylthiazol-5-yl)benzyl)pyrrolidine-2-carboxamide |

TABLE 1-continued
The structure of compounds and its name
| Compound No. | Structure of compound | Name of the compound |
|---|---|---|
| SIAIS172 079 | 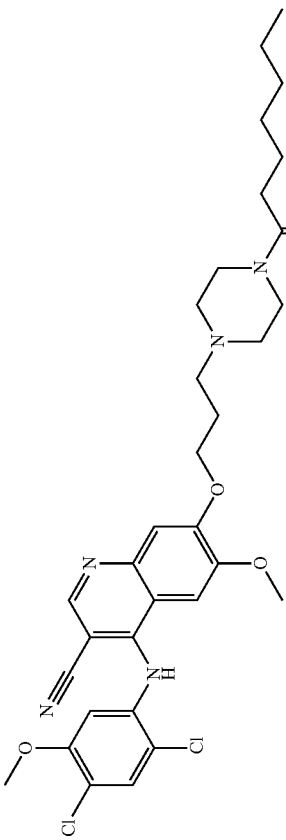 | (2S,4R)-1-((S)-2-(11-(4-(3-((3-cyano-4-((2,4-dichloro-5-methoxyphenyl)amino)-6-methoxyquinolin-7-yl)oxy)propyl)piperazin-1-yl)-11-oxoundecanamido)-3,3-dimethylbutanoyl)-4-hydroxy-N-(4-(4-methylthiazol-5-yl)benzyl)pyrrolidine-2-carboxamide |

TABLE 1-continued
The structure of compounds and its name
| Compound No. | Structure of compound | Name of the compound |
|---|---|---|
| | 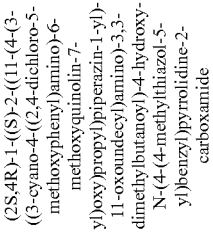 | (2S,4R)-1-((S)-2-(11-(4-(3-((3-cyano-4-((2,4-dichloro-5-methoxyphenyl)amino)-6-methoxyquinolin-7-yl)oxy)propyl)piperazin-1-yl)-11-oxoundecyl)amino)-3,3-dimethylbutanoyl)-4-hydroxy-N-(4-(4-methylthiazol-5-yl)benzyl)pyrrolidine-2-carboxamide |

TABLE 1-continued
The structure of compounds and its name
| Compound No. | Structure of compound | Name of the compound |
|---|---|---|
| | 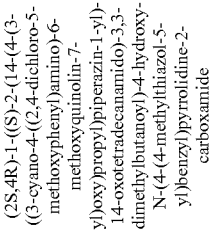 | (2S,4R)-1-((S)-2-(14-(4-(3-((3-cyano-4-((2,4-dichloro-5-methoxyphenyl)amino)-6-methoxyquinolin-7-yl)oxy)propyl)piperazin-1-yl)-14-oxotetradecanamido)-3,3-dimethylbutanoyl)-4-hydroxy-N-(4-(4-methylthiazol-5-yl)benzyl)pyrrolidine-2-carboxamide |

TABLE 1-continued
The structure of compounds and its name
| Compound No. | Structure of compound | Name of the compound |
|---|---|---|
| | 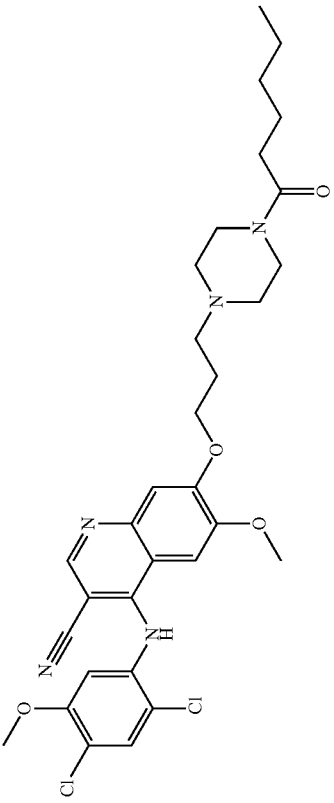 | (2S,4R)-1-((S)-2-(16-(4-(3-((3-cyano-4-((2,4-dichloro-5-methoxyphenyl)amino)-6-methoxyquinolin-7-yl)oxy)propyl)piperazin-1-yl)-16-oxohexadecanamido)-3,3-dimethylbutanoyl)-4-hydroxy-N-(4-(4-methylthiazol-5-yl)benzyl)pyrrolidine-2-carboxamide |

TABLE 1-continued

The structure of compounds and its name

| Compound No. | Structure of compound | Name of the compound |
|---|---|---|
|  |  | 4-((4-(6-(2-(2-((6-((2-(2,6-dioxopiperidin-3-yl)-1,3-dioxoisoindolin-4-yl)amino)-6-oxohexyl)oxy)ethoxy)ethoxy)hexanoyl)piperazin-1-yl)methyl)-N-(4-methyl-3-((4-(pyridin-3-yl)pyrimidin-2-yl)amino)phenyl)benzamide |

TABLE 1-continued

The structure of compounds and its name

| Compound No. | Structure of compound | Name of the compound |
|---|---|---|
| | 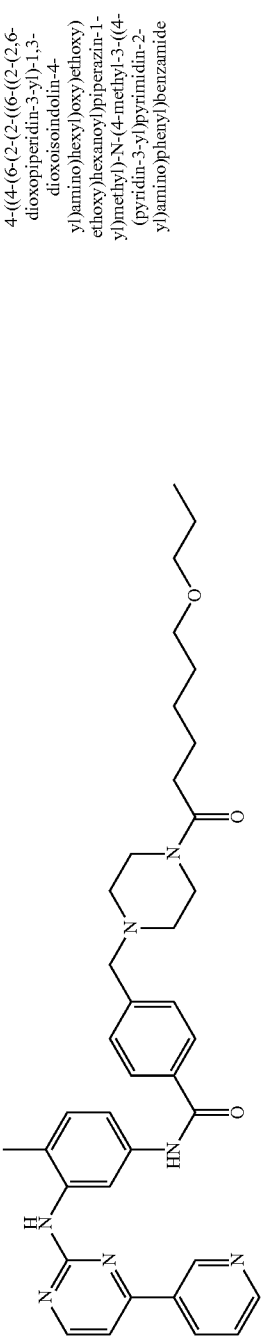 | 4-((4-(6-(2-(2-(6-(2-(2,6-dioxopiperidin-3-yl)-1,3-dioxoisoindolin-4-yl)amino)hexanoyl)oxy)ethoxy)ethoxy)hexyl)oxy)piperazin-1-yl)methyl)-N-(4-methyl-3-((4-(pyridin-3-yl)pyrimidin-2-yl)amino)phenyl)benzamide |
| SIAIS119 7001 | 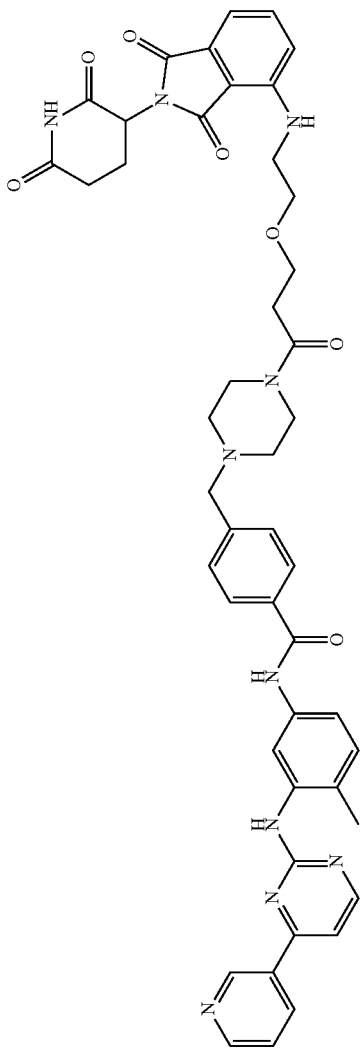 | 4-((4-(3-(2-((2-(2,6-dioxopiperidin-3-yl)-1,3-dioxoisoindolin-4-yl)amino)ethoxy)propanoyl)piperazin-1-yl)methyl)-N-(4-methyl-3-((4-(pyridin-3-yl)pyrimidin-2-yl)amino)phenyl)benzamide |

TABLE 1-continued

The structure of compounds and its name

| Compound No. | Structure of compound | Name of the compound |
|---|---|---|
| SIAIS1197015 | 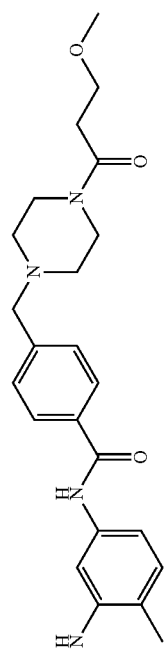 | 4-((4-(3-(2-(2-((2-(2,6-dioxopiperidin-3-yl)-1,3-dioxoisoindolin-4-yl)amino)ethoxy)ethoxy)propanoyl)piperazin-1-yl)methyl)-N-(4-methyl-3-((4-(pyridin-3-yl)pyrimidin-2-yl)amino)phenyl)benzamide |
| SIAIS1197017 | 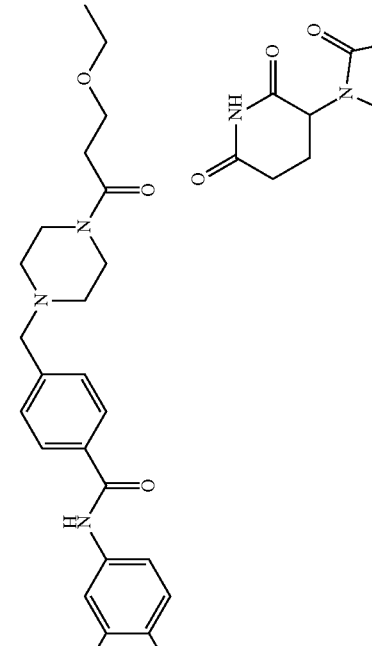 | 4-((4-(3-(2-(2-(2-((2-(2,6-dioxopiperidin-3-yl)-1,3-dioxoisoindolin-4-yl)amino)ethoxy)ethoxy)ethoxy)propanoyl)piperazin-1-yl)methyl)-N-(4-methyl-3-((4-(pyridin-3-yl)pyrimidin-2-yl)amino)phenyl)benzamide |

TABLE 1-continued

| Compound No. | Structure of compound | Name of the compound |
|---|---|---|
| SIAIS1197019 | | 4-((4-(1-((2-(2,6-dioxopiperidin-3-yl)-1,3-dioxoisoindolin-4-yl)amino)-3,6,9,12-tetraoxapentadecan-15-oyl)piperazin-1-yl)methyl)-N-(4-methyl-3-((4-(pyridin-3-yl)pyrimidin-2-yl)amino)phenyl)benzamide |
| SIAIS1197021 | | 4-((4-(1-((2-(2,6-dioxopiperidin-3-yl)-1,3-dioxoisoindolin-4-yl)amino)-3,6,9,12,15-pentaoxaoctadecan-18-oyl)piperazin-1-yl)methyl)-N-(4-methyl-3-((4-(pyridin-3-yl)pyrimidin-2-yl)amino)phenyl)benzamide |

TABLE 1-continued

The structure of compounds and its name

| Compound No. | Structure of compound | Name of the compound |
|---|---|---|
| | 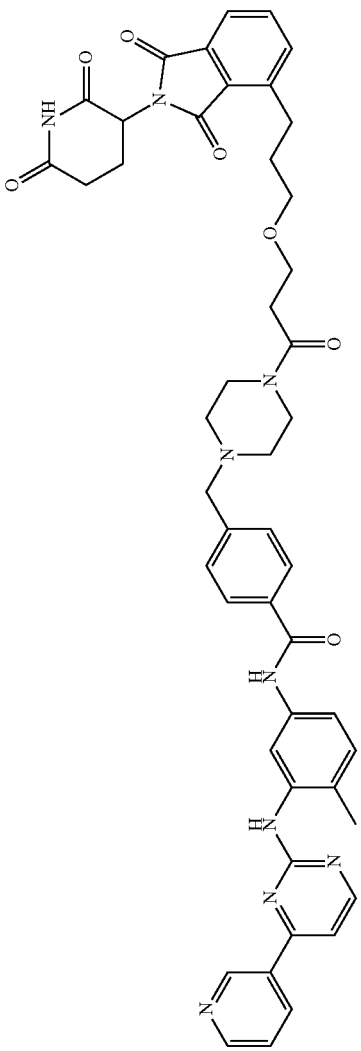 | 4-((4-(3-(3-(2-(2,6-dioxopiperidin-3-yl)-1,3-dioxoisoindolin-4-yl)propoxy)propanoyl)piperazin-1-yl)methyl)-N-(4-methyl-3-((4-(pyridin-3-yl)pyrimidin-2-yl)amino)phenyl)benzamide |
| | 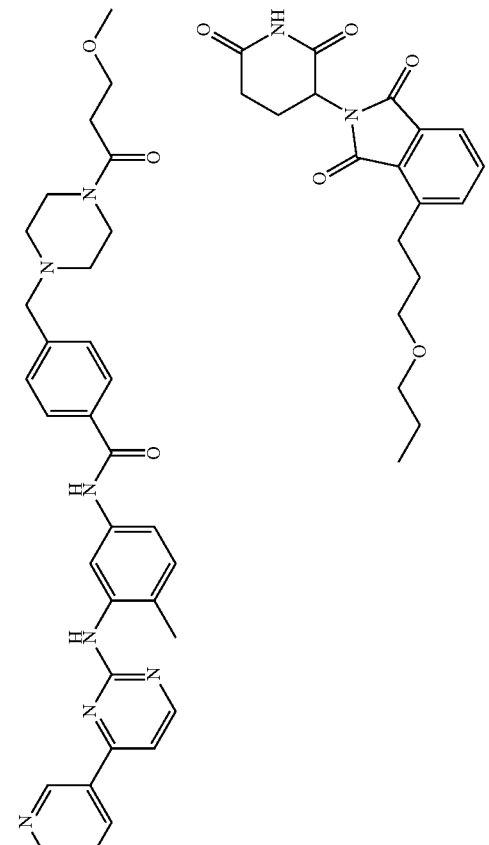 | 4-((4-(3-(2-(2-(2,6-dioxopiperidin-3-yl)-1,3-dioxoisoindolin-4-yl)propoxy)ethoxy)propanoyl)piperazin-1-yl)methyl)-N-(4-methyl-3-((4-(pyridin-3-yl)pyrimidin-2-yl)amino)phenyl)benzamide |

TABLE 1-continued

The structure of compounds and its name

| Compound No. | Structure of compound | Name of the compound |
|---|---|---|
| | 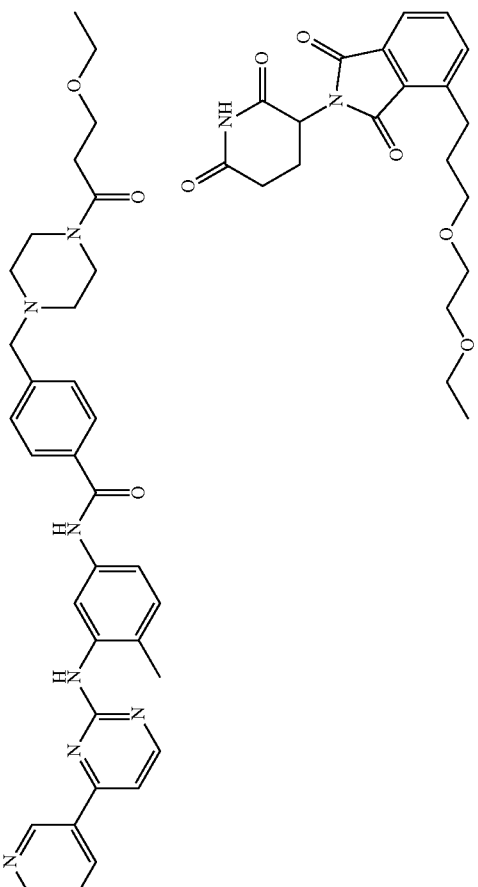 | 4-((4-(3-(2-(3-(2-(2,6-dioxopiperidin-3-yl)-1,3-dioxoisoindolin-4-yl)propoxy)ethoxy)propanoyl)piperazin-1-yl)methyl)-N-(4-methyl-3-((4-(pyridin-3-yl)pyrimidin-2-yl)amino)phenyl)benzamide |
| SIAIS119 7003 | | 4-((4-((2-(2,6-dioxopiperidin-3-yl)-1,3-dioxoisoindolin-4-yl)glycyl)piperazin-1-yl)methyl)-N-(4-methyl-3-((4-(pyridin-3-yl)pyrimidin-2-yl)amino)phenyl)benzamide |

TABLE 1-continued

The structure of compounds and its name

| Compound No. | Structure of compound | Name of the compound |
|---|---|---|
| SIAIS1197005 | | 4-((4-(3-((2-(2,6-dioxopiperidin-3-yl)-1,3-dioxoisoindolin-4-yl)amino)propanoyl)piperazin-1-yl)methyl)-N-(4-methyl-3-((4-(pyridin-3-yl)pyrimidin-2-yl)amino)phenyl)benzamide |
| SIAIS1197007 | | 4-((4-(4-((2-(2,6-dioxopiperidin-3-yl)-1,3-dioxoisoindolin-4-yl)amino)butanoyl)piperazin-1-yl)methyl)-N-(4-methyl-3-((4-(pyridin-3-yl)pyrimidin-2-yl)amino)phenyl)benzamide |
| SIAIS1197009 | | 4-((4-(5-((2-(2,6-dioxopiperidin-3-yl)-1,3-dioxoisoindolin-4-yl)amino)pentanoyl)piperazin-1-yl)methyl)-N-(4-methyl-3-((4-(pyridin-3-yl)pyrimidin-2-yl)amino)phenyl)benzamide |

TABLE 1-continued

The structure of compounds and its name

| Compound No. | Structure of compound | Name of the compound |
|---|---|---|
| SIAIS119 7011 | | 4-(4-(6-((2-(2,6-dioxopiperidin-3-yl)-1,3-dioxoisoindolin-4-yl)amino)hexanoyl)piperazin-1-yl)methyl)-N-(4-methyl-3-(((4-(pyridin-3-yl)pyrimidin-2-yl)amino)phenyl)benzamide |
| SIAIS119 7095 | | 4-((4-(7-((2-(2,6-dioxopiperidin-3-yl)-1,3-dioxoisoindolin-4-yl)amino)heptanoyl)piperazin-1-yl)methyl)-N-(4-methyl-3-(((4-(pyridin-3-yl)pyrimidin-2-yl)amino)phenyl)benzamide |

TABLE 1-continued

The structure of compounds and its name

| Compound No. | Structure of compound | Name of the compound |
|---|---|---|
| | 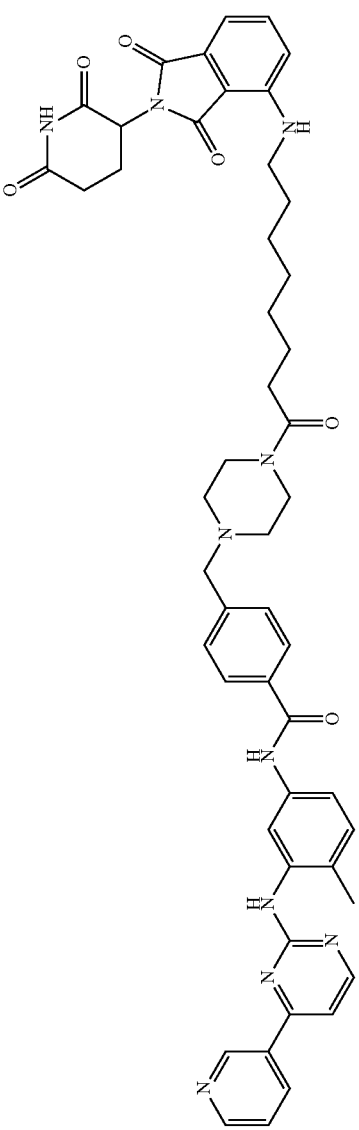 | 4-((4-(8-((2-(2,6-dioxopiperidin-3-yl)-1,3-dioxoisoindolin-4-yl)amino)octanoyl)piperazin-1-yl)methyl)-N-(4-methyl-3-((4-(pyridin-3-yl)pyrimidin-2-yl)amino)phenyl)benzamide |
| | 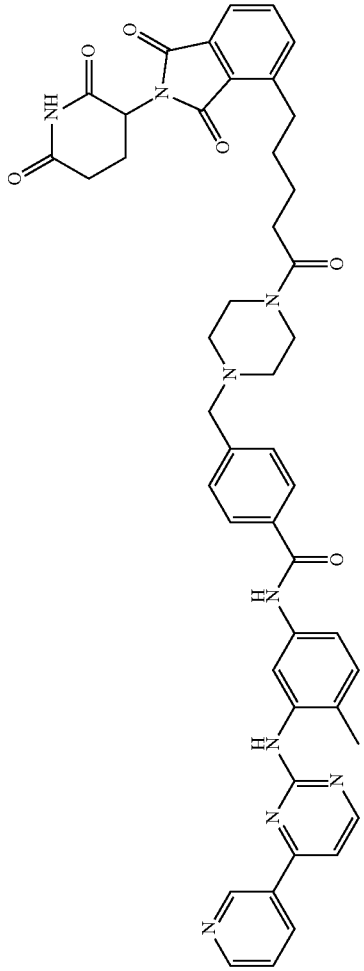 | 4-((4-(5-(2-(2,6-dioxopiperidin-3-yl)-1,3-dioxoisoindolin-4-yl)pentanoyl)piperazin-1-yl)methyl)-N-(4-methyl-3-((4-(pyridin-3-yl)pyrimidin-2-yl)amino)phenyl)benzamide |

TABLE 1-continued

The structure of compounds and its name

| Compound No. | Structure of compound | Name of the compound |
|---|---|---|
| | | 4-((4-(6-(2-(2,6-dioxopiperidin-3-yl)-1,3-dioxoisoindolin-4-yl)hexanoyl)piperazin-1-yl)methyl)-N-(4-methyl-3-((4-(pyridin-3-yl)pyrimidin-2-yl)amino)phenyl)benzamide |
| | | 4-((4-(7-(2-(2,6-dioxopiperidin-3-yl)-1,3-dioxoisoindolin-4-yl)heptanoyl)piperazin-1-yl)methyl)-N-(4-methyl-3-((4-(pyridin-3-yl)pyrimidin-2-yl)amino)phenyl)benzamide |
| | | 4-((4-(8-(2-(2,6-dioxopiperidin-3-yl)-1,3-dioxoisoindolin-4-yl)octanoyl)piperazin-1-yl)methyl)-N-(4-methyl-3-((4-(pyridin-3-yl)pyrimidin-2-yl)amino)phenyl)benzamide |

TABLE 1-continued

The structure of compounds and its name

| Compound No. | Structure of compound | Name of the compound |
|---|---|---|
| | 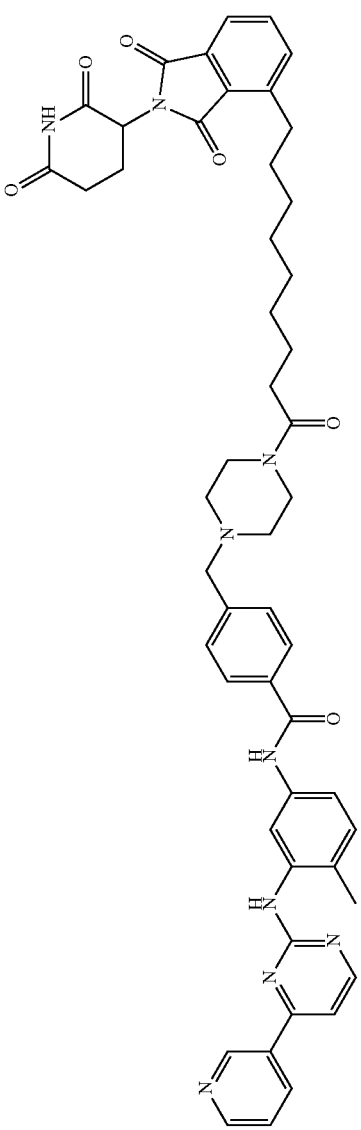 | 4-((4-(9-(2-(2,6-dioxopiperidin-3-yl)-1,3-dioxoisoindolin-4-yl)nonanoyl)piperazin-1-yl)methyl)-N-(4-methyl-3-((4-(pyridin-3-yl)pyrimidin-2-yl)amino)phenyl)benzamide |
| | 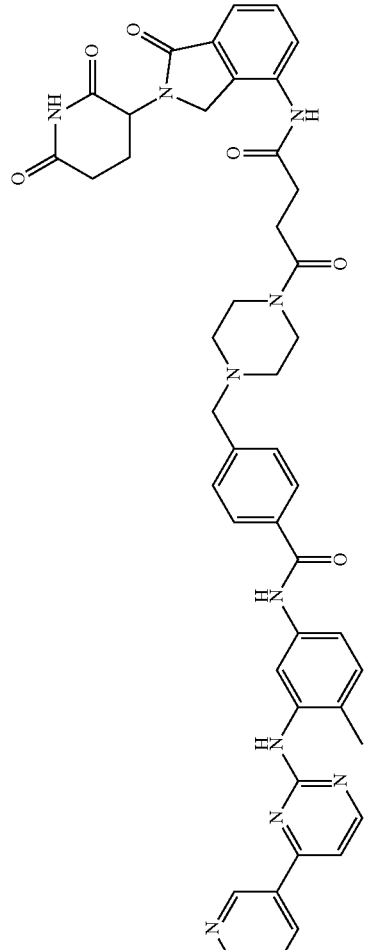 | 4-((4-(4-((2-(2,6-dioxopiperidin-3-yl)-1-oxoisoindolin-4-yl)amino)-4-oxobutanoyl)piperazin-1-yl)methyl)-N-(4-methyl-3-((4-(pyridin-3-yl)pyrimidin-2-yl)amino)phenyl)benzamide |

TABLE 1-continued

The structure of compounds and its name

| Compound No. | Structure of compound | Name of the compound |
|---|---|---|
| | | 4-((4-(5-((2-(2,6-dioxopiperidin-3-yl)-1-oxoisoindolin-4-yl)amino)-5-oxopentanoyl)piperazin-1-yl)methyl)-N-(4-methyl-3-((4-(pyridin-3-yl)pyrimidin-2-yl)amino)phenyl)benzamide |
| | | 4-((4-(6-((2-(2,6-dioxopiperidin-3-yl)-1-oxoisoindolin-4-yl)amino)-6-oxohexanoyl)piperazin-1-yl)methyl)-N-(4-methyl-3-((4-(pyridin-3-yl)pyrimidin-2-yl)amino)phenyl)benzamide |
| | | 4-((4-(7-((2-(2,6-dioxopiperidin-3-yl)-1-oxoisoindolin-4-yl)amino)-7-oxoheptanoyl)piperazin-1-yl)methyl)-N-(4-methyl-3-((4-(pyridin-3-yl)pyrimidin-2-yl)amino)phenyl)benzamide |

TABLE 1-continued

The structure of compounds and its name

| Compound No. | Structure of compound | Name of the compound |
|---|---|---|
| | 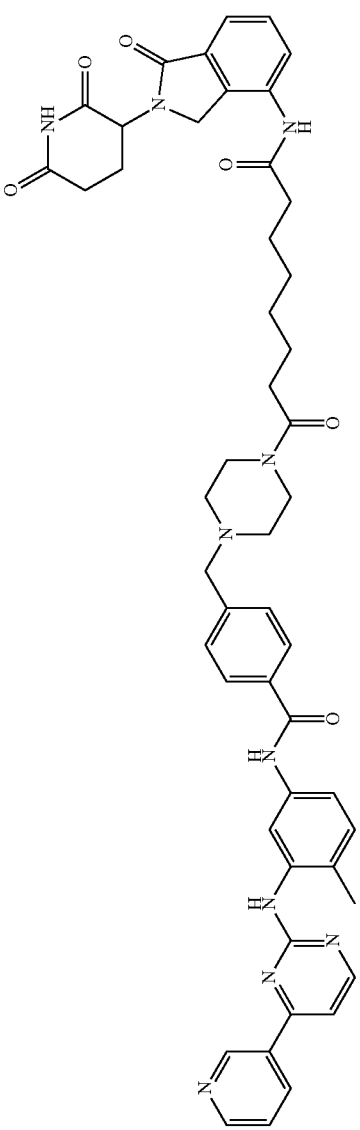 | 4-((4-(8-((2-(2,6-dioxopiperidin-3-yl)-1-oxoisoindolin-4-yl)amino)-8-oxooctanoyl)piperazin-1-yl)methyl)-N-(4-methyl-3-((4-(pyridin-3-yl)pyrimidin-2-yl)amino)phenyl)benzamide |
| | | 4-((4-(9-((2-(2,6-dioxopiperidin-3-yl)-1-oxoisoindolin-4-yl)amino)-9-oxononanoyl)piperazin-1-yl)methyl)-N-(4-methyl-3-((4-(pyridin-3-yl)pyrimidin-2-yl)amino)phenyl)benzamide |

TABLE 1-continued
The structure of compounds and its name
| Compound No. | Structure of compound | Name of the compound |
|---|---|---|
| | 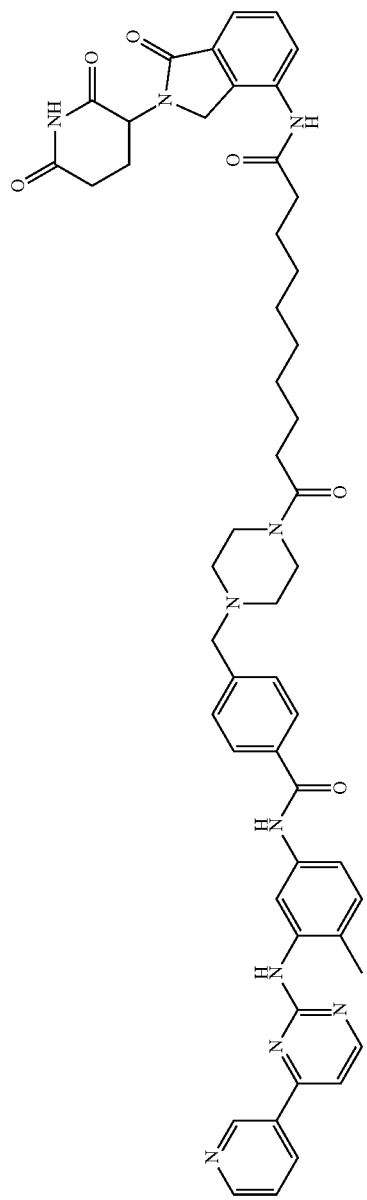 | 4-((4-(10-((2-(2,6-dioxopiperidin-3-yl)-1-oxoisoindolin-4-yl)amino)-10-oxodecanoyl)piperazin-1-yl)methyl)-N-(4-methyl-3-((4-(pyridin-3-yl)pyrimidin-2-yl)amino)phenyl)benzamide |

TABLE 1-continued
The structure of compounds and its name
| Compound No. | Structure of compound | Name of the compound |
|---|---|---|
| | 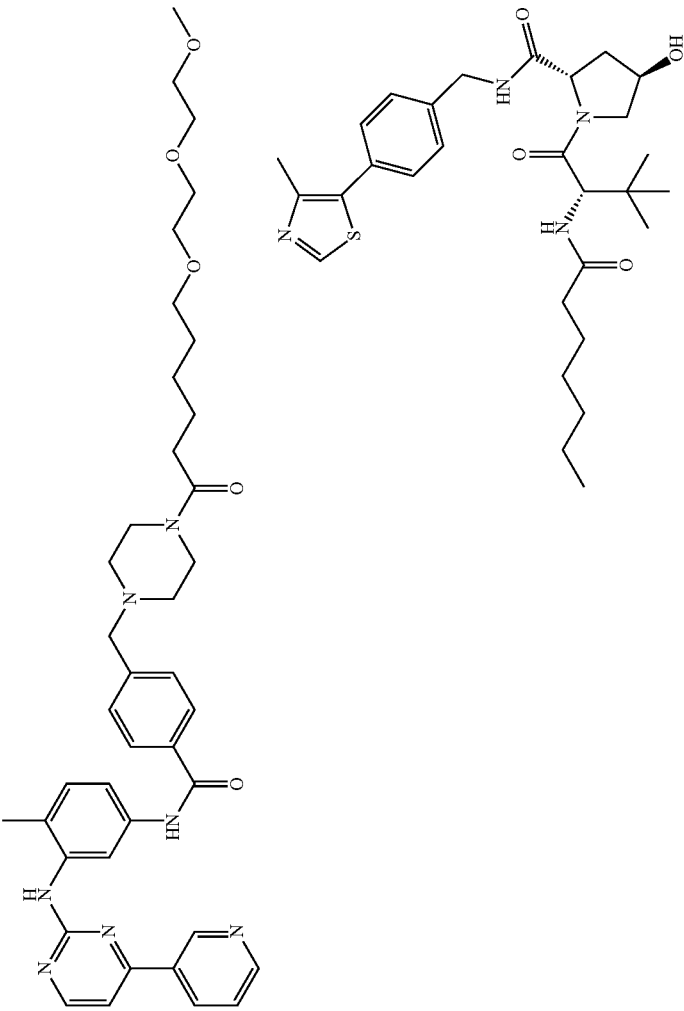 | (2S,4R)-1-((S)-2-(tert-butyl)-22-(4-(4-methyl-3-((4-(pyridin-3-yl)pyrimidin-2-yl)amino)phenyl)carbamoyl)benzyl)piperazin-1-yl)-4,22-dioxo-10,13,16-trioxa-3-azadocosanoyl)-4-hydroxy-N-(4-(4-methylthiazol-5-yl)benzyl)pyrrolidine-2-carboxamide |

TABLE 1-continued
The structure of compounds and its name
| Compound No. | Structure of compound | Name of the compound |
|---|---|---|
| | 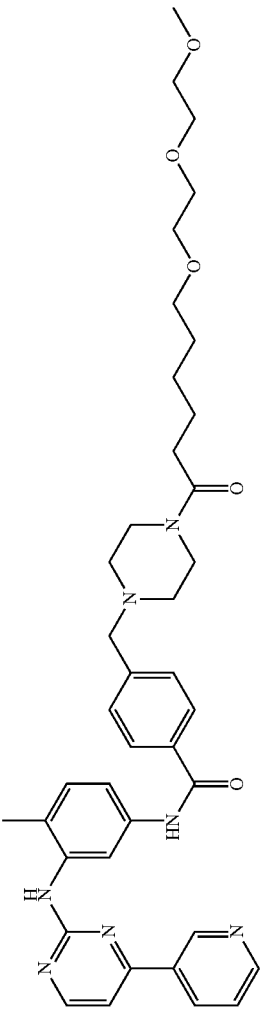 | (2S,4R)-1-((S)-2-(tert-butyl)-22-(4-(4-((4-methyl-3-((4-(pyridin-3-yl)pyrimidin-2-yl)amino)phenyl)carbamoyl)benzyl)piperazin-1-yl)-22-oxo-10,13,16-trioxa-3-azadocosanoyl)-4-hydroxy-N-(4-(4-methylthiazol-5-yl)benzyl)pyrrolidine-2-carboxamide |

TABLE 1-continued
The structure of compounds and its name
| Compound No. | Structure of compound | Name of the compound |
|---|---|---|
| SIAIS119 7043 | 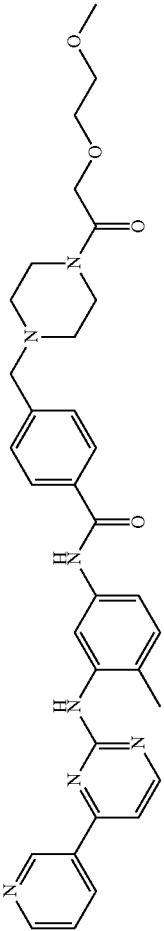 | (2S,4R)-1-((S)-3,3-dimethyl-2-(2-(2-(4-(4-methyl-3-((4-(pyridin-3-yl)pyrimidin-2-yl)amino)phenyl)carbamoyl)benzyl)piperazin-1-yl)-2-oxoethoxy)ethoxy)acetamido)butanoyl)-4-hydroxy-N-(4-(4-methylthiazol-5-yl)benzyl)pyrrolidine-2-carboxamide |

TABLE 1-continued
The structure of compounds and its name
| Compound No. | Structure of compound | Name of the compound |
|---|---|---|
| SIAIS119 7029 | 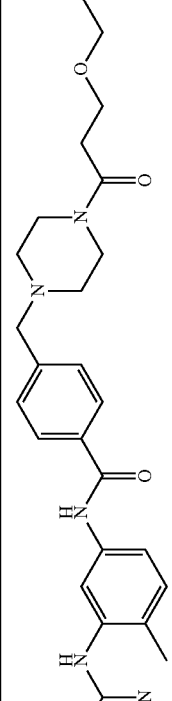 | (2S,4R)-1-((S)-3,3-dimethyl-2-(3-(2-(3-(4-(4-methyl-3-((4-(pyridin-3-yl)pyrimidin-2-yl)amino)phenyl)carbamoyl)benzyl)piperazin-1-yl)-3-oxopropoxy)ethoxy)propanamido)butanoyl)-4-hydroxy-N-(4-(4-methylthiazol-5-yl)benzyl)pyrrolidine-2-carboxamide |

TABLE 1-continued

The structure of compounds and its name

| Compound No. | Structure of compound | Name of the compound |
|---|---|---|
| | | (2S,4R)-1-((S)-3,3-dimethyl-2-((3-(2-(3-(4-(4-methyl-3-((4-(pyridin-3-yl)pyrimidin-2-yl)amino)phenyl)carbamoyl)benzyl)piperazin-1-yl)-3-oxopropoxy)ethoxy)propyl)amino)butanoyl)-4-hydroxy-N-(4-(4-methylthiazol-5-yl)benzyl)pyrrolidine-2-carboxamide |

TABLE 1-continued
The structure of compounds and its name
| Compound No. | Structure of compound | Name of the compound |
|---|---|---|
| SIAIS119 7031 | 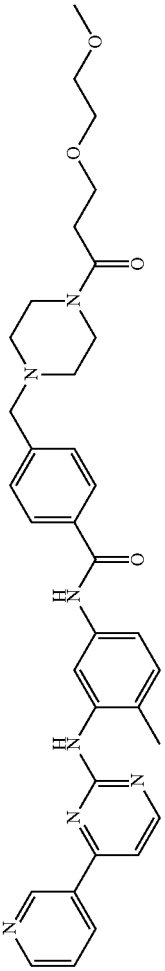 | (2S,4R)-1-((S)-2-(tert-butyl)-16-(4-(4-methyl-3-((4-(pyridin-3-yl)pyrimidin-2-yl)amino)phenyl)carbamoyl)benzyl)piperazin-1-yl)-4,16-dioxo-7,10,13-trioxa-3-azahexadecanoyl)-4-hydroxy-N-(4-(4-methylthiazol-5-yl)benzyl)pyrrolidine-2-carboxamide |

TABLE 1-continued
The structure of compounds and its name
| Compound No. | Structure of compound | Name of the compound |
|---|---|---|
| SIAIS119 7039 | 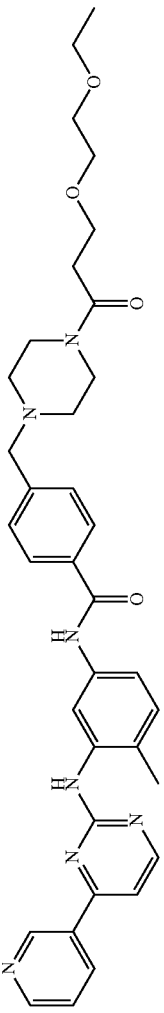 | (2S,4R)-1-((S)-2-(tert-butyl)-19-(4-(4-((4-methyl-3-((4-(pyridin-3-yl)pyrimidin-2-yl)amino)phenyl)carbamoyl)benzyl)piperazin-1-yl)-4,19-dioxo-7,10,13,16-tetraoxa-3-azanonadecanoyl)-4-hydroxy-N-(4-(4-methylthiazol-5-yl)benzyl)pyrrolidine-2-carboxamide |

TABLE 1-continued
The structure of compounds and its name
| Compound No. | Structure of compound | Name of the compound |
|---|---|---|
| SIAIS119 7041 | 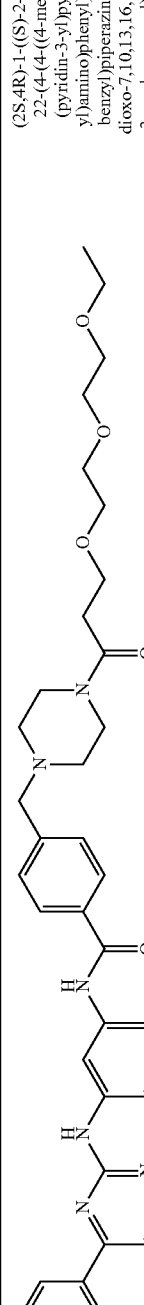 | (2S,4R)-1-((S)-2-(tert-butyl)-22-(4-(4-methyl-3-((4-(pyridin-3-yl)pyrimidin-2-yl)amino)phenyl)carbamoyl)benzyl)piperazin-1-yl)-4,22-dioxo-7,10,13,16,19-pentaoxa-3-azadocosanoyl)-4-hydroxy-N-(4-(4-methylthiazol-5-yl)benzyl)pyrrolidine-2-carboxamide |

TABLE 1-continued

The structure of compounds and its name

| Compound No. | Structure of compound | Name of the compound |
|---|---|---|
| SIAIS074 027 | 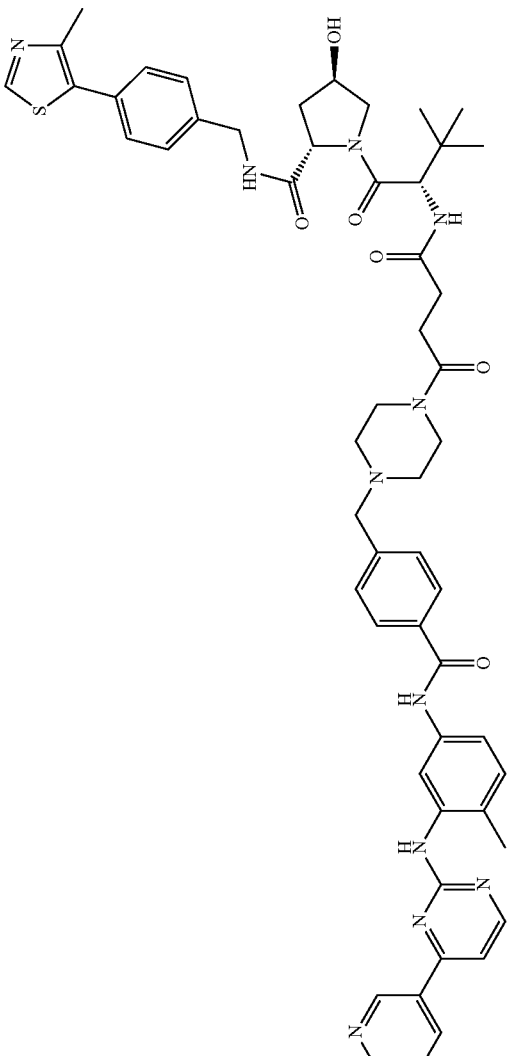 | (2S,4R)-1-((S)-3,3-dimethyl-2-(4-(4-(4-methyl-3-((4-(pyridin-3-yl)pyrimidin-2-yl)amino)phenyl)carbamoyl)benzyl)piperazin-1-yl)-4-oxobutanamido)butanoyl)-4-hydroxy-N-(4-(4-methylthiazol-5-yl)benzyl)pyrrolidine-2-carboxamide |
| SIAIS074 028 | 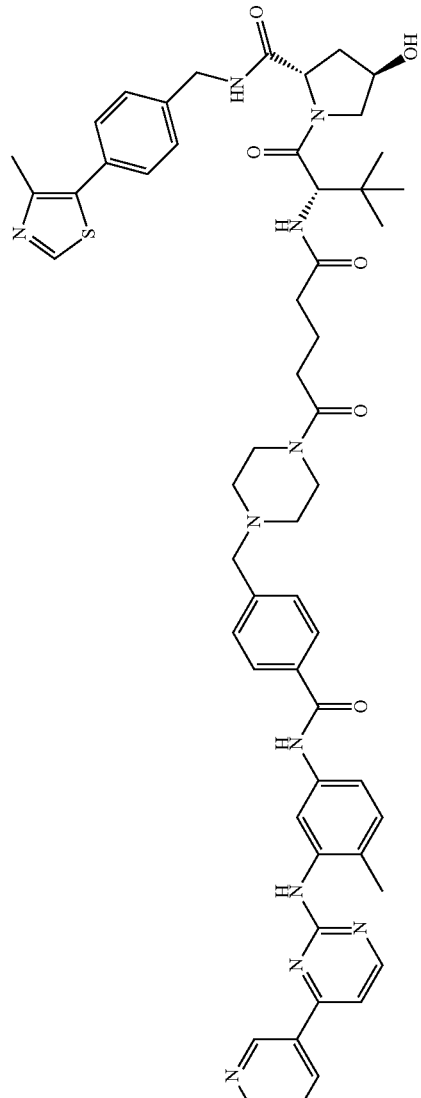 | (2S,4R)-1-((S)-3,3-dimethyl-2-(5-(4-(4-(4-methyl-3-((4-(pyridin-3-yl)pyrimidin-2-yl)amino)phenyl)carbamoyl)benzyl)piperazin-1-yl)-5-oxopentanamido)butanoyl)-4-hydroxy-N-(4-(4-methylthiazol-5-yl)benzyl)pyrrolidine-2-carboxamide |

TABLE 1-continued

The structure of compounds and its name

| Compound No. | Structure of compound | Name of the compound |
| --- | --- | --- |
| SIAIS074 029 | | (2S,4R)-1-((S)-3,3-dimethyl-2-(6-(4-(4-methyl-3-((4-(pyridin-3-yl)pyrimidin-2-yl)amino)phenyl)carbamoyl)benzyl)piperazin-1-yl)-6-oxohexanamido)butanoyl)-4-hydroxy-N-(4-(4-methylthiazol-5-yl)benzyl)pyrrolidine-2-carboxamide |
| SIAIS074 030 | | (2S,4R)-1-((S)-3,3-dimethyl-2-(7-(4-(4-methyl-3-((4-(pyridin-3-yl)pyrimidin-2-yl)amino)phenyl)carbamoyl)benzyl)piperazin-1-yl)-7-oxoheptanamido)butanoyl)-4-hydroxy-N-(4-(4-methylthiazol-5-yl)benzyl)pyrrolidine-2-carboxamide |

TABLE 1-continued
The structure of compounds and its name
| Compound No. | Structure of compound | Name of the compound |
|---|---|---|
| SIAIS074031 | 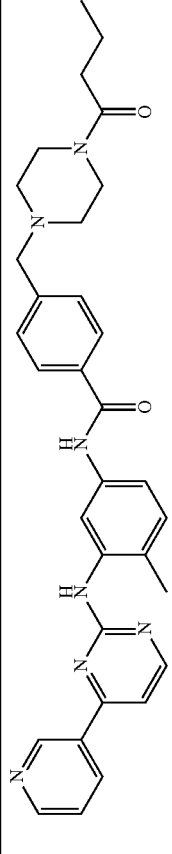 | (2S,4R)-1-((S)-3,3-dimethyl-2-(8-(4-(4-methyl-3-((4-(pyridin-3-yl)pyrimidin-2-yl)amino)phenyl)carbamoyl)benzyl)piperazin-1-yl)-8-oxooctanamido)butanoyl)-4-hydroxy-N-(4-(4-methylthiazol-5-yl)benzyl)pyrrolidine-2-carboxamide |

TABLE 1-continued
The structure of compounds and its name
| Compound No. | Structure of compound | Name of the compound |
|---|---|---|
| SIAIS074032 | 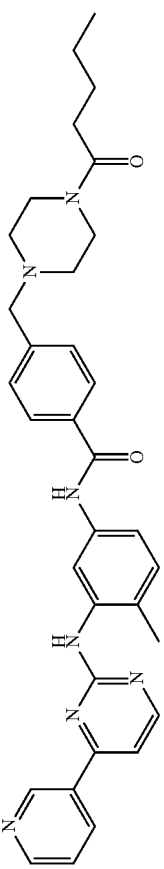 | (2S,4R)-1-((S)-3,3-dimethyl-2-(9-(4-(4-((4-methyl-3-((4-(pyridin-3-yl)pyrimidin-2-yl)amino)phenyl)carbamoyl)benzyl)piperazin-1-yl)-9-oxononanamido)butanoyl)-4-hydroxy-N-(4-(4-methylthiazol-5-yl)benzyl)pyrrolidine-2-carboxamide |

TABLE 1-continued
The structure of compounds and its name
| Compound No. | Structure of compound | Name of the compound |
|---|---|---|
| SIAIS074 033 | 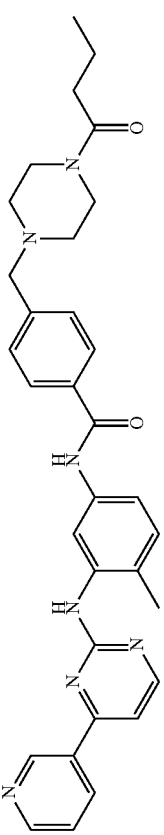 | (2S,4R)-1-((S)-3,3-dimethyl-2-(10-(4-(4-((4-(pyridin-3-yl)pyrimidin-2-yl)amino)phenyl)carbamoyl)benzyl)piperazin-1-yl)-10-oxodecanamido)butanoyl)-4-hydroxy-N-(4-(4-methylthiazol-5-yl)benzyl)pyrrolidine-2-carboxamide |

TABLE 1-continued
The structure of compounds and its name
| Compound No. | Structure of compound | Name of the compound |
|---|---|---|
| SIAIS074034 | 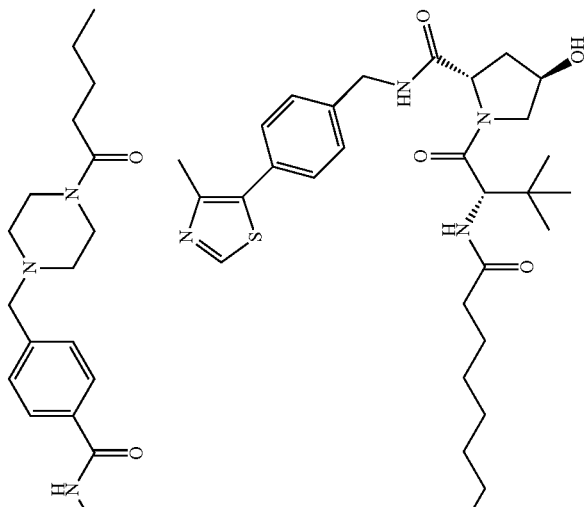 | (2S,4R)-1-((S)-3,3-dimethyl-2-(11-(4-(4-((4-(pyridin-3-yl)pyrimidin-2-yl)amino)phenyl)carbamoyl)benzyl)piperazin-1-yl)-11-oxoundecanamido)butanoyl)-4-hydroxy-N-(4-(4-methylthiazol-5-yl)benzyl)pyrrolidine-2-carboxamide |

TABLE 1-continued

The structure of compounds and its name

| Compound No. | Structure of compound | Name of the compound |
|---|---|---|
| | | (2S,4R)-1-((S)-3,3-dimethyl-2-(14-(4-(4-methyl-3-((4-(pyridin-3-yl)pyrimidin-2-yl)amino)phenyl)carbamoyl)benzyl)piperazin-1-yl)-14-oxotetradecanamido)butanoyl)-4-hydroxy-N-(4-(4-methylthiazol-5-yl)benzyl)pyrrolidine-2-carboxamide |

TABLE 1-continued
The structure of compounds and its name
| Compound No. | Structure of compound | Name of the compound |
|---|---|---|
| | 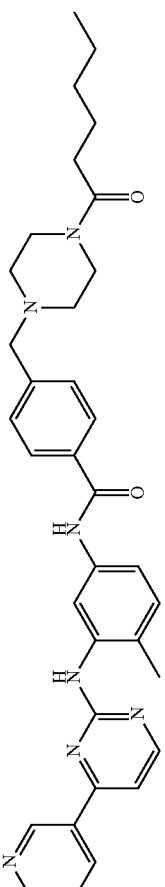 | (2S,4R)-1-((S)-3,3-dimethyl-2-(16-(4-(4-methyl-3-((4-(pyridin-3-yl)pyrimidin-2-yl)amino)phenyl)carbamoyl)benzyl)piperazin-1-yl)-16-oxohexadecanamido)butanoyl)-4-hydroxy-N-(4-(4-methylthiazol-5-yl)benzyl)pyrrolidine-2-carboxamide |

TABLE 1-continued
The structure of compounds and its name
| Compound No. | Structure of compound | Name of the compound |
|---|---|---|
| | 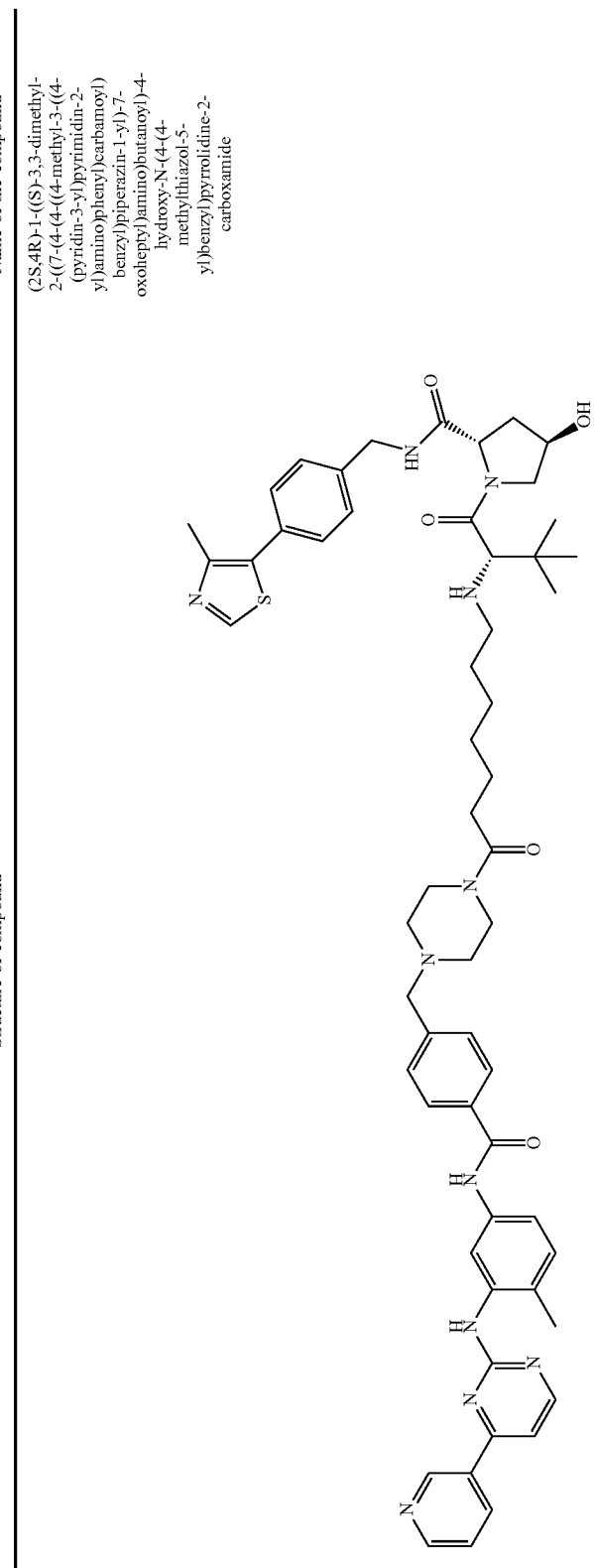 | (2S,4R)-1-((S)-3,3-dimethyl-2-((7-(4-(4-methyl-3-((4-(pyridin-3-yl)pyrimidin-2-yl)amino)phenyl)carbamoyl)benzyl)piperazin-1-yl)-7-oxoheptyl)amino)butanoyl)-4-hydroxy-N-(4-(4-methylthiazol-5-yl)benzyl)pyrrolidine-2-carboxamide |

TABLE 1-continued

The structure of compounds and its name

| Compound No. | Structure of compound | Name of the compound |
|---|---|---|
|  |  | (2S,4R)-1-((S)-3,3-dimethyl-2-((8-(4-((4-methyl-3-((4-(pyridin-3-yl)pyrimidin-2-yl)amino)phenyl)carbamoyl)benzyl)piperazin-1-yl)-8-oxooctyl)amino)butanoyl)-4-hydroxy-N-(4-(4-methylthiazol-5-yl)benzyl)pyrrolidine-2-carboxamide |

TABLE 1-continued
The structure of compounds and its name
| Compound No. | Structure of compound | Name of the compound |
|---|---|---|
| | 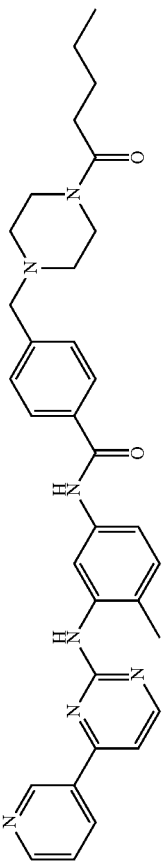 | (2S,4R)-1-((S)-3,3-dimethyl-2-((9-(4-((4-methyl-3-((4-(pyridin-3-yl)pyrimidin-2-yl)amino)phenyl)carbamoyl)benzyl)piperazin-1-yl)-9-oxononyl)amino)butanoyl)-4-hydroxy-N-(4-(4-methylthiazol-5-yl)benzyl)pyrrolidine-2-carboxamide |

It is to be understood that the compound of formula (I) may have a stereo configuration and can therefore exist in more than one stereoisomer form. The present disclosure also relates to compounds of formula (I) having a stereo configuration in pure or substantially pure isomeric form, e.g., greater than about 90% enantiomeric/diastereomeric excess ("ee"), such as greater than about 95% ee or 97% ee, or greater than about 99% ee, and mixtures thereof, including racemic mixtures. The purification of said isomers and the separation of said isomeric mixtures may be achieved by standard techniques known in the art (e.g., column chromatography, preparative TLC, preparative HPLC, asymmetric synthesis (for example, by using chiral intermediates) and/or chiral resolution and the like).

In another aspect, the present disclosure also provides a pharmaceutical composition, including, as an active ingredient, the compound of formula (I) according to the present disclosure or a pharmaceutically acceptable salt thereof, and a pharmaceutically acceptable carrier.

In the present disclosure, the pharmaceutical composition further includes at least one additional agent for treating or preventing a cancer.

In another aspect of the present disclosure, the compound of formula (I) according to the present disclosure or a pharmaceutical acceptable salt thereof, is for use as a medicament.

In another aspect of the present disclosure, the compound of formula (I) according to the present disclosure or a pharmaceutical acceptable salt thereof, is used for treating and/or preventing a cancer.

In one embodiment, the cancer is selected from the group consisting of: $Ph^+$ chronic myeloid leukemia (CML) (the CML relate to chronic phase (CP), accelerated phase (AP) and acute blast crisis (BC) patient); $Ph^+$ acute lymphoblastic leukemia (ALL); PDGFR (platelet-derived growth factor receptor) gene rearrangement-related myelodysplastic/myeloproliferative diseases (MDS/MPD); aggressive systemic mastocytosis (ASM); Hypereosinophilic Syndrome (HES); Chronic Eosinophilic Leukemia (CEL); Dermatofibrosarcoma protuberans (DFSP); and ($Kit^+$) gastrointestinal stromal tumor (GIST).

In a sub-embodiment, the $Ph^+$ chronic myeloid leukemia (CML) is in the phase of chronic, accelerated, or acute.

The compound of formula (I) according to the present disclosure and a pharmaceutically acceptable salt thereof, can be used as a medicament in the form of a pharmaceutical composition for gastrointestinal or parenteral administration.

The pharmaceutical composition can be prepared according to any method known to those skilled in the art, through optionally combining the compound of formula (I) or a pharmaceutically acceptable salt thereof with other substances of medical vaule, together with suitable, non-toxic, inert, therapeutically compatible solid or liquid carrier materials and (if necessary) commonly used pharmaceutical adjuvants to produce an appropriate desired formulation for administration. In the pharmaceutical composition, the content of the active ingredient compound is sufficient to generate the desired effect on the process of disease or conditions.

The pharmaceutical composition can be prepared into varities of dosage forms after sterilization based on available mehods known in the pharmaceutical field. According to the desired route of administration, the pharmaceutical composition according to the present disclosure can be formulated into powders, lozenges, tablets (such as conventional tablets, dispersible tablets, orally disintegrating tablets), granules, pills, emulsions, aqueous or oily suspensions, capsules (such as soft capsules, hard capsules, enteric capsules); or an injectable solution suitable for intravenous, intramuscular, intraluminal, intra-tissue, intradermal or subcutaneous administration (e.g., a sterile injection solution prepared using water, Ringer's solution or isotonic sodium chloride solution, etc., as a carrier or solvent based on available methods known in the art), etc.; or sprays, troches, or suppositories suitable for topical administration or absorption through the skin or mucous membranes, etc.

In another aspect of the present disclosure, the compound of formula (I) according to the present disclosure or a pharmaceutically acceptable salt thereof, can be used for preparing a medicament for treating and/or preventing a cancer. In a sub-embodiment, the cancer is selected from the group consisting of: $Ph^+$ chronic myeloid leukemia (CML) (the CML relating to chronic phase (CP), accelerated phase (AP) and acute blast crisis (BC) patients); $Ph^+$ acute lymphoblastic leukemia (ALL); PDGFR (platelet-derived growth factor receptor) gene rearrangement-related myelodysplastic/myeloproliferative diseases (MDS/MPD); aggressive systemic mastocytosis (ASM); Hypereosinophilic Syndrome (HES); Chronic Eosinophilic Leukemia (CEL); Dermatofibrosarcoma protuberans (DFSP); and ($Kit^+$) gastrointestinal stromal tumor (GIST). In one embodiment, the $Ph^+$ chronic myeloid leukemia (CML) is in a chronic, accelerated, or acute phase.

In another aspect, the present disclosure also provides the method of treatment or prevention of a cancer in a subject, comprising adiministering to the subject a therapeutically effective amount of the compound of fomular (I) accordign to the present disclosure, or a pharmaceutically acceptable salt thereof, or the pharmaceutical composition thereof. In one embodiment, the cancer is selected from the group consisting of: $Ph^+$ chronic myeloid leukemia (CML) (the CML relating to chronic phase (CP), accelerated phase (AP) and acute blast crisis (BC) patient); $Ph^+$ acute lymphoblastic leukemia (ALL); PDGFR (platelet-derived growth factor receptor) gene rearrangement-related myelodysplastic/myeloproliferative diseases (MDS/MPD); aggressive systemic mastocytosis (ASM); Hypereosinophilic Syndrome (HES); Chronic Eosinophilic Leukemia (CEL); Dermatofibrosarcoma protuberans (DFSP); and ($Kit^+$) gastrointestinal stromal tumor (GIST). In a sub-embodiment, the $Ph^+$ chronic myeloid leukemia (CML) is in a chronic, accelerated, or acute phase.

In the method of treatment or prevention of a cancer according to the present disclosure, the compound of formula (I) or a pharmaceutically acceptable salt thereof, or the pharmaceutical composition, can be administered via any suitable routes, such as by at least one route selected from the group consisting of nasal administration, inhalation administration, topical administration, oral administration, oral mucosal administration, rectal administration, pleural cavity administration, peritoneal administration, vaginal administration, intramuscular administration, subcutaneous, transdermal, epidural, intrathecal, and intravenous administration to the subject.

Definition

Generally, the nomenclature used herein and the laboratory procedures described below comprising those for cell culture, organic chemistry, analytical chemistry, and pharmacology and the like are those well known and commonly used in the art. Unless otherwise defined, all the scientific and technical terms used herein in combination with the present disclosure described herein have the same meaning commonly understood by those skilled in the art. In addition, the use of the word "a" or "an" when used in combination with the term "comprising" or a noun word in the claims and/or the specification may mean "one", but it is also consistent with the meaning of "one or more", "at least one", and "one or more than one". Similarly, the word "another" or "other" may mean at least a second or more.

It should be understood that whenever various aspects are described herein with term "comprising", other similar aspects described with "consisting of" and/or "consisting essentially of" are also provided.

The term "about" used herein refers to approximately, roughly, approximately, or around. When the term "about" is used in combination with a numerical range, it modifies that range by extending the boundaries above and below the stated numerical value. For example, the term "about" used herein may modify a numerical value above and below the stated value by a variance of, for example, ±20%, or ±15%, or ±10%, ±5%, or ±1%.

The term "absent" used herein in combination with a substituent(s) or group(s) means that the substituent(s) or group(s) is not present. In other words, when the substituent(s) or group(s) is not present, it becomes a bond or a bond connector. For example, in the ULM represented by the structure of formula (II) according to the present disclosure, when the group Z is absent, the ULM moiety is directly covalently bonded (or connected) to the LIN.

As used herein, the term "interrupted" of "the linear or branched alkylene chain interrupted . . . by . . . " used alone or in combination has a definition known in the art, i.e., can refer to there is a group as defined herein (e.g., a group selected from the group consisting of O, C(O)NH, NHC(O), NH, alkynylene, alkenylene, cycloalkylene, arylene, heterocyclylene, or heteroarylene group, or any combination thereof, as described herein) inserted between any two adjacent carbon atoms in the backbone chain of the linear or branched alkylene chain. For example, the term "the linear or branched alkylene chain interrupted one or more times by one or more "O" radicals" used alone or in combination refers to one or more pairs of any two adjacent carbon atoms in the backbone chain of the linear or branched alkylene chain are inserted therebetween with the —O— radical, to from a linear or branched oxaalkylene radical containing one or more (e.g., 1-10, 1-8, 1-7, 1-6, 1-5, 1-4, 1-3, 1-2, or 1) "—CH₂—O—CH₂—" fragments.

In the present disclosure, the structure represented by formula (Ia):

(Ia)

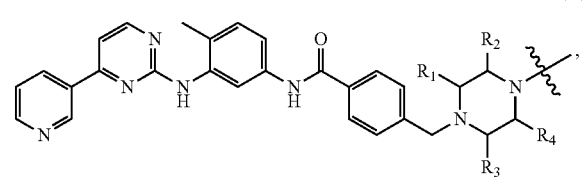

can be obtained by removing the methyl group on the piperazine ring of imatinib, wherein $R_1$, $R_2$, $R_3$, and $R_4$ are as defined above.

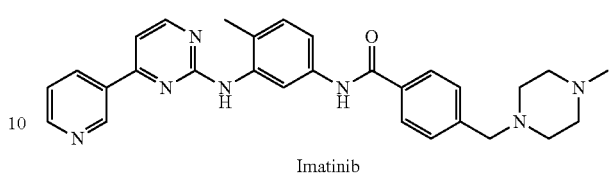

Imatinib

In the present disclosure, the structure represented by the formula (Ib):

(Ib)

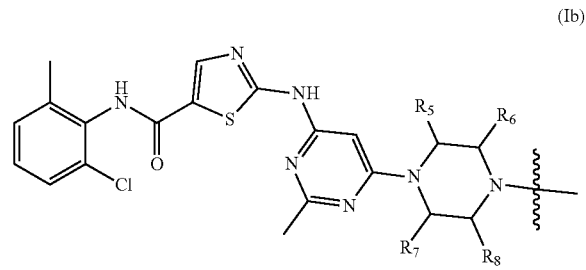

can be obtained by removing the hydroxyethyl group on the piperazine ring of Dasatinib, wherein $R_5$, $R_6$, $R_7$, and $R_8$ are as defined above.

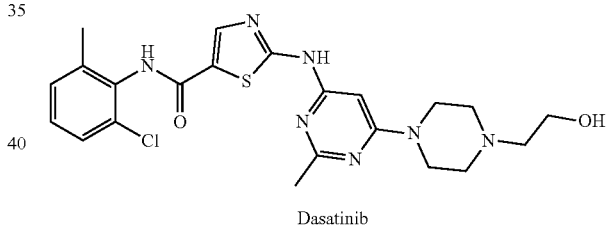

Dasatinib

In the present disclosure, the structure represented by the formula (Ic):

(Ic)

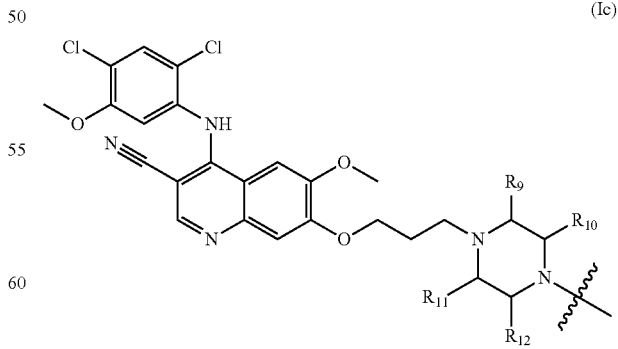

can be obtained by removing the methyl group on the piperazine ring of the Bosutinib, wherein $R_9$, $R_{10}$, $R_{11}$, and $R_{12}$ are as defined above

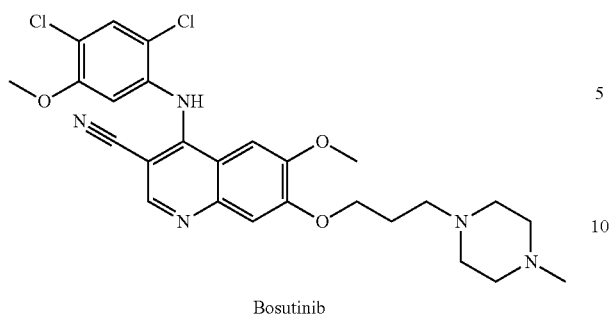

Bosutinib

In the present disclosure, a bond interrupted by a wavy line shows the point of attachment of the radical depicted. For example, the group depicted below (Ia)

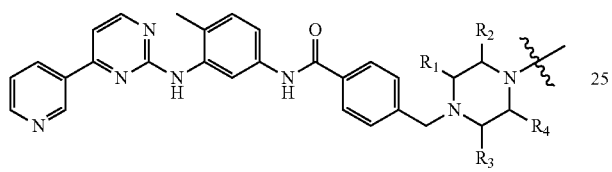

means that the chemical moiety represented by formula (Ia), which is covalently bonded to the group A of the compound of formula (I) via the N atom of piperazinyl.

Herein, ULM can represents a structure of formula (II)

formula (II)

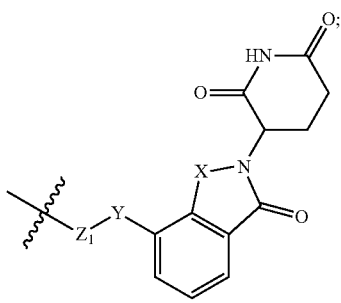

wherein X is —$CH_2$— or —CO—, Y is —$CH_2$—, —NH— or —O—, and $Z_1$ is carbonyl or $Z_1$ is absent, which is an analog derived from CRBN ubiquitin ligase small molecule ligand thalidomide, lenalidomide or pomalidomide.

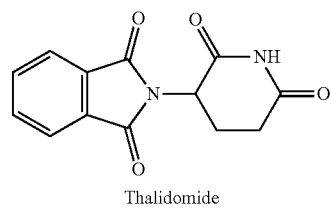

Thalidomide

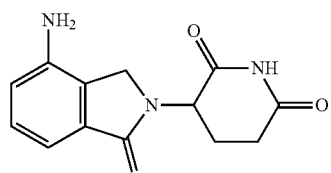

Lenalidomide

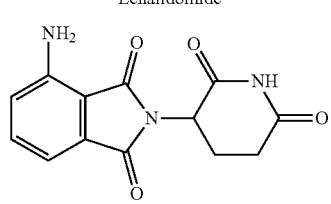

Pomalidomide

Herein, ULM can represents a structure of formula(III)

Formula(III)

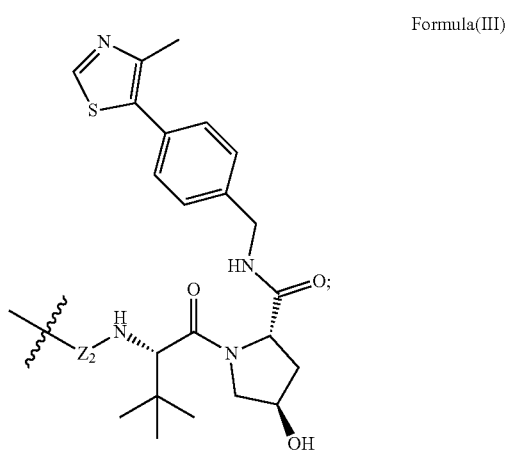

wherein $Z_2$ is carbonyl or $Z_1$ is absent, which is an analog derived from VHL-1 (chemical name: (2S,4R)-1-((S)-2-amino-3,3-dimethylbutanoyl)-4-hydroxy-N-(4-(4-methyl-thiazol-5-yl)benzyl)pyrrolidine-2-carboxamide).

VHL-1

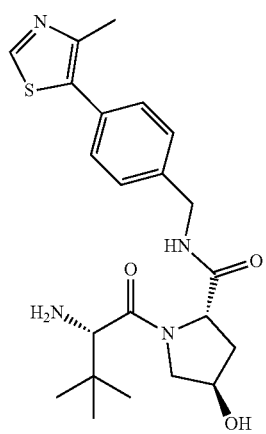

In the present disclosure, the compound of formula (I) is also referred to as PROTAD compound, PROTAD (small) molecule, or degrader (or a degradation agent), which can be used interchangeably.

In the present disclosure, the terms "LIN" and "linker" are used interchangeably, and both of them refer to the linker group (LIN) of the compound of formula (I).

In the present disclosure, the term "halogen atom" or "halogen" used individually or in combination refers to fluorine, chlorine, bromine or iodine, and preferably F, Cl or Br.

In the present disclosure, the term "alkyl" used individually or in combination refers to a linear or branched alkyl group. The term "$C_x$-$C_y$ alkyl" (x and y are each an integer) refers to a linear or branched alkyl group containing x to y carbon atoms. In the present disclosure, the term "$C_{1-10}$ alkyl" used individually or in combination refers to a linear or branched alkyl group containing 1 to 10 carbon atoms. The $C_{1-10}$ alkyl group of the present disclosure is preferably a $C_{1-9}$ alkyl group, more preferably a $C_{1-8}$ alkyl group, still more preferably a $C_{2-8}$ alkyl group, more preferably a $C_{1-7}$ alkyl group, and even more preferably a $C_{1-6}$ alkyl, $C_{1-5}$ alkyl, or $C_{1-4}$ alkyl. The representative examples include, but are not limit to, methyl, ethyl, n-propyl, isopropyl, n-butyl, isobutyl, sec-butyl, tert-butyl, pentyl, isopentyl, neopentyl, tert-pentyl, hexyl, heptyl, octyl, nonyl and decyl. The term "$C_{1-3}$ alkyl group" in the present disclosure refers to an alkyl group containing 1 to 3 carbon atoms, and its representative examples include methyl, ethyl, n-propyl and isopropyl.

In the present disclosure, the term "alkylene" (which is used interchangeably with alkylene chain) used individually or in combination refers to a linear or branched divalent saturated hydrocarbon group composed of carbon and hydrogen atoms. The term "$C_x$-$C_y$ alkylene" or "$C_{x-y}$ alkylene" (x and y are each an integer) refers to a linear or branched alkylene group containing from x to y carbon atoms. In the present disclosure, the $C_1$-$C_{30}$ alkylene group is preferably $C_1$-$C_{29}$ alkylene group, $C_1$-$C_{28}$ alkylene group, $C_1$-$C_{27}$ alkylene group, $C_1$-$C_{26}$ alkylene group, $C_1$-$C_{25}$ alkylene group, $C_1$-$C_{24}$ alkylene group, $C_1$-$C_{23}$ alkylene, $C_1$-$C_{22}$ alkylene, $C_1$-$C_{21}$ alkylene, $C_1$-$C_{20}$ alkylene, $C_1$-$C_{19}$ alkylene, $C_1$-$C_{18}$ alkylene, $C_1$-$C_{17}$ alkylene, $C_1$-$C_{16}$ alkylene, $C_1$-$C_{15}$ alkylene, $C_1$-$C_{14}$ alkylene, $C_1$-$C_{13}$ alkylene, $C_1$-$C_{12}$ alkylene, $C_1$-$C_{11}$ alkylene, $C_1$-$C_{10}$ alkylene, $C_1$-$C_9$ alkylene, $C_1$-$C_8$ alkylene, $C_1$-$C_7$ alkylene, $C_1$-$C_6$ alkylene, $C_1$-$C_5$ alkylene, $C_1$-$C_4$ alkylene, $C_1$-$C_3$ alkylene, or $C_1$-$C_2$ alkylene. Representative examples include, but are not limit to, methylene, ethylene, propylene, isopropylidene, butylene, isobutylene, sec-butylene, tert-butylene, pentylene, isopentylene, neopentylene, tert-pentylene, hexylene, heptylene, octylene, nonylene, decylene, undecylene, dodecylene, tridecylene, tetradecylene, pentadecylene, hexadecylene, heptadecylene, octadecylene, nonadecylene, eicosylene, heneicosylene, docosylene, tricosylene, tetracosylene, pentacosylene, hexacosylene, peptacosylene, octacosylene, nonacosylene, and triacontylene.

In the present disclosure, the term "arylene" used individually or in combination refers to a divalent aromatic hydrocarbon group containing 5 to 14 carbon atoms and optionally one or more fused rings, such as phenylene or naphthylene or fluorenylene group. In the present disclosure, the "arylene" as defined herein is an optionally substituted arylene. The substituted arylene refers to an arylene group optionally substituted 1 to 3 times by one or more substituents selected from the group consisting of $C_{1-3}$ alkyl, $C_{1-3}$ alkoxy, halogen, amino, hydroxyl, or any combination thereof.

In the present disclosure, the term "$C_{1-3}$ alkoxy" used individually or in combination refers to a linear or branched alkoxy group containing from 1 to 3 carbon atoms. Representative examples of $C_{1-3}$ alkoxy include, but are not limit to, methoxy, ethoxy, n-propoxy and isopropoxy.

Preferred are methoxy and ethoxy.

In the present disclosure, the term "cycloalkyl" used individually or in combination refers to a saturated or partially unsaturated (e.g., containing one or more double bonds, but not having a completely conjugated 7-electron system) monovalent monocyclic or bicyclic cyclic hydrocarbon radical, which may include fused, bridged, or spiro ring system, having from 3 to 12 carbon atoms, e.g., having from 3 to 10 carbon atoms, or from 3 to 8 carbon atoms, or from 3 to 6 carbon atoms. The term "$C_3$-$C_{10}$ cycloalkyl" refers to a saturated or partially unsaturated (e.g., containing one or more double bonds, but not having a completely conjugated 7-electron system) monovalent monocyclic or bicyclic cyclic hydrocarbon radical, which may include fused, bridged, or spiro ring system, having from 3 to 10 carbon atoms. Representative examples include, but are not limit to, cyclopropyl, cyclobutyl, cyclopentyl, cyclopentenyl, cyclohexyl, cyclohexenyl, cycloheptyl, cyclooctyl, decalinyl, octahydropentalenyl, octahydro-1H-indenyl, and spiro-cycloalkyl. The cycloalkyl group may be unsubstituted or substituted. A substituted cycloalkyl group refers to a cycloalkyl group optionally substituted 1-3 times by a substituent(s) (that is, the cycloalkyl group optionally has 1-3 same or different substituent(s)). In a further embodiment, the substituent can be any one optionally selected from the group consisting of $C_{1-3}$ alkyl, $C_{1-3}$ alkoxy, cyano, trifluoromethyl, heterocyclyl, halogen, amino, hydroxyl, or any combination thereof.

In the present disclosure, the term "cycloalkylene" used individually or in combination refers to a saturated and partially unsaturated (e.g., containing one or more double bonds, but not having a fully conjugated π-electron system) divalent monocyclic or bicyclic cyclic hydrocarbon group, which may include fused, bridged, or spiro ring system, having from 3 to 12 carbon atoms, e.g., having from 3 to 10 carbon atoms, or from 3 to 8 carbon atoms, or from 3 to 6 carbon atoms. Representative examples include, but are not limit to, cyclopropylene, cyclobutylene, cyclopentylene, cyclopentenylene, cyclohexylene, cyclohexenylene, cycloheptylene, cyclooctylene, decalinylene, octahydropentalenylene, octahydro-1H-indenylene, and spiro-cycloalkylene. The cycloalkylene group may be unsubstituted or substituted. A substituted cycloalkylene group refers to a cycloalkylene group optionally substituted 1-3 times by a substituent(s) (that is, the cycloalkylene group optionally has 1-3 same or different substituent(s)). In a further embodiment, the substituent can be any one optionally selected from the group consisting of $C_{1-3}$ alkyl, $C_{1-3}$ alkoxy, cyano, trifluoromethyl, heterocyclyl, halogen, amino, hydroxyl, or any combination thereof.

In the present disclosure, the term "heteroarylene" used individually or in combination refers to a 5- to 10-membered monocyclic or bicyclic divalent aromatic ring group containing one or more (e.g., from 1 to 6, or from 1 to 5, or from 1 to 4, or from 1 to 3) heteroatoms independently selected from the group consisting of oxygen, nitrogen, and sulfur. Representative examples of such heteroarylene groups include, but are not limited to, furanylene, oxazolylene, isoxazolylene, oxadiazolylene, thienylene, thiazolylene, isothiazolylene, thiadiazolylene, pyrrolylene, imidazolylene, triazolylene, pyridylene, pyrimidinylene, pyridazinylene, pyrazinylene, indolylene, isoindolylene, benzofuranylene, isobenzofuranylene, benzothienylene, indazolylene, benzimidazolylene, benzoxazolylene, benzoisoxazolylene, benzothiazolylene, benzoisothiazolylene, benzotriazolylene, benzo[2,1,3]oxadiazolylene, benzo[2,1,3]thiadiazolylene, benzo[1,2,3]thiadiazolylene, quinolylene, isoquinolylene, naphthyridinylene, cinnolinylene, quinazolinylene, quinoxalinylene, phthalazinylene, pyrazolo[1,5-a]pyridinylene, pyrazolo[1,5-a]pyrimidinylene, imidazo[1,2-a]pyridinylene, 1H-pyrrolo[3,2-b]pyridinylene, 1H-pyrrolo[2,3-b]pyridinylene, 4H-fluoro[3,2-b]pyrrolylene, pyrrolo[2,1-b]thiazolylene, and imidazo[2,1-b]thiazolylene. According to a clear definition, the heteroarylene group may be unsubstituted or substituted. A substituted heteroarylene group refers to a heteroarylene group optionally substituted 1-3 times by a substituent(s) (that is, the heteroarylene group optionally has 1-3 same or different substituent(s)). In a further embodiment, the substituent can be any one optionally selected from the group consisting of $C_{1\text{-}3}$ alkyl, $C_{1\text{-}3}$ alkoxy, cyano, trifluoromethyl, heterocyclyl, halogen, amino, hydroxyl, or any combination thereof.

In the present disclosure, the term "heterocyclylene" used individually or in combination refers to a 4- to 6-membered saturated monocyclic divalent cyclic hydrocarbon group containing one or more (e.g., from 1 to 4, or from 1 to 3, or from 1 to 2, or 1) heteroatoms independently selected from the group consisting of sulfur, oxygen, and nitrogen. Representative examples of the heterocyclylene group include, but are not limited to, azetidinylene, oxetanylene, pyrrolidinylene, imidazolidylene, pyrazolidylene, triazolylene, tetrahydrofuranylene, tetrahydrothienylene, tetrahydrothiopyranylene, oxazolidinylene, thiazolidinylene, piperidinylene, piperazinylene, morpholinylene, thiomorpholinylene, and dioxanylene. The heterocyclylene group may be unsubstituted or substituted as explicitly defined. A substituted heterocycloalkylene refers to a heterocycloalkylene group optionally substituted 1-3 times by a substituent(s) (that is, the heterocycloalkylene group optionally has 1-3 same or different substituent(s)). In a further embodiment, the substituent can be any one optionally selected from the group consisting of $C_{1\text{-}3}$ alkyl, $C_{1\text{-}3}$ alkoxy, cyano, trifluoromethyl, heterocyclyl, halogen, amino, hydroxyl, or any combination thereof.

In the present disclosure, the term "alkynylene" used individually or in combination refers to a linear or branched divalent hydrocarbon group containing one or more carbon-carbon triple bonds and containing from 2 to 10 (e.g., from 2 to 6, or from 2 to 4, or from 2 to 3, or 2) carbon atoms. Examples of alkynylene group include, but are not limit to, ethynylene, 1-propynylene, 1-butynylene, and 1,3-diynylene.

In the present disclosure, the term "alkenylene" used individually or in combination refers to a linear or branched divalent hydrocarbon group containing one or more carbon-carbon double bonds and containing from 2 to 10 carbon atoms (preferably from 2 to 6, more preferably from 2 to 4, or from 2 to 3, or 2 carbon atoms). Examples of alkynylene preferably include, but are not limit to, vinylidene (e.g., —CH=CH—), 1-propenylene, and 1-butenylene.

In the present disclosure, salts or pharmaceutically acceptable salts, enantiomers, stereoisomers, solvates, polymorphs of the compound of formula (I) according to the disclosure are also encompassed within the scope of this invention.

In all embodiments of the present disclosure, the salt or pharmaceutically acceptable salt of the compound of formula (I) refers to non-toxic inorganic or organic acid and/or base addition salts. Examples include, but are not limited to, sulfate, hydrochloride, citrate, maleate, sulfonate, or p-toluenesulfonate, etc.

The term "pharmaceutically acceptable carrier" refers to pharmaceutically acceptable materials, such as fillers, stabilizers, dispersants, suspending agents, diluents, excipients, thickeners, solvents or encapsulating materials, the useful compounds in the present disclosure are carried or transported to a subject or administrating it to a subject so that it can perform its desired effect. Usually, such a building blocks can be carried or transported from one organ or part of body to another organ or part of body. Therefore, both carriers and the other element of preparations are not only compatible but also no harmful to a subject, and the carriers also must be "acceptable". Some embodiments of materials can be served as pharmaceutically acceptable carriers including sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil, and soybean oil; glycols, such as propylene glycol; polyols, such as glycerol, sorbitol, mannitol, and polyethylene glycol; esters, such as ethyl oleate and ethyl laurate; agar; Buffers, such as magnesium hydroxide and aluminum hydroxide; surfactant phosphate buffer solutions; and other non-toxic compatible substances are used in the pharmaceutical preparations.

The "therapeutically effective amount" of the compound according to the present disclosure depends on the age, sex and weight of a subject, the current medical condition of he subject and cancer progression in the treatment of subject. Those skilled in this art can determine a suitable dose based on these and other factors.

In the present disclosure, the term "room temperature" refers to ambient temperature, such as a temperature of 20-30° C.

In the present disclosure, the developed compounds belong to a protein degradation targeting small molecule compound, which is mainly comprised of four moieties, the first moiety: BCR-ABL-TKIs are compounds with BCR-ABL tyrosine kinase inhibited activity; the second moiety: the LIN being a link unit; the third moiety: the ULM being a small molecule ligand for VHL or CRBN proteases with ubiquitination; and the four moiety: the group A being carbonyl group that covalently binds to BCR-ABL-TKIs and LIN, in addition, the LIN is also covalently bonded to ULM. Through the inhibition of the BCR-ABL tyrosine kinase activity by the Bcr-abl-TKIs specifically recognizing the targeted proteins as well as the E3 ligase specifically leading to Bcr-abl protein ubiquitinated and further degraded by the protesome, the small molecule PROTAD targeting BCR-ABL protein can degrade and eliminate the pathogenic BCR-ABL fusion protein, so that in one aspect, it can achieve genetic or molecular biological remission to subject with $Ph^+$ leukemia, in another aspect, it is also of great significance to overcome the resistance of targeted drugs. In addition, the designed and developed small molecule PROTAD can also degrade other tyrosine kinase receptors, such as KIT, SRC protein kinase and PDGFR etc., which also show potential treatment value for these targets relevant cancer.

EXAMPLES

In the following description, numerous specific details are set forth in order to provide a thorough understanding of the invention. The invention may be practiced without some or all of these specific details. In other cases, well-known process operations have not been described in detail in order not to unnecessarily obscure the present invention. Although the present invention will be described in conjunction with specific embodiments, it should be understood that this is not intended to limit the present invention to these embodiments.

The description and examples use the following Abbreviates:
Boc Tert-butoxycarbonyl
n-BuOH 1-Butanol
'BuOH Tert-Butanol
Con. Concentration
DCM Dichloromethane
DME 1,2-Dimethoxyethane
DMF N,N-dimethyl formamide
DMSO Dimethylsulfoxide
DIPEA N,N-diisopropylethylamine
EDCI N-(3-dimethylaminopropyl)-N'-ethylcarbodiimide hydrochloride
ESI Electrospray ionization
equiv Equivalent
EtOH Ethanol
HATU 1-[Bis(dimethylamino)methylene]-1H-1,2,3-triazolo[4,5-b]pyridinium 3-oxid hexafluorophosphate
HOAT 1-Hydroxy-7-azabenotriazole
HPLC High performance liquid chromatography
HRMS High-resolution mass spectrometer
LC-MS Liquid chromatograph mass spectrometer
LRMS Low-resolution mass spectrometer
LC Liquid chromatograph
Me Methyl-
MeCN Acetonitrile
MeOH Methanol
MS Mass spectrometer
MW Microwave
NMM N-methylmorpholine
NMP 1-methyl-2-pyrrolidinone
$^1$H NMR $^1$H-nuclear magnetic resonance spectrum
rt Room temperature
TFA Trifluoroacetic acid
THF Tetrahydrofuran
TLC Thin-Layer chromatography
TMS Trimethylsilyl-
HO$_2$C-LIN-ULM Linker covalent with ULM(Ubiquitin Ligase binding Moiety) formed analog
PROTAD Proteolysis Targeting Drug In present disclosure, $^1$H NMR spectra were measured on a Bruker Advance 500 MHz spectrometer. $^1$H NMR spectra were reported in parts per million (ppm) downfield from tetramethylsilane (TMS). CD$_3$OD containing 0.1% TMS was used as solvent, then it ($\delta$=3.31 ppm) was used as internal standard in $^1$H NMR spectra; or CDCl$_3$ containing 0.1% TMS was used as solvent, then it ($\delta$=7.26 ppm) was used as internal standard in $^1$H NMR spectra; or DMSO-d$_6$ containing 0.1% TMS was used as solvent, then it ($\delta$=2.50 ppm) was used as internal standard in $^1$H NMR spectra. LRMS spectra were measured on a AB Triple 4600, the preparative HPLC was performed in a SHIMADZU LC-20AP, HPLC purity was measured on a SHIMADZU LC-30AP or Waters 1525. The target products were purified by flash column chromatography (silica gel: 200-300 mesh) or C18 reverse phase preparative HPLC column. All reactions were carried out under room temperature except as otherwise noted. These reactions were monitored by TLC or LC-MS.

The reaction solvents and reagents were treated as follows:

The reaction solvents, such as DCM, DMF, NMP, anhydrous ethanol and methanol etc., were purchased from Chinese Sinopharm Group;

The reverse phase preparative HPLC used e.g., deionized water and acetonitrile as eluent;

Unless otherwise stated, the commercially available starting matericals contain demethylated imatinib analog, dasatinib analog, bosutinib analog and varties of different length linker units, were purchased from suppliers.

Unless otherwise stated, other solvents and reagents were also easy to obtain from suppliers.

Synthesis of Intermediates

Intermediate Example 1: Preparation of Dasatinib Analog

Scheme 1

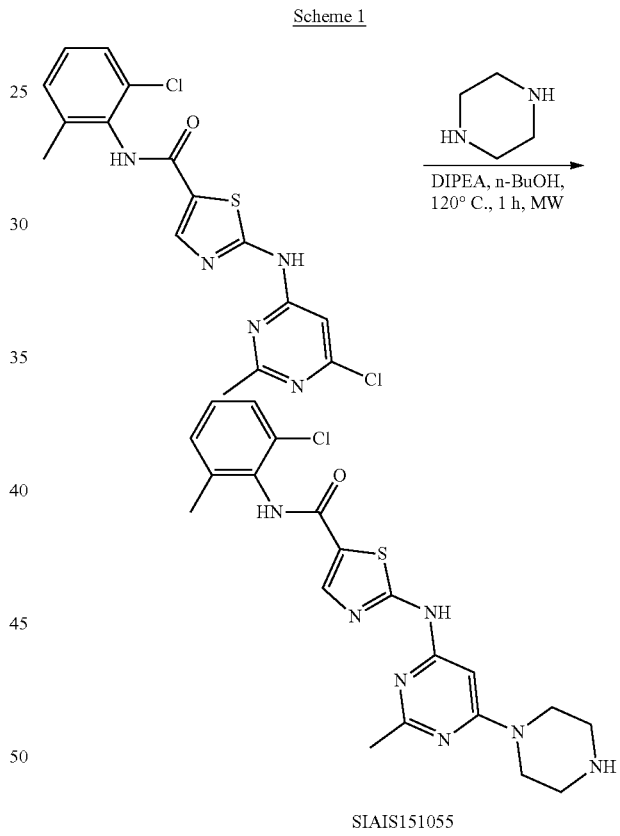

SIAIS151055

Preparation of N-(2-chloro-6-methylphenyl)-2-((2-methyl-6-(piperazin-1-yl)pyrimidin 4-yl)amino)thiazole-5-carboxamide (SIAIS151055) Based on Scheme 1

In a 30 mL microwave reaction tube, to a stirred solution of 2-((6-chloro-2-methylpyrimidin-4-yl)amino)-N-(2-chloro-6-methylphenyl)thiazole-5-carboxamide (1.0 g, 2.54 mmol), anhydrous piperazine (1.31 g, 15.21 mmol) and N,N-diisopropylethylamine (4.9 g, 38.0 mmol) was added n-BuOH (8 mL), the mixture was filled with Ar and stirring for 10 minutes at room temperature, then it was heated to 120° C. in microwave reactor and stirring for another 1 h. The reaction mixture was then cooled to room temperature, a large amount of white solid was formed, filtered, washed by n-BuOH, and concentrated under reduced pressure to afford compound SIAIS151055 as a white solid (0.9 g, 80% yield). $^1$H NMR (500 MHz, DMSO) δ 9.88 (s, 1H), 8.23 (s, 1H), 7.43-7.38 (m, 1H), 7.31-7.24 (m, 2H), 6.04 (s, 1H), 3.45 (d, J=4.6 Hz, 4H), 2.79-2.71 (m, 4H), 2.44-2.37 (m, 3H), 2.25 (s, 3H). HRMS (ESI) m/z: calcd $C_{20}H_{23}CN_7OS^+$ [M+H]$^+$, 444.1368; found, 444.1301.

Intermediate Example 2: Preparation of Bosutinib Analog brown solid (0.55 g, 50% yield). $^1$H NMR (500 MHz, DMSO) δ 8.39 (s, 1H), 7.82 (s, 1H), 7.72 (s, 1H), 7.30 (s, 1H), 7.28 (s, 1H), 5.75 (s, 1H), 4.19 (t, J=6.4 Hz, 2H), 3.94 (s, 3H), 3.85 (s, 3H), 2.76 (t, J=4.8 Hz, 4H), 2.43 (t, J=7.1 Hz, 2H), 2.39-2.32 (m, 4H), 1.99-1.91 (m, 2H). HRMS (ESI) m/z: calcd $C_{25}H_{28}Cl_2N_5O_3^+$[M+H]$^+$, 516.1564; found, 516.1699.

The general method of preparation of pomalidomide PEG series of HO$_2$C-LIN-ULM analogs:

Scheme 2

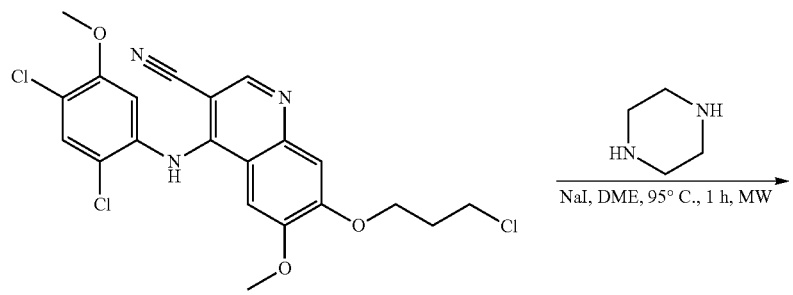

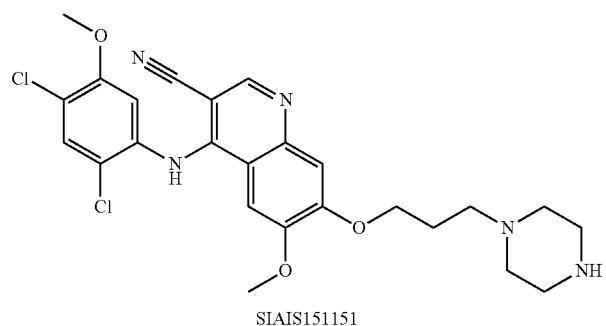

SIAIS151151

Preparation of 4-((2,4-dichloro-5-methoxyphenyl)amino)-6-methoxy-7-(3-(piperazin-1-yl)propoxy)quinoline-3-carbonitrile (SIAIS151151) Based on Scheme 2

In a 30 mL microwave reaction tube, to a stirred solution of 7-(3-chloropropoxy)-4-((2,4-dichloro-5-methoxyphenyl)amino)-6-methoxyquinoline-3-carbonitrile (1.0 g, 2.14 mmol), anhydrous piperazine (0.93 g, 10.7 mmol) and NaI (0.4 g, 2.14 mmol) was added DME (8 mL), the mixture was filled with Ar and stirring for 10 minutes at room temperature, then it was heated to 95° C. in microwave reactor and stirring for another 1 h. The reaction mixture was then cooled to room temperature, the reaction solvent was removed under the reduced pressure, the mixture was then poured into 20% NaHCO$_3$ aqueous (20 mL) followed by extracted with EtOAc (4×50 mL), the combined organic layers were washed with brine (20 mL), dried over Na$_2$SO$_4$, and concentrated under reduced pressure, the residue was subjected to flash column chromatography with DCM/MeOH (10:1) to afford compound SIAIS151151 as a light Scheme 3

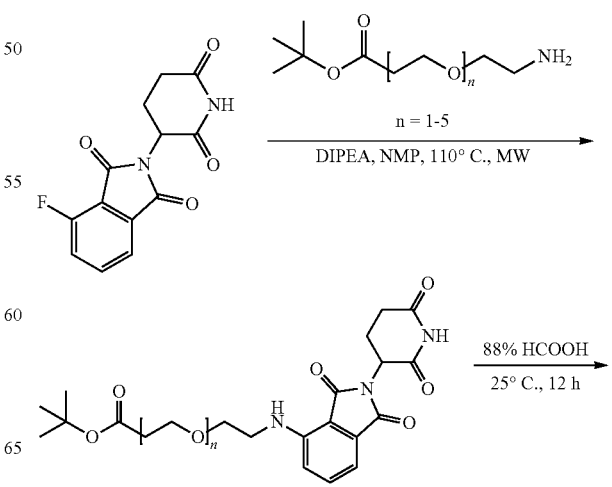

-continued

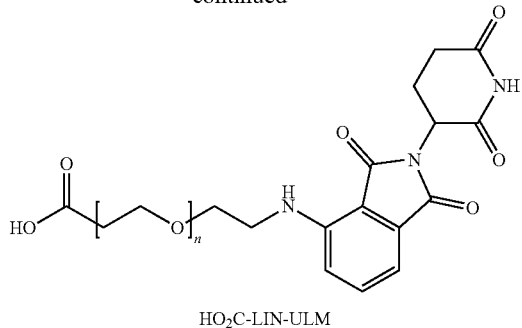

HO$_2$C-LIN-ULM

In a 30 mL microwave reaction tube, to a stirred solution of 2-(2,6-dioxopiperidin-3-yl)-4-fluoroisoindoline-1,3-dione (5 mmol, 1.0 equiv), relevant linker amine (6 mmol, 1.2 equiv) and N,N-diisopropylethylamine (25 mmol, 5.0 equiv) was added NMP (8 mL), the mixture was stirred for 10 minutes at room temperature, then it was heated to 110° C. in microwave reactor and stirred for another 2 h at Ar atmosphere. The reaction mixture was then cooled to room temperature, poured into 90% NaCl aqueous followed by extraction with EtOAc (4×50 mL), the combined organic layers were washed with water (2×30 mL) and brine (20 mL), dried over Na$_2$SO$_4$, and concentrated under reduced pressure, the residue was subjected to flash column chromatography with PE/EtOAc (1:1) to afford intermediate; the obtained intermediate and 88% HCOOH (20 mL) were added to a 50 mL of round-bottom flask, and then the mixture was stirred for 12 h at room temperature. The reaction solvent was removed under reduced pressure, then the residue was treated by addition of water, freeze-drying to afford target compound HO$_2$C-LIN-ULM.

Intermediate Example 3: Preparation of 3-(2-((2-(2,6-dioxopiperidin-3-yl)-1,3-dioxoisoindolin-4-yl)amino)ethoxy)propanoic acid (SIAIS151001)

Based on the method of scheme 3, the 2-(2,6-dioxopiperidin-3-yl)-4-fluoroisoindoline-1,3-dione was reacted with tert-butyl 3-(2-aminoethoxy)propanoate to provide the intermediate, followed by hydrolyzation to afford compound SIAIS151001 as a yellow solid (1.0 g, 48% yield). $^1$H NMR (500 MHz, DMSO) δ 12.17 (s, 1H), 11.09 (s, 1H), 7.57 (dd, J=8.5, 7.5 Hz, 1H), 7.13 (d, J=8.6 Hz, 1H), 7.04 (d, J=7.0 Hz, 1H), 6.59 (t, J=5.7 Hz, 1H), 5.05 (dd, J=12.8, 5.4 Hz, 1H), 3.65 (t, J=6.3 Hz, 2H), 3.59 (t, J=5.5 Hz, 2H), 3.46 (q, J=5.5 Hz, 2H), 2.91-2.83 (m, 1H), 2.61-2.52 (m, 2H), 2.46 (t, J=6.3 Hz, 2H), 2.05-2.00 (m, 1H); HRMS (ESI) m/z: calcd C$_{18}$H$_{20}$N$_3$O$_7{}^+$[M+H]$^+$, 390.1301; found, 390.1261.

Intermediate Example 4: Preparation of 3-(2-((2-(2-(2,6-dioxopiperidin-3-yl)-1,3-dioxoisoindolin-4-yl)amino)ethoxy)ethoxy)propanoic acid (SIAIS151004)

Based on the method of scheme 3, the 2-(2,6-dioxopiperidin-3-yl)-4-fluoroisoindoline-1,3-dione was reacted with tert-butyl 3-(2-(2-aminoethoxy)ethoxy)propanoate to provide the intermediate, followed by hydrolyzation to afford compound SIAIS151004 as a yellow solid (0.95 g, 51% yield). $^1$H NMR (500 MHz, DMSO) δ 11.09 (s, 1H), 7.58 (dd, J=8.0, 7.5 Hz, 1H), 7.14 (d, J=8.6 Hz, 1H), 7.04 (d, J=7.0 Hz, 1H), 6.60 (t, J=5.7 Hz, 1H), 5.05 (dd, J=12.8, 5.4 Hz, 1H), 3.62-3.58 (m, 4H), 3.56-3.54 (m, 2H), 3.52-3.49 (m, 2H), 3.46 (dd, J=11.1, 5.5 Hz, 2H), 2.92-2.84 (m, 1H), 2.66-2.51 (m, 2H), 2.42 (t, J=6.4 Hz, 2H), 2.06-1.98 (m, 1H). HRMS (ESI) m/z: calcd C$_{20}$H$_{24}$N$_3$O$_8{}^+$[M+H]$^+$, 434.1558; found, 434.1445.

Intermediate Example 5: Preparation of 3-(2-(2-(2-((2-(2,6-dioxopiperidin-3-yl)-1,3-dioxoisoindolin-4-yl)amino)ethoxy)ethoxy)ethoxy)propanoic acid (SIAIS151005)

Based on the method of scheme 3, the 2-(2,6-dioxopiperidin-3-yl)-4-fluoroisoindoline-1,3-dione was reacted with tert-butyl 3-(2-(2-(2-aminoethoxy)ethoxy)ethoxy)propanoate to provide the intermediate, followed by hydrolyzation to afford compound SIAIS151005 as a yellow solid (0.95 g, 61% yield). $^1$H NMR (500 MHz, DMSO) δ 11.09 (s, 1H), 7.58 (dd, J=8.0, 7.0 Hz, 1H), 7.15 (d, J=8.6 Hz, 1H), 7.04 (d, J=7.0 Hz, 1H), 6.61 (t, J=5.8 Hz, 1H), 5.05 (dd, J=12.8, 5.4 Hz, 1H), 3.63-3.48 (m, 14H), 2.92-2.83 (m, 1H), 2.64-2.52 (m, 2H), 2.18 (t, J=8.1 Hz, 2H), 2.07-1.99 (m, 1H). HRMS (ESI) m/z: calcd C$_{22}$H$_{28}$N$_3$O$_9{}^+$[M+H]$^+$, 478.1820; found, 478.1159.

Intermediate Example 6: Preparation of 1-((2-(2,6-dioxopiperidin-3-yl)-1,3-dioxoisoindolin-4-yl)amino)-3,6,9,12-tetraoxapentadecan-15-oic acid (SIAIS151006)

Based on the method of scheme 3, the 2-(2,6-dioxopiperidin-3-yl)-4-fluoroisoindoline-1,3-dione was reacted with tert-butyl 1-amino-3,6,9,12-tetraoxapentadecan-15-oate to provide the intermediate, followed by hydrolyzation to afford compound SIAIS151006 as a yellow solid (0.87 g, 53% yield). $^1$H NMR (500 MHz, DMSO) δ 11.09 (s, 1H), 7.58 (dd, J=8.5, 7.5 Hz, 1H), 7.15 (d, J=8.6 Hz, 1H), 7.04 (d, J=7.0 Hz, 1H), 6.60 (t, J=5.7 Hz, 1H), 5.05 (dd, J=12.8, 5.4 Hz, 1H), 3.63-3.48 (m, 18H), 2.92-2.84 (m, 1H), 2.63-2.52 (m, 2H), 2.41 (t, J=6.4 Hz, 2H), 2.07-1.98 (m, 1H). HRMS (ESI) m/z: calcd C$_{24}$H$_{32}$N$_3$O$_{10}{}^+$[M+H]$^+$, 522.2082; found, 522.2178.

Intermediate Example 7: Preparation of 1-((2-(2,6-dioxopiperidin-3-yl)-1,3-dioxoisoindolin-4-yl)amino)-3,6,9,12,15-pentaoxaoctadecan-18-oic acid (SIAIS151007)

Based on the method of scheme 3, the 2-(2,6-dioxopiperidin-3-yl)-4-fluoroisoindoline-1,3-dione was reacted with tert-butyl 1-amino-3,6,9,12,15-pentaoxaoctadecan-18-oate to provide the intermediate, followed by hydrolyzation to afford compound SIAIS151007 as a yellow solid (0.80 g, 51% yield). $^1$H NMR (500 MHz, DMSO) δ 11.09 (s, 1H), 7.58 (t, J=8.0 Hz, 1H), 7.14 (d, J=8.6 Hz, 1H), 7.04 (d, J=7.0 Hz, 1H), 6.60 (t, J=5.7 Hz, 1H), 5.05 (dd, J=12.8, 5.4 Hz, 1H), 3.63-3.54 (m, 8H), 3.54-3.48 (m, 12H), 3.30 (dd, J=7.0 Hz, 4H), 2.92-2.84 (m, 1H), 2.63-2.52 (m, 2H), 2.06-1.99 (m, 1H). HRMS (ESI) m/z: calcd C$_{26}$H$_{36}$N$_3$O$_{11}{}^+$[M+H]$^+$, 566.2344; found, 566.2679.

The general method of preparation of pomalidomide alkyl carbon chain series of HO₂C-LIN-ULM analogs:

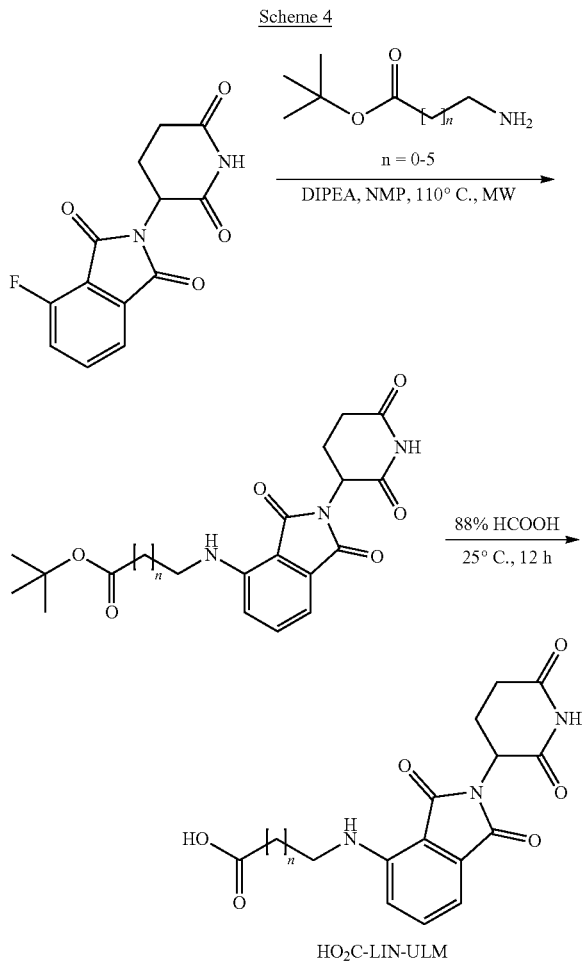

In a 30 mL microwave reaction tube, to a stirred solution of 2-(2,6-dioxopiperidin-3-yl)-4-fluoroisoindoline-1,3-dione (7 mmol, 1.0 equiv), corresponding linkers amine (8.4 mmol, 1.2 equiv) and N,N-diisopropylethylamine (35 mmol, 5.0 equiv) was added NMP (8 mL), the mixture was stirred for 10 minitues at room temperature, then it was heated to 110° C. in microwave reactor and stirred for another 2 h at Argon atmosphere. The reaction mixture was then cooled to room temperature, the mixture was then poured into 90% NaCl aqueous followed by extracted with EtOAc (4×50 mL), the combined organic layers were washed with water (2×30 mL) and brine (20 mL), dried over Na₂SO₄, and concentrated under reduced pressure, the residue was subjected to flash column chromatography with PE/EtOAc (1:1) to afford analog; the obtained analog and 88% HCOOH (20 mL) were added to a 50 mL of round-bottom flask, and then the mixture was stirred for 12 h at room temperature. The reaction solvent was removed under the reduced pressure, then the residue was treated by addition of water, freeze-drying to afford target compound HO₂C-LIN-ULM.

Intermediate Example 8: Preparation of (2-(2,6-dioxopiperidin-3-yl)-1,3-dioxoisoindolin-4-yl)glycine (SIAIS151025)

Based on the method of scheme 4, the 2-(2,6-dioxopiperidin-3-yl)-4-fluoroisoindoline-1,3-dione was reacted with tert-butyl glycinate to provide the intermediate, followed by hydrolyzation to afford compound SIAIS151025 as a yellow solid (1.2 g, 48% yield). $^1$H NMR (500 MHz, DMSO) δ 11.10 (s, 1H), 7.59 (dd, J=15.9, 8.5 Hz, 1H), 7.07 (d, J=7.0 Hz, 1H), 6.99 (d, J=8.6 Hz, 1H), 6.86 (t, J=5.7 Hz, 1H), 5.06 (dt, J=15.1, 7.6 Hz, 1H), 4.08 (d, J=5.7 Hz, 2H), 2.92-2.84 (m, 1H), 2.63-2.52 (m, 2H), 2.07-2.02 (m, 1H). HRMS (ESI) m/z: calcd $C_{18}H_{20}N_3O_6^+$[M+H]$^+$, 332.0877; found, 332.0720.

Intermediate Example 9: Preparation of 3-((2-(2,6-dioxopiperidin-3-yl)-1,3-dioxoisoindolin-4-yl)amino)propanoic acid (SIAIS151026)

Based on the method of scheme 4, the 2-(2,6-dioxopiperidin-3-yl)-4-fluoroisoindoline-1,3-dione was reacted with tert-butyl 3-aminopropanoate to provide the intermediate, followed by hydrolyzation to afford compound SIAIS151026 as a yellow solid (0.93 g, 39% yield). $^1$H NMR (500 MHz, DMSO) δ 11.09 (s, 1H), 7.59 (dd, J=8.0, 7.5 Hz, 1H), 7.15 (d, J=8.6 Hz, 1H), 7.04 (d, J=7.0 Hz, 1H), 6.67 (t, J=6.0 Hz, 1H), 5.05 (dd, J=12.8, 5.4 Hz, 1H), 3.53 (dd, J=12.6, 6.3 Hz, 2H), 2.92-2.84 (m, 1H), 2.65-2.53 (m, 4H), 2.08-1.98 (m, 1H). HRMS (ESI) m/z: calcd $C_{16}H_{16}N_3O_6^+$[M+H]$^+$, 346.1034; found, 346.0868.

Intermediate Example 10: Preparation of 4-((2-(2,6-dioxopiperidin-3-yl)-1,3-dioxoisoindolin-4-yl)amino)butanoic acid (SIAIS151019)

Based on the method of scheme 4, the 2-(2,6-dioxopiperidin-3-yl)-4-fluoroisoindoline-1,3-dione was reacted with tert-butyl 4-aminobutanoate to provide the intermediate, followed by hydrolyzation to afford compound SIAIS151019 as a yellow solid (0.80 g, 61% yield). $^1$H NMR (500 MHz, DMSO) δ 12.14 (s, 1H), 11.09 (s, 1H), 7.58 (dd, J=8.4, 7.3 Hz, 1H), 7.13 (d, J=8.6 Hz, 1H), 7.02 (d, J=7.0 Hz, 1H), 6.65 (t, J=6.0 Hz, 1H), 5.05 (dd, J=12.8, 5.4 Hz, 1H), 3.32 (dd, J=13.7, 6.7 Hz, 2H), 2.94-2.82 (m, 1H), 2.66-2.51 (m, 2H), 2.30 (t, J=7.2 Hz, 2H), 2.05-2.00 (m, 1H), 1.82-1.75 (m, 2H). HRMS (ESI) m/z: calcd $C_{17}H_{18}N_3O_6^+$ [M+H]$^+$, 360.1190; found, 360.1223.

Intermediate Example 11: Preparation of 5-((2-(2,6-dioxopiperidin-3-yl)-1,3-dioxoisoindolin-4-yl)amino)pentanoic acid (SIAIS151020)

Based on the method of scheme 4, the 2-(2,6-dioxopiperidin-3-yl)-4-fluoroisoindoline-1,3-dione was reacted with tert-butyl 5-aminopentanoate to provide the intermediate, followed by hydrolyzation to afford compound SIAIS151020 as a yellow solid (0.90 g, 50% yield). $^1$H NMR (500 MHz, DMSO) δ 12.05 (s, 1H), 11.11 (s, 1H), 7.57 (dd, J=8.3, 7.4 Hz, 1H), 7.09 (d, J=8.6 Hz, 1H), 7.02 (d, J=7.0 Hz, 1H), 6.56 (t, J=5.9 Hz, 1H), 5.05 (dd, J=12.7, 5.4 Hz, 1H), 3.32-3.28 (m, 2H), 2.94-2.82 (m, 1H), 2.62-2.51 (m, 2H), 2.27-2.25 (m, 2H), 2.06-1.99 (m, 1H), 1.62-1.53 (m, 4H). HRMS (ESI) m/z: calcd $C_{18}H_{20}N_3O_6^+$ [M+H]$^+$, 374.1347; found, 374.1384.

Intermediate Example 12: Preparation of 6-((2-(2,6-dioxopiperidin-3-yl)-1,3-dioxoisoindolin-4-yl)amino)hexanoic acid (SIAIS151027)

Based on the method of scheme 4, the 2-(2,6-dioxopiperidin-3-yl)-4-fluoroisoindoline-1,3-dione was reacted with tert-butyl 6-aminohexanoate to provide the intermediate, followed by hydrolyzation to afford compound SIAIS151027 as a yellow solid (1.26 g, 61% yield). $^1$H NMR (500 MHz, DMSO) δ 12.00 (s, 1H), 11.09 (s, 1H), 7.58 (dd, J=8.3, 7.4 Hz, 1H), 7.09 (d, J=8.6 Hz, 1H), 7.02 (d, J=7.0 Hz, 1H), 6.54 (t, J=5.9 Hz, 1H), 5.05 (dd, J=12.8, 5.4 Hz, 1H), 3.30-3.27 (m, 2H), 2.92-2.84 (m, 1H), 2.63-2.51 (m, 2H), 2.21 (t, J=7.5 Hz, 2H), 2.08-1.98 (m, 1H), 1.60-1.50 (m, 4H), 1.38-1.31 (m, 2H). HRMS (ESI) m/z: calcd $C_{19}H_{22}N_3O_6^+$ [M+H]$^+$, 388.1503; found, 388.1119.

Intermediate Example 13: Preparation of 7-((2-(2,6-dioxopiperidin-3-yl)-1,3-dioxoisoindolin-4-yl)amino)heptanoic acid (SIAIS151086)

Based on the method of scheme 4, the 2-(2,6-dioxopiperidin-3-yl)-4-fluoroisoindoline-1,3-dione was reacted with tert-butyl 7-aminoheptanoate to provide the intermediate, followed by hydrolyzation to afford compound SIAIS151086 as a yellow solid (1.3 g, 64% yield). $^1$H NMR (500 MHz, DMSO) δ 12.04 (s, 1H), 11.09 (s, 1H), 7.58 (dd, J=8.3, 7.3 Hz, 1H), 7.09 (d, J=8.6 Hz, 1H), 7.02 (d, J=7.0 Hz, 1H), 6.53 (t, J=5.9 Hz, 1H), 5.05 (dd, J=12.7, 5.4 Hz, 1H), 3.28 (dd, J=13.4, 6.7 Hz, 2H), 2.94-2.82 (m, 1H), 2.65-2.51 (m, 2H), 2.19 (t, J=7.3 Hz, 2H), 2.05-2.00 (m, 1H), 1.60-1.53 (m, 2H), 1.53-1.46 (m, 2H), 1.37-1.28 (m, 4H). HRMS (ESI) m/z: calcd $C_{20}H_{24}N_3O_6^+$ [M+H]$^+$, 402.1660; found, 402.1643.

The general method of synthesis of lenalidomide alkyl carbon chain series of HO$_2$C-LIN-ULM analogs:

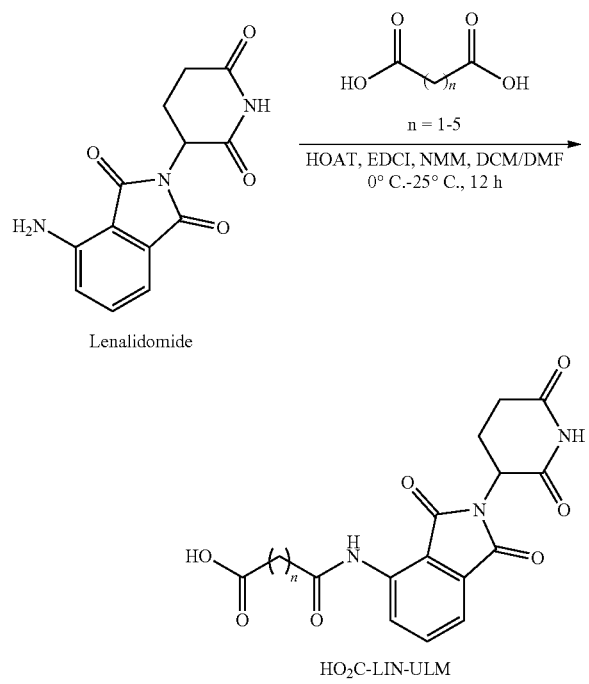

Scheme 5

In a 250 mL of round-bottom flask, to a stirred solution of relevant diacid linker (5.0 mmol, 2.5 equiv) in anhydrous DMF (10 mL) and DCM (150 mL) at 0° C. was added NMM (10.0 mmol, 5equiv), lenalidomide (2 mmol, 1 equiv), HOAT (2.4 mmol, 1.2equiv) and EDCI.HCl (2.4 mmol, 1.2equiv), respectively. After addition, the mixture was allowed to stir for another 12 h at room temperature. The mixture was quenched with water (1 mL) once consumed completely, concentrated to dryness under reduced pressure, the residue was purified via C18 reverse phase preparative HPLC column (eluent gradient: acetonitrile/(H$_2$O+0.1% TFA)=10%-100%) to afford desired product HO$_2$C-LIN-ULM.

Intermediate Example 14: Preparation of 3-((2-(2,6-dioxopiperidin-3-yl)-1-oxoisoindolin-4-yl)amino)-3-oxopropanoic acid (SIAIS171004)

Based on the method of scheme 5, coupling of 3-(4-amino-1-oxoisoindolin-2-yl)piperidine-2,6-dione with malonic acid was performed under suitable standard coupling conditions to afford compound SIAIS171004 as a white solid (0.32 g, 24% yield). $^1$H NMR (500 MHz, DMSO) δ 11.02 (s, 1H), 10.03 (s, 1H), 7.86 (d, J=7.1 Hz, 1H), 7.62-7.43 (m, 2H), 5.15 (dd, J=13.4, 4.9 Hz, 1H), 4.36 (dd, J=35.5, 17.5 Hz, 2H), 3.42 (s, 2H), 2.95-2.87 (m, 1H), 2.63-2.59 (m, 1H), 2.38-2.28 (m, 1H), 2.07-2.01 (m, 1H). HRMS (ESI) m/z: calcd $C_{16}H_{16}N_3O_6^+$ [M+H]$^+$, 346.1034; found, 346.1015.

Intermediate Example 15: Preparation of 4-((2-(2,6-dioxopiperidin-3-yl)-1-oxoisoindolin-4-yl)amino)-4-oxobutanoic acid (SIAIS164084)

Based on the method of scheme 5, coupling of 3-(4-amino-1-oxoisoindolin-2-yl)piperidine-2,6-dione with succinic acid was performed under suitable standard coupling conditions to afford compound SIAIS164084 as a white solid (0.11 g, 44% yield). $^1$H NMR (500 MHz, DMSO) δ 12.16 (s, 1H), 11.02 (s, 1H), 9.86 (s, 1H), 7.81 (dd, J=7.1, 1.7 Hz, 1H), 7.57-7.40 (m, 2H), 5.15 (dd, J=13.3, 5.1 Hz, 1H), 4.35 (dd, J=35.5, 17.5 Hz, 2H), 2.96-2.87 (m, 1H), 2.65-2.58 (m, 3H), 2.55-2.53 (m, 2H), 2.37-2.29 (m, 1H), 2.06-2.00 (m, 1H). HRMS (ESI) m/z: calcd $C_{17}H_{18}N_3O_6^+$ [M+H]$^+$, 360.1190; found, 360.1198.

Intermediate Example 16: Preparation of 5-((2-(2,6-dioxopiperidin-3-yl)-1-oxoisoindolin-4-yl)amino)-5-oxopentanoic acid (SIAIS171005)

Based on the method of scheme 5, coupling of 3-(4-amino-1-oxoisoindolin-2-yl)piperidine-2,6-dione with glutaric acid was performed under suitable standard coupling conditions to afford compound SIAIS171005 as a white solid (0.52 g, 35% yield). $^1$H NMR (500 MHz, DMSO) δ 11.01 (s, 1H), 9.80 (s, 1H), 7.81 (d, J=5.8 Hz, 1H), 7.54-7.46 (m, 2H), 5.15 (dd, J=13.3, 5.1 Hz, 1H), 4.36 (dd, J=35.5, 17.5 Hz, 2H), 2.97-2.85 (m, 1H), 2.77-2.75 (m, 2H), 2.66-2.57 (m, 1H), 2.42-2.39 (m, 1H), 2.35 (dd, J=13.1, 4.4 Hz, 1H), 2.30-2.27 (m, 1H), 2.03-1.97 (m, 1H), 1.85-1.79 (m, 2H). HRMS (ESI) m/z: calcd $C_{18}H_{20}N_3O_6^+$ [M+H]$^+$, 374.1347; found, 374.1526.

Intermediate Example 17: Preparation of 6-((2-(2,6-dioxopiperidin-3-yl)-1-oxoisoindolin-4-yl)amino)-6-oxohexanoic acid (SIAIS164101)

Based on the method of scheme 5, coupling of 3-(4-amino-1-oxoisoindolin-2-yl)piperidine-2,6-dione with adipic acid was performed under suitable standard coupling conditions to afford compound SIAIS164101 as a white solid (0.4 g, 27% yield). $^1$H NMR (500 MHz, MeOD) δ 7.70 (d, J=7.9 Hz, 1H), 7.66 (d, J=7.4 Hz, 1H), 7.52 (t, J=7.7 Hz, 1H), 5.16 (dd, J=13.4, 5.2 Hz, 1H), 4.53-4.43 (m, 2H), 2.95-2.87 (m, 1H), 2.81-2.76 (m, 1H), 2.55-2.48 (m, 1H), 2.46 (t, J=7.2 Hz, 2H), 2.36 (t, J=7.0 Hz, 2H), 2.22-2.16 (m, 1H), 1.79-1.66 (m, 4H). HRMS (ESI) m/z: calcd $C_{19}H_{22}N_3O_6^+$ [M+H]$^+$, 388.1503; found, 388.1714.

Intermediate Example 18: Preparation of 7-((2-(2,6-dioxopiperidin-3-yl)-1-oxoisoindolin-4-yl)amino)-7-oxoheptanoic acid (SIAIS164102)

Based on the method of scheme 5, coupling of 3-(4-amino-1-oxoisoindolin-2-yl)piperidine-2,6-dione with heptanedioic acid was performed under suitable standard coupling conditions to afford compound SIAIS164102 as a white solid (0.45 g, 28% yield). $^1$H NMR (500 MHz, MeOD) δ 7.70 (d, J=7.9 Hz, 1H), 7.65 (d, J=7.4 Hz, 1H), 7.52 (t, J=7.7 Hz, 1H), 5.16 (dd, J=13.4, 5.2 Hz, 1H), 4.49 (t, J=10.1 Hz, 2H), 2.94-2.87 (m, 1H), 2.81-2.76 (m, 1H), 2.54-2.48 (m, 1H), 2.45 (t, J=7.5 Hz, 2H), 2.32 (t, J=7.0 Hz, 2H), 2.22-2.16 (m, 1H), 1.77-1.72 (m, 2H), 1.70-1.63 (m, 2H), 1.48-1.42 (m, 2H). HRMS (ESI) m/z: calcd $C_{20}H_{24}N_3O6+$[M+H]$^+$, 402.1660; found, 402.1890.

The general method of preparation of VHL-1 PEG series of HO$_2$C-LIN-ULM analogs:

Intermediate Example 19: Preparation of 2-(2-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)ethoxy) acetic acid (SIAIS151010)

Based on the method of scheme 6, coupling of VHL-1 with 2,2'-(ethane-1,2-diylbis(oxy))diacetic acid was performed under suitable standard coupling conditions to afford compound SIAIS151010 as a white solid (0.2 g, 23% yield). $^1$H NMR (500 MHz, DMSO) δ 8.98 (s, 1H), 8.60 (t, J=5.9 Hz, 1H), 7.48 (d, J=9.5 Hz, 1H), 7.40 (s, 4H), 4.57 (d, J=9.6 Hz, 1H), 4.47-4.37 (m, 2H), 4.35 (s, 1H), 4.29-4.22 (m, 1H), 4.07 (d, J=12.5 Hz, 1H), 3.97 (s, 2H), 3.69-3.59 (m, 8H), 2.44 (s, 3H), 2.07-2.03 (m, 1H), 1.93-1.87 (m, 1H), 0.94 (s, 9H). HRMS (ESI) m/z: calcd $C_2H_{39}N_4O_8S^+$ [M+H]$^+$, 591.2483; found, 591.2365.

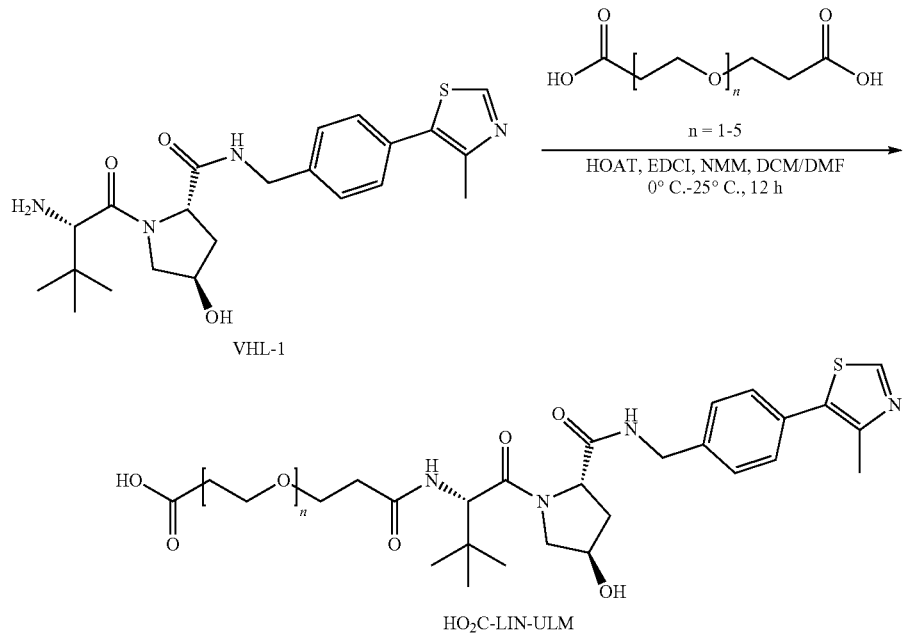

Scheme 6

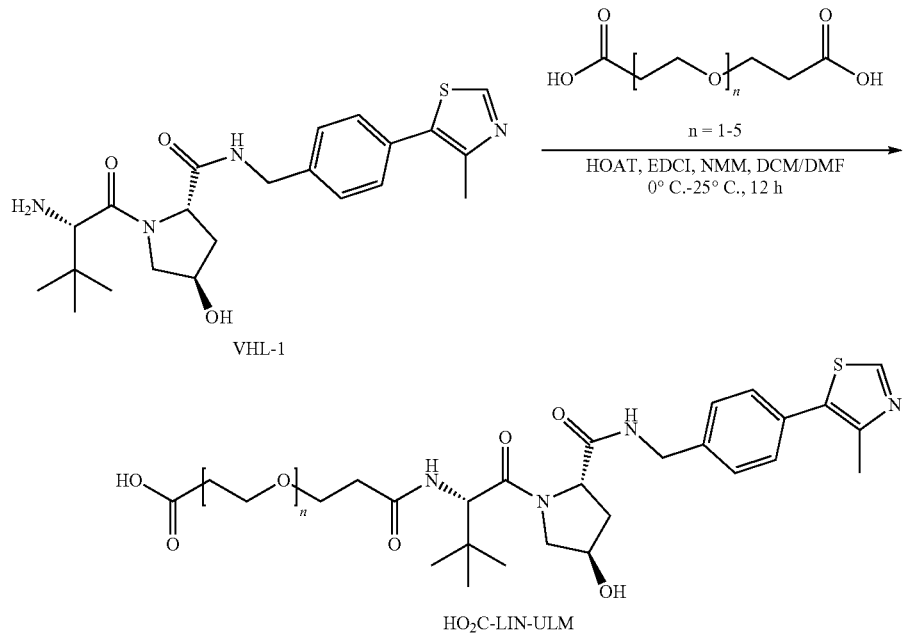

In a 250 mL of round-bottom flask, to a stirred solution of corresponding diacid linker (5.0 mmol, 2.5 equiv) in anhydrous DMF (10 mL) and DCM (150 mL) at 0° C. was added NMM (10.0 mmol, 5equiv), VHL-1 (2 mmol, 1 equiv), HOAT (2.4 mmol, 1.2equiv) and EDCI.HCl (2.4 mmol, 1.2equiv), respectively. After addition, the mixture was allowed to stir for another 12 h at room temperature. The mixture was quenched with water (1 mL) once consumed completely, concentrated to dryness under reduced pressure, the residue was purified via C18 reverse phase preparative HPLC column (eluent gradient: acetonitrile/(H$_2$O+0.1% TFA)=10%-100%) to afford desired product HO$_2$C-LIN-ULM.

Intermediate Example 20: Preparation of 3-(2-(3-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-3-oxopropoxy) ethoxy)propanoic acid (SIAIS151002)

Based on the method of scheme 6, coupling of VHL-1 with 3,3'-(ethane-1,2-diylbis(oxy))dipropionic acid was performed under suitable standard coupling conditions to afford compound SIAIS151002 as a white solid (0.53 g, 44% yield). $^1$H NMR (500 MHz, DMSO) δ 12.17 (s, 1H), 8.99 (s, 1H), 8.57 (t, J=6.0 Hz, 1H), 7.92 (d, J=9.3 Hz, 1H), 7.41 (dd, J=18.5, 8.2 Hz, 4H), 4.55 (d, J=9.5 Hz, 1H), 4.46-4.40 (m, 2H), 4.36 (s, 1H), 4.23 (dd, J=15.8, 5.4 Hz, 1H), 3.69-3.56 (m, 7H), 3.49-3.46 (m, 4H), 2.58-2.53 (m, 1H), 2.47-2.42

(m, 2H), 2.45 (s, 3H), 2.39-2.32 (m, 1H), 2.06-2.01 (m, 1H), 1.95-1.88 (m, 1H), 0.94 (s, 9H). HRMS (ESI) m/z: calcd $C_{30}H_{43}N_4O_8S^+$ [M+H]$^+$, 619.2796; found, 619.2973.

Intermediate Example 21: Preparation of (S)-15-((2S,4R)-4-hydroxy-2-((4-(4-methylthiazol-5-yl)benzyl)carbamoyl)pyrrolidine-1-carbonyl)-16,16-dimethyl-13-oxo-4,7,10-trioxa-14-azaheptadecanoic acid (SIAIS151003)

Based on the method of scheme 6, coupling of VHL-1 with 3,3'-((oxybis(ethane-2,1-diyl))bis(oxy))dipropionic acid was performed under suitable standard coupling conditions to afford compound SIAIS151003 as a white solid (0.63 g, 59% yield). $^1$H NMR (500 MHz, DMSO) δ 8.99 (s, 1H), 8.57 (t, J=6.0 Hz, 1H), 7.92 (d, J=9.4 Hz, 1H), 7.41 (dd, J=18.5, 8.2 Hz, 4H), 4.56 (d, J=9.4 Hz, 1H), 4.47-4.41 (m, 2H), 4.36 (s, 1H), 4.23 (dd, J=15.9, 5.5 Hz, 1H), 3.70-3.57 (m, 8H), 3.51-3.47 (m, 7H), 2.58-2.52 (m, 1H), 2.47-2.42 (m, 2H), 2.45 (s, 3H), 2.39-2.32 (m, 1H), 2.08-2.00 (m, 1H), 1.94-1.88 (m, 1H), 0.94 (s, 9H). HRMS (ESI) m/z: calcd $C_{32}H_{47}N_4O_9S^+$ [M+H]$^+$, 663.3058; found, 663.3008.

Intermediate Example 22: Preparation of (S)-18-((2S,4R)-4-hydroxy-2-((4-(4-methylthiazol-5-yl)benzyl)carbamoyl)pyrrolidine-1-carbonyl)-19,19-dimethyl-16-oxo-4,7,10,13-tetraoxa-17-azaicosanoic acid (SIAIS151008)

Based on the method of scheme 6, coupling of VHL-1 with 4,7,10,13-tetraoxahexadecanedioic acid was performed under suitable standard coupling conditions to afford compound SIAIS151008 as a white solid (0.53 g, 51% yield). $^1$H NMR (500 MHz, DMSO) δ 8.98 (s, 1H), 8.56 (t, J=6.0 Hz, 1H), 7.91 (d, J=9.4 Hz, 1H), 7.40 (dd, J=18.8, 8.3 Hz, 4H), 4.55 (d, J=9.4 Hz, 1H), 4.45-4.40 (m, 2H), 4.35 (s, 1H), 4.22 (dd, J=15.8, 5.5 Hz, 1H), 3.69-3.54 (m, 10H), 3.48 (d, J=2.7 Hz, 9H), 2.56-2.52 (m, 1H), 2.45-2.41 (m, 2H), 2.45 (s, 3H), 2.38-2.32 (m, 1H), 2.06-2.00 (m, 1H), 1.94-1.88 (m, 1H), 0.93 (s, 9H). HRMS (ESI) m/z: calcd $C_{34}H_{51}N_4O_{10}S^+$ [M+H]$^+$, 707.3320; found, 707.2945.

Intermediate Example 23: Preparation of (S)-21-((2S,4R)-4-hydroxy-2-((4-(4-methylthiazol-5-yl)benzyl)carbamoyl)pyrrolidine-1-carbonyl)-22,22-dimethyl-19-oxo-4,7,10,13,16-pentaoxa-20-azatricosanoic acid (SIAIS151009)

Based on the method of scheme 6, coupling of VHL-1 with 4,7,10,13,16-pentaoxanonadecanedioic acid was performed under suitable standard coupling conditions to afford compound SIAIS151009 as a white solid (0.82 g, 85% yield). $^1$H NMR (500 MHz, DMSO) δ 8.98 (s, 1H), 8.56 (d, J=5.7 Hz, 1H), 7.91 (d, J=9.3 Hz, 1H), 7.40 (dd, J=18.6, 7.9 Hz, 4H), 4.55 (d, J=9.3 Hz, 1H), 4.47-4.40 (m, 2H), 4.35 (s, 1H), 4.22 (dd, J=15.7, 5.2 Hz, 1H), 3.68-3.56 (m, 11H), 3.51-3.49 (s, 9H), 2.56-2.53 (m, 1H), 2.45-2.41 (m, 5H), 2.44 (s, 3H), 2.36 (dd, J=13.4, 7.0 Hz, 1H), 2.08-2.00 (m, 1H), 1.94-1.86 (m, 1H), 0.93 (s, 9H). HRMS (ESI) m/z: calcd $C_{36}H_{55}N_4O_{11}S^+$ [M+H]$^+$, 751.3583; found, 751.3199.

The general method of preparation of VHL-1 alkyl carbon chain series of $HO_2C$-LIN-ULM analogs:

Scheme 7

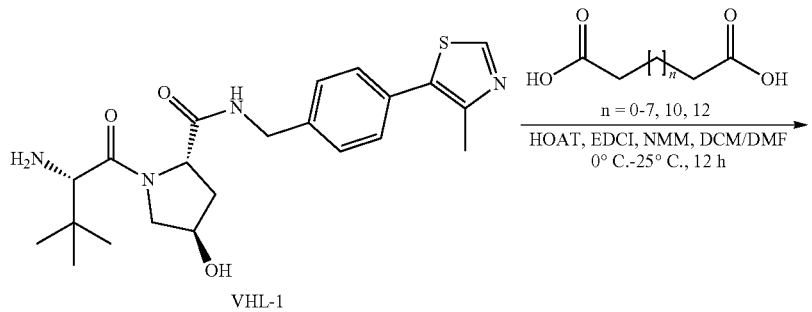

VHL-1

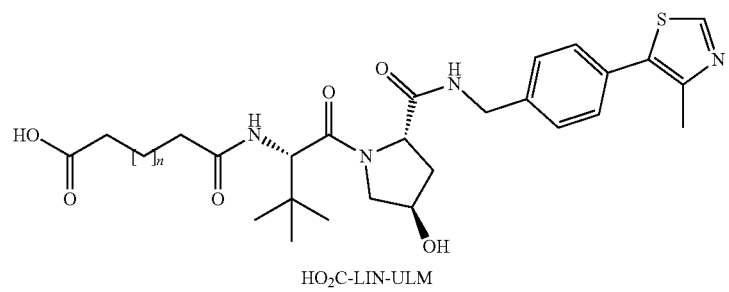

$HO_2C$-LIN-ULM

In a 250 mL of round-bottom flask, to a stirred solution of corresponding diacid linker (5.0 mmol, 2.5 equiv) in anhydrous DMF (10 mL) and DCM (150 mL) at 0° C. was added NMM (10.0 mmol, 5equiv), VHL-1 (2 mmol, 1 equiv), HOAT (2.4 mmol, 1.2equiv) and EDCI.HCl (2.4 mmol, 1.2equiv), respectively. After addition, the mixture was allowed to stir for another 12 h at room temperature. The mixture was quenched with water (1 mL) once consumed completely, concentrated to dryness under reduced pressure, the residue was purified via C18 reverse phase preparative HPLC column (eluent gradient: acetonitrile/($H_2O$+0.1% TFA)=10%-100%) to afford desired product $HO_2$C-LIN-ULM

Intermediate Example 24: Preparation of 4-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-4-oxobutanoic acid (SIAIS074011)

Based on the method of scheme 7, coupling of VHL-1 with succinic acid was performed under suitable standard coupling conditions to afford compound SIAIS074011 as a white solid (0.82 g, 65% yield). $^1$H NMR (500 MHz, CDCl$_3$) δ 11.88 (s, 1H), 8.85 (s, J=11.2 Hz, 1H), 7.69 (s, 1H), 7.37-7.29 (m, 4H), 6.09 (br, 1H), 4.67-4.54 (m, 3H), 4.49 (s, 1H), 4.29 (dd, J=15.0, 5.0 Hz, 1H), 4.05 (d, J=11.3 Hz, 1H), 3.73-3.63 (m, 1H), 2.73-2.58 (m, 1H), 2.57-2.41 (m, 3H), 2.50 (s, 3H), 2.31-2.14 (m, 2H), 0.96 (s, 9H). HRMS (ESI) m/z: calcd $C_{26}H_{35}N_4O_6S^+$ [M+H]$^+$, 531.2272; found, 531.2275.

Intermediate Example 25: Preparation of 5-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-5-oxopentanoic acid (SIAIS074012)

Based on the method of scheme 7, coupling of VHL-1 with glutaric acid was performed under suitable standard coupling conditions to afford compound SIAIS074012 as a white solid (0.85 g, 67% yield). $^1$H NMR (500 MHz, CDCl$_3$) δ 9.08 (s, 1H), 8.65 (br, 1H), 8.10 (s, 1H), 7.38-7.29 (m, 4H), 4.72-4.64 (m, 3H), 4.52 (s, 1H), 4.25 (dd, J=15.4, 5.0 Hz, 1H), 4.09 (d, J=10.5 Hz, 1H), 3.73 (d, J=10.0 Hz, 1H), 2.48 (s, 3H), 2.39-2.13 (m, 6H), 1.92-1.74 (m, 2H), 0.96 (s, 9H). HRMS (ESI) m/z: calcd $C_{27}H_{37}N_4O_6S^+$ [M+H]$^+$, 545.2428; found, 545.2428.

Intermediate Example 26: Preparation of 6-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-6-oxohexanoic acid (SIAIS074013)

Based on the method of scheme 7, coupling of VHL-1 with adipic acid was performed under suitable standard coupling conditions to afford compound SIAIS074013 as a white solid (0.79 g, 55% yield). $^1$H NMR (500 MHz, CDCl$_3$) δ 8.99 (s, 1H), 7.66 (s, 1H), 7.39-7.33 (m, 4H), 7.30 (d, J=7.5 Hz, 1H). 7.14 (br, 1H), 4.67-4.61 (m, 3H), 4.52 (s, 1H). 4.28 (dd, J=15.4, 5.0 Hz, 1H), 4.09 (d, J=11.4 Hz, 1H), 3.74-3.63 (m, 1H), 2.52 (s, 3H), 2.31-2.17 (m, 6H), 1.65-1.53 (m, 4H), 0.96 (s, 9H). HRMS (ESI) m/z: calcd $C_{28}H_{40}N_4O_6S^+$ [M+H]$^+$, 559.2585; found, 559.3632.

Intermediate Example 27: Preparation of 7-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-7-oxoheptanoic acid (SIAIS074014)

Based on the method of scheme 7, coupling of VHL-1 with heptanedioic acid was performed under suitable standard coupling conditions to afford compound SIAIS074014 as a white solid (0.8 g, 57% yield). $^1$H NMR (500 MHz, CDCl$_3$) δ 8.90 (s, 1H), 7.42-7.38 (m, 1H), 7.41-7.33 (m, 4H), 7.31 (d, J=9.0 Hz, 1H), 6.38 (br, 1H), 4.79-4.46 (m, 3H), 4.55 (s, 1H), 4.28 (dd, J=15.2, 5.1 Hz, 1H), 4.12 (d, J=11.3 Hz, 1H), 3.72-3.63 (m, 1H), 2.51 (s, 3H), 2.38-2.33 (m, 1H), 2.28-2.21 (m, 4H), 2.18-2.12 (m, 1H), 1.62-1.52 (m, 3H), 1.33-1.23 (m, 3H), 0.96 (s, 9H). HRMS (ESI) m/z: calcd $C_{29}H_{41}N_4O_6S^+$ [M+H]$^+$, 573.2741; found, 573.3804.

Intermediate Example 28: Preparation of 8-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-8-oxooctanoic acid (SIAIS074015)

Based on the method of scheme 7, coupling of VHL-1 with octanedioic acid was performed under suitable standard coupling conditions to afford compound SIAIS074015 as a white solid (0.95 g, 68% yield). $^1$H NMR (500 MHz, CDCl$_3$) δ 8.82 (s, 1H), 7.43 (t, J=6.0 Hz, 1H), 7.34 (s, 4H), 6.98 (d, J=8.5 Hz, 1H), 6.10 (s, 1H), 4.69-4.65 (m, 1H), 4.63-4.51 (m, 2H), 4.55-4.50 (m, 1H), 4.38-4.27 (m, 1H), 4.11 (d, J=16.7 Hz, 1H), 3.72-3.62 (m, 1H), 2.51 (s, 3H), 2.39-2.13 (m, 6H), 1.58-1.54 (m, 4H), 1.33-1.21 (m, 4H), 0.95 (s, 9H). HRMS (ESI) m/z: calcd $C_{30}H_{43}N_4O_6S^+$ [M+H]$^+$, 587.2898; found, 587.2917.

Intermediate Example 29: Preparation of 9-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-9-oxononanoic acid (SIAIS074016)

Based on the method of scheme 7, coupling of VHL-1 with nonanedioic acid was performed under suitable standard coupling conditions to afford compound SIAIS074016 as a white solid (0.92 g, 64% yield). $^1$H NMR (500 MHz, CDCl$_3$) δ 8.82 (s, 1H), 7.35 (s, 4H), 7.02 (t, J=14.3 Hz, 1H), 5.99 (s, 1H), 4.74-4.49 (m, 4H), 4.30 (dd, J=15.2, 5.1 Hz, 1H), 4.13 (d, J=11.3 Hz, 1H), 3.67 (dd, J=11.5, 3.5 Hz, 1H), 2.51 (s, 3H), 2.42-2.36 (m, 1H), 2.28 (t, J=7.5 Hz, 2H), 2.24-2.12 (m, 3H), 1.67-1.48 (m, 4H), 1.35-1.22 (m, 6H), 0.95 (s, 9H). HRMS (ESI) m/z: calcd $C_{31}H_{45}N_4O_6S^+$ [M+H]$^+$, 601.3054; found, 601.3150.

Intermediate Example 30: Preparation of 10-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-10-oxodecanoic acid (SIAIS074019)

Based on the method of scheme 7, coupling of VHL-1 with decanedioic acid was performed under suitable standard coupling conditions to afford compound SIAIS074019 as a white solid (0.96 g, 66% yield). $^1$H NMR (500 MHz, CDCl$_3$) δ 8.79 (s, 1H), 7.39-7.36 (m, 1H), 7.35 (s, 4H), 7.01 (d, J=9.0 Hz, 1H), 5.80 (s, 1H), 4.68-4.52 (m, 4H), 4.29 (dd, J=15.2, 5.0 Hz, 1H), 4.12 (d, J=11.2 Hz, 1H), 3.72-3.62 (m, 1H), 2.51 (s, 3H), 2.41-2.33 (m, 1H), 2.32-2.23 (m, 2H), 2.23-2.11 (m, 3H), 1.65-1.48 (m, 4H), 1.32-1.21 (m, 8H), 0.95 (s, 9H). HRMS (ESI) m/z: calcd $C_{32}H_{47}N_4O_6S^+$ [M+H]$^+$, 615.3211; found, 615.4391.

Intermediate Example 31: Preparation of 11-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-11-oxoundecanoic acid (SIAIS074020)

Based on the method of scheme 7, coupling of VHL-1 with undecanedioic acid was performed under suitable standard coupling conditions to afford compound SIAIS074020 as a white solid (1.0 g, 67% yield). $^1$H NMR (500 MHz, CDCl$_3$) δ 8.77 (s, 1H), 7.39-7.32 (m, 4H), 7.30 (m, 1H), 7.01 (d, J=8.8 Hz, 1H), 5.52 (br, 1H), 4.69-4.59 (m, 3H), 4.53 (s, 1H), 4.29 (dd, J=15.2, 5.0 Hz, 1H), 4.14 (d, J=11.3 Hz, 1H), 3.68-3.64 (m, 1H), 2.51 (s, 3H), 2.44-2.40 (m, 1H), 2.29 (t, J=7.1 Hz, 2H), 2.26-2.12 (m, 3H), 1.68-1.48 (m, 4H), 1.30-1.20 (m, 10H), 0.95 (s, 9H). HRMS (ESI) m/z: calcd $C_{33}H_{49}N_4O_6S^+$ [M+H]$^+$, 629.3367; found, 629.4540.

Intermediate Example 32: Preparation of 14-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-14-oxotetradecanoic acid (SIAIS164185)

Based on the method of scheme 7, coupling of VHL-1 with tetradecanedioic acid was performed under suitable standard coupling conditions to afford compound SIAIS164185 as a white solid (523 mg, 70% yield). $^1$H NMR (500 MHz, MeOD) δ 8.95 (s, 1H), 7.48 (d, J=8.4 Hz, 2H), 7.44-7.41 (m, 2H), 4.64 (s, 1H), 4.58-4.49 (m, 3H), 4.36 (d, J=15.4 Hz, 1H), 3.91 (d, J=11.0 Hz, 1H), 3.81 (dd, J=10.9, 3.9 Hz, 1H), 2.48 (s, 3H), 2.32-2.22 (m, 11H), 2.12-2.05 (m, 1H), 1.63-1.56 (m, 10H), 1.29-1.28 (m, 8H), 1.04 (s, 9H). HRMS (ESI) m/z: calcd $C_{36}H_{55}N_4O_6S^+$ [M+H]$^+$, 671.3837; found, 671.0892.

Intermediate Example 33: Preparation of 16-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-16-oxohexadecanoic acid (SIAIS164189)

Based on the method of scheme 7, coupling of VHL-1 with hexadecanedioic acid was performed under suitable standard coupling conditions to afford compound SIAIS164189 as a white solid (488 mg, 68% yield). $^1$H NMR (500 MHz, MeOD) δ 8.90 (s, 1H), 7.49-7.44 (m, 2H), 7.44-7.40 (m, 2H), 4.64 (s, 1H), 4.59-4.48 (m, 3H), 4.40-4.31 (m, 1H), 3.90 (d, J=11.1 Hz, 1H), 3.80 (dd, J=10.9, 3.9 Hz, 1H), 2.48 (s, 3H), 2.30-2.25 (m, 8H), 2.23-2.19 (m, 1H), 2.11-2.06 (m, 1H), 1.62-1.59 (m, 10H), 1.30-1.29 (m, 6H), 1.04 (s, 9H). HRMS (ESI) m/z: calcd $C_{38}H_{59}N_4O_6S^+$ [M+H]$^+$, 699.4150; found, 699.0566.

The general method of preparation of other HO$_2$C-LIN-ULM analogs:

Intermediate Example 34: Preparation of 6-(2-(2-((6-((2-(2,6-dioxopiperidin-3-yl)-1,3-dioxoisoindolin-4-yl)amino)-6-oxohexyl)oxy)ethoxy)ethoxy)hexanoic acid (SIAIS171104B)

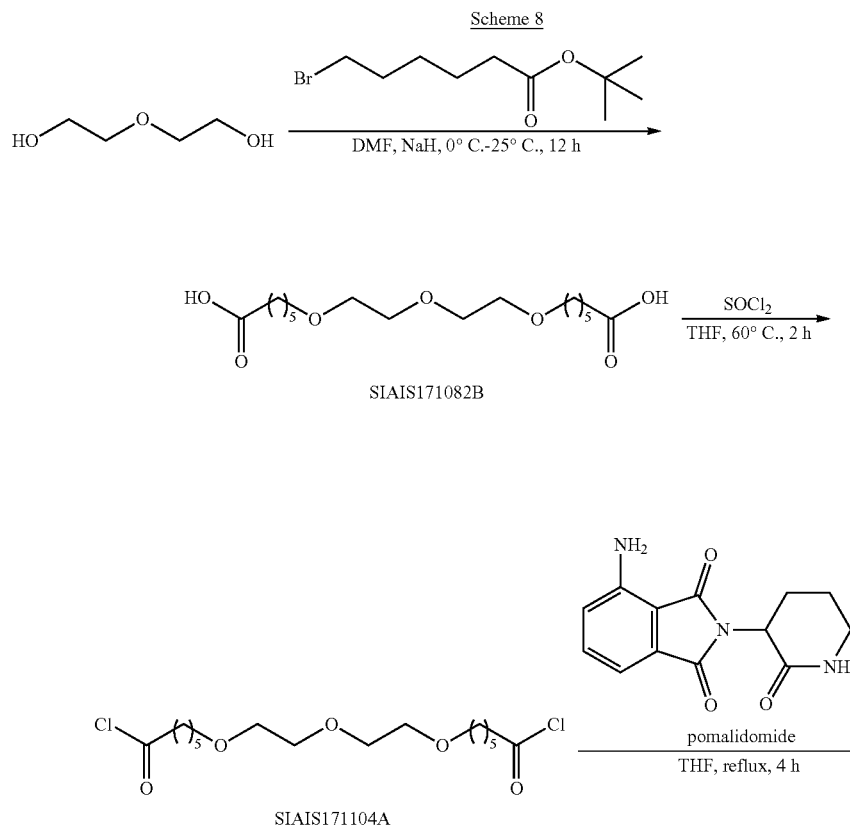

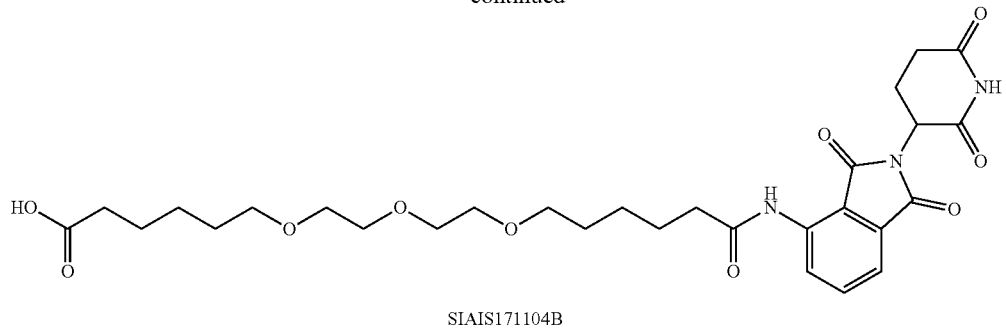

SIAIS171104B

Step 1: Based on Scheme 8, Preparation of 6,6'-((oxybis(ethane-2,1-diyl))bis(oxy))dihexanoic acid (SIAIS171082B)

In a 100 mL of round-bottom flask, to a stirred solution of 2,2'-oxybis(ethan-1-ol) (500 mg, 4.71 mmol) and tert-butyl 6-bromohexanoate (2370 mg, 9.42 mmol) in anhydrous DMF (15 mL) was added slowly NaH (566 mg, 14.13 mmol, 60% in oil) at 0° C. under nitrogen atmosphere. After addition, the mixture was stirred for 10 min at 0° C., then stirred for another 12 h at room temperature. The mixture was slowly quenched with water at 0° C. when the starting material was consumed completely, extracted with EtOAc (50 mL×3), the combined organic layers was washed with water (50 mL×3) and brine (500 mL), respectively, dried over $Na_2SO_4$, filtered, concentrated to dryness under reduced pressure to afford desired product (SIAIS171082B) as a light yellow oil (620 mg, 39% yield), which was directly used for the next step without further purification. $^1$H NMR (500 MHz, $CDCl_3$) δ 3.67-3.62 (m, 4H), 3.60-3.54 (m, 4H), 3.49-3.45 (m, 4H), 2.38-2.35 (m, 4H), 1.68-1.57 (m, 8H), 1.46-1.40 (m, 4H). HRMS (ESI) m/z: calcd $C_{16}H_{31}O_7^+$ [M+H]$^+$, 335.2064; found, 334.9111.

Step 2: Based on Scheme 8, Preparation of 6,6'-((oxybis(ethane-2,1-diyl))bis(oxy))dihexanoyl chloride (SIAIS171104A)

In a 50 mL of round-bottom flask, to a stirred solution of (SIAIS171082B) (100 mg, 0.30 mmol) in anhydrous THF (15 mL) was dropwise added thionyl chloride (0.2 mL) at room temperature. After addition, the mixture was stirred for 2 h at refluxing condition. Once the starting material was consumed completely, The reaction solvent was removed under reduced pressure to afford desired product (SIAIS171104A) as a rufous oil (150 mg), which was directly used for the next step without further purification.

Step 3: Based on Scheme 8, Preparation of 6-(2-(2-((6-((2-(2,6-dioxopiperidin-3-yl)-1,3-dioxoisoindolin-4-yl)amino)-6-oxohexyl)oxy)ethoxy)ethoxy)hexanoic acid (SIAIS171104B)

In a 25 mL of round-bottom flask, to a stirred suspension solution of pomalidomide (40 mg, 0.15 mmol) in anhydrous THF (3 mL) was dropwise added SIAIS171104A (150 mg, residue) at room temperature. After addition, the mixture was stirred for 4 h at refluxing condition. The mixture was cooled to room temperature when the starting material was consumed completely, then quenched with water (1 mL), and stirred for 30 min, concentrated to dryness under reduced pressure, the residue was purified via C18 reverse phase preparative HPLC column (eluent gradient: acetonitrile/($H_2O$+0.1% TFA)=10%-100%) to afford desired product (SIAIS171104B) as a light yellow solid (20 mg, 23% yield). HRMS (ESI) m/z: calcd $C_{29}H_{40}N_3O_{10}^+$ [M+H]$^+$, 590.2708; found, 590.2694.

The general method of preparation of other $HO_2C$-LIN-ULM analogs:

Scheme 9

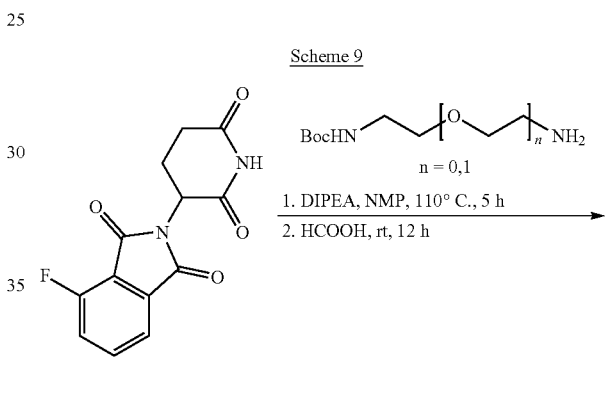

n = 0, SIAIS151103
n = 1, SIAIS151012B n = 0, SIAIS164119
n = 1, SIAIS164118

Intermediate Example 35: Preparation of 4-((2-aminoethyl)amino)-2-(2,6-dioxopiperidin-3-yl)isoindoline-1,3-dione (SIAIS151103)

Step 1: Based on Scheme 9, Preparation of 4-((2-aminoethyl)amino)-2-(2,6-dioxopiperidin-3-yl)isoindoline-1,3-dione (SIAIS151103)

In a 30 mL microwave reaction tube, to a stirred solution of 2-(2,6-dioxopiperidin-3-yl)-4-fluoroisoindoline-1,3-dione (2.0 g, 7.24 mmol), tert-butyl (2-aminoethyl)carbamate (1.28 g, 7.96 mmol) and N,N-diisopropylethylamine (4.68 g, 36.2 mmol) was added NMP (10 mL), the mixture was stirred for 10 minitues at room temperature, then it was heated to 110° C. in microwave reactor and stirred for another 2 h at Argon atmosphere. The reaction mixture was then cooled to room temperature, the mixture was poured into 90% NaCl aqueous, followed by extraction with EtOAc (4×50 mL), the combined organic layers were washed with water (2×30 mL) and brine (20 mL), dried over $Na_2SO_4$, and concentrated under reduced pressure, the residue was subjected to flash column chromatography with PE/EtOAc (1:1) to afford analog; the obtained analog and 88% HCOOH (20 mL) were added to a 50 mL of round-bottom flask, and then the mixture was stirred for 12 h at room temperature. The reaction solvent was removed under reduced pressure, then the residue was treated by addition of water, freeze-drying to afford desired product (SIAIS151103) as a yellow solid (1.6 g, 70% yield: two steps). $^1$H NMR (500 MHz, DMSO) δ 8.36 (s, 2H), 7.64-7.58 (m, 1H), 7.18 (t, J=6.2 Hz, 1H), 7.07 (d, J=7.1 Hz, 1H), 6.84 (t, J=6.2 Hz, 1H), 5.06 (dd, J=12.7, 5.4 Hz, 1H), 3.56 (dd, J=12.2, 6.0 Hz, 2H), 2.96 (t, J=6.1 Hz, 2H), 2.93-2.85 (m, 1H), 2.61-2.51 (m, 2H), 2.06-2.00 (m, 1H). HRMS (ESI) m/z: calcd $C_{15}H_{17}N_4O_4^+$ [M+H]$^+$, 317.1244; found, 317.1236.

Intermediate Example 36: Preparation of 4-((2-(2-aminoethoxy)ethyl)amino)-2-(2,6-dioxopiperidin-3-yl)isoindoline-1,3-dione (SIAIS151012B)

Step 1: Based on Scheme 9, Preparation of 4-((2-(2-aminoethoxy)ethyl)amino)-2-(2,6-dioxopiperidin-3-yl)isoindoline-1,3-dione (SIAIS151012B)

In a 30 mL microwave reaction tube, to a stirred solution of 2-(2,6-dioxopiperidin-3-yl)-4-fluoroisoindoline-1,3-dione (1.35 g, 4.90 mmol), tert-butyl (2-aminoethyl)carbamate (1.5 g, 5.39 mmol) and N,N-diisopropylethylamine (3.16 g, 24.5 mmol) was added NMP (10 mL), the mixture was stirred for 10 minutes at room temperature, then it was heated to 110° C. in microwave reactor and stirring for another 2 h at Argon atmosphere. The reaction mixture was then cooled to room temperature, the mixture was then poured into 90% NaCl aqueous followed by extracted with EtOAc (4×50 mL), the combined organic layers were washed with water (2×30 mL) and brine (20 mL), dried over $Na_2SO_4$, and concentrated to dryness under reduced pressure, the residue was subjected to flash column chromatography with PE/EtOAc (1:1) to afford intermediate; the obtained intermediate and 88% HCOOH (20 mL) were added to a 50 mL of round-bottom flask, and then the mixture was stirred for 12 h at room temperature. The reaction solvent was removed under reduced pressure, then the residue was treated by addition of water, freeze-drying to afford desired product (SIAIS151012B) as a yellow solid (856.6 mg, 49% yield: two steps). $^1$H NMR (500 MHz, DMSO) δ 8.33 (s, 1H), 7.61-7.57 (m, 1H), 7.16 (dd, J=8.5, 6.4 Hz, 1H), 7.05 (dd, J=7.0, 4.3 Hz, 1H), 6.67-6.57 (m, 1H), 5.05 (dd, J=12.8, 5.4 Hz, 1H), 3.64-3.60 (m, 3H), 3.58-3.55 (m, 2H), 3.51-3.46 (m, 3H), 2.90-2.88 (m, 1H), 2.63-2.51 (m, 2H), 2.06-2.00 (m, 1H). HRMS (ESI) m/z: calcd $C_{17}H_{21}N_4O_5^+$ [M+H]$^+$, 361.1506; found, 361.1685.

Intermediate Example 37: Preparation of 4-((2-((2-(2,6-dioxopiperidin-3-yl)-1,3-dioxoisoindolin-4-yl)amino)ethyl)amino)-4-oxobutanoic acid (SIAIS164119)

Based on Scheme 9, Preparation of 4-((2-((2-(2,6-dioxopiperidin-3-yl)-1,3-dioxoisoindolin-4-yl)amino)ethyl)amino)-4-oxobutanoic acid (SIAIS164119)

In a 100 mL of round-bottom flask, to a stirred solution of succinic acid linker (325 mg, 2.75 mmol) in anhydrous DMF (5 mL) and DCM (50 mL) at 0° C. was added NMM (1.12 g, 11 mmol), compound (SIAIS151103) (350 mg, 1.10 mmol), HOAt (180 mg, 1.32 mmol) and EDCI.HCl (252 mg, 1.32 mmol), respectively. After addition, the mixture was allowed to stir for another 12 h at room temperature. The mixture was quenched with water (1 mL) once the starting material was consumed completely, concentrated to dryness under reduced pressure, the residue was purified via C18 reverse phase preparative HPLC column (eluent gradient: acetonitrile/($H_2O$+0.1% TFA)=10%-100%) to afford desired product (SIAIS164119) as a yellow solid (170 mg, 41% yield). $^1$H NMR (500 MHz, MeOD) δ 7.55-7.50 (m, 1H), 7.10 (d, J=8.6 Hz, 1H), 7.04 (t, J=6.3 Hz, 1H), 5.05 (dd, J=12.4, 5.5 Hz, 1H), 3.47-3.39 (m, 4H), 2.89-2.82 (m, 1H), 2.79-2.65 (m, 2H), 2.58 (t, J=7.0 Hz, 2H), 2.45 (t, J=7.0 Hz, 2H), 2.16-2.05 (m, 1H). HRMS (ESI) m/z: calcd $C_{19}H_{21}N_4O_7^+$ [M+H]$^+$, 417.1405; found, 417.0916.

Intermediate Example 38: Preparation of 4-((2-(2-((2-(2,6-dioxopiperidin-3-yl)-1,3-dioxoisoindolin-4-yl)amino)ethoxy)ethyl)amino)-4-oxobutanoic acid (SIAIS164118)

Based on Scheme 9, Preparation of 4-((2-(2-((2-(2,6-dioxopiperidin-3-yl)-1,3-dioxoisoindolin-4-yl)amino)ethoxy)ethyl)amino)-4-oxobutanoic acid (SIAIS164118)

In a 100 mL of round-bottom flask, to a stirred solution of succinic acid linker (325 mg, 2.75 mmol) in anhydrous DMF (5 mL) and DCM (50 mL) at 0° C. was added NMM (1.12 g, 11 mmol), compound (SIAIS151012B) (390 mg, 1.10 mmol), HOAt (180 mg, 1.32 mmol) and EDCI.HCl (252 mg, 1.32 mmol), respectively. After addition, the mixture was allowed to stir for another 12 h at room temperature. The mixture was quenched with water (1 mL) once the starting material was consumed completely, concentrated to dryness under reduced pressure, the residue was purified via C18 reverse phase preparative HPLC column (eluent gradient: acetonitrile/($H_2O$+0.1% TFA)=10%-100%) to afford desired product (SIAIS164118) as a yellow solid (280 mg, 61% yield). $^1$H NMR (500 MHz, MeOD) δ 7.59-7.53 (m, 1H), 7.12-7.04 (m, 2H), 5.11-5.03 (m, 1H), 3.71 (t, J=5.2 Hz, 2H), 3.58 (dd, J=11.4, 5.6 Hz, 2H), 3.50 (dd, J=10.8, 5.4 Hz, 2H), 3.45-3.37 (m, 2H), 3.32-3.31 (m, 2H), 2.92-2.82 (m, 1H), 2.79-2.65 (m, 2H), 2.63-2.56 (m, 1H), 2.55-2.48 (m, 1H), 2.15-2.07 (m, 1H). HRMS (ESI) m/z: calcd $C_{21}H_{25}N_4O_8^+$ [M+H]$^+$, 461.1667; found, 461.1672.

Intermediate Example 39: Preparation of 5-((2-(2,6-dioxopiperidin-3-yl)-1,3-dioxoisoindolin-4-yl)amino)-5-oxopentanoic acid (SIAIS184044)

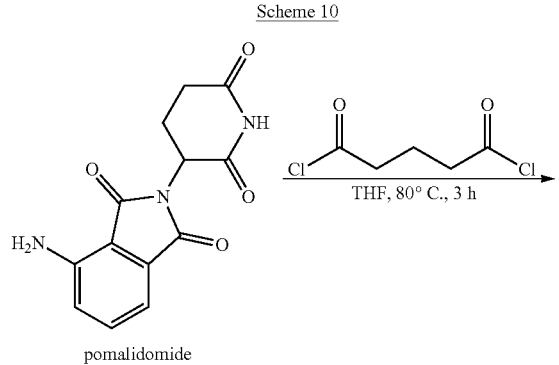

General Preparation Method of Other HO₂C-LIN-ULM Analogs

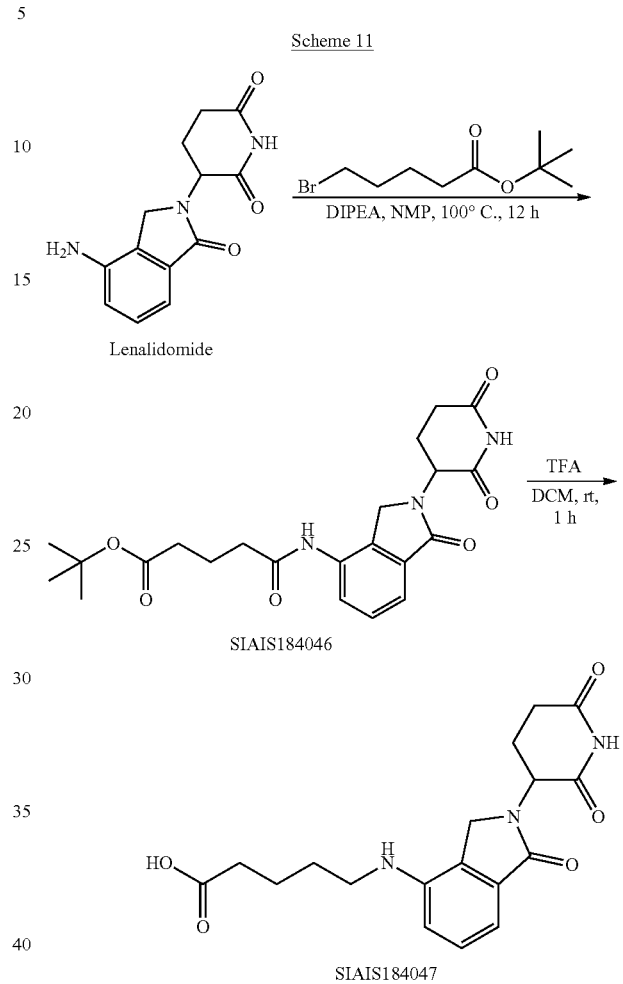

Intermediate Example 40: Preparation of tert-butyl 5-((2-(2,6-dioxopiperidin-3-yl)-1-oxoisoindolin-4-yl)amino)pentanoate (SIAIS184046)

Based on Scheme 10, Preparation of 5-((2-(2,6-dioxopiperidin-3-yl)-1,3-dioxoisoindolin-4-yl)amino)-5-oxopentanoic acid (SIAIS184044)

In a 100 mL of round-bottom flask, to a stirred solution of pomalidomide (273.2 mg, 1.0 mmol) in anhydrous THF (15 mL) was dropwise added glutaroyl dichloride (0.64 mL, 5.0 mmol) at room temperature. After addition, the mixture was stirred for 3 h at 80° C. The mixture was cooled to room temperature, quenched with water (0.5 mL), concentrated to dryness under reduced pressure, the residue was purified via C18 reverse phase preparative HPLC column (eluent gradient: acetonitrile/(H₂O+0.1% TFA)=10%-100%) to afford desired product (SIAIS184044) as a light solid (193.7 mg, 50% yield). $^1$H NMR (500 MHz, DMSO) δ 11.14 (s, 1H), 9.73 (s, 1H), 8.44 (d, J=8.4 Hz, 1H), 7.83 (dd, J=8.3, 7.5 Hz, 1H), 7.62 (d, J=7.3 Hz, 1H), 5.14 (dd, J=12.9, 5.4 Hz, 1H), 2.93-2.86 (m, 1H), 2.65-2.51 (m, 4H), 2.37-2.26 (m, 2H), 2.12-2.02 (m, 1H), 1.91-1.78 (m, 2H). HRMS (ESI) m/z: calcd $C_{18}H_{18}N_3O_7^+$ [M+H]⁺, 388.1139; found, 388.1149.

Based on Scheme 11, Preparation of tert-butyl 5-((2-(2,6-dioxopiperidin-3-yl)-1-oxoisoindolin-4-yl)amino)pentanoate (SIAIS184046)

In a 25 mL of round-bottom flask, to a stirred solution of Lenalidomide (259.3 mg, 1 mmol) in NMP (8 mL) was added N,N-diisopropylethylamine (25 mmol, 5.0 equiv) and tert-butyl 5-bromopentanoate (284.6 mg, 1.2 mmol). After addition, the mixture was stirred for 12 h at 100° C. Once the starting material was consumed completely, the mixture was purified via $C_{18}$ reverse phase preparative HPLC column (eluent gradient: acetonitrile/(H₂O+0.1% TFA)=10%-100%) to afford desired product (SIAIS184046) as a light yellow solid (260 mg, 63% yield). $^1$H NMR (500 MHz, DMSO) δ 11.00 (s, 1H), 7.28 (t, J=7.7 Hz, 1H), 6.92 (d, J=7.2 Hz, 1H), 6.74 (d, J=8.0 Hz, 1H), 5.58 (s, 1H), 5.11 (dd, J=13.3, 5.1 Hz, 1H), 4.22 (d, J=17.1 Hz, 1H), 4.12 (d, J=17.1 Hz, 1H), 3.12 (t, J=6.1 Hz, 2H), 2.95-2.89 (m, 1H), 2.62 (d, J=16.7 Hz, 1H), 2.36-2.19 (m, 3H), 2.08-1.96 (m, 1H), 1.59

(dd, J=8.4, 5.1 Hz, 4H), 1.39 (d, J=6.1 Hz, 9H). HRMS (ESI) m/z: calcd $C_{22}H_{30}N_3O_5^+$ [M+H]$^+$, 416.2180; found, 416.1274.

Intermediate Example 41: preparation of tert-butyl 5-((2-(2,6-dioxopiperidin-3-yl)-1-oxoisoindolin-4-yl)amino)pentanoic acid (SIAIS184047)

Based on Scheme 11, Preparation of tert-butyl 5-((2-(2,6-dioxopiperidin-3-yl)-1-oxoisoindolin-4-yl)amino)pentanoic acid (SIAIS184047)

To a stirred solution of (SIAIS184046) (260 mg, 0.63 mmol) in DCM (5 mL) was added TFA (15 mL) in a 25 mL of round-bottom flask. After addition, the mixture was stirred for 1 h at room temperature. The reaction solvent was removed under reduced pressure, the residue was added water, freeze-dried to afford desired product (SIAIS184047) as a light yellow solid (210 mg, 93% yield). $^1$H NMR (500 MHz, DMSO) δ 11.00 (s, 1H), 7.28 (t, J=7.7 Hz, 1H), 6.92 (t, J=10.9 Hz, 1H), 6.76 (d, J=8.0 Hz, 1H), 5.11 (dd, J=13.3, 5.1 Hz, 1H), 5.07-4.83 (m, 3H), 4.23 (d, J=17.2 Hz, 1H), 4.13 (d, J=17.1 Hz, 1H), 3.13 (d, J=6.4 Hz, 2H), 2.97-2.87 (m, 1H), 2.61 (d, J=16.7 Hz, 1H), 2.38-2.21 (m, 3H), 2.06-1.98 (m, 1H), 1.67-1.55 (m, 4H); HRMS (ESI) m/z: calcd $C_{18}H_{22}N_3O_5^+$ [M+H]$^+$, 360.1554; found, 360.0739.

Intermediate Example 42: preparation of (S)-3-((2S, 4R)-4-hydroxy-2-((4-(4-methylthiazol-5-yl)benzyl) carbamoyl)pyrrolidine-1-carbonyl)-2,2-dimethyl-5-oxo-11,14,17-trioxa-4-azatricosan-23-oic acid (SIAIS180127)

Scheme 12

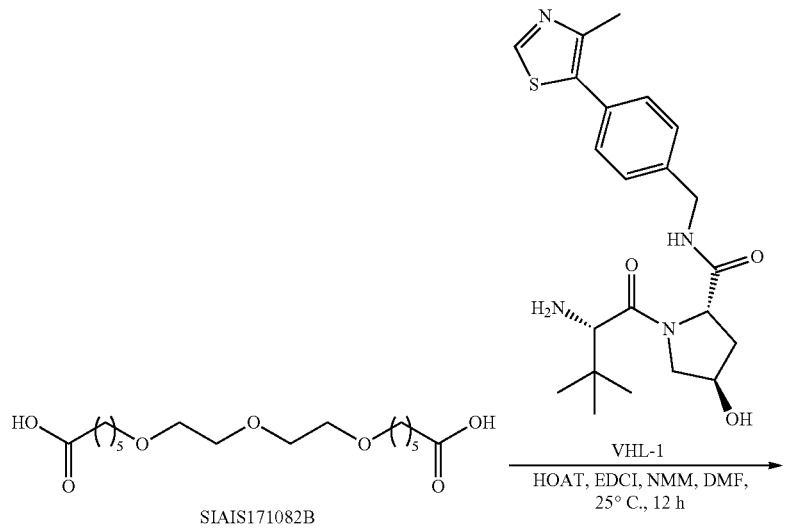

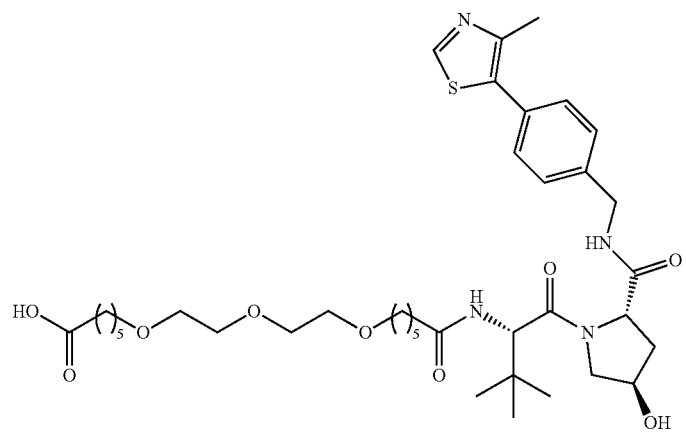

SIAIS180127

Based on Scheme 12, Preparation of (S)-3-((2S,4R)-4-hydroxy-2-((4-(4-methylthiazol-5-yl)benzyl)carbamoyl)pyrrolidine-1-carbonyl)-2,2-dimethyl-5-oxo-11,14,17-trioxa-4-azatricosan-23-oic acid (SIAIS180127)

In a 10 mL of round-bottom flask, to a stirred solution of SIAIS171082B (46 mg, 0.14 mmol) in anhydrous DMF (0.3 mL) and DCM (1.2 mL) at room temperature was added VHL-1 (32 mg, 0.07 mmol), HOAt (14 mg, 0.10 mmol), EDC.HCl (20 mg, 0.10 mmol) and NMM (35 mg, 0.34 mmol). After addition, the mixture was stirred for 12 h at room temperature. LC-MS analysis showed the product peak, then the mixture was purified via C18 reverse phase preparative HPLC column (eluent gradient: acetonitrile/($H_2O$+0.1% TFA)=10%-100%) to afford desired product (SIAIS180127) as a white solid (33 mg, 64% yield). $^1$H NMR (500 MHz, MeOD) δ 9.05 (s, 1H), 7.49 (d, J=8.1 Hz, 2H), 7.43 (d, J=8.2 Hz, 2H), 4.64 (s, 1H), 4.59-4.49 (m, 3H), 4.36 (d, J=15.5 Hz, 1H), 3.91 (d, J=11.2 Hz, 1H), 3.80 (dd, J=11.0, 3.8 Hz, 1H), 3.63-3.61 (m, 4H), 3.58-3.56 (m, 4H), 3.50-3.44 (m, 4H), 2.50 (s, 3H), 2.36-2.19 (m, 5H), 2.11-2.05 (m, 1H), 1.66-1.55 (m, 8H), 1.44-1.36 (m, 4H), 1.04 (s, 9H). HRMS (ESI) m/z: calcd $C_{38}H_{59}N_4O_9S^+$ $[M+H]^+$, 747.3997; found, 746.6856.

Intermediate Example 43: Preparation of 5-(10-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-10-oxodecanamido)pentanoicacid (SIAIS164178B)

Based on Scheme 13, Preparation of 5-(10-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-10-oxodecanamido)pentanoic acid (SIAIS164178B)

To a stirred solution of compound SIAIS074019 (40 mg, 0.07 mmol) in anhydrous DMF (2 mL) at room temperature was added tert-butyl 5-aminopentanoate (11.3 mg, 0.07 mmol), HOAt (17.7 mg, 0.14 mmol), EDCI.HCl (24.9 mg, 0.14 mmol) and NMM (32.9 mg, 0.35 mmol). After addition, the mixture was stirred for 12 h at room temperature. LC-MS analysis showed the product peak, then the mixture was purified via C18 reverse phase preparative HPLC column (eluent gradient: acetonitrile/($H_2O$+0.1% TFA)=10%-100%) to afford the analog. The obtained analog was added to a 25 mL of round-bottom flask with DCM (1 mL) and TFA (3 mL), then the mixture was stirred for 2 h. Once the starting material was consumed completely, concentrated to dryness under reduced pressure, the residue was added water, freeze-dried to afford desired product (SIAIS164178B) as a white solid (24 mg, 92% yield), which was used for the next step without further purification. $^1$H NMR (500 MHz, DMSO) δ 8.99 (s, 1H), 8.58-8.51 (m, 1H), 7.83 (d, J=9.4 Hz, 1H), 7.73 (t, J=5.6 Hz, 1H), 7.40 (q, J=8.4 Hz, 4H), 4.54 (d, J=9.4 Hz, 1H), 4.45-4.40 (m, 2H), 4.35 (s, 1H), 4.24-4.20 (m, 2H), 3.69-3.63 (m, 3H), 3.03-2.97 (m, 2H), 2.45 (s, 3H), 2.22-2.17 (m, 2H), 2.13-2.07 (m, 1H), 2.05-1.99 (m, 2H), 1.94-1.86 (m, 1H), 1.49-1.44 (m, 6H), 1.41-1.34 (m, 2H), 1.23 (d, J=6.7 Hz, 8H), 0.92 (s, 9H). HRMS (ESI) m/z: calcd $C_{37}H_{56}N_5O_7S^+$ $[M+H]^+$, 714.3895; found, 714.1117.

Scheme 13

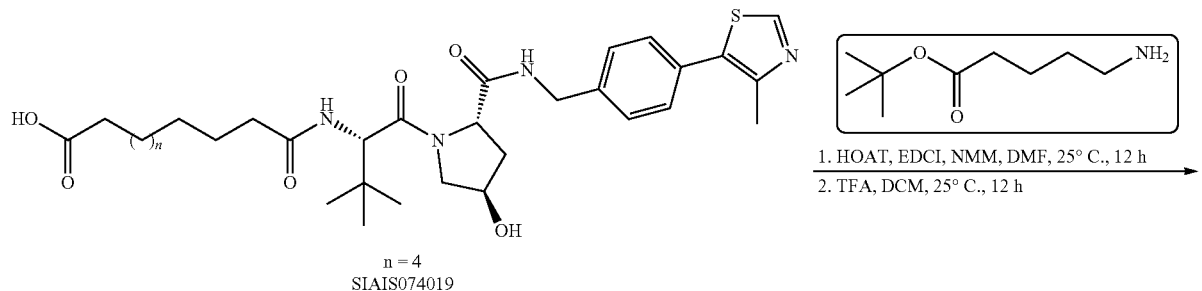

n = 4
SIAIS074019

1. HOAT, EDCI, NMM, DMF, 25° C., 12 h
2. TFA, DCM, 25° C., 12 h

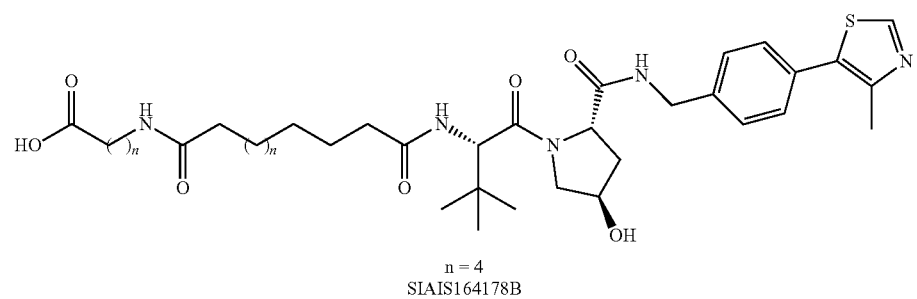

n = 4
SIAIS164178B

General Preparation Method of Other HO₂C-LIN-ULM Analogs

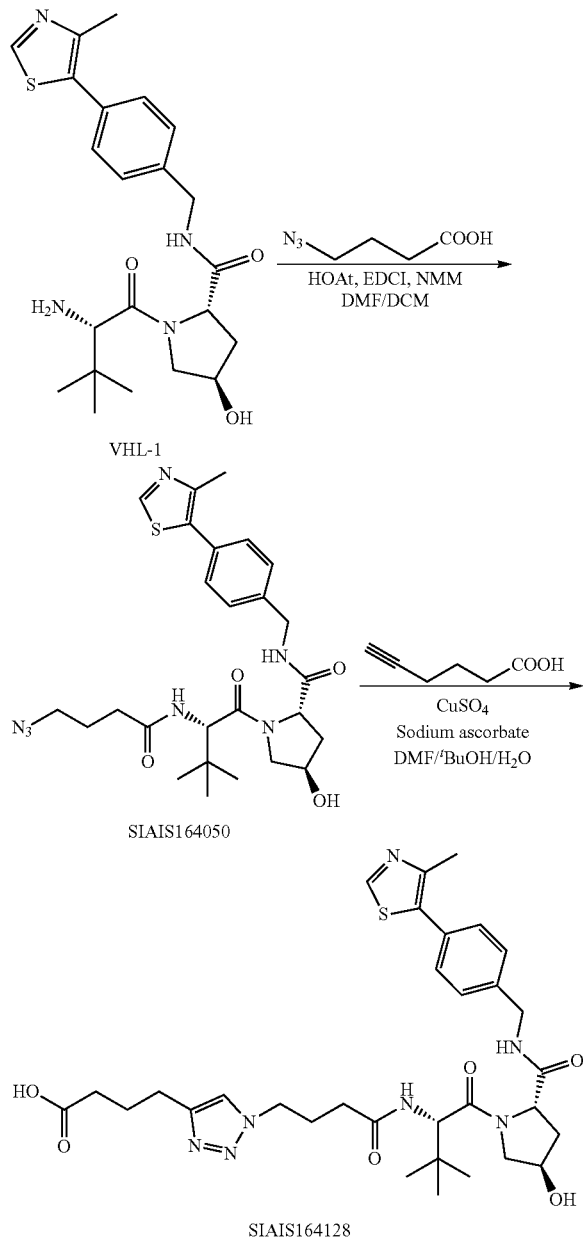

Intermediate Example 44: Preparation of (2S,4R)-1-((S)-2-(4-azidobutanamido)-3,3-dimethylbutanoyl)-4-hydroxy-N-(4-(4-methylthiazol-5-yl)benzyl)pyrrolidine-2-carboxamide (SIAIS164050)

Based on Scheme 14, Preparation of 5(2S,4R)-1-((S)-2-(4-azidobutanamido)-3,3-dimethylbutanoyl)-4-hydroxy-N-(4-(4-methylthiazol-5-yl)benzyl)pyrrolidine-2-carboxamide (SIAIS164050)

To a stirred solution of VHL-1 (934 mg, 2.0 mmol) in anhydrous DMF (5 mL) and DCM (20 mL) at room temperature was added 4-azidobutanoic acid (258.2 mg, 2.0 mmol), HOAt (54.4 mg, 0.4 mmol), EDCI.HCl (766.8 mg, 4 mmol) and NMM (2.02 g, 20 mmol). After addition, the mixture was stirred for 12 h at room temperature. LC-MS analysis showed the product peak, the solvent was removed under reduced pressure, the mixture was poured into 90% NaCl aqueous, extracted with EtOAc (4×50 mL), the combined organic layers were washed with water (2×30 mL) and brine (50 mL), dried over Na₂SO₄, concentrated to dryness in vaccum, the residue was subjected to flash column chromatography with DCM/MeOH (40:1) to afford desired product (SIAIS164050) as a light yellow oil (734 mg, 68% yield). $^1$H NMR (500 MHz, MeOD) δ 8.87 (s, 1H), 7.48-7.41 (m, 4H), 4.62 (s, 1H), 4.58-4.50 (m, 3H), 4.38-4.33 (m, 1H), 3.91 (d, J=11.0 Hz, 1H), 3.80 (dd, J=10.9, 3.9 Hz, 1H), 3.33 (t, J=5.0 Hz, 2H), 2.48 (d, J=5.3 Hz, 3H), 2.41-2.32 (m, 2H), 2.22 (dd, J=13.1, 7.6 Hz, 1H), 2.11-2.06 (m, 1H), 1.90-1.82 (m, 2H), 1.04 (s, 9H). HRMS (ESI) m/z: calcd $C_{26}H_{36}N_7O_4S^+$ [M+H]⁺, 542.2544; found, 542.2256.

Intermediate Example 45: Preparation of 4-(1-(4-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-4-oxobutyl)-1H-1,2,3-triazol-4-yl)butanoic acid (SIAIS164128)

Based on Scheme 14, Preparation of 4-(1-(4-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-4-oxobutyl)-1H-1,2,3-triazol-4-yl)butanoic acid (SIAIS164128)

To a stirred solution of compound (SIAIS164050) (108.3 mg, 0.2 mmol) in DMF (1 mL), ᵗBuOH (1mL) and H₂O (1 mL) at room temperature was added hex-5-ynoic acid (22.4 mg, 0.2 mmol), CuSO4 (31.9 mg, 0.2 mmol) and sodium ascorbate (39.6 mg, 0.2 mmol). After addition, the mixture was stirred for 2 h at room temperature. LC-MS analysis showed the product peak, then the mixture was purified via C18 reverse phase preparative HPLC column (eluent gradient: acetonitrile/(H₂O+0.1% TFA)=10%-100%) to afford desired product (SIAIS164128) as a white solid (100 mg, 76% yield). $^1$H NMR (500 MHz, MeOD) δ 9.19 (d, J=3.4 Hz, 1H), 7.87 (s, 1H), 7.51-7.42 (m, 4H), 4.60 (s, 1H), 4.59-4.54 (m, 2H), 4.51 (s, 1H), 4.43 (t, J=6.8 Hz, 2H), 4.36 (d, J=15.3 Hz, 1H), 3.93 (d, J=11.1 Hz, 1H), 3.80 (dd, J=11.0, 3.8 Hz, 1H), 2.77 (t, J=7.6 Hz, 2H), 2.51 (d, J=3.8 Hz, 3H), 2.36 (t, J=7.3 Hz, 2H), 2.32-2.28 (m, 2H), 2.25-2.15 (m, 3H), 2.11-2.06 (m, 1H), 2.00-1.94 (m, 2H), 1.04 (s, 9H). HRMS (ESI) m/z: calcd $C_{32}H_{44}N_7O_6S^+$ [M+H]⁺, 654.3068; found, 654.2990.

Intermediate Example 46: Preparation of N-(2-(2,6-dioxopiperidin-3-yl)-1,3-dioxoisoindolin-4-yl)-6-(2-(2-((6-iodohexyl)oxy)ethoxy)ethoxy)hexanamide (SIAIS171116)

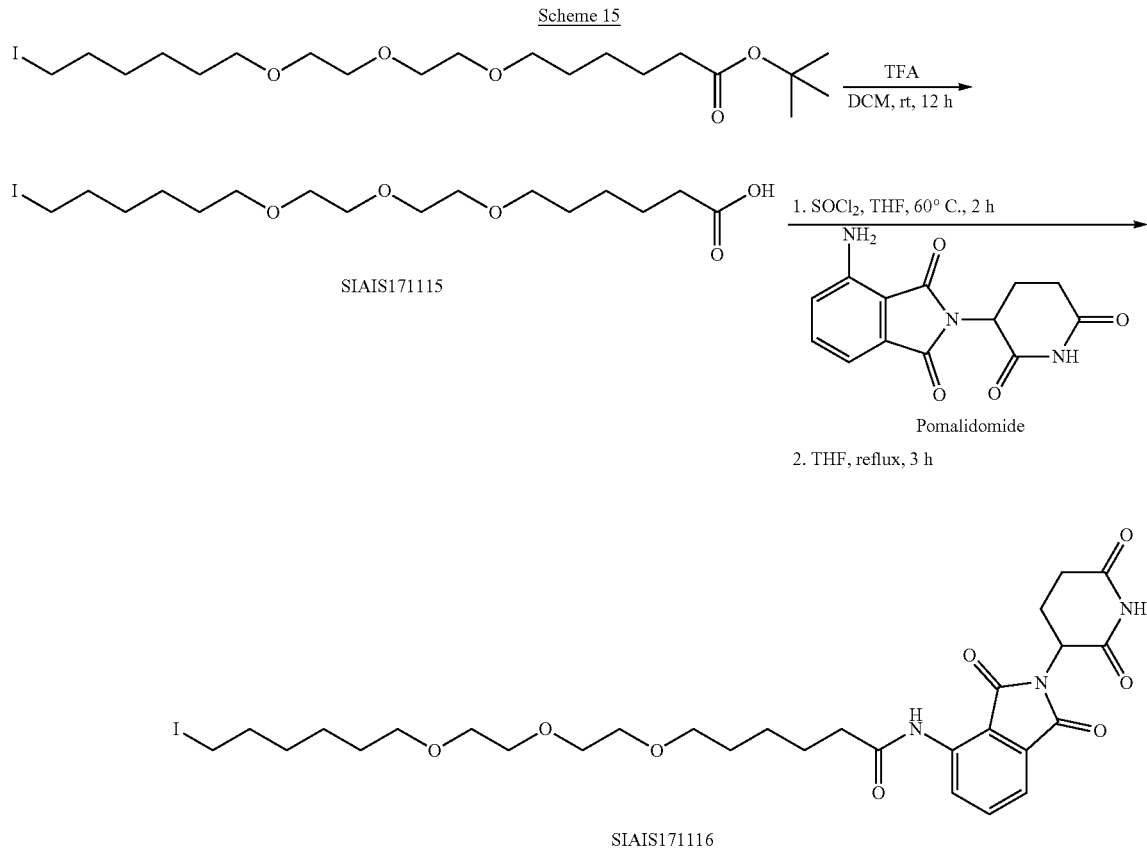

A solution of tert-butyl 6-(2-(2-((6-iodohexyl)oxy)ethoxy)ethoxy)hexanoate (500 mg, 1.03 mmol) in DCM (3 mL) and TFA (3 mL) was stirred for 12 h at room temperature. Once the starting material was consumed completely, concentrated to dryness under reduced pressure, the residue was added water, freeze-dried to afford crude (SIAIS171115) as a light yellow solid (440 mg). In a 25 mL of round-bottom flask, to a stirred solution of compound (SIAIS171115) (440 mg, crude) in anhydrous THF (3 mL) was dropwise added $SOCl_2$ (0.2 mL) at room temperature. After addition, the mixture was stirred for 2 h at refluxing condition, then concentrated in vacuum to afford the crude acyl chloride, which was dissolved in anhydrous THF (3 mL), then the mixture was added pomalidomide (40 mg, 0.15 mmol) and stirred for 4 h at refluxing condition. The mixture was cooled to room temperature once the starting material was consumed completely, quenched with water (1 mL) and stirred for 30 min, concentrated to dryness in vaccum, the residue was purified via C18 reverse phase preparative HPLC column (eluent gradient: acetonitrile/($H_2O$+0.1% TFA)=10%-100%) to afford desired product (SIAIS171116) as a light yellow solid (50 mg, 50% yield). $^1$H NMR (500 MHz, $CDCl_3$) δ 9.42 (s, 1H), 8.83 (d, J=8.3 Hz, 1H), 8.18 (s, 1H), 7.72 (dd, J=8.4, 7.5 Hz, 1H), 7.53 (dd, J=36.0, 18.0 Hz, 1H), 4.96 (dd, J=12.4, 5.4 Hz, 1H), 3.68-3.62 (m, 4H), 3.61-3.54 (m, 4H), 3.47 (dt, J=13.1, 6.6 Hz, 4H), 3.18 (t, J=7.0 Hz, 2H), 2.96-2.88 (m, 1H), 2.85-2.72 (m, 2H), 2.47 (t, J=7.6 Hz, 2H), 2.23-2.13 (m, 1H), 1.87-1.74 (m, 4H), 1.67-1.56 (m, 4H), 1.49-1.33 (m, 6H). HRMS (ESI) m/z: calcd $C_{29}H_{40}IN_3O_8^+$ [M+H]$^+$, 686.1933; found, 686.1941.

Intermediate Example 47: Preparation of (2S,4R)-1-((S)-2-(tert-butyl)-22-chloro-4-oxo-10,13,16-trioxa-3-azadocosanoyl)-4-hydroxy-N-(4-(4-methylthiazol-5-yl)benzyl)pyrrolidine-2-carboxamide (SIAIS180114)

Scheme 16

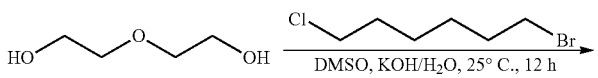

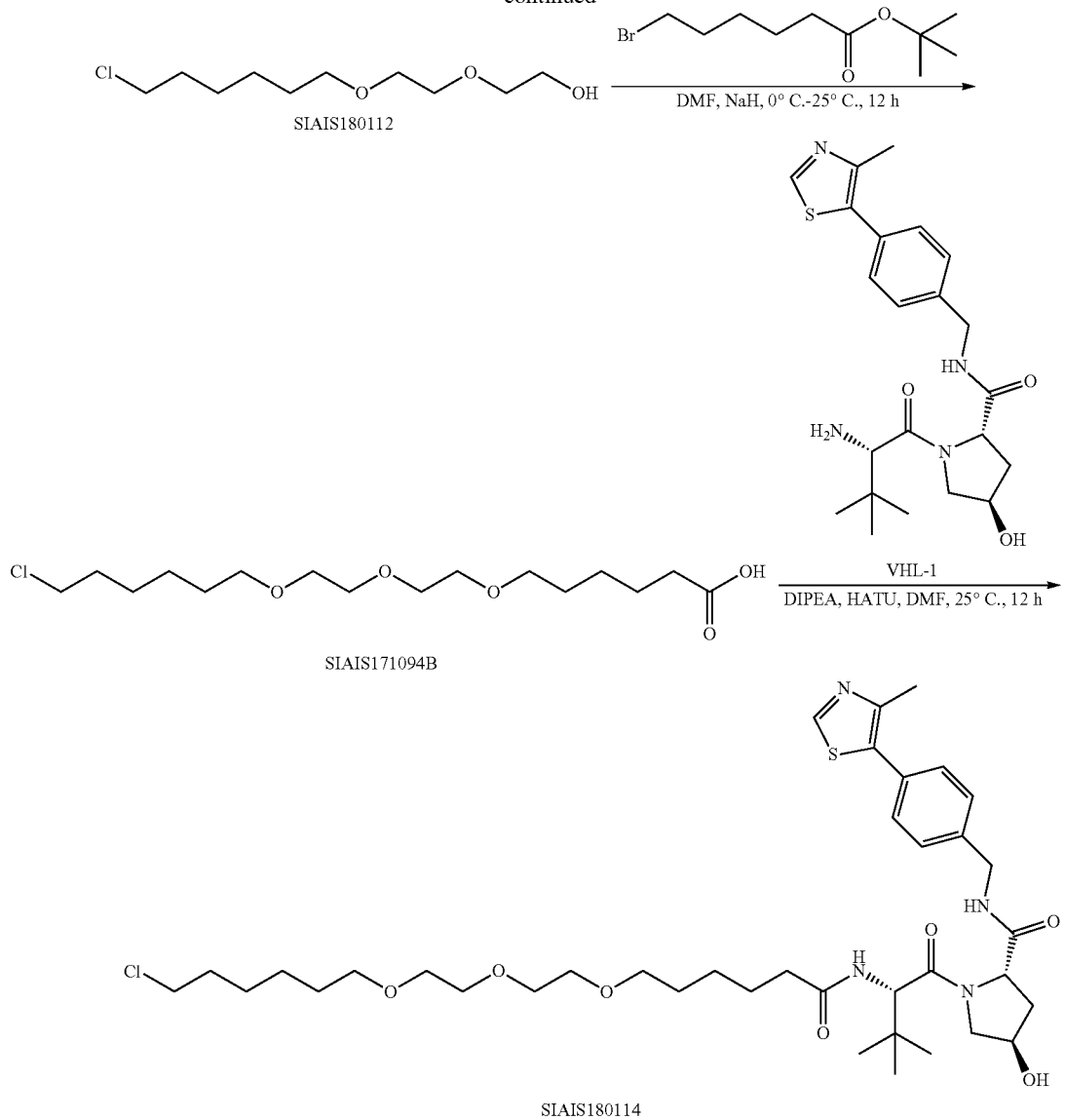

Step 1: Based on Scheme 16, Preparation of 2-(2-((6-chlorohexyl)oxy)ethoxy)ethan-1-ol (SIAIS180112)

In 250 mL of round-bottom flask, to a stirred solution of 2,2'-oxybis(ethan-1-ol) (5.3 g, 50.12 mmol) and 1-bromo-6-chlorohexane (10 g, 50.12 mmol) in DMSO (100 mL) was dropwise added 15% KOH aqueous solution (50 mL) at 0° C. After addition, the mixture was stirred overnight at room temperature. The mixture was extracted with EtOAc (150 mL×3), and the combined organic layer was washed with water (100 mL×3) and brine (100 mL), dried over $Na_2SO_4$, concentrated to dryness in vacuum. The residue was subjected to flash column chromatography with PE/EtOAc (3:1) to afford desired product (SIAIS1801112) as a light yellow oil (1.7 g, 15% yield). $^1$H NMR (500 MHz, $CDCl_3$) δ 3.76-3.71 (m, 2H), 3.69-3.67 (m, 2H), 3.64-3.61 (m, 2H), 3.59 (dd, J=5.7, 3.6 Hz, 2H), 3.53 (t, J=6.7 Hz, 2H), 3.47 (t, J=6.6 Hz, 2H), 2.49 (s, 1H), 1.84-1.73 (m, 2H), 1.71-1.53 (m, 4H), 1.49-1.43 (m, 2H), 1.41-1.35 (m, 2H). HRMS (ESI) m/z: calcd $C_{10}H_{22}ClO_3^+$ $[M+H]^+$, 225.1252; found, 225.0804.

Step 2: Based on Scheme 16, Preparation of 6-(2-(2-((6-chlorohexyl)oxy)ethoxy)ethoxy)hexanoic acid (SIAIS171094B)

In a 100 mL of round-bottom flask, to a stirred solution of SIAIS180112 (700 mg, 3.11 mmol) and tert-butyl 6-bromo-hexanoate (784 mg, 3.11 mmol) in anhydrous DMF (100 mL) was slowly added NaH (375 mg, 9.30 mmol, 60% in oil) at 0° C. under nitrogen atmosphere. After addition, the mixture was stirred for 10 min at 0° C. and allowed to stir overnight at room temperature. The mixture was slowly quenched with water, extracted with EtOAc (50 mL), and the pH of aqueous moiety was acidified to 2-3 with 2N HCl aqueous solution, and extracted with EtOAc (50 mL×3). The combined organic layer was washed with water (50 mL×3) and brine (500 mL), dried over $Na_2SO_4$, concentrated to dryness in vacuum to obtain the crude (SIAIS171094B) as a light yellow oil (600 mg, 57% yield), which was used for the next step without further purification. $^1$H NMR (500 MHz, CDCl$_3$) δ 3.65-3.63 (m, 4H), 3.60-3.57 (m, 4H), 3.53 (t, J=6.7 Hz, 2H), 3.47 (td, J=6.6, 1.6 Hz, 4H), 2.37-2.33 (m, 2H), 1.79-1.73 (m, 2H), 1.68-1.57 (m, 6H), 1.46-1.33 (m, 6H). HRMS (ESI) m/z: calcd C$_{16}$H$_{32}$ClO*$_5^+$ [M+H]$^+$, 339.1933; found, 338.8928.

Step 3: Based on Scheme 16, Preparation of (2S, 4R)-1-((S)-2-(tert-butyl)-22-chloro-4-oxo-10,13,16-trioxa-3-azadocosanoyl)-4-hydroxy-N-(4-(4-methyl-thiazol-5-yl)benzyl)pyrrolidine-2-carboxamide (SIAIS180114)

In a 50 mL of round-bottom flask, to a stirred solution of compound (SIAIS171094B) (210 mg, 0.62 mmol), VHL-1 (289.4 mg, 0.62 mmol) and HATU (471.3 mg, 1.24 mmol) in anhydrous DMF (10 mL) was added N,N-Diisopropyl-ethylamine (400.5 mg, 3.10 mmol). After addition, the mixture was stirred overnight at room temperature. The mixture was purified via C18 reverse phase preparative HPLC column (eluent gradient: acetonitrile/(H$_2$O+0.1% TFA)=10%-100%) to afford desired product (SIAIS180114) as a white solid (270 mg, 58% yield). $^1$H NMR (500 MHz, MeOD) δ 8.89 (s, 1H), 7.52-7.45 (m, 2H), 7.43-7.41 (m, 2H), 4.64 (s, 1H), 4.60-4.52 (m, 2H), 4.50 (m, 1H), 4.39-4.32 (m, 1H), 3.90 (d, J=11.0 Hz, 1H), 3.80 (dd, J=11.0, 3.9 Hz, 1H), 3.62-3.55 (m, 10H), 3.49-3.46 (m, 4H), 2.49-2.48 (m, 3H), 2.34-2.18 (m, 3H), 2.10-2.08 (m, 1H), 1.80-1.72 (m, 2H), 1.63-1.56 (m, 6H), 1.49-1.36 (m, 6H), 1.03 (m, 9H). HRMS (ESI) m/z: calcd C$_{38}$H$_{60}$ClN$_4$O$_7$S$^+$ [M+H]$^+$, 751.3866; found, 750.6442.

General Preparation Method of Other HO$_2$C-LIN-ULM Analogs

Scheme 17

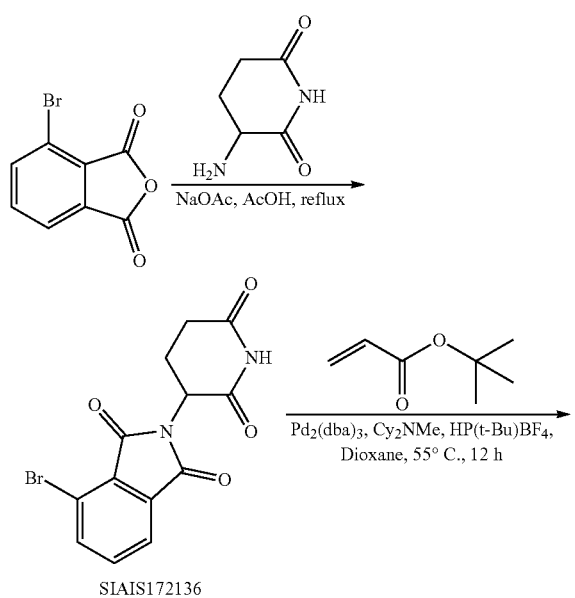

SIAIS172136

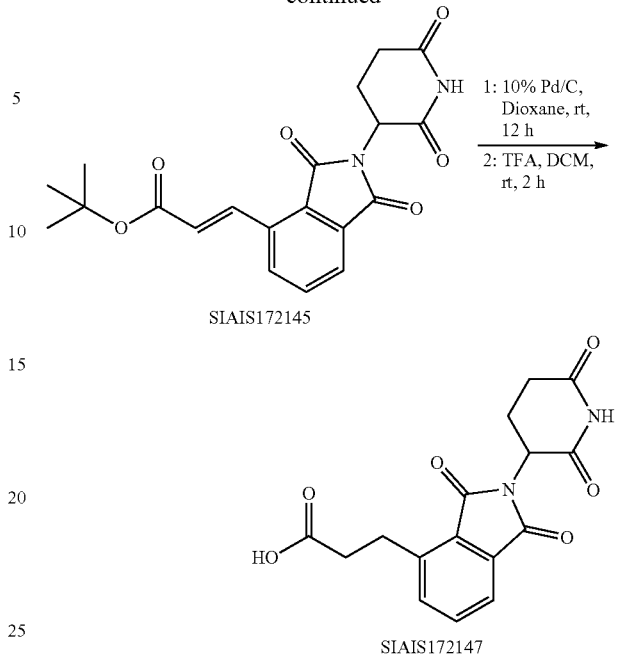

SIAIS172145

SIAIS172147

Intermediate Example 48: Preparation of 4-bromo-2-(2,6-dioxopiperidin-3-yl)isoindoline-1,3-dione (SIAIS172136)

Based on Scheme 17, Preparation of 4-bromo-2-(2,6-dioxopiperidin-3-yl)isoindoline-1,3-dione (SIAIS172136)

In a 100 mL of round-bottom flask, to a stirred solution of 4-bromoisobenzofuran-1,3-dione (500 mg, 2.20 mmol) and 3-aminopiperidine-2,6-dione (400 mg, 2.42 mmol) in acetic acid (10 mL) was added anhydrous sodium acetate (220 mg, 2.64 mmol). After addition, the mixture was stirred for 12 h at 140° C. The mixture was cooled to room temperature, filtered, and the obtained solid was mixed with water (10 mL) and methanol (2 mL), and stirred for another 30 min, then filtered, washed with water, dried under reduced pressure to afford desired product (SIAIS172136) as a white solid (700 mg, 94% yield). $^1$H NMR (500 MHz, DMSO) δ 11.14 (s, 1H), 8.14 (d, J=1.4 Hz, 1H), 8.09 (dd, J=7.9, 1.7 Hz, 1H), 7.86 (d, J=7.9 Hz, 1H), 5.16 (dd, J=12.9, 5.4 Hz, 1H), 2.93-2.85 (m, 1H), 2.65-2.50 (m, 2H), 2.08-2.04 (m, 1H). HRMS (ESI) m/z: calcd C$_{13}$H$_{10}$BrN$_2$O$_4^+$ [M+H]$^+$, 336.9818; found, 336.9810.

Intermediate Example 49: Preparation of tert-butyl (E)-3-(2-(2,6-dioxopiperidin-3-yl)-1,3-dioxoisoindo-lin-4-yl)acrylate (SIAIS172145)

Based on scheme 17, preparation of tert-butyl (E)-3-(2-(2,6-dioxopiperidin-3-yl)-1,3-dioxoisoindolin-4-yl)acrylate (SIAIS172145):

In a 50 mL of round-bottom flask, the mixture of Tri-tert-butylphosphine tetrafluoroborate ligand (110 mg, 0.38 mmol), N,N-Dicyclohexylmethylamine (250 mg, 1.28 mmol) and Pd$_2$(dba)$_3$ (163 mg, 0.64 mmol) in anhydrous dioxane (6 mL) was stirred for 30 min at room temperature, followed by addition of compound (SIAIS172136) (300 mg, 0.89 mmol) and tert-butyl acrylate (228 mg, 1.98 mmol). After addition, the mixture was stirred for 12 h at 55° C. under nitrogen atmosphere. Concentrated under reduced pressure, the residue was subjected to flash column chromatography with (40% EtOAc in PE) to afford desired product (SIAIS172145) as a light yellow solid (270 mg, 79% yield). $^1$H NMR (500 MHz, CDCl$_3$) δ 8.11 (s, 1H), 8.02 (s, 1H), 7.89 (d, J=7.7 Hz, 1H), 7.84 (dd, J=7.8, 1.2 Hz, 1H), 7.65 (d, J=16.0 Hz, 1H), 6.54 (d, J=16.0 Hz, 1H), 5.00 (dd, J=12.5, 5.3 Hz, 1H), 2.94-2.72 (m, 3H), 2.20-2.13 (m, 1H), 1.54 (s, 9H). HRMS (ESI) m/z: calcd $C_{20}H_{21}N_2O_6^+$ [M+H]$^+$, 385.1394; found, 385.1389.

Intermediate Example 50: Preparation of 3-(2-(2,6-dioxopiperidin-3-yl)-1,3-dioxoisoindolin-4-yl)propanoic acid (SIAIS172147)

Based on Scheme 17, Preparation of 3-(2-(2,6-dioxopiperidin-3-yl)-1,3-dioxoisoindolin-4-yl)propanoic acid (SIAIS172147)

In a 100 mL of round-bottom flask, to a stirred solution of SIAIS172145 (250 mg, 0.65 mmol) in dioxane (20 mL) was added 10% wet Pd/C, then the mixture was purged and refilled with H$_2$ (25 psi), and was stirred overnight at room temperature. After completion, the mixture was filtered, washed with dioxane, concentrated under reduced pressure to afford the residue as a light yellow oil, which was used for the next step without further purification. The obtained residue was dissolved in DCM (5 mL) and TFA (1 mL) in a 50 mL of round-bottom flask, then the mixture was stirred for 12 h at room temperature. Once the starting material was consumed completely, the mixture was concentrated to dryness in vaccum, and the obtained residue was purified via C18 reverse phase preparative HPLC column (eluent gradient: acetonitrile/(H$_2$O+0.1% TFA)=10%-100%) to afford desired product (SIAIS172147) as a white solid (180 mg, two steps: 58% yield). $^1$H NMR (500 MHz, DMSO) δ 12.22 (s, 1H), 11.12 (s, 1H), 7.86-7.79 (m, 2H), 7.77-7.70 (m, 1H), 5.13 (dd, J=12.8, 5.4 Hz, 1H), 3.01 (t, J=7.4 Hz, 2H), 2.93-2.85 (m, 1H), 2.64 (t, J=7.4 Hz, 2H), 2.62-2.50 (m, 2H), 2.08-2.02 (m, 1H). HRMS (ESI) m/z: calcd $C_{16}H_{15}N_2O_6^+$ [M+H]$^+$, 331.0925; found, 331.0919.

Intermediate Example 51: Preparation of 2-((2-(2,6-dioxopiperidin-3-yl)-1,3-dioxoisoindolin-4-yl)oxy)acetic acid (SIAIS172101B)

Scheme 18

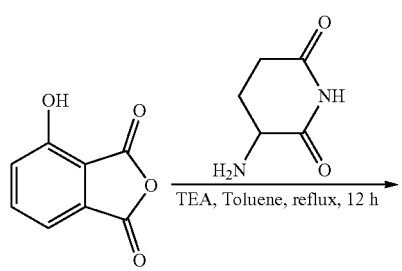

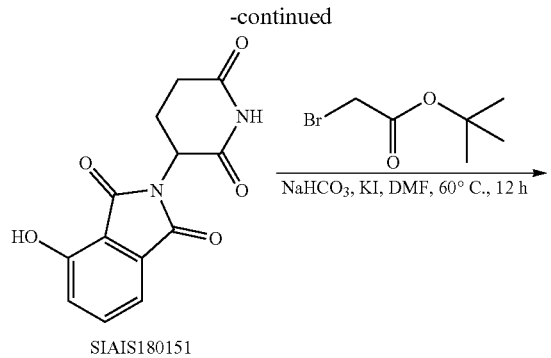

SIAIS180151

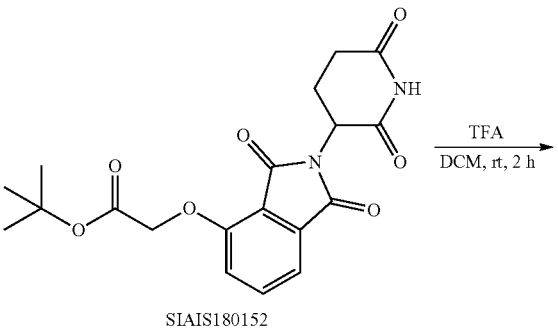

SIAIS180152

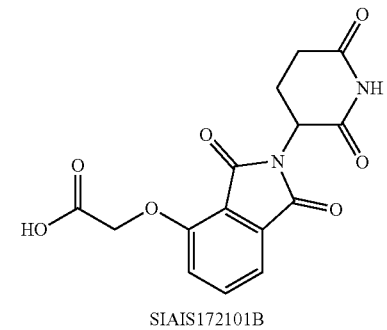

SIAIS172101B

Step 1: Based on Scheme 18, Preparation of 2-(2,6-dioxopiperidin-3-yl)-4-hydroxyisoindoline-1,3-dione (SIAIS180151)

In a 100 mL of round-bottom flask, to a stirred solution of 4-hydroxyisobenzofuran-1,3-dione (500 mg, 3.05 mmol) and 3-aminopiperidine-2,6-dione (502 mg, 3.05 mmol) in anhydrous toluene (20 mL) was added triethylamine (340 mg, 3.36 mmol). After addition, the mixture was stirred for 12 h at 110° C. The mixture was cooled to room temperature, filtered, and the obtained filtered cake was mixed with EtOAc/PE (3:10), and stirred for another 12 min, then filtered, washed with PE, dried under reduced pressure to afford desired product (SIAIS180151) as a white solid (770 mg, 92% yield). $^1$H NMR (500 MHz, DMSO) δ 11.17 (s, 1H), 11.08 (s, 1H), 7.65 (dd, J=8.3, 7.3 Hz, 1H), 7.32 (d, J=7.1 Hz, 1H), 7.25 (d, J=8.3 Hz, 1H), 5.07 (dd, J=12.8, 5.4 Hz, 1H), 2.92-2.85 (m, 1H), 2.62-2.51 (m, 2H), 2.07-1.96 (m, 1H). HRMS (ESI) m/z: calcd $C_{13}H_{11}N_2O_5^+$ [M+H]$^+$, 275.0662; found, 275.0666.

Step 2: Based on Scheme 18, Preparation of tert-butyl 2-((2-(2,6-dioxopiperidin-3-yl)-1,3-dioxoisoindolin-4-yl)oxy)acetate (SIAIS180152)

In a 50 mL of round-bottom flask, a mixed suspension solution of SIAIS180151 (412 mg, 1.50 mmol), tert-butyl 2-bromoacetate (350 mg, 1.80 mmol), anhydrous NaHCO$_3$ (190 mg, 2.25 mmol), KI (25 mg, 0.15 mmol) in anhydrous DMF (10 mL) was stirred for 12 h at 60° C. The mixture was poured into water, extracted with EtOAc, and the combined organic layer was washed water and brine, dried over Na$_2$SO$_4$, and concentrated under reduced pressure. The obtained residue was subjected to flash column chromatography with (40% EtOAc in PE) to afford desired product (SIAIS180152) as a light yellow solid (520 mg, 89% yield). $^1$H NMR (500 MHz, DMSO) δ 11.11 (s, 1H), 7.82-7.78 (m, 1H), 7.48 (d, J=7.1 Hz, 1H), 7.38 (d, J=8.5 Hz, 1H), 5.10 (dd, J=12.8, 5.4 Hz, 1H), 4.97 (s, 2H), 2.95-2.83 (m, 1H), 2.62-2.52 (m, 2H), 2.08-1.98 (m, 1H), 1.44-1.43 (m, 9H). HRMS (ESI) m/z: calcd $C_{19}H_{21}N_2O_7^+$ [M+H]$^+$, 389.1343; found, 389.1339.

Step 3: based on scheme 18, preparation of 2-((2-(2,6-dioxopiperidin-3-yl)-1,3-dioxoisoindolin-4-yl)oxy)acetic acid (SIAIS172101B)

The compound SIAIS180152 (500 mg, 1.29 mmol) was dissolved in DCM (10 mL) and TFA (2 mL) in a 50 mL of round-bottom flask, then the mixture was stirred for 2 h at room temperature. Once the starting material was consumed completely, the mixture was concentrated to dryness in vacuum, and the obtained residue was purified via C18 reverse phase preparative HPLC column (eluent gradient: acetonitrile/(H$_2$O+0.1% TFA)=10%-100%) to afford desired product (SIAIS172101B) as a white solid (400 mg, 92% yield). $^1$H NMR (500 MHz, DMSO) δ 13.25 (s, 1H), 11.11 (s, 1H), 7.79 (dd, J=8.5, 7.3 Hz, 1H), 7.47 (d, J=7.2 Hz, 1H), 7.39 (d, J=8.6 Hz, 1H), 5.10 (dd, J=12.8, 5.4 Hz, 1H), 4.98 (s, 2H), 2.93-2.85 (m, 1H), 2.63-2.51 (m, 2H), 2.08-2.00 (m, 1H). HRMS (ESI) m/z: calcd $C_{15}H_{13}N_2O_7^+$ [M+H]$^+$, 333.0717; found, 333.0719.

General Synthetic Method of PROTAD Compounds Targeting and Degrading BCR-ABL Protein:

Scheme 19

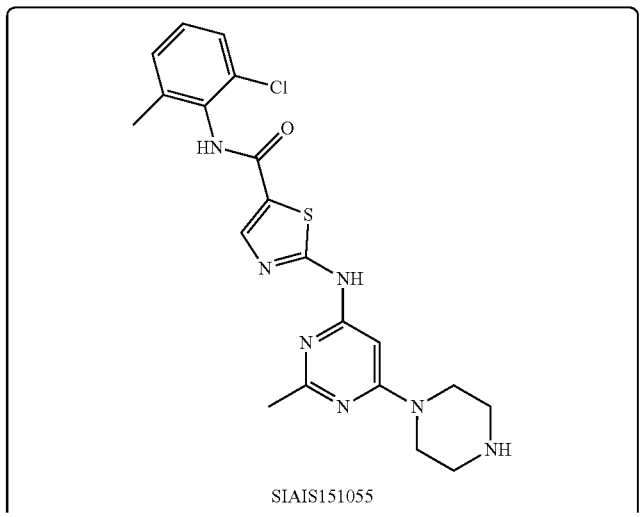

SIAIS151055

-continued
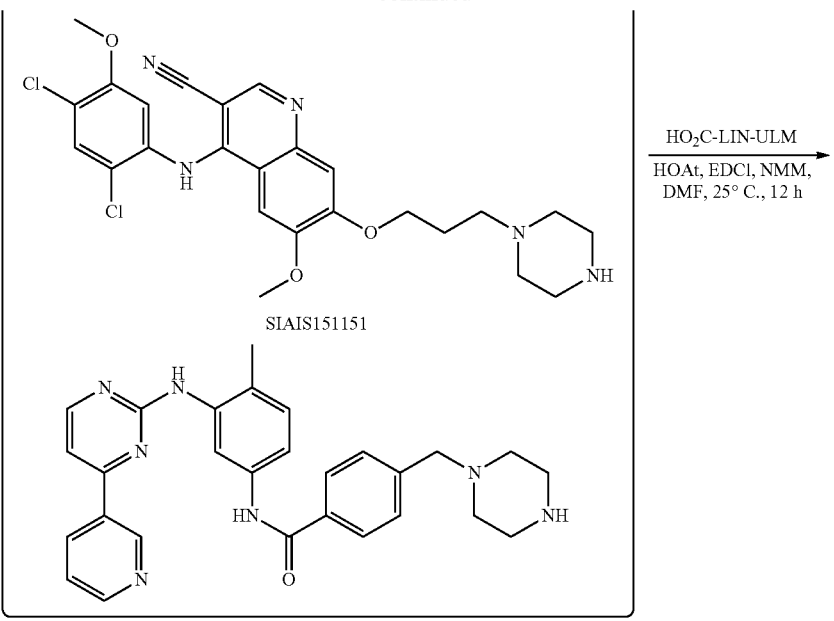
SIAIS151151
inhibitors
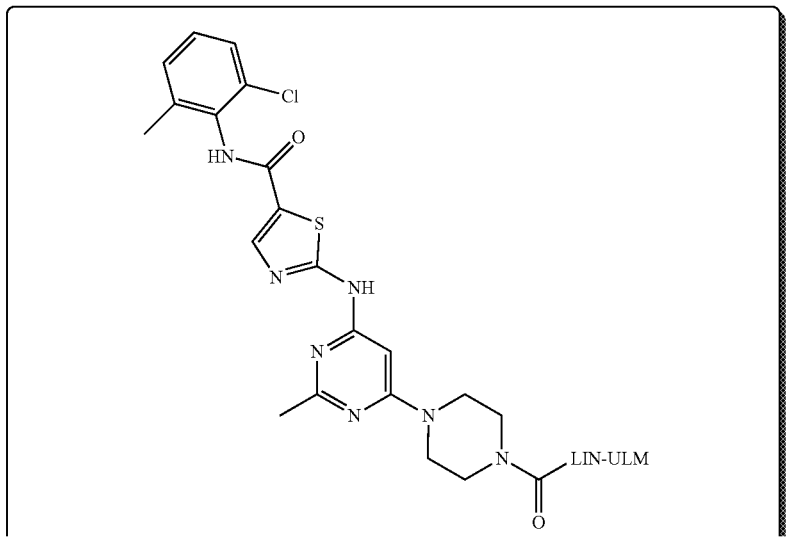
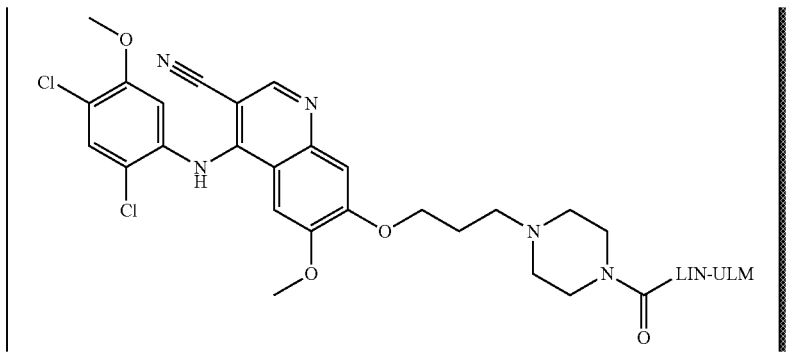

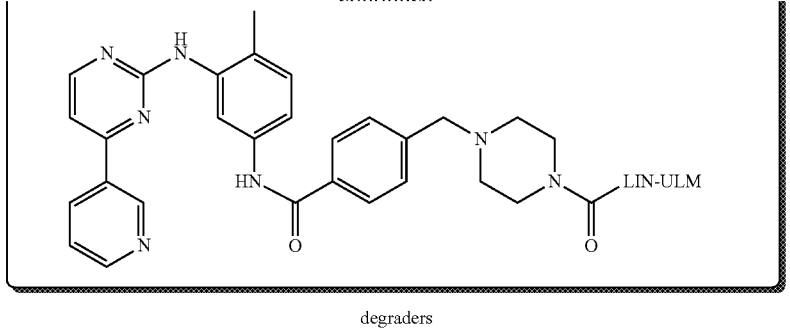

degraders

Based on scheme 19, to a mixed solution of relevant inhibitor (1 equiv), corresponding $HO_2C$-LIN-ULM analog (1 equiv), HOAt (2 equiv), EDCI.HC (2 equiv) and NMM (5 equiv) in anhydrous DMF (2 mL) was stirred overnight at room temperature. After LC-MS analysis showed the product peak, the mixture was purified via C18 reverse phase preparative HPLC column (eluent gradient: acetonitrile/($H_2O$+0.1% TFA)=10%-100%) to afford desired compounds.

PREPARATION EXAMPLES

Example 1: Preparation of N-(2-chloro-6-methylphenyl)-2-((6-(4-(3-(2-((2-(2,6-dioxopiperidin-3-yl)-1,3-dioxoisoindolin-4-yl)amino)ethoxy)propanoyl)piperazin-1-yl)-2-methylpyrimidin-4-yl)amino)thiazole-5-carboxamide (SIAIS151063)

Based on the general method of scheme 19 as described herein, compound (SIAIS151063) was obtained by coupling reaction of (SIAIS151055) with $HO_2C$-LIN-ULM analog (SIAIS151001) as a yellow solid (30.2 mg, 82% yield). $^1H$ NMR (500 MHz, MeOD) δ 8.21 (s, 1H), 7.55-7.47 (m, 1H), 7.37 (dd, J=7.5, 1.5 Hz, 1H), 7.30-7.21 (m, 2H), 7.04 (d, J=8.5 Hz, 1H), 6.95 (d, J=7.1 Hz, 1H), 6.13 (s, 1H), 5.02 (dd, J=12.8, 5.4 Hz, 1H), 3.84 (t, J=5.8 Hz, 2H), 3.79-3.62 (m, 10H), 3.52-3.45 (m, 2H), 2.87-2.79 (m, 1H), 2.77-2.61 (m, 4H), 2.54 (s, 3H), 2.33 (s, 3H), 2.13-2.05 (m, 1H). HRMS (ESI) m/z: calcd $C_{38}H_{40}ClN_{10}O_7S^+$ $[M+H]^+$, 815.2485; found, 815.3241.

Example 2: Preparation of N-(2-chloro-6-methylphenyl)-2-((6-(4-(3-(2-(2-((2-(2,6-dioxopiperidin-3-yl)-1,3-dioxoisoindolin-4-yl)amino)ethoxy)ethoxy)propanoyl)piperazin-1-yl)-2-methylpyrimidin-4-yl)amino)thiazole-5-carboxamide (SIAIS151064)

Based on the general method of scheme 19 as described herein, compound (SIAIS151064) was obtained by coupling reaction of (SIAIS151055) with $HO_2C$-LIN-ULM analog (SIAIS151004) as a yellow solid (13.7 mg, 35% yield). $^1H$ NMR (500 MHz, MeOD) δ 8.18 (s, 1H), 7.49-7.43 (m, 1H), 7.38-7.34 (m, 1H), 7.29-7.21 (m, 2H), 6.97 (d, J=8.6 Hz, 1H), 6.92 (d, J=7.1 Hz, 1H), 6.09 (s, 1H), 5.05 (dd, J=12.7, 5.5 Hz, 1H), 3.79 (t, J=5.8 Hz, 4H), 3.70 (dd, J=11.6, 6.3 Hz, 6H), 3.64 (t, J=3.8 Hz, 6H), 3.42 (t, J=5.2 Hz, 2H), 2.89-2.79 (m, 1H), 2.78-2.65 (m, 4H), 2.50 (s, 3H), 2.33 (s, 3H), 2.15-2.09 (m, 1H). HRMS (ESI) m/z: calcd $C_{40}H_{44}ClN_{10}O_8S^+$ $[M+H]^+$, 859.2747; found, 859.3538.

Example 3: Preparation of N-(2-chloro-6-methylphenyl)-2-((6-(4-(3-(2-(2-(2-((2-(2,6-dioxopiperidin-3-yl)-1,3-dioxoisoindolin-4-yl)amino)ethoxy)ethoxy)ethoxy)propanoyl)piperazin-1-yl)-2-methylpyrimidin-4-yl)amino)thiazole-5-carboxamide (SIAIS151067)

Based on the general method of scheme 19 as described herein, compound (SIAIS151067) was obtained by coupling reaction of (SIAIS151055) with $HO_2C$-LIN-ULM analog (SIAIS151005) as a yellow solid (15.7 mg, 38% yield). $^1H$ NMR (500 MHz, MeOD) δ 8.17 (s, 1H), 7.54-7.46 (m, 1H), 7.37 (d, J=6.0 Hz, 1H), 7.29-7.22 (m, 2H), 6.99 (dd, J=14.0, 7.8 Hz, 2H), 6.17 (s, 1H), 5.05 (dd, J=12.8, 5.5 Hz, 1H), 3.84-3.72 (m, 10H), 3.68 (t, J=5.2 Hz, 2H), 3.65-3.62 (m, 6H), 3.61-3.59 (m, 2H), 3.43 (t, J=5.2 Hz, 2H), 2.92-2.81 (m, 1H), 2.77-2.66 (m, 4H), 2.54 (s, 3H), 2.33 (s, 3H), 2.15-2.09 (m, 1H). HRMS (ESI) m/z: calcd $C_{42}H_{48}ClN_{10}O_9S^+$ $[M+H]^+$, 903.3009; found, 903.2500.

Example 4: Preparation of N-(2-chloro-6-methylphenyl)-2-((6-(4-(1-((2-(2,6-dioxopiperidin-3-yl)-1,3-dioxoisoindolin-4-yl)amino)-3,6,9,12-tetraoxapentadecan-15-oyl)piperazin-1-yl)-2-methylpyrimidin-4-yl)amino)thiazole-5-carboxamide (SIAIS151068)

Based on the general method of scheme 19 as described herein, compound (SIAIS151068) was obtained by coupling reaction of (SIAIS151055) with $HO_2C$-LIN-ULM analog (SIAIS151006) as a yellow solid (18.6 mg, 43% yield). $^1H$ NMR (500 MHz, MeOD) δ 8.17 (s, 1H), 7.50 (t, J=7.8 Hz, 1H), 7.36 (d, J=7.2 Hz, 1H), 7.31-7.21 (m, 2H), 7.06-6.95 (m, 2H), 6.19 (s, 1H), 5.05 (dd, J=12.8, 5.5 Hz, 1H), 3.85-3.71 (m, 10H), 3.70 (t, J=5.2 Hz, 2H), 3.66-3.57 (m, 12H), 3.44 (t, J=5.0 Hz, 2H), 2.90-2.82 (m, 1H), 2.76-2.65 (m, 4H), 2.55 (s, 3H), 2.33 (s, 3H), 2.16-2.07 (m, 1H). HRMS (ESI) m/z: calcd $C_{44}H_{52}ClN_{10}O_{10}S^+[M+H]^+$, 947.3272; found, 947.2704.

Example 5: Preparation of N-(2-chloro-6-methylphenyl)-2-((6-(4-(1-((2-(2,6-dioxopiperidin-3-yl)-1,3-dioxoisoindolin-4-yl)amino)-3,6,9,12,15-pentaoxaoctadecan-18-oyl)piperazin-1-yl)-2-methylpyrimidin-4-yl)amino)thiazole-5-carboxamide (SIAIS151069)

Based on the general method of scheme 19 as described herein, compound (SIAIS151069) was obtained by coupling reaction of (SIAIS151055) with $HO_2C$-LIN-ULM analog (SIAIS151007) as a yellow solid (35 mg, 78% yield). $^1H$ NMR (500 MHz, MeOD) δ 8.18 (s, 1H), 7.54-7.48 (m, 1H), 7.36 (d, J=7.4 Hz, 1H), 7.28-7.22 (m, 2H), 7.03 (dd, J=16.0, 7.8 Hz, 2H), 6.23 (s, 1H), 5.04 (dd, J=12.8, 5.4 Hz, 1H), 3.86-3.73 (m, 10H), 3.71 (t, J=5.1 Hz, 2H), 3.78-3.68 (m, 10H), 3.65-3.60 (m, 7H), 3.59-3.57 (m, 9H), 3.46 (t, J=5.1 Hz, 2H), 2.89-2.81 (m, 1H), 2.76-2.65 (m, 4H), 2.57 (s, 3H), 2.32 (s, 3H), 2.15-2.08 (m, 1H). HRMS (ESI) m/z: calcd $C_{46}H_{56}ClN_{10}O_{11}S^+$ [M+H]$^+$, 991.3534; found, 991.2469.

Example 6: Preparation of N-(2-chloro-6-methylphenyl)-2-((6-(4-((2-(2,6-dioxopiperidin-3-yl)-1,3-dioxoisoindolin-4-yl)glycyl)piperazin-1-yl)-2-methylpyrimidin-4-yl)amino)thiazole-5-carboxamide (SIAIS151072)

Based on the general method of scheme 19 as described herein, compound (SIAIS151072) was obtained by coupling reaction of (SIAIS151055) with HO$_2$C-LIN-ULM analog (SIAIS151025) as a yellow solid (19.1 mg, 56% yield). $^1$H NMR (500 MHz, MeOD) δ 8.11 (s, 1H), 7.51-7.46 (m, 1H), 7.27 (d, J=7.9 Hz, 1H), 7.19-7.12 (m, 2H), 7.01 (d, J=7.0 Hz, 1H), 6.94 (d, J=8.5 Hz, 1H), 6.19 (s, 1H), 4.98 (dd, J=12.6, 5.3 Hz, 1H), 4.19 (s, 2H), 3.83-3.63 (m, 8H), 2.82-2.73 (m, 1H), 2.69-2.61 (m, 2H), 2.50 (s, 3H), 2.22 (s, 3H), 2.06-1.99 (m, 1H). HRMS (ESI) m/z: calcd $C_{35}H_{34}ClN_{10}O_6S^+$ [M+H]$^+$, 757.2067; found, 757.1286.

Example 7: Preparation of N-(2-chloro-6-methylphenyl)-2-((6-(4-(3-((2-(2,6-dioxopiperidin-3-yl)-1,3-dioxoisoindolin-4-yl)amino)propanoyl)piperazin-1-yl)-2-methylpyrimidin-4-yl)amino)thiazole-5-carboxamide (SIAIS151074)

Based on the general method of scheme 19 as described herein, compound (SIAIS151074) was obtained by coupling reaction of (SIAIS151055) with HO$_2$C-LIN-ULM analog (SIAIS151026) as a yellow solid (24.4 mg, 70% yield). $^1$H NMR (500 MHz, MeOD) δ 8.20 (s, 1H), 7.60-7.53 (m, 1H), 7.36 (d, J=7.4 Hz, 1H), 7.28-7.22 (m, 2H), 7.13 (d, J=8.6 Hz, 1H), 7.05 (d, J=7.1 Hz, 1H), 6.22 (s, 1H), 5.03 (dd, J=12.7, 5.5 Hz, 1H), 3.78-3.66 (m, 10H), 2.90-2.82 (m, 1H), 2.79 (t, J=6.2 Hz, 2H), 2.75-2.63 (m, 2H), 2.57 (s, 3H), 2.32 (s, 3H), 2.10-2.03 (m, 1H). HRMS (ESI) m/z: calcd $C_{36}H_{36}ClN_{10}O_6S^+$ [M+H]$^+$, 771.2223; found, 771.1824.

Example 8: Preparation of N-(2-chloro-6-methylphenyl)-2-((6-(4-(4-((2-(2,6-dioxopiperidin-3-yl)-1,3-dioxoisoindolin-4-yl)amino)butanoyl)piperazin-1-yl)-2-methylpyrimidin-4-yl)amino)thiazole-5-carboxamide (SIAIS151070)

Based on the general method of scheme 19 as described herein, compound (SIAIS151070) was obtained by coupling reaction of (SIAIS151055) with HO$_2$C-LIN-ULM analog (SIAIS151019) as a yellow solid (31.2 mg, 88% yield). $^1$H NMR (500 MHz, DMSO) δ 11.53 (s, 1H), 11.09 (s, 1H), 9.89 (s, 1H), 8.22 (s, 1H), 7.59 (dd, J=8.5, 7.1 Hz, 1H), 7.40 (d, J=7.7 Hz, 1H), 7.31-7.23 (m, 2H), 7.19 (d, J=8.7 Hz, 1H), 7.02 (d, J=7.0 Hz, 1H), 6.68 (s, 1H), 6.07 (t, 1H), 5.05 (dd, J=12.7, 5.4 Hz, 1H), 3.51-3.48 (m, 8H), 3.34 (t, J=7.1 Hz, 2H), 2.92-2.84 (m, 1H), 2.64-2.52 (m, 2H), 2.45 (t, J=7.1 Hz, 2H), 2.43 (s, 3H), 2.24 (s, 3H), 2.04-2.00 (m, 1H), 1.86-1.79 (m, 2H). HRMS (ESI) m/z: calcd $C_{37}H_{38}ClN_{10}O_6S^+$ [M+H]$^+$, 785.2380; found, 785.1578.

Example 9: Preparation of N-(2-chloro-6-methylphenyl)-2-((6-(4-(5-((2-(2,6-dioxopiperidin-3-yl)-1,3-dioxoisoindolin-4-yl)amino)pentanoyl)piperazin-1-yl)-2-methylpyrimidin-4-yl)amino)thiazole-5-carboxamide (SIAIS151071)

Based on the general method of scheme 19 as described herein, compound (SIAIS151071) was obtained by coupling reaction of (SIAIS151055) with HO$_2$C-LIN-ULM analog (SIAIS151020) as a yellow solid (10.0 mg, 28% yield). $^1$H NMR (500 MHz, MeOD) δ 8.21 (s, 1H), 7.56 (dd, J=8.5, 7.2 Hz, 1H), 7.37 (d, J=7.1 Hz, 1H), 7.26 (t, J=7.7 Hz, 2H), 7.08 (d, J=8.6 Hz, 1H), 7.04 (d, J=7.1 Hz, 1H), 6.30 (s, 1H), 5.04 (dd, J=12.6, 5.5 Hz, 1H), 3.83-3.69 (m, 8H), 3.40 (t, J=6.1 Hz, 2H), 2.89-2.80 (m, 1H), 2.76-2.67 (m, 2H), 2.61 (s, 3H), 2.53 (d, J=6.4 Hz, 2H), 2.32 (s, 3H), 2.13-2.07 (m, 1H), 1.80-1.72 (m, 4H). HRMS (ESI) m/z: calcd $C_{38}H_4OClN_{10}O_6S^+$ [M+H]$^+$, 799.2536; found, 799.1711.

Example 10: Preparation of N-(2-chloro-6-methylphenyl)-2-((6-(4-(6-((2-(2,6-dioxopiperidin-3-yl)-1,3-dioxoisoindolin-4-yl)amino)hexanoyl)piperazin-1-yl)-2-methylpyrimidin-4-yl)amino)thiazole-5-carboxamide (SIAIS151075)

Based on the general method of scheme 19 as described herein, compound (SIAIS151075) was obtained by coupling reaction of (SIAIS151055) with HO$_2$C-LIN-ULM analog (SIAIS151027) as a yellow solid (26.7 mg, 73% yield). $^1$H NMR (500 MHz, MeOD) δ 8.19 (s, 1H), 7.53 (t, J=7.0 Hz, 1H), 7.36 (d, J=7.6 Hz, 1H), 7.28-7.22 (m, 2H), 7.05 (d, J=8.6 Hz, 1H), 7.00 (d, J=7.1 Hz, 1H), 6.17 (s, 1H), 5.04 (dd, J=12.4, 5.5 Hz, 1H), 3.81-3.64 (m, 8H), 3.35 (t, J=6.8 Hz, 2H), 2.88-2.80 (m, 1H), 2.76-2.65 (m, 2H), 2.56 (s, 3H), 2.48 (t, J=7.4 Hz, 2H), 2.32 (s, 3H), 2.13-2.07 (m, 1H), 1.74-1.67 (m, 4H), 1.53-1.47 (m, 2H). HRMS (ESI) m/z: calcd $C_{39}H_{42}ClN_{10}O_6S^+$ [M+H]$^+$, 813.2693; found, 813.2278.

Example 11: Preparation of N-(2-chloro-6-methylphenyl)-2-((6-(4-(7-((2-(2,6-dioxopiperidin-3-yl)-1,3-dioxoisoindolin-4-yl)amino)heptanoyl)piperazin-1-yl)-2-methylpyrimidin-4-yl)amino)thiazole-5-carboxamide (SIAIS151181)

Based on the general method of scheme 19 as described herein, compound (SIAIS151118) was obtained by coupling reaction of (SIAIS151055) with HO$_2$C-LIN-ULM analog (SIAIS151086) as a yellow solid (22.3 mg, 60% yield). $^1$H NMR (500 MHz, MeOD) δ 7.54 (dd, J=8.5, 7.1 Hz, 1H), 7.36 (d, J=6.1 Hz, 1H), 7.28-7.22 (m, 3H), 7.03 (dd, J=10.7, 7.8 Hz, 2H), 6.15 (s, 1H), 5.04 (dd, J=12.6, 5.5 Hz, 1H), 3.89-3.62 (m, 8H), 3.34 (t, J=7.5 Hz, 2H), 2.87-2.80 (m, 1H), 2.77-2.68 (m, 2H), 2.56 (s, 3H), 2.45 (t, J=7.5 Hz, 2H), 2.32 (s, 3H), 2.13-2.08 (m, 1H), 1.72-1.64 (m, 4H), 1.53-1.39 (m, 4H). HRMS (ESI) m/z: calcd $C_{40}H_{44}ClN_{10}O_6S^+$ [M+H]$^+$, 827.2849; found, 827.3884.

Example 12: Preparation of N-(2-chloro-6-methylphenyl)-2-((6-(4-(3-((2-(2,6-dioxopiperidin-3-yl)-1-oxoisoindolin-4-yl)amino)-3-oxopropanoyl)piperazin-1-yl)-2-methylpyrimidin-4-yl)amino)thiazole-5-carboxamide (SIAIS164108)

Based on the general method of scheme 19 as described herein, compound (SIAIS164108) was obtained by coupling reaction of (SIAIS151055) with HO$_2$C-LIN-ULM analog (SIAIS171004) as a white solid (12.6 mg, 49% yield). $^1$H NMR (500 MHz, MeOD) δ 8.22 (s, 1H), 7.81 (d, J=7.7 Hz, 1H), 7.67 (d, J=7.5 Hz, 1H), 7.54 (t, J=7.8 Hz, 1H), 7.37 (d, J=7.2 Hz, 1H), 7.29-7.23 (m, 2H), 6.32 (s, 1H), 5.15 (dd, J=13.0, 5.0 Hz, 1H), 4.51 (dd, J=22.0, 17.5 Hz, 2H), 3.83 (s, 8H), 2.96-2.88 (m, 1H), 2.81-2.75 (m, 1H), 2.70 (s, 1H), 2.62 (s, 3H), 2.53-2.43 (m, 2H), 2.32 (s, 3H), 2.23-2.17 (m, 1H).HRMS (ESI) m/z: calcd C$_{36}$H$_{36}$ClN$_{10}$O$_6$S [M+H]$^+$, 771.2223; found, 771.3122.

Example 13: Preparation of N-(2-chloro-6-methylphenyl)-2-((6-(4-(4-((2-(2,6-dioxopiperidin-3-yl)-1-oxoisoindolin-4-yl)amino)-4-oxobutanoyl)piperazin-1-yl)-2-methylpyrimidin-4-yl)amino)thiazole-5-carboxamide (SIAIS164109)

Based on the general method of scheme 19 as described herein, compound (SIAIS164109) was obtained by coupling reaction of (SIAIS151055) with HO$_2$C-LIN-ULM analog (SIAIS164084) as a white solid (12.7 mg, 48% yield). $^1$H NMR (500 MHz, MeOD) δ 8.23 (s, 1H), 7.74 (d, J=7.5 Hz, 1H), 7.64 (d, J=7.4 Hz, 1H), 7.51 (t, J=7.8 Hz, 1H), 7.37 (dd, J=7.2, 1.9 Hz, 1H), 7.29-7.22 (m, 2H), 6.32 (s, 1H), 5.18 (dd, J=13.3, 5.2 Hz, 1H), 4.48 (dd, J=20.0, 17.5 Hz, 2H), 4.04-3.65 (m, 8H), 2.96-2.88 (m, 1H), 2.86-2.76 (m, 5H), 2.63 (s, 3H), 2.50-2.42 (m, 1H), 2.31 (s, 3H), 2.23-2.16 (m, 1H). HRMS (ESI) m/z: calcd C$_{37}$H$_{38}$ClN$_{10}$O$_6$S$^+$ [M+H]$^+$, 785.2380; found, 785.3319.

Example 14: Preparation of N-(2-chloro-6-methylphenyl)-2-((6-(4-(5-((2-(2,6-dioxopiperidin-3-yl)-1-oxoisoindolin-4-yl)amino)-5-oxopentanoyl)piperazin-1-yl)-2-methylpyrimidin-4-yl)amino)thiazole-5-carboxamide (SIAIS164110)

Based on the general method of scheme 19 as described herein, compound (SIAIS164110) was obtained by coupling reaction of (SIAIS151055) with HO$_2$C-LIN-ULM analog (SIAIS171005) as a white solid (13.1 mg, 49% yield). $^1$H NMR (500 MHz, DMSO) δ 11.65 (s, 1H), 11.01 (s, 1H), 9.94 (s, 1H), 9.85 (s, 1H), 8.26 (s, 1H), 7.83 (dd, J=7.1, 1.6 Hz, 1H), 7.54-7.46 (m, 2H), 7.40 (d, J=6.4 Hz, 1H), 7.34-7.21 (m, 2H), 6.13 (s, 1H), 5.14 (dd, J=13.3, 5.1 Hz, 1H), 4.38 (dd, J=22.0, 17.5 Hz, 2H), 3.62-3.51 (m, 8H), 2.97-2.86 (m, 1H), 2.63-2.58 (m, 1H), 2.45 (s, 3H), 2.47-2.40 (m, 4H), 2.39-2.30 (m, 1H), 2.24 (s, 3H), 2.06-1.99 (m, 1H), 1.91-1.82 (m, 2H).HRMS (ESI) m/z: calcd C$_{38}$H$_4$OClN$_{10}$O$_6$S$^+$ [M+H]$^+$, 799.2536; found, 799.3481.

Example 14: Preparation of N-(2-chloro-6-methylphenyl)-2-((6-(4-(6-((2-(2,6-dioxopiperidin-3-yl)-1-oxoisoindolin-4-yl)amino)-6-oxohexanoyl)piperazin-1-yl)-2-methylpyrimidin-4-yl)amino)thiazole-5-carboxamide (SIAIS164181)

Based on the general method of scheme 19 as described herein, compound (SIAIS164181) was obtained by coupling reaction of (SIAIS151055) with HO$_2$C-LIN-ULM analog (SIAIS164101) as a white solid (7 mg, 38% yield). $^1$H NMR (500 MHz, MeOD) δ 8.23 (s, 1H), 7.71 (d, J=7.3 Hz, 1H), 7.64 (d, J=7.0 Hz, 1H), 7.52 (t, J=7.8 Hz, 1H), 7.37 (dd, J=7.1, 2.0 Hz, 1H), 7.30-7.22 (m, 2H), 6.34 (s, 1H), 5.18 (dd, J=13.3, 5.2 Hz, 1H), 4.55-4.44 (m, 2H), 3.76 (s, 8H), 2.91 (dd, J=22.3, 9.1 Hz, 1H), 2.78 (d, J=15.5 Hz, 1H), 2.65 (s, 3H), 2.57-2.44 (m, 5H), 2.32 (s, 3H), 2.22-2.14 (m, 1H), 1.84-1.69 (m, 4H).HRMS (ESI) m/z: calcd C$_{39}$H$_{42}$ClN$_{10}$O$_6$S$^+$ [M+H]$^+$, 813.2693; found, 813.2683.

Example 15: Preparation of N-(2-chloro-6-methylphenyl)-2-((6-(4-(7-((2-(2,6-dioxopiperidin-3-yl)-1-oxoisoindolin-4-yl)amino)-7-oxoheptanoyl)piperazin-1-yl)-2-methylpyrimidin-4-yl)amino)thiazole-5-carboxamide (SIAIS164182)

Based on the general method of scheme 19 as described herein, compound (SIAIS164182) was obtained by coupling reaction of (SIAIS151055) with HO$_2$C-LIN-ULM analog (SIAIS164102) as a white solid (9.7 mg, 52% yield). $^1$H NMR (500 MHz, MeOD) δ 8.24 (s, 1H), 7.70 (d, J=7.9 Hz, 1H), 7.64 (d, J=7.0 Hz, 1H), 7.51 (dd, J=9.0, 5.9 Hz, 1H), 7.37 (dd, J=7.2, 2.1 Hz, 1H), 7.30-7.22 (m, 2H), 6.33 (s, 1H), 5.17 (dd, J=13.3, 5.2 Hz, 1H), 4.48 (t, J=9.6 Hz, 3H), 3.75 (s, 8H), 2.91 (ddd, J=18.7, 13.5, 5.4 Hz, 1H), 2.81-2.75 (m, 1H), 2.65 (s, 3H), 2.49 (dt, J=15.8, 6.0 Hz, 6H), 2.32 (s, 3H), 2.23-2.16 (m, 1H), 1.80-1.66 (m, 5H).HRMS (ESI) m/z: calcd C$_{39}$H$_{42}$ClN$_{10}$O$_6$S$^+$ [M+H]$^+$, 827.2849; found, 826.8941.

Example 16: Preparation of N-(2-chloro-6-methylphenyl)-2-((6-(4-(2-(2-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)ethoxy)acetyl)piperazin-1-yl)-2-methylpyrimidin-4-yl)amino)thiazole-5-carboxamide (SIAIS151080)

Based on the general method of scheme 19 as described herein, compound (SIAIS151080) was obtained by coupling reaction of (SIAIS151055) with HO$_2$C-LIN-ULM analog (SIAIS151010) as a white solid (23 mg, 45% yield). $^1$H NMR (500 MHz, MeOD) δ 8.92 (s, 1H), 8.19 (s, 1H), 7.44-7.35 (m, 5H), 7.28-7.22 (m, 2H), 6.20 (s, 1H), 4.73 (s, 1H), 4.58 (t, J=8.5 Hz, 1H), 4.53-4.46 (m, 2H), 4.44-4.35 (m, 3H), 4.07 (dd, J=21.0, 16.0 Hz, 2H), 3.88-3.66 (m, 14H), 2.55 (s, 3H), 2.46 (s, 3H), 2.32 (s, 3H), 2.29-2.24 (m, 1H), 2.14-2.06 (m, 1H), 1.04 (s, 9H). HRMS (ESI) m/z: calcd C$_{48}$H$_9$CN$_{11}$O$_8$S$_2^+$ [M+H]$^+$, 1016.3673; found, 1016.3214.

Example 17: Preparation of N-(2-chloro-6-methylphenyl)-2-((6-(4-(2-(2-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)ethoxy)acetyl)piperazin-1-yl)-2-methylpyrimidin-4-yl)amino)thiazole-5-carboxamide (SIAIS151076)

Based on the general method of scheme 19 as described herein, compound (SIAIS151076) was obtained by coupling reaction of (SIAIS151055) with HO$_2$C-LIN-ULM analog (SIAIS151002) as a white solid (26.7 mg, 73% yield). $^1$H NMR (500 MHz, MeOD) δ 8.93 (s, 1H), 8.21 (s, 1H), 7.47 (d, J=8.2 Hz, 2H), 7.44-7.39 (m, 2H), 7.37 (dd, J=7.2, 1.4 Hz, 1H), 7.28-7.23 (m, 2H), 6.27 (s, 1H), 4.66 (s, 1H), 4.59-4.49 (m, 3H), 4.36 (d, J=15.5 Hz, 1H), 3.89 (d, J=11.0 Hz, 1H), 3.86-3.69 (m, 13H), 3.64-3.60 (m, 4H), 2.71 (t, J=6.1 Hz, 2H), 2.58 (s, 3H), 2.56-2.52 (m, 1H), 2.50 (d, J=6.1 Hz, 1H), 2.48 (s, 3H), 2.32 (s, 3H), 2.25-2.20 (m, 1H), 2.11-2.06 (m, 1H), 1.04 (s, 9H). HRMS (ESI) m/z: calcd $C_{50}H_{63}CN_{11}O_8S_2^+$ [M+H]$^+$, 1044.3986; found, 1044.3367.

Example 18: Preparation of N-(2-chloro-6-methylphenyl)-2-((6-(4-((S)-15-((2S,4R)-4-hydroxy-2-((4-(4-methylthiazol-5-yl)benzyl)carbamoyl)pyrrolidine-1-carbonyl)-16,16-dimethyl-13-oxo-4,7,10-trioxa-14-azaheptadecanoyl)piperazin-1-yl)-2-methylpyrimidin-4-yl)amino)thiazole-5-carboxamide (SIAIS151077)

Based on the general method of scheme 19 as described herein, compound (SIAIS151077) was obtained by coupling reaction of (SIAIS151055) with HO$_2$C-LIN-ULM analog (SIAIS151003) as a white solid (41.5 mg, 84% yield). $^1$H NMR (500 MHz, MeOD) δ 8.85 (s, 1H), 8.11 (s, 1H), 7.36 (d, J=8.2 Hz, 2H), 7.34-7.30 (m, 2H), 7.28-7.24 (m, 1H), 7.18-7.12 (m, 2H), 6.20 (s, 1H), 4.54 (s, 1H), 4.49-4.37 (m, 3H), 4.25 (d, J=15.5 Hz, 1H), 3.78-3.65 (m, 12H), 3.62-3.57 (m, 2H), 3.54-3.46 (m, 8H), 2.61 (t, J=6.1 Hz, 2H), 2.49 (s, 3H), 2.47-2.43 (m, 1H), 2.39-2.34 (m, 4H), 2.22 (s, 3H), 2.15-2.09 (m, 1H), 2.01-1.95 (m, 1H), 0.93 (s, 9H). HRMS (ESI) m/z: calcd $C_{52}H_{67}CN_{11}O_9S_2^+$ [M+H]$^+$, 1088.4248; found, 1088.3640.

Example 19: Preparation of N-(2-chloro-6-methylphenyl)-2-((6-(4-((S)-18-((2S,4R)-4-hydroxy-2-((4-(4-methylthiazol-5-yl)benzyl)carbamoyl)pyrrolidine-1-carbonyl)-19,19-dimethyl-16-oxo-4,7,10,13-tetraoxa-17-azaicosanoyl)piperazin-1-yl)-2-methylpyrimidin-4-yl)amino)thiazole-5-carboxamide (SIAIS151078)

Based on the general method of scheme 19 as described herein, compound (SIAIS151078) was obtained by coupling reaction of (SIAIS151055) with HO$_2$C-LIN-ULM analog (SIAIS151008) as a white solid (23 mg, 45% yield). $^1$H NMR (500 MHz, MeOD) δ 8.95 (s, 1H), 8.20 (s, 1H), 7.46 (d, J=8.1 Hz, 2H), 7.44-7.39 (m, 2H), 7.36 (d, J=7.2 Hz, 1H), 7.28-7.22 (m, 2H), 6.29 (s, 1H), 4.64 (s, 1H), 4.59-4.47 (m, 3H), 4.35 (d, J=15.5 Hz, 1H), 3.91-3.82 (m, 3H), 3.81-3.75 (m, 9H), 3.73-3.67 (m, 2H), 3.62-3.57 (m, 12H), 2.71 (t, J=6.0 Hz, 2H), 2.59 (s, 3H), 2.57-2.53 (m, 1H), 2.49-2.44 (m, 4H), 2.32 (s, 3H), 2.27-2.18 (m, 1H), 2.11-2.05 (m, 1H), 1.03 (s, 9H). HRMS (ESI) m/z: calcd $C_{54}H_{71}CN_{11}O_{10}S_2^+$ [M+H]$^+$, 1132.4510; found, 1132.3996.

Example 20: Preparation of N-(2-chloro-6-methylphenyl)-2-((6-(4-((S)-21-((2S,4R)-4-hydroxy-2-((4-(4-methylthiazol-5-yl)benzyl)carbamoyl)pyrrolidine-1-carbonyl)-22,22-dimethyl-19-oxo-4,7,10,13,16-pentaoxa-20-azatricosanoyl)piperazin-1-yl)-2-methylpyrimidin-4-yl)amino)thiazole-5-carboxamide (SIAIS151079)

Based on the general method of scheme 19 as described herein, compound (SIAIS151079) was obtained by coupling reaction of (SIAIS151055) with HO$_2$C-LIN-ULM analog (SIAIS151009) as a white solid (27.5 mg, 53% yield). $^1$H NMR (500 MHz, MeOD) δ 8.86 (s, 1H), 8.11 (s, 1H), 7.37 (d, J=8.1 Hz, 2H), 7.34-7.29 (m, 2H), 7.26 (d, J=7.2 Hz, 1H), 7.19-7.12 (m, 2H), 6.22 (s, 1H), 4.54 (s, 1H), 4.53-4.38 (m, 3H), 4.35 (d, J=15.5 Hz, 1H), 3.80-3.73 (m, 3H), 3.71-3.65 (m, 9H), 3.63-3.57 (m, 2H), 3.52-3.48 (m, 16H), 2.62 (t, J=6.0 Hz, 2H), 2.49 (s, 3H), 2.47-2.43 (m, 1H), 2.39-2.34 (m, 1H), 2.38 (s, 3H), 2.22 (s, 3H), 2.15-2.09 (m, 1H), 2.00-1.95 (m, 1H), 1.03 (s, 9H). HRMS (ESI) m/z: calcd $C_{56}H_{75}CN_{11}O_{11}S_2^+$ [M+H]$^+$, 1176.4772; found, 1176.4277.

Example 21: Preparation of N-(2-chloro-6-methylphenyl)-2-((6-(4-4-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-4-oxobutanoyl)piperazin-1-yl)-2-methylpyrimidin-4-yl)amino)thiazole-5-carboxamide (SIAIS151174)

Based on the general method of scheme 19 as described herein, compound (SIAIS151174) was obtained by coupling reaction of (SIAIS151055) with HO$_2$C-LIN-ULM analog (SIAIS074011) as a white solid (8.5 mg, 26% yield). $^1$H NMR (500 MHz, MeOD) δ 9.40 (s, 1H), 8.24 (s, 1H), 7.52-7.46 (m, 4H), 7.37 (d, J=6.8 Hz, 1H), 7.30-7.22 (m, 2H), 6.39 (s, 1H), 4.61 (s, 1H), 4.58-4.47 (m, 3H), 4.40-4.36 (m, 1H), 4.08-3.67 (m, 10H), 2.79-2.57 (m, 4H), 2.65 (s, 3H), 2.53 (s, 3H), 2.32 (s, 3H), 2.25-2.18 (m, 1H), 2.10-2.04 (m, 1H), 1.03 (s, 9H). HRMS (ESI) m/z: calcd $C_{46}H_{55}CN_{11}O_6S_2^+$ [M+H]$^+$, 956.3461; found, 956.2902.

Example 22: Preparation of N-(2-chloro-6-methylphenyl)-2-((6-(4-(5-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-5-oxopentanoyl)piperazin-1-yl)-2-methylpyrimidin-4-yl)amino)thiazole-5-carboxamide (SIAIS151175)

Based on the general method of scheme 19 as described herein, compound (SIAIS151175) was obtained by coupling reaction of (SIAIS151055) with HO$_2$C-LIN-ULM analog (SIAIS074012) as a white solid (7.6 mg, 24% yield). $^1$H NMR (500 MHz, MeOD) δ 9.44 (s, 1H), 8.23 (s, 1H), 7.53-7.49 (m, 2H), 7.48-7.45 (m, 2H), 7.39-7.35 (m, 1H), 7.30-7.22 (m, 2H), 6.39 (s, 1H), 4.62 (s, 1H), 4.59-4.49 (m, 3H), 4.41-4.36 (m, 1H), 3.98-3.66 (m, 10H), 2.64 (s, 3H), 2.53 (s, 3H), 2.48 (t, J=7.5 Hz, 2H), 2.40-2.34 (m, 2H), 2.32 (s, 3H), 2.25-2.21 (m, 1H), 2.13-2.05 (m, 1H), 2.10-2.05 (m, 2H), 1.09-1.03 (m, 9H). HRMS (ESI) m/z: calcd $C_{47}H_{57}CN_{11}O_6S_2^+$ [M+H]$^+$, 970.3618; found, 970.3060.

Example 23: Preparation of N-(2-chloro-6-methylphenyl)-2-((6-(4-(6-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-6-oxohexanoyl)piperazin-1-yl)-2-methylpyrimidin-4-yl)amino)thiazole-5-carboxamide (SIAIS151176)

Based on the general method of scheme 19 as described herein, compound (SIAIS151176) was obtained by coupling reaction of (SIAIS151055) with HO$_2$C-LIN-ULM analog (SIAIS074013) as a white solid (7.8 mg, 23% yield). $^1$H NMR (500 MHz, MeOD) δ 9.49 (s, 1H), 8.23 (s, 1H), 7.53-7.51 (m, 2H), 7.48-7.46 (m, 2H), 7.38-7.35 (m, 1H), 7.30-7.23 (m, 2H), 6.39 (s, 1H), 4.63 (s, 1H), 4.58-4.48 (m, 3H), 4.41-4.37 (m, 1H), 3.96-3.74 (m, 10H), 2.65 (s, 3H), 2.55 (s, 3H), 2.48 (t, J=6.4 Hz, 2H), 2.35-2.29 (m, 5H), 2.25-2.19 (m, 1H), 2.10-2.05 (m, 1H), 1.70-1.62 (m, 4H), 1.04 (s, 9H). HRMS (ESI) m/z: calcd $C_{48}H_{59}CN_{11}O_6S_2^+$ [M+H]$^+$, 984.3774; found, 984.3125.

Example 24: Preparation of N-(2-chloro-6-methylphenyl)-2-((6-(4-(7-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-7-oxoheptanoyl)piperazin-1-yl)-2-methylpyrimidin-4-yl)amino)thiazole-5-carboxamide (SIAIS151177)

Based on the general method of scheme 19 as described herein, compound (SIAIS151177) was obtained by coupling reaction of (SIAIS151055) with HO₂C-LIN-ULM analog (SIAIS074014) as a white solid (8.3 mg, 25% yield). ¹H NMR (500 MHz, MeOD) δ 9.45 (s, 1H), 8.24 (s, 1H), 7.52 (d, J=8.1 Hz, 2H), 7.49-7.46 (m, 2H), 7.37 (d, J=7.0 Hz, 1H), 7.28-7.23 (m, 2H), 6.39 (s, 1H), 4.64 (s, 1H), 4.60-4.48 (m, 3H), 4.41-4.37 (m, 1H), 4.05-3.65 (m, 10H), 2.65 (s, 3H), 2.54 (s, 3H), 2.46 (t, J=7.5 Hz, 2H), 2.36-2.19 (m, 3H), 2.32 (s, 3H), 2.10-2.05 (m, 1H), 1.68-1.62 (m, 4H), 1.43-1.37 (m, 2H), 1.02 (s, 9H). HRMS (ESI) m/z: calcd $C_{49}H_{61}ClN_{11}O_6S_2^+$ [M+H]⁺, 998.3931; found, 998.3324.

Example 25: Preparation of N-(2-chloro-6-methylphenyl)-2-((6-(4-(8-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-8-oxooctanoyl)piperazin-1-yl)-2-methylpyrimidin-4-yl)amino)thiazole-5-carboxamide (SIAIS151178)

Based on the general method of scheme 19 as described herein, compound (SIAIS151178) was obtained by coupling reaction of (SIAIS151055) with HO₂C-LIN-ULM analog (SIAIS074015) as a white solid (12.1 mg, 36% yield). ¹H NMR (500 MHz, MeOD) δ 9.34 (s, 1H), 8.23 (s, 1H), 7.53-7.49 (m, 2H), 7.48-7.45 (m, 2H), 7.37 (d, J=7.0 Hz, 1H), 7.30-7.22 (m, 2H), 6.38 (s, 1H), 4.64 (s, 1H), 4.59-4.49 (m, 3H), 4.40-4.36 (m, 1H), 4.03-3.68 (m, 10H), 2.65 (s, 3H), 2.53 (s, 3H), 2.46 (t, J=7.5 Hz, 2H), 2.32 (s, 3H), 2.30-2.19 (m, 3H), 2.11-2.04 (m, 1H), 1.67-1.60 (m, 4H), 1.42-1.35 (m, 4H), 1.03 (s, 9H). HRMS (ESI) m/z: calcd $C_{50}H_{63}ClN_{11}O_6S_2^+$ [M+H]⁺, 1012.4087; found, 1012.3439.

Example 26: Preparation of N-(2-chloro-6-methylphenyl)-2-((6-(4-(9-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-9-oxononanoyl)piperazin-1-yl)-2-methylpyrimidin-4-yl)amino)thiazole-5-carboxamide (SIAIS151179)

Based on the general method of scheme 19 as described herein, compound (SIAIS151179) was obtained by coupling reaction of (SIAIS151055) with HO₂C-LIN-ULM analog (SIAIS074016) as a white solid (9.3 mg, 27% yield). ¹H NMR (500 MHz, MeOD) δ 9.43 (s, 1H), 8.23 (s, 1H), 7.54-7.51 (m, 2H), 7.49-7.46 (m, 2H), 7.41-7.33 (m, 1H), 7.30-7.23 (m, 2H), 6.39 (s, 1H), 4.64 (s, 1H), 4.59-4.49 (m, 3H), 4.40-4.36 (m, 1H), 4.09-3.69 (m, 10H), 2.65 (s, 3H), 2.54 (s, 3H), 2.45 (t, J=7.6 Hz, 2H), 2.32 (s, 3H), 2.30-2.19 (m, 3H), 2.10-2.04 (m, 1H), 1.66-1.59 (m, 4H), 1.40-1.32 (m, 6H), 1.03 (s, 9H). HRMS (ESI) m/z: calcd $C_{51}H_{65}ClN_{11}O_6S_2^+$ [M+H]⁺, 1026.4244; found, 1026.5215.

Example 27: Preparation of N-(2-chloro-6-methylphenyl)-2-((6-(4-(10-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-10-oxodecanoyl)piperazin-1-yl)-2-methylpyrimidin-4-yl)amino)thiazole-5-carboxamide (SIAIS151180)

Based on the general method of scheme 19 as described herein, compound (SIAIS151180) was obtained by coupling reaction of (SIAIS151055) with HO₂C-LIN-ULM analog (SIAIS074019) as a white solid (8.4 mg, 24% yield). ¹H NMR (500 MHz, MeOD) δ 9.33 (s, 1H), 8.23 (s, 1H), 7.53-7.49 (m, 2H), 7.47-7.45 (m, 2H), 7.38-7.35 (m, 1H), 7.28-7.23 (m, 2H), 6.38 (s, 1H), 4.63 (s, 1H), 4.59-4.48 (m, 3H), 4.41-4.35 (m, 1H), 3.96-3.72 (m, 10H), 2.64 (s, 3H), 2.52 (s, 3H), 2.45 (t, J=7.5 Hz, 2H), 2.31 (s, 3H), 2.29-2.19 (m, 3H), 2.10-2.04 (m, 1H), 1.64-1.58 (m, 4H), 1.40-1.30 (m, 8H), 1.03 (s, 9H). HRMS (ESI) m/z: calcd $C_{52}H_{67}ClN_{11}O_6S_2^+$ [M+H]⁺, 1040.4400; found, 1040.3784.

Example 28: Preparation of N-(2-chloro-6-methylphenyl)-2-((6-(4-(14-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-14-oxotetradecanoyl)piperazin-1-yl)-2-methylpyrimidin-4-yl)amino)thiazole-5-carboxamide (SIAIS164193)

Based on the general method of scheme 19 as described herein, compound (SIAIS164193) was obtained by coupling reaction of (SIAIS151055) with HO₂C-LIN-ULM analog (SIAIS164185) as a white solid (6.2 mg, 25% yield). ¹H NMR (500 MHz, DMSO) δ 11.56 (s, 1H), 9.90 (s, 1H), 9.00 (s, 1H), 8.56 (t, J=5.8 Hz, 1H), 8.24 (s, 1H), 7.83 (d, J=9.4 Hz, 1H), 7.40 (q, J=8.1 Hz, 5H), 7.31-7.23 (m, 3H), 6.09 (s, 1H), 4.54 (d, J=9.4 Hz, 1H), 4.44-4.41 (m, 2H), 4.34 (s, 1H), 4.21 (dd, J=15.7, 5.4 Hz, 1H), 3.50-3.45 (m, 8H), 3.43-3.40 (m, 2H), 2.46-2.41 (m, 8H), 2.33 (t, J=7.6 Hz, 3H), 2.28-2.23 (m, 6H), 2.13-2.08 (m, 1H), 2.07-1.99 (m, 1H), 1.50 (s, 6H), 1.24-1.22 (m, 10H), 0.93 (s, 9H). HRMS (ESI) m/z: calcd $C_{56}H_{74}ClN_{11}O_6S_2^+$ [M+H]⁺, 1096.5026; found, 1096.6575.

Example 29: Preparation of N-(2-chloro-6-methylphenyl)-2-((6-(4-(16-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-16-oxohexadecanoyl)piperazin-1-yl)-2-methylpyrimidin-4-yl)amino)thiazole-5-carboxamide (SIAIS164194)

Based on the general method of scheme 19 as described herein, compound (SIAIS164194) was obtained by coupling reaction of (SIAIS151055) with HO₂C-LIN-ULM analog (SIAIS164189) as a white solid (6.8 mg, 27% yield). ¹H NMR (500 MHz, DMSO) δ 11.56 (s, 1H), 9.91 (s, 1H), 9.00 (s, 1H), 8.57 (t, J=6.1 Hz, 1H), 8.24 (s, 1H), 7.84 (d, J=9.3 Hz, 1H), 7.40 (t, J=8.7 Hz, 5H), 7.31-7.25 (m, 3H), 6.09 (s, 1H), 4.55 (d, J=9.4 Hz, 1H), 4.48-4.41 (m, 2H), 4.35 (s, 1H), 4.22 (dd, J=16.0, 5.5 Hz, 1H), 3.48-3.45 (m, 8H), 3.43-3.38 (m, 2H), 2.45 (t, J=5.0 Hz, 8H), 2.34 (t, J=6.5 Hz, 3H), 2.27-2.24 (m, 6H), 2.14-2.08 (m, 1H), 2.04-2.00 (m, 1H), 1.50 (d, J=6.2 Hz, 6H), 1.24-1.23 (m, 14H), 0.94 (s, 9H). HRMS (ESI) m/z: calcd $C_{58}H_{78}ClN_{11}O_6S_2^+$ [M+H]⁺, 1124.5339; found, 1123.6957.

Example 30: Preparation of N-(2-chloro-6-methylphenyl)-2-((6-(4-(6-(2-(2-((6-((2-(2,6-dioxopiperidin-3-yl)-1,3-dioxoisoindolin-4-yl)amino)-6-oxohexyl)oxy)ethoxy)ethoxy)hexanoyl)piperazin-1-yl)-2-methylpyrimidin-4-yl)amino)thiazole-5-carboxamide (SIAIS171114)

Based on the general method of scheme 19 as described herein, compound (SIAIS171114) was obtained by coupling reaction of (SIAIS151055) with HO₂C-LIN-ULM analog (SIAIS171104B) as a yellow solid (3.0 mg, 17% yield). ¹H NMR (500 MHz, MeOD) δ 8.63 (d, J=8.4 Hz, 1H), 8.22 (s, 1H), 7.81-7.71 (m, 1H), 7.57 (t, J=9.4 Hz, 1H), 7.37 (d, J=7.0 Hz, 1H), 7.27-7.24 (m, 2H), 6.36 (s, 1H), 5.13 (dd, J=12.5, 5.5 Hz, 1H), 4.00-3.75 (m, 8H), 3.66-3.53 (m, 8H), 3.50-3.42 (m, 4H), 2.94-2.82 (m, 1H), 2.80-2.70 (m, 2H), 2.66 (s, 3H), 2.51 (t, J=7.5 Hz, 2H), 2.48-2.42 (m, 2H), 2.31

(s, 3H), 2.20-2.11 (m, 1H), 1.77-1.74 (m, 2H), 1.70-1.55 (m, 6H), 1.52-1.35 (m, 4H). HRMS (ESI) m/z: calcd $C_{49}H_{60}ClN_{10}O_{10}S^+$ [M+H]$^+$, 1015.3898; found, 1015.3921.

Example 31: Preparation of N-(2-chloro-6-methylphenyl)-2-((6-(4-(4-((2-(2-(2,6-dioxopiperidin-3-yl)-1,3-dioxoisoindolin-4-yl)amino)ethyl)amino)-4-oxobutanoyl)piperazin-1-yl)-2-methylpyrimidin-4-yl)amino)thiazole-5-carboxamide (SIAIS164133)

Based on the general method of scheme 19 as described herein, compound (SIAIS164133) was obtained by coupling reaction of (SIAIS151055) with HO$_2$C-LIN-ULM analog (SIAIS164119) as a yellow solid (11.4 mg, 60% yield). $^1$H NMR (500 MHz, MeOD) δ 8.23 (s, 1H), 7.55 (dd, J=8.5, 7.2 Hz, 1H), 7.37 (dd, J=7.2, 2.0 Hz, 1H), 7.30-7.22 (m, 2H), 7.13 (d, J=8.5 Hz, 1H), 7.04 (d, J=7.1 Hz, 1H), 6.33 (s, 1H), 5.05 (dd, J=12.6, 5.5 Hz, 1H), 3.75 (s, 8H), 3.50-3.41 (m, 4H), 2.88-2.81 (m, 1H), 2.76-2.65 (ddd, J=20.8, 15.5, 5.6 Hz, 7H), 2.52 (t, J=6.6 Hz, 2H), 2.32 (s, 3H), 2.15-2.05 (m, 1H). HRMS (ESI) m/z: calcd $C_{39}H_{41}ClN_{11}O_7S^+$ [M+H]$^+$, 842.2594; found, 842.0407.

Example 32: Preparation of N-(2-chloro-6-methylphenyl)-2-((6-(4-(4-((2-(2-((2-(2,6-dioxopiperidin-3-yl)-1,3-dioxoisoindolin-4-yl)amino)ethoxy)ethyl)amino)-4-oxobutanoyl)piperazin-1-yl)-2-methylpyrimidin-4-yl)amino)thiazole-5-carboxamide (SIAIS164132)

Based on the general method of scheme 19 as described herein, compound (SIAIS164132) was obtained by coupling reaction of (SIAIS151055) with HO$_2$C-LIN-ULM analog (SIAIS164118) as a yellow solid (7.9 mg, 40% yield). $^1$H NMR (500 MHz, MeOD) δ 8.23 (s, 1H), 7.57 (dd, J=8.5, 7.2 Hz, 1H), 7.38-7.34 (m, 1H), 7.30-7.22 (m, 2H), 7.07 (dd, J=17.6, 7.8 Hz, 2H), 6.36 (s, 1H), 5.10 (dd, J=12.5, 5.4 Hz, 1H), 3.97-3.69 (m, 10H), 3.59 (t, J=5.2 Hz, 2H), 3.49 (t, J=5.1 Hz, 2H), 3.42 (t, J=4.9 Hz, 2H), 2.92-2.84 (m, 1H), 2.77-2.55 (m, 9H), 2.32 (s, 3H), 2.13-2.09 (m, 1H). HRMS (ESI) m/z: calcd $C_{41}H_{45}ClN_{11}O_8S^+$ [M+H]$^+$, 886.2856; found, 886.0532.

Example 33: Preparation of N-(2-chloro-6-methylphenyl)-2-((6-(4-(5-((2-(2,6-dioxopiperidin-3-yl)-1,3-dioxoisoindolin-4-yl)amino)-5-oxopentanoyl)piperazin-1-yl)-2-methylpyrimidin-4-yl)amino)thiazole-5-carboxamide (SIAIS184053)

Based on the general method of scheme 19 as described herein, compound (SIAIS184053) was obtained by coupling reaction of (SIAIS151055) with HO$_2$C-LIN-ULM analog (SIAIS184044) as a yellow solid (10 mg, 55% yield). $^1$H NMR (500 MHz, DMSO) δ 11.59 (s, 1H), 11.14 (s, 1H), 9.92 (s, 1H), 9.73 (s, 1H), 8.45 (d, J=8.4 Hz, 1H), 8.24 (s, 1H), 7.93-7.76 (m, 1H), 7.62 (d, J=7.0 Hz, 1H), 7.40 (d, J=7.7 Hz, 1H), 7.35-7.20 (m, 2H), 6.11 (s, 1H), 5.14 (dd, J=12.8, 5.4 Hz, 1H), 3.76-3.68 (m, 8H), 2.96-2.82 (m, 1H), 2.60 (dd, J=26.0, 6.5 Hz, 2H), 2.53 (d, J=4.4 Hz, 2H), 2.47 (d, J=7.4 Hz, 2H), 2.44 (s, 3H), 2.24 (s, 3H), 2.10-2.01 (m, 1H), 1.94-1.81 (m, 2H). HRMS (ESI) m/z: calcd $C_{38}H_{38}ClN_{10}O_7S^+$ [M+H]$^+$, 813.2329; found, 813.2346.

Example 34: Preparation of N-(2-chloro-6-methylphenyl)-2-((6-(4-(5-((2-(2,6-dioxopiperidin-3-yl)-1-oxoisoindolin-4-yl)amino)pentanoyl)piperazin-1-yl)-2-methylpyrimidin-4-yl)amino)thiazole-5-carboxamide (SIAIS184052)

Based on the general method of scheme 19 as described herein, compound (SIAIS184052) was obtained by coupling reaction of (SIAIS151055) with HO$_2$C-LIN-ULM analog (SIAIS184047) as a white solid (10.9 mg, 41% yield). $^1$H NMR (500 MHz, DMSO) δ 11.63 (s, 1H), 11.00 (s, 1H), 9.93 (s, 1H), 8.25 (s, 1H), 7.40 (d, J=7.9 Hz, 1H), 7.28 (td, J=15.2, 7.4 Hz, 3H), 6.96 (d, J=7.4 Hz, 1H), 6.80 (d, J=8.1 Hz, 1H), 6.12 (s, 1H), 5.11 (dd, J=13.2, 5.3 Hz, 1H), 4.25 (d, J=16.7 Hz, 1H), 4.15 (d, J=17.3 Hz, 1H), 3.59 (s, 8H), 3.16 (s, 2H), 2.92 (t, J=12.8 Hz, 1H), 2.61 (d, J=16.9 Hz, 1H), 2.45 (s, 3H), 2.41 (s, 2H), 2.30 (d, J=8.6 Hz, 1H), 2.24 (s, 3H), 2.04 (s, 1H), 1.63 (s, 4H). HRMS (ESI) m/z: calcd $C_{38}H_{42}ClN_{10}O_5S^+$ [M+H]$^+$, 785.2743; found, 785.2776.

Example 35: Preparation of N-(2-chloro-6-methylphenyl)-2-((6-(4-((S)-3-((2S,4R)-4-hydroxy-2-((4-(4-methylthiazol-5-yl)benzyl)carbamoyl)pyrrolidine-1-carbonyl)-2,2-dimethyl-5-oxo-11,14,17-trioxa-4-azatricosan-23-oyl)piperazin-1-yl)-2-methylpyrimidin-4-yl)amino)thiazole-5-carboxamide (SIAIS180147)

Based on the general method of scheme 19 as described herein, compound (SIAIS180147) was obtained by coupling reaction of (SIAIS151055) with HO$_2$C-LIN-ULM analog (SIAIS180127) as a white solid (2.9 mg, 8% yield). $^1$H NMR (500 MHz, MeOD) δ 9.54 (d, J=5.5 Hz, 1H), 8.24 (s, 1H), 7.53 (d, J=8.1 Hz, 2H), 7.48 (d, J=8.3 Hz, 2H), 7.39-7.35 (m, 1H), 7.29-7.23 (m, 2H), 6.40 (s, 1H), 4.63 (s, 1H), 4.58-4.53 (m, 2H), 4.49 (s, 1H), 4.38 (d, J=15.7 Hz, 1H), 3.95-3.73 (m, 10H), 3.63-3.61 (m, 4H), 3.59-3.55 (m, 4H), 3.50-3.45 (m, 4H), 2.65 (s, 3H), 2.55 (s, 3H), 2.47 (t, J=7.5 Hz, 2H), 2.31 (s, 3H), 2.30-2.19 (m, 3H), 2.10-2.05 (m, 1H), 1.67-1.57 (m, 8H), 1.46-1.37 (m, 4H), 1.03 (s, 9H). HRMS (ESI) m/z: calcd $C_{58}H_{79}ClN_{11}O_9S_2^+$ [M+H]$^+$, 1172.5187; found, 1172.3144.

Example 36: Preparation of N1-(5-(4-(6-((5-((2-chloro-6-methylphenyl)carbamoyl)thiazol-2-yl)amino)-2-methylpyrimidin-4-yl)piperazin-1-yl)-5-oxopentyl)-N10-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)decanediamide (SIAIS184032)

Based on the general method of scheme 19 as described herein, compound (SIAIS184032) was obtained by coupling reaction of (SIAIS151055) with HO$_2$C-LIN-ULM analog (SIAIS164178B) as a white solid (10.2 mg, 45% yield). $^1$H NMR (500 MHz, MeOD) δ 9.88 (s, 1H), 8.24 (s, 1H), 7.56 (d, J=8.3 Hz, 2H), 7.51 (d, J=8.3 Hz, 2H), 7.38-7.35 (m, 1H), 7.27-7.22 (m, 2H), 4.63 (s, 1H), 4.56 (dd, J=16.1, 8.0 Hz, 2H), 4.49 (s, 1H), 4.40 (d, J=15.8 Hz, 1H), 3.95-3.87 (m, 4H), 3.82-3.75 (m, 6H), 3.20 (t, J=6.7 Hz, 2H), 2.66 (s, 2H), 2.58 (s, 3H), 2.49 (t, J=7.3 Hz, 2H), 2.31 (s, 3H), 2.30-2.26 (m, 1H), 2.25-2.21 (m, 2H), 2.18 (t, J=7.5 Hz, 3H), 2.12-2.02 (m, 1H), 1.65-1.56 (m, 8H), 1.32 (s, 8H), 1.03 (s, 9H). HRMS (ESI) m/z: calcd $C_{57}H_{76}ClN_{12}O_7S_2^+$ [M+H]$^+$, 1139.5084; found, 1139.4847.

Example 37: Preparation of N-(2-chloro-6-methylphenyl)-2-((6-(4-(4-(1-(4-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-4-oxobutyl)-1H-1,2,3-triazol-4-yl)butanoyl)piperazin-1-yl)-2-methylpyrimidin-4-yl)amino)thiazole-5-carboxamide (SIAIS164134)

Based on the general method of scheme 19 as described herein, compound (SIAIS164134) was obtained by coupling reaction of (SIAIS151055) with HO₂C-LIN-ULM analog (SIAIS164128) as a white solid (9.1 mg, 37% yield). $^1$H NMR (500 MHz, MeOD) δ 9.73 (s, 1H), 8.24 (s, 1H), 8.11 (s, 1H), 7.54 (d, J=8.2 Hz, 2H), 7.50 (d, J=8.2 Hz, 2H), 7.38-7.36 (m, 1H), 7.29-7.24 (m, 2H), 6.40 (s, 1H), 4.62-4.55 (m, 3H), 4.53-4.50 (m, 3H), 4.43-4.39 (m, 1H), 3.94-3.75 (m, 10H), 2.86 (t, J=7.7 Hz, 2H), 2.65 (s, 3H), 2.58-2.54 (m, 5H), 2.38-2.31 (m, 5H), 2.26-2.22 (m, 3H), 2.10-2.02 (m, 3H), 1.04 (s, 9H). HRMS (ESI) m/z: calcd $C_{52}H_{64}ClN_{14}O_6S_2^+$ [M+H]⁺, 1079.4258; found, 1079.1240.

Example 38: Preparation of N-(2-chloro-6-methylphenyl)-2-((6-(4-(3-(2-(2,6-dioxopiperidin-3-yl)-1,3-dioxoisoindolin-4-yl)propanoyl)piperazin-1-yl)-2-methylpyrimidin-4-yl)amino)thiazole-5-carboxamide (SIAIS172150)

Based on the general method of scheme 19 as described herein, compound (SIAIS172150) was obtained by coupling reaction of (SIAIS151055) with HO₂C-LIN-ULM analog (SIAIS172147) as a white solid (24.2 mg, 47% yield). $^1$H NMR (500 MHz, DMSO) δ 11.12 (s, 1H), 9.94 (s, 1H), 8.25 (s, 1H), 7.88-7.82 (m, 2H), 7.78 (dd, J=7.8, 1.1 Hz, 1H), 7.40 (d, J=7.7 Hz, 1H), 7.31-7.23 (m, 2H), 6.12 (s, 1H), 5.14 (dd, J=12.8, 5.4 Hz, 1H), 3.59 (s, 6H), 3.49 (dd, J=7.8, 3.0 Hz, 1H), 3.41 (dd, J=7.8, 3.0 Hz, 1H), 3.04 (t, J=7.5 Hz, 2H), 2.93-2.85 (m, 1H), 2.80 (t, J=7.5 Hz, 2H), 2.64-2.52 (m, 2H), 2.45 (s, 3H), 2.24 (s, 3H), 2.06-2.02 (m, 1H). HRMS (ESI) m/z: calcd $C_{36}H_{35}CN_9O_6S^+$ [M+H]⁺, 756.2114; found, 756.2140.

Example 39: Preparation of N-(2-chloro-6-methylphenyl)-2-((6-(4-(2-((2-(2,6-dioxopiperidin-3-yl)-1,3-dioxoisoindolin-4-yl)oxy)acetyl)piperazin-1-yl)-2-methylpyrimidin-4-yl)amino)thiazole-5-carboxamide (SIAIS184128)

Based on the general method of scheme 19 as described herein, compound (SIAIS184128) was obtained by coupling reaction of (SIAIS151055) with HO₂C-LIN-ULM analog (SIAIS172101B) as a white solid (18.5 mg, 52% yield). $^1$H NMR (500 MHz, MeOD) δ 8.21 (s, 1H), 7.77 (dd, J=8.5, 7.3 Hz, 1H), 7.51 (d, J=7.1 Hz, 1H), 7.42 (d, J=8.5 Hz, 1H), 7.36 (dd, J=7.2, 1.9 Hz, 1H), 7.28-7.22 (m, 2H), 6.30 (s, 1H), 5.17 (d, J=2.3 Hz, 2H), 5.14-5.08 (m, 1H), 3.80 (d, J=29.3 Hz, 8H), 2.90-2.80 (m, 1H), 2.78-2.68 (m, 2H), 2.61 (s, 3H), 2.31 (s, 3H), 2.16-2.10 (m, 1H). HRMS (ESI) m/z: calcd $C_{35}H_{33}CN_9O_7S^+$ [M+H]⁺, 758.1907; found, 758.1913.

Example 40: Preparation of 4-((2,4-dichloro-5-methoxyphenyl)amino)-7-(3-(4-(3-(2-((2-(2,6-dioxopiperidin-3-yl)-1,3-dioxoisoindolin-4-yl)amino)ethoxy)propanoyl)piperazin-1-yl)propoxy)-6-methoxyquinoline-3-carbonitrile (SIAIS151157)

Based on the general method of scheme 19 as described herein, compound (SIAIS151157) was obtained by coupling reaction of (SIAIS151151) with HO₂C-LIN-ULM analog (SIAIS151001) as a yellow solid (12.3 mg, 48% yield). $^1$H NMR (500 MHz, MeOD) δ 8.86 (s, 1H), 8.00 (s, 1H), 7.66 (s, 1H), 7.55 (dd, J=8.4, 7.2 Hz, 1H), 7.42 (s, 1H), 7.38 (s, 1H), 7.08 (d, J=8.6 Hz, 1H), 6.99 (d, J=7.0 Hz, 1H), 5.05 (dd, J=12.6, 5.4 Hz, 1H), 4.77-4.69 (m, 1H), 4.38 (t, J=4.9 Hz, 3H), 4.06 (s, 3H), 3.94 (s, 3H), 3.88-3.80 (m, 2H), 3.78-3.68 (s, 4H), 3.53-3.49 (m, 2H), 3.36 (t, J=7.2 Hz, 2H), 3.23-2.94 (m, 3H), 2.90-2.81 (m, 2H), 2.74-2.66 (m, 2H), 2.43-2.35 (m, 2H), 2.14-2.08 (m, 1H). HRMS (ESI) m/z: calcd $C_{43}H_{45}Cl_2N_8O_9^+$[M+H]⁺, 887.2681; found, 887.2507.

Example 41: Preparation of 4-((2,4-dichloro-5-methoxyphenyl)amino)-7-(3-(4-(3-(2-(2-((2-(2,6-dioxopiperidin-3-yl)-1,3-dioxoisoindolin-4-yl)amino)ethoxy)ethoxy)propanoyl)piperazin-1-yl)propoxy)-6-methoxyquinoline-3-carbonitrile (SIAIS151158)

Based on the general method of scheme 19 as described herein, compound (SIAIS151158) was obtained by coupling reaction of (SIAIS151151) with HO₂C-LIN-ULM analog (SIAIS151004) as a yellow solid (14 mg, 52% yield). $^1$H NMR (500 MHz, MeOD) δ 8.83 (s, 1H), 7.96 (s, 1H), 7.66 (s, 1H), 7.51-7.45 (m, 1H), 7.41 (s, 1H), 7.36 (s, 1H), 7.04 (d, J=8.6 Hz, 1H), 6.94 (d, J=7.1 Hz, 1H), 5.07 (dd, J=12.6, 5.5 Hz, 1H), 4.78-4.65 (m, 1H), 4.38 (t, J=5.5 Hz, 2H), 4.36-4.24 (m, 1H), 4.06 (s, 3H), 3.95 (s, 3H), 3.81-3.60 (m, 12H), 3.48 (t, J=5.1 Hz, 2H), 3.46-3.40 (m, 2H), 3.28-3.12 (m, 2H), 3.10-2.95 (m, 1H), 2.92-2.83 (m, 2H), 2.76-2.66 (m, 2H), 2.46-2.39 (m, 2H), 2.14-2.09 (m, 1H). HRMS (ESI) m/z: calcd $C_{45}H_{49}Cl_2N_8O_{10}^+$ [M+H]⁺, 931.2943; found, 931.2866.

Example 42: Preparation of 4-((2,4-dichloro-5-methoxyphenyl)amino)-7-(3-(4-(3-(2-(2-(2-((2-(2,6-dioxopiperidin-3-yl)-1,3-dioxoisoindolin-4-yl)amino)ethoxy)ethoxy)ethoxy)propanoyl)piperazin-1-yl)propoxy)-6-methoxyquinoline-3-carbonitrile (SIAIS151159)

Based on the general method of scheme 19 as described herein, compound (SIAIS151159) was obtained by coupling reaction of (SIAIS151151) with HO₂C-LIN-ULM analog (SIAIS151005) as a yellow solid (13.2 mg, 46% yield). $^1$H NMR (500 MHz, MeOD) δ 8.83 (s, 1H), 7.94 (s, 1H), 7.66 (s, 1H), 7.47 (dd, J=8.0, 7.0 Hz, 1H), 7.41 (s, 1H), 7.36 (s, 1H), 7.00 (d, J=8.5 Hz, 1H), 6.96 (d, J=7.1 Hz, 1H), 5.07 (dd, J=12.6, 5.5 Hz, 1H), 4.78-4.70 (m, 1H), 4.46-4.32 (m, 3H), 4.05 (s, 3H), 3.95 (s, 3H), 3.81-3.58 (m, 16H), 3.50-3.43 (m, 4H), 3.27-3.00 (m, 3H), 2.95-2.83 (m, 2H), 2.78-2.65 (m, 2H), 2.48-2.39 (m, 2H), 2.15-2.08 (m, 1H). HRMS (ESI) m/z: calcd $C_{47}H_{53}Cl_2N_8O_{11}^+$ [M+H]⁺, 975.3205; found, 975.3144.

Example 43: Preparation of 4-((2,4-dichloro-5-methoxyphenyl)amino)-7-(3-(4-(1-((2-(2,6-dioxopiperidin-3-yl)-1,3-dioxoisoindolin-4-yl)amino)-3,6,9,12-tetraoxapentadecan-15-oyl)piperazin-1-yl)propoxy)-6-methoxyquinoline-3-carbonitrile (SIAIS151160)

Based on the general method of scheme 19 as described herein, compound (SIAIS151160) was obtained by coupling reaction of (SIAIS151151) with HO₂C-LIN-ULM analog (SIAIS151006) as a yellow solid (9.8 mg, 33% yield). $^1$H NMR (500 MHz, MeOD) δ 8.83 (s, 1H), 7.96 (s, 1H), 7.66 (s, 1H), 7.48 (dd, J=8.4, 7.2 Hz, 1H), 7.41 (s, 1H), 7.37 (s, 1H), 7.01 (d, J=8.6 Hz, 1H), 6.96 (d, J=7.1 Hz, 1H), 5.06 (dd, J=12.6, 5.5 Hz, 1H), 4.76 (s, 1H), 4.45-4.34 (m, 3H), 4.07 (s, 3H), 3.95 (s, 3H), 3.76-3.72 (m, 6H), 3.65-3.55 (m, 14H), 3.49-3.44 (m, 4H), 3.24-3.04 (m, 3H), 2.90-2.83 (m, 2H), 2.77-2.67 (m, 2H), 2.53-2.43 (m, 2H), 2.13-2.08 (m, 1H). HRMS (ESI) m/z: calcd $C_{49}H_{57}Cl_2N_8O_{12}^+$ [M+H]⁺, 1019.3468; found, 1019.3348.

Example 44: Preparation of 4-((2,4-dichloro-5-methoxyphenyl)amino)-7-(3-(4-(1-((2-(2,6-dioxopiperidin-3-yl)-1,3-dioxoisoindolin-4-yl)amino)-3,6,9,12,15-pentaoxaoctadecan-18-oyl)piperazin-1-yl)propoxy)-6-methoxyquinoline-3-carbonitrile (SIAIS151161)

Based on the general method of scheme 19 as described herein, compound (SIAIS151161) was obtained by coupling reaction of (SIAIS151151) with HO$_2$C-LIN-ULM analog (SIAIS151007) as a yellow solid (13.2 mg, 43% yield). $^1$H NMR (500 MHz, MeOD) δ 8.84 (s, 1H), 7.98 (s, 1H), 7.65 (d, J=4.0 Hz, 1H), 7.49 (dd, J=8.3, 7.3 Hz, 1H), 7.41 (t, J=9.8 Hz, 2H), 7.00 (dd, J=18.1, 7.8 Hz, 2H), 5.05 (dd, J=12.7, 5.4 Hz, 1H), 4.73 (s, 1H), 4.44 (t, J=5.3 Hz, 2H), 4.39-4.30 (m, 1H), 4.07 (s, 3H), 3.95 (s, 3H), 3.80-3.70 (m, 6H), 3.67-3.58 (m, 18H), 3.50-3.44 (m, 4H), 3.28-3.00 (m, 3H), 2.91-2.82 (m, 2H), 2.76-2.63 (m, 2H), 2.52-2.4 (m, 2H), 2.16-2.07 (m, 1H). HRMS (ESI) m/z: calcd C$_{51}$H$_{61}$Cl$_2$N$_8$O$_{13}$$^+$ [M+H]$^+$, 1063.3730; found, 1063.3582.

Example 45: Preparation of 4-((2,4-dichloro-5-methoxyphenyl)amino)-7-(3-(4-((2-(2,6-dioxopiperidin-3-yl)-1,3-dioxoisoindolin-4-yl)glycyl)piperazin-1-yl)propoxy)-6-methoxyquinoline-3-carbonitrile (SIAIS151164)

Based on the general method of scheme 19 as described herein, compound (SIAIS151164) was obtained by coupling reaction of (SIAIS151151) with HO$_2$C-LIN-ULM analog (SIAIS151025) as a yellow solid (8.6 mg, 36% yield). $^1$H NMR (500 MHz, MeOD) δ 8.85 (s, 1H), 8.00 (s, 1H), 7.66 (s, 1H), 7.57-7.51 (m, 1H), 7.40 (d, J=4.4 Hz, 2H), 7.07 (d, J=7.1 Hz, 1H), 7.00 (d, J=8.4 Hz, 1H), 5.08 (dd, J=12.5, 5.5 Hz, 1H), 4.76-4.58 (m, 1H), 4.50-4.42 (m, 2H), 4.26 (s, 3H), 4.09 (s, 3H), 4.40-4.14 (m, 3H), 3.81-3.61 (s, 3H), 3.57-3.47 (m, 2H), 3.30-2.97 (m, 3H), 2.91-2.82 (m, 1H), 2.77-2.69 (m, 2H), 2.52-2.45 (m, 2H), 2.18-2.10 (m, 1H). HRMS (ESI) m/z: calcd C$_{40}$H$_{39}$Cl$_2$N$_8$O$_8$$^+$ [M+H]$^+$, 829.2262; found, 829.2137.

Example 46: Preparation of 4-((2,4-dichloro-5-methoxyphenyl)amino)-7-(3-(4-(3-((2-(2,6-dioxopiperidin-3-yl)-1,3-dioxoisoindolin-4-yl)amino)propanoyl)piperazin-1-yl)propoxy)-6-methoxyquinoline-3-carbonitrile (SIAIS151165)

Based on the general method of scheme 19 as described herein, compound (SIAIS151165) was obtained by coupling reaction of (SIAIS151151) with HO$_2$C-LIN-ULM analog (SIAIS151026) as a yellow solid (9.2 mg, 38% yield). $^1$H NMR (500 MHz, MeOD) δ 8.85 (s, 1H), 8.00 (s, 1H), 7.66 (s, 1H), 7.58 (dd, J=8.4, 7.2 Hz, 1H), 7.40 (s, 2H), 7.14 (d, J=8.6 Hz, 1H), 7.06 (d, J=7.1 Hz, 1H), 5.04 (dd, J=12.5, 5.5 Hz, 1H), 4.79-4.64 (m, 1H), 4.44 (t, J=5.3 Hz, 2H), 4.33-4.13 (m, 1H), 4.08 (s, 3H), 3.94 (s, 3H), 3.82-3.52 (m, 5H), 3.47-3.42 (m, 2H), 3.26-2.92 (m, 3H), 2.90-2.79 (m, 2H), 2.79-2.63 (m, 3H), 2.47-2.43 (m, 2H), 2.13-2.08 (m, 1H). HRMS (ESI) m/z: calcd C$_{41}$H$_{41}$Cl$_2$N$_8$O$_8$$^+$ [M+H]$^+$, 843.2419; found, 843.1989.

Example 47: Preparation of 4-((2,4-dichloro-5-methoxyphenyl)amino)-7-(3-(4-(4-((2-(2,6-dioxopiperidin-3-yl)-1,3-dioxoisoindolin-4-yl)amino)butanoyl)piperazin-1-yl)propoxy)-6-methoxyquinoline-3-carbonitrile (SIAIS151162)

Based on the general method of scheme 19 as described herein, compound (SIAIS151162) was obtained by coupling reaction of (SIAIS151151) with HO$_2$C-LIN-ULM analog (SIAIS151019) as a yellow solid (11.3 mg, 45% yield). $^1$H NMR (500 MHz, MeOD) δ 8.84 (s, 1H), 8.00 (s, 1H), 7.66 (s, 1H), 7.57 (dd, J=8.5, 7.2 Hz, 1H), 7.40 (d, J=3.8 Hz, 2H), 7.13 (d, J=8.6 Hz, 1H), 7.05 (d, J=7.0 Hz, 1H), 5.06 (dd, J=12.6, 5.5 Hz, 1H), 4.78-4.62 (m, 1H), 4.44 (t, J=5.5 Hz, 2H), 4.34-4.14 (m, 1H), 4.08 (s, 3H), 3.94 (s, 3H), 3.79-3.52 (m, 3H), 3.49-3.40 (m, 4H), 3.25-2.95 (m, 3H), 2.91-2.78 (m, 1H), 2.76-2.68 (m, 2H), 2.59 (s, 2H), 2.49-2.43 (m, 2H), 2.13-2.08 (m, 1H), 2.03-1.98 (m, 2H). HRMS (ESI) m/z: calcd C$_{42}$H$_{43}$Cl$_2$N$_8$O$_8$$^+$ [M+H]$^+$, 857.2575; found, 857.2471.

Example 48: Preparation of 4-((2,4-dichloro-5-methoxyphenyl)amino)-7-(3-(4-(5-((2-(2,6-dioxopiperidin-3-yl)-1,3-dioxoisoindolin-4-yl)amino)pentanoyl)piperazin-1-yl)propoxy)-6-methoxyquinoline-3-carbonitrile (SIAIS151163)

Based on the general method of scheme 19 as described herein, compound (SIAIS151163) was obtained by coupling reaction of (SIAIS151151) with HO$_2$C-LIN-ULM analog (SIAIS151020) as a yellow solid (12 mg, 47% yield). $^1$H NMR (500 MHz, MeOD) δ 8.86 (s, 1H), 8.01 (s, 1H), 7.67 (s, 1H), 7.56 (dd, J=8.4, 7.2 Hz, 1H), 7.41 (s, 2H), 7.07 (d, J=8.5 Hz, 1H), 7.04 (d, J=7.0 Hz, 1H), 5.05 (dd, J=12.6, 5.4 Hz, 1H), 4.77-4.62 (m, 1H), 4.45 (t, J=5.3 Hz, 2H), 4.32-4.15 (s, 1H), 4.08 (s, 3H), 3.94 (s, 3H), 3.82-3.56 (m, 3H), 3.50-3.43 (m, 2H), 3.42-3.36 (m, 2H), 3.22-2.94 (m, 3H), 2.87-2.80 (m, 1H), 2.75-2.67 (m, 2H), 2.55 (s, 2H), 2.49-2.43 (m, 2H), 2.12-2.06 (m, 1H), 1.80-1.71 (m, 4H). HRMS (ESI) m/z: calcd C$_{43}$H$_{45}$Cl$_2$N$_8$O$_8$$^+$[M+H]$^+$, 871.2732; found, 871.2615.

Example 49: Preparation of 4-((2,4-dichloro-5-methoxyphenyl)amino)-7-(3-(4-(6-((2-(2,6-dioxopiperidin-3-yl)-1,3-dioxoisoindolin-4-yl)amino)hexanoyl)piperazin-1-yl)propoxy)-6-methoxyquinoline-3-carbonitrile (SIAIS151166)

Based on the general method of scheme 19 as described herein, compound (SIAIS151166) was obtained by coupling reaction of (SIAIS151151) with HO$_2$C-LIN-ULM analog (SIAIS151027) as a yellow solid (12.8 mg, 50% yield). $^1$H NMR (500 MHz, MeOD) δ 8.85 (s, 1H), 8.00 (s, 1H), 7.66 (s, 1H), 7.55 (dd, J=8.0, 7.0 Hz, 1H), 7.40 (d, J=3.9 Hz, 2H), 7.04 (dd, J=12.2, 7.8 Hz, 2H), 5.05 (dd, J=12.4, 5.5 Hz, 1H), 4.79-4.64 (m, 1H), 4.45 (t, J=5.5 Hz, 2H), 4.35-4.18 (m, 1H), 4.08 (s, 3H), 3.93 (s, 3H), 3.84-3.54 (m, 3H), 3.48 (t, J=7.2 Hz, 2H), 3.36 (t, J=6.8 Hz, 2H), 3.27-2.95 (m, 3H), 2.89-2.82 (m, 1H), 112.78-2.65 (m, 2H), 2.54-2.43 (m, 4H), 2.13-2.08 (m, 1H), 1.76-1.65 (m, 4H), 1.53-1.47 (m, 2H). HRMS (ESI) m/z: calcd C$_{44}$H$_{47}$Cl$_2$N$_8$O$_8$$^+$ [M+H]$^+$, 885.2888; found, 885.2423.

Example 50: Preparation of 4-((2,4-dichloro-5-methoxyphenyl)amino)-7-(3-(4-(7-((2-(2,6-dioxopiperidin-3-yl)-1,3-dioxoisoindolin-4-yl)amino)heptanoyl)piperazin-1-yl)propoxy)-6-methoxyquinoline-3-carbonitrile (SIAIS151167)

Based on the general method of scheme 19 as described herein, compound (SIAIS151167) was obtained by coupling reaction of (SIAIS151151) with HO$_2$C-LIN-ULM analog (SIAIS151086) as a yellow solid (14.1 mg, 54% yield). $^1$H NMR (500 MHz, MeOD) δ 8.82 (s, 1H), 7.97 (s, 1H), 7.66 (s, 1H), 7.55 (dd, J=8.5, 7.5 Hz, 1H), 7.39 (d, J=6.1 Hz, 2H), 7.05 (t, J=8.3 Hz, 2H), 5.05 (dd, J=12.4, 5.5 Hz, 1H), 4.79-4.63 (m, 1H), 4.44 (t, J=5.5 Hz, 2H), 4.32-4.14 (m, 1H), 4.08 (s, 3H), 3.93 (s, 3H), 3.80-3.54 (m, 3H), 3.48 (t, J=7.2 Hz, 2H), 3.35 (t, J=6.8 Hz, 2H), 3.25-3.00 (m, 3H), 2.89-2.81 (m, 1H), 2.78-2.65 (m, 2H), 2.54-2.43 (m, 4H), 2.14-2.07 (m, 1H), 1.72-1.62 (m, 4H), 1.52-1.43 (m, 4H). HRMS (ESI) m/z: calcd $C_{45}H_{49}Cl_2N_8O_8^+$ [M+H]$^+$, 899.3045; found, 899.2559.

Example 51: Preparation of 3-(4-(3-((3-cyano-4-((2,4-dichloro-5-methoxyphenyl)amino)-6-methoxyquinolin-7-yl)oxy)propyl)piperazin-1-yl)-N-(2-(2,6-dioxopiperidin-3-yl)-1-oxoisoindolin-4-yl)-3-oxopropanamide (SIAIS164104)

Based on the general method of scheme 19 as described herein, compound (SIAIS164104) was obtained by coupling reaction of (SIAIS151151) with HO$_2$C-LIN-ULM analog (SIAIS171004) as a yellow solid (13.2 mg, 54% yield). $^1$H NMR (500 MHz, DMSO) δ 11.32 (s, 1H), 11.03 (s, 1H), 10.22 (s, 1H), 8.95 (s, 1H), 8.23 (s, 1H), 7.88 (dd, J=7.4, 1.3 Hz, 1H), 7.84 (s, 1H), 7.57-7.47 (m, 4H), 5.16 (dd, J=13.3, 5.1 Hz, 1H), 4.51-4.42 (m, 2H), 4.38-4.30 (m, 3H), 4.14 (d, J=15.1 Hz, 1H), 4.02 (s, 3H), 3.88 (s, 3H), 3.72 (s, 2H), 3.65-3.59 (m, 2H), 3.34-3.28 (m, 2H), 3.25-3.08 (m, 3H), 3.03-2.88 (m, 2H), 2.64-2.60 (m, 1H), 2.41-2.28 (m, 3H), 2.09-2.02 (m, 1H).HRMS (ESI) m/z: calcd $C_{41}H_{41}Cl_2N_8O_8^+$ [M+H]$^+$, 843.2419; found, 843.3409.

Example 52: Preparation of 4-(4-(3-((3-cyano-4-((2,4-dichloro-5-methoxyphenyl)amino)-6-methoxyquinolin-7-yl)oxy)propyl)piperazin-1-yl)-N-(2-(2,6-dioxopiperidin-3-yl)-1-oxoisoindolin-4-yl)-4-oxobutanamide (SIAIS164105)

Based on the general method of scheme 19 as described herein, compound (SIAIS164105) was obtained by coupling reaction of (SIAIS151151) with HO$_2$C-LIN-ULM analog (SIAIS164084) as a yellow solid (11.8 mg, 48% yield). $^1$H NMR (500 MHz, MeOD) δ 8.87 (s, 1H), 8.01 (s, 1H), 7.72 (d, J=7.9 Hz, 1H), 7.67 (s, 1H), 7.63 (d, J=7.4 Hz, 1H), 7.51 (t, J=7.7 Hz, 1H), 7.41 (d, J=6.2 Hz, 2H), 5.18 (dd, J=13.3, 5.1 Hz, 1H), 4.77-4.66 (m, 1H), 4.48 (s, 2H), 4.45 (t, J=5.6 Hz, 2H), 4.40-4.32 (m, 1H), 4.07 (s, 3H), 3.94 (s, 3H), 3.80-3.72 (m, 2H), 3.71-3.61 (m, 1H), 3.51-3.45 (m, 2H), 3.25-3.15 (m, 1H), 3.12-3.03 (m, 1H), 3.00-2.55 (m, 7H), 2.50-2.43 (m, 3H), 2.22-2.16 (m, 1H). HRMS (ESI) m/z: calcd $C_{42}H_{43}Cl_2N_8O_8^+$ [M+H]$^+$, 857.2575; found, 857.3555.

Example 53: Preparation of 5-(4-(3-((3-cyano-4-((2,4-dichloro-5-methoxyphenyl)amino)-6-methoxyquinolin-7-yl)oxy)propyl)piperazin-1-yl)-N-(2-(2,6-dioxopiperidin-3-yl)-1-oxoisoindolin-4-yl)-5-oxopentanamide (SIAIS164106)

Based on the general method of scheme 19 as described herein, compound (SIAIS164106) was obtained by coupling reaction of (SIAIS151151) with HO$_2$C-LIN-ULM analog (SIAIS171005) as a yellow solid (14.1 mg, 56% yield). $^1$H NMR (500 MHz, DMSO) δ 11.18 (s, 1H), 11.02 (s, 1H), 9.92 (s, 1H), 8.92 (s, 1H), 8.21 (s, 1H), 7.84-7.81 (m, 2H), 7.56-7.45 (m, 4H), 5.15 (dd, J=13.3, 5.1 Hz, 1H), 4.51-4.44 (m, 1H), 4.42-4.30 (m, 4H), 4.09 (d, J=13.8 Hz, 1H), 4.01 (s, 3H), 3.88 (s, 3H), 3.57-3.54 (m, 3H), 3.31-3.24 (m, 2H), 3.16-3.05 (m, 3H), 2.98-2.87 (m, 2H), 2.63-2.59 (m, 3H), 2.47-2.42 (m, 3H), 2.38-2.30 (m, 3H), 2.08-1.99 (m, 1H), 1.88-1.82 (m, 2H).HRMS (ESI) m/z: calcd $C_{43}H_{45}Cl_2N_8O_8^+$ [M+H]$^+$, 871.2732; found, 871.3725.

Example 54: Preparation of (2S,4R)-1-((S)-2-(tert-butyl)-16-(4-(3-((3-cyano-4-((2,4-dichloro-5-methoxyphenyl)amino)-6-methoxyquinolin-7-yl)oxy)propyl)piperazin-1-yl)-4,16-dioxo-7,10,13-trioxa-3-azahexadecanoyl)-4-hydroxy-N-(4-(4-methylthiazol-5-yl)benzyl)pyrrolidine-2-carboxamide (SIAIS172082)

Based on the general method of scheme 19 as described herein, compound (SIAIS172082) was obtained by coupling reaction of (SIAIS151151) with HO$_2$C-LIN-ULM analog (SIAIS151003) as a white solid (6.2 mg, 46% yield). $^1$H NMR (500 MHz, MeOD) δ 9.95 (s, 1H), 8.88 (s, 1H), 8.04 (s, 1H), 7.67 (s, 1H), 7.57 (d, J=7.7 Hz, 2H), 7.52 (d, J=8.1 Hz, 2H), 7.42 (d, J=6.1 Hz, 2H), 4.64 (s, 1H), 4.60-4.56 (m, 2H), 4.50-4.47 (m, 3H), 4.42 (d, J=15.9 Hz, 1H), 4.09 (s, 3H), 3.94 (s, 3H), 3.90 (d, J=11.1 Hz, 1H), 3.82-3.76 (m, 4H), 3.74-3.70 (m, 3H), 3.67-3.59 (m, 10H), 3.53-3.47 (m, 2H), 3.27-3.17 (m, 2H), 3.11-3.05 (m, 1H), 2.88-2.80 (m, 1H), 2.69-2.55 (m, 6H), 2.51-2.45 (m, 3H), 2.26-2.22 (m, 1H), 2.11-2.03 (m, 1H), 1.04 (s, 9H).HRMS (ESI) m/z: calcd $C_{57}H_{72}Cl_2N_9O_{11}S^+$ [M+H]$^+$, 1160.4444; found, 1160.4225.

Example 55: Preparation of (2S,4R)-1-((S)-2-(tert-butyl)-19-(4-(3-((3-cyano-4-((2,4-dichloro-5-methoxyphenyl)amino)-6-methoxyquinolin-7-yl)oxy)propyl)piperazin-1-yl)-4,19-dioxo-7,10,13,16-tetraoxa-3-azanonadecanoyl)-4-hydroxy-N-(4-(4-methylthiazol-5-yl)benzyl)pyrrolidine-2-carboxamide (SIAIS172083)

Based on the general method of scheme 19 as described herein, compound (SIAIS172083) was obtained by coupling reaction of (SIAIS151151) with HO$_2$C-LIN-ULM analog (SIAIS151008) as a white solid (5.0 mg, 36% yield). $^1$H NMR (500 MHz, MeOD) δ 9.90 (s, 1H), 8.88 (s, 1H), 8.03 (s, 1H), 7.67 (s, 1H), 7.56 (d, J=8.4 Hz, 2H), 7.52 (d, J=8.3 Hz, 2H), 7.42 (d, J=5.0 Hz, 2H), 4.64 (s, 1H), 4.59-4.52 (m, 2H), 4.50-4.46 (m, 3H), 4.42 (d, J=15.7 Hz, 1H), 4.09 (s, 3H), 3.94 (s, 3H), 3.90 (d, J=10.9 Hz, 1H), 3.82-3.71 (m, 7H), 3.64-3.60 (m, 14H), 3.53-3.47 (m, 2H), 3.26-3.15 (m, 2H), 3.12-3.05 (m, 1H), 2.92-2.84 (m, 1H), 2.63-2.55 (m, 5H), 2.51-2.46 (m, 3H), 2.28-2.21 (m, 1H), 2.10-2.04 (m, 1H), 1.04 (s, 9H). HRMS (ESI) m/z: calcd $C_{63}H_{84}Cl_2N_9O_8S^+$ [M+H]$^+$, 1204.4706; found, 1204.4476.

Example 56: Preparation of (2S,4R)-1-((S)-2-(tert-butyl)-22-(4-(3-((3-cyano-4-((2,4-dichloro-5-methoxyphenyl)amino)-6-methoxyquinolin-7-yl)oxy)propyl)piperazin-1-yl)-4,22-dioxo-7,10,13,16,19-pentaoxa-3-azadocosanoyl)-4-hydroxy-N-(4-(4-methylthiazol-5-yl)benzyl)pyrrolidine-2-carboxamide (SIAIS172084)

Based on the general method of scheme 19 as described herein, compound (SIAIS172084) was obtained by coupling reaction of (SIAIS151151) with HO$_2$C-LIN-ULM analog (SIAIS151009) as a white solid (6.0 mg, 42% yield). $^1$H NMR (500 MHz, MeOD) δ 9.57 (d, J=4.9 Hz, 1H), 8.88 (d, J=3.7 Hz, 1H), 8.02 (s, 1H), 7.67 (s, 1H), 7.53 (d, J=8.3 Hz, 2H), 7.48 (d, J=8.3 Hz, 2H), 7.41 (d, J=4.4 Hz, 2H), 4.63 (s, 1H), 4.58-4.52 (m, 2H), 4.49-4.45 (m, 3H), 4.41-4.37 (m, 1H), 4.08 (s, 3H), 3.93 (s, 3H), 3.89 (d, J=11.1 Hz, 1H), 3.81-3.68 (m, 9H), 3.62-3.60 (m, 20H), 3.50-3.46 (m, 2H), 2.63-2.53 (m, 3H), 2.55 (s, 3H), 2.51-2.45 (m, 3H), 2.25-2.21 (m, 1H), 2.10-2.04 (m, 1H), 1.03 (s, 9H), HRMS (ESI) m/z: calcd $C_{61}H_{80}Cl_2N_9O_{13}S^+$ [M+H]$^+$, 1248.4968; found, 1248.4678.

Example 57: Preparation of (2S,4R)-1-((S)-2-(4-(4-(3-((3-cyano-4-((2,4-dichloro-5-methoxyphenyl)amino)-6-methoxyquinolin-7-yl)oxy)propyl)piperazin-1-yl)-4-oxobutanamido)-3,3-dimethylbutanoyl)-4-hydroxy-N-(4-(4-methylthiazol-5-yl)benzyl)pyrrolidine-2-carboxamide (SIAIS172072)

Based on the general method of scheme 19 as described herein, compound (SIAIS172072) was obtained by coupling reaction of (SIAIS151151) with HO$_2$C-LIN-ULM analog (SIAIS074011) as a white solid (10 mg, 83% yield). $^1$H NMR (500 MHz, MeOD) δ 8.97 (s, 1H), 8.86 (s, 1H), 7.99 (s, 1H), 7.67 (s, 1H), 7.47 (d, J=8.3 Hz, 2H), 7.43-7.39 (m, 4H), 4.62-4.48 (m, 4H), 4.44 (t, J=5.4 Hz, 2H), 4.37 (d, J=15.5 Hz, 1H), 4.08 (s, 3H), 3.93 (s, 3H), 3.89 (d, J=11.0 Hz, 1H), 3.80 (dd, J=11.0, 4.0 Hz, 1H), 3.49 (t, J=7.3 Hz, 2H), 3.33-3.31 (m, 6H), 2.78-2.58 (m, 4H), 2.48 (s, 3H), 2.48-2.43 (m, 2H), 2.24-2.20 (m, 1H), 2.11-2.06 (m, 1H), 1.05 (s, 9H). HRMS (ESI) m/z: calcd $C_{51}H_{60}Cl_2N_9O_8S^+$ [M+H]$^+$, 1028.3657; found, 1028.3466.

Example 58: Preparation of (2S,4R)-1-((S)-2-(5-(4-(3-((3-cyano-4-((2,4-dichloro-5-methoxyphenyl)amino)-6-methoxyquinolin-7-yl)oxy)propyl)piperazin-1-yl)-5-oxopentanamido)-3,3-dimethylbutanoyl)-4-hydroxy-N-(4-(4-methylthiazol-5-yl)benzyl)pyrrolidine-2-carboxamide (SIAIS172073)

Based on the general method of scheme 19 as described herein, compound (SIAIS172073) was obtained by coupling reaction of (SIAIS151151) with HO$_2$C-LIN-ULM analog (SIAIS074012) as a white solid (10.7 mg, 87% yield). $^1$H NMR (500 MHz, MeOD) δ 9.61 (s, 1H), 8.88 (s, 1H), 8.01 (s, 1H), 7.67 (s, 1H), 7.55-7.51 (m, 2H), 7.49-7.47 (m, 2H), 7.41 (d, J=2.7 Hz, 2H), 4.63-4.49 (m, 4H), 4.46 (t, J=5.4 Hz, 2H), 4.40 (d, J=15.7 Hz, 1H), 4.08 (s, 3H), 3.93 (s, 3H), 3.82-3.59 (m, 4H), 3.51-3.45 (m, 2H), 3.34-3.31 (m, 2H), 3.30-3.00 (m, 4H), 2.55 (s, 3H), 2.47 (s, 4H), 2.37 (t, J=7.1 Hz, 2H), 2.28-2.21 (m, 1H), 2.11-2.04 (m, 1H), 1.97-1.89 (m, 2H), 1.05 (s, 9H). HRMS (ESI) m/z: calcd $C_{52}H_{62}Cl_2N_9O_8S^+$ [M+H]$^+$, 1042.3814; found, 1042.3593.

Example 59: Preparation of (2S,4R)-1-((S)-2-(6-(4-(3-((3-cyano-4-((2,4-dichloro-5-methoxyphenyl)amino)-6-methoxyquinolin-7-yl)oxy)propyl)piperazin-1-yl)-6-oxohexanamido)-3,3-dimethylbutanoyl)-4-hydroxy-N-(4-(4-methylthiazol-5-yl)benzyl)pyrrolidine-2-carboxamide (SIAIS172074)

Based on the general method of scheme 19 as described herein, compound (SIAIS172074 was obtained by coupling reaction of (SIAIS151151) with HO$_2$C-LIN-ULM analog (SIAIS074013) as a white solid (9.0 mg, 73% yield). $^1$H NMR (500 MHz, MeOD) δ 9.93 (s, 1H), 8.88 (s, 1H), 8.03 (s, 1H), 7.67 (s, 1H), 7.58-7.56 (m, 2H), 7.53-7.51 (m, 2H), 7.42 (d, J=4.2 Hz, 2H), 4.64-4.45 (m, 6H), 4.41 (d, J=15.7 Hz, 1H), 4.09 (s, 3H), 3.94 (s, 3H), 3.91 (d, J=11.2 Hz, 1H), 3.83-3.73 (m, 3H), 3.70-3.46 (m, 4H), 3.30-3.06 (m, 4H), 2.60 (s, 3H), 2.53-2.44 (m, 4H), 2.38-2.28 (m, 2H), 2.27-2.20 (m, 1H), 2.10-2.02 (m, 1H), 1.72-1.62 (m, 4H), 1.04 (s, 9H). HRMS (ESI) m/z: calcd $C_{53}H_{64}Cl_2N_9O_8S^+$ [M+H]$^+$, 1056.3970; found, 1056.3754.

Example 60: Preparation of (2S,4R)-1-((S)-2-(7-(4-(3-((3-cyano-4-((2,4-dichloro-5-methoxyphenyl)amino)-6-methoxyquinolin-7-yl)oxy)propyl)piperazin-1-yl)-7-oxoheptanamido)-3,3-dimethylbutanoyl)-4-hydroxy-N-(4-(4-methylthiazol-5-yl)benzyl)pyrrolidine-2-carboxamide (SIAIS172075)

Based on the general method of scheme 19 as described herein, compound (SIAIS172075) was obtained by coupling reaction of (SIAIS151151) with HO$_2$C-LIN-ULM analog (SIAIS074014) as a white solid (9.6 mg, 77% yield). $^1$H NMR (500 MHz, MeOD) δ 9.99 (s, 1H), 8.88 (s, 1H), 8.04 (s, 1H), 7.66 (s, 1H), 7.58-7.56 (m, 2H), 7.53-7.51 (m, 2H), 7.42 (d, J=5.5 Hz, 2H), 4.64-4.45 (m, 6H), 4.41 (d, J=15.8 Hz, 1H), 4.09 (s, 3H), 3.94 (s, 3H), 3.90 (d, J=11.1 Hz, 1H), 3.83-3.73 (m, 3H), 3.72-3.43 (m, 4H), 3.30-3.04 (m, 4H), 2.60 (s, 3H), 2.52-2.44 (m, 4H), 2.34-2.21 (m, 3H), 2.11-2.04 (m, 1H), 1.68-1.61 (m, 4H), 1.42-1.36 (m, 2H), 1.03 (s, 9H). HRMS (ESI) m/z: calcd $C_{54}H_{66}Cl_2N_9O_8S^+$ [M+H]$^+$, 1070.4127; found, 1070.3939.

Example 61: Preparation of (2S,4R)-1-((S)-2-(8-(4-(3-((3-cyano-4-((2,4-dichloro-5-methoxyphenyl)amino)-6-methoxyquinolin-7-yl)oxy)propyl)piperazin-1-yl)-8-oxooctanamido)-3,3-dimethylbutanoyl)-4-hydroxy-N-(4-(4-methylthiazol-5-yl)benzyl)pyrrolidine-2-carboxamide (SIAIS172076)

Based on the general method of scheme 19 as described herein, compound (SIAIS172076) was obtained by coupling reaction of (SIAIS151151) with HO$_2$C-LIN-ULM analog (SIAIS074015) as a white solid (6.0 mg, 48% yield). $^1$H NMR (500 MHz, MeOD) δ 9.99 (s, 1H), 8.88 (s, 1H), 8.04 (s, 1H), 7.67 (s, 1H), 7.59-7.57 (m, 2H), 7.54-7.52 (m, 2H), 7.43 (d, J=4.2 Hz, 2H), 4.64 (s, 1H), 4.59-4.54 (m, 2H), 4.50-4.46 (m, 3H), 4.41 (d, J=15.7 Hz, 1H), 4.09 (s, 3H), 3.94 (s, 3H), 3.91 (d, J=11.1 Hz, 1H), 3.83-3.73 (m, 3H), 3.70-3.46 (m, 4H), 3.30-3.04 (m, 4H), 2.61 (s, 3H), 2.51-2.45 (m, 4H), 2.33-2.22 (m, 3H), 2.10-2.04 (m, 1H), 1.66-1.60 (m, 4H), 1.42-1.36 (m, 4H), 1.04 (s, 9H). HRMS (ESI) m/z: calcd $C_{55}H_{68}Cl_2N_9O_8S^+$ [M+H]$^+$, 1084.4238; found, 1084.4072.

Example 62: Preparation of (2S,4R)-1-((S)-2-(9-(4-(3-((3-cyano-4-((2,4-dichloro-5-methoxyphenyl)amino)-6-methoxyquinolin-7-yl)oxy)propyl)piperazin-1-yl)-9-oxononanamido)-3,3-dimethylbutanoyl)-4-hydroxy-N-(4-(4-methylthiazol-5-yl)benzyl)pyrrolidine-2-carboxamide (SIAIS172077)

Based on the general method of scheme 19 as described herein, compound (SIAIS172077) was obtained by coupling reaction of (SIAIS151151) with HO$_2$C-LIN-ULM analog (SIAIS074016) as a white solid (6.4 mg, 48% yield). $^1$H NMR (500 MHz, MeOD) δ 9.93 (s, 1H), 8.88 (s, 1H), 8.03 (s, 1H), 7.67 (s, 1H), 7.57 (d, J=8.3 Hz, 2H), 7.53-7.51 (m, 2H), 7.42 (d, J=2.6 Hz, 2H), 4.64 (s, 1H), 4.60-4.53 (m, 2H), 4.50-4.46 (m, 3H), 4.41 (d, J=15.7 Hz, 1H), 4.09 (s, 3H), 3.94 (s, 3H), 3.91 (d, J=11.1 Hz, 1H), 3.83-3.73 (m, 3H), 3.68-3.46 (m, 4H), 3.30-3.08 (m, 4H), 2.60 (s, 3H), 2.51-2.44 (m, 4H), 2.34-2.20 (m, 3H), 2.10-2.04 (m, 1H), 1.66-

1.60 (m, 4H), 1.38-1.34 (m, 6H), 1.03 (s, 9H). HRMS (ESI) m/z: calcd $C_{56}H_{70}Cl_2N_9O_8S^+$ [M+H]$^+$, 1098.4440; found, 1098.4216.

Example 63: Preparation of (2S,4R)-1-((S)-2-(10-(4-(3-((3-cyano-4-((2,4-dichloro-5-methoxyphenyl)amino)-6-methoxyquinolin-7-yl)oxy)propyl)piperazin-1-yl)-10-oxodecanamido)-3,3-dimethylbutanoyl)-4-hydroxy-N-(4-(4-methylthiazol-5-yl)benzyl)pyrrolidine-2-carboxamide (SIAIS172078)

Based on the general method of scheme 19 as described herein, compound (SIAIS172078) was obtained by coupling reaction of (SIAIS151151) with HO$_2$C-LIN-ULM analog (SIAIS074019) as a white solid (7.3 mg, 56% yield). $^1$H NMR (500 MHz, MeOD) δ 9.80 (d, J=2.7 Hz, 1H), 8.88 (s, 1H), 8.03 (s, 1H), 7.67 (s, 1H), 7.56 (d, J=8.3 Hz, 2H), 7.51 (d, J=8.3 Hz, 2H), 7.42 (d, J=1.8 Hz, 2H), 4.64 (s, 1H), 4.56 (dd, J=11.8, 6.1 Hz, 2H), 4.50-4.46 (m, 3H), 4.40 (d, J=15.7 Hz, 1H), 4.09 (s, 3H), 3.94 (s, 3H), 3.91 (d, J=11.0 Hz, 1H), 3.83-3.72 (m, 3H), 3.70-3.46 (m, 4H), 3.30-3.06 (m, 4H), 2.59 (s, 3H), 2.51-2.44 (m, 4H), 2.33-2.20 (m, 3H), 2.10-2.05 (m, 1H), 1.66-1.58 (m, 4H), 1.38-1.32 (s, 8H), 1.03 (s, 9H). HRMS (ESI) m/z: calcd $C_{57}H_{72}Cl_2N_9O_8S^+$ [M+H]$^+$, 1112.4596; found, 1112.4366.

Example 64: Preparation of (2S,4R)-1-((S)-2-(11-(4-(3-((3-cyano-4-((2,4-dichloro-5-methoxyphenyl)amino)-6-methoxyquinolin-7-yl)oxy)propyl)piperazin-1-yl)-11-oxoundecanamido)-3,3-dimethylbutanoyl)-4-hydroxy-N-(4-(4-methylthiazol-5-yl)benzyl)pyrrolidine-2-carboxamide (SIAIS172079)

Based on the general method of scheme 19 as described herein, compound (SIAIS172079) was obtained by coupling reaction of (SIAIS151151) with HO$_2$C-LIN-ULM analog (SIAIS074020) as a white solid (6.6 mg, 50% yield). $^1$H NMR (500 MHz, MeOD) δ 9.86 (s, 1H), 8.88 (s, 1H), 8.03 (s, 1H), 7.67 (s, 1H), 7.56 (d, J=8.4 Hz, 2H), 7.52 (d, J=8.4 Hz, 2H), 7.42 (d, J=1.5 Hz, 2H), 4.64 (s, 1H), 4.56 (dd, J=16.5, 9.5 Hz, 2H), 4.50-4.46 (m, 3H), 4.41 (d, J=15.7 Hz, 1H), 4.09 (s, 3H), 3.94 (s, 3H), 3.91 (d, J=11.0 Hz, 1H), 3.83-3.73 (m, 3H), 3.66-3.46 (m, 4H), 3.30-3.04 (m, 4H), 2.59 (s, 3H), 2.50-2.44 (m, 4H), 2.33-2.21 (m, 3H), 2.10-2.04 (m, 1H), 1.64-1.58 (m, 4H), 1.38-1.32 (m, 10H), 1.03 (s, 9H). HRMS (ESI) m/z: calcd $C_{58}H_{74}Cl_2N_9O_8S^+$ [M+H]$^+$, 1126.4753; found, 1126.4546.

Example 65: Preparation of 4-(4-(3-((3-cyano-4-((2,4-dichloro-5-methoxyphenyl)amino)-6-methoxyquinolin-7-yl)oxy)propyl)piperazin-1-yl)-N-(2-((2-(2,6-dioxopiperidin-3-yl)-1,3-dioxoisoindolin-4-yl)amino)ethyl)-4-oxobutanamide (SIAIS164136)

Based on the general method of scheme 19 as described herein, compound (SIAIS164136) was obtained by coupling reaction of (SIAIS151151) with HO$_2$C-LIN-ULM analog (SIAIS164119) as a yellow solid (12.4 mg, 71% yield). $^1$H NMR (500 MHz, MeOD) δ 8.87 (s, 1H), 8.00 (s, 1H), 7.68 (s, 1H), 7.56 (dd, J=8.4, 7.2 Hz, 1H), 7.40 (d, J=5.8 Hz, 2H), 7.14 (d, J=8.6 Hz, 1H), 7.05 (d, J=7.1 Hz, 1H), 5.05 (dd, J=12.6, 5.5 Hz, 1H), 4.68 (s, 1H), 4.45 (t, J=5.4 Hz, 2H), 4.26 (s, 1H), 4.08 (s, 3H), 3.94 (s, 3H), 3.73 (s, 2H), 3.53 (d, J=59.0 Hz, 8H), 3.10 (s, 2H), 2.86 (ddd, J=19.1, 13.9, 5.2 Hz, 1H), 2.78-2.67 (m, 3H), 2.49 (dd, J=26.8, 20.9 Hz, 5H), 2.11 (dd, J=10.2, 5.1 Hz, 1H). HRMS (ESI) m/z: calcd $C_{44}H_{46}Cl_2N_9O_9^+$ [M+H]$^+$, 914.2790; found, 914.0165.

Example 66: Preparation of 4-((4-(3-(2-((2-(2,6-dioxopiperidin-3-yl)-1,3-dioxoisoindolin-4-yl)amino)ethoxy)propanoyl)piperazin-1-yl)methyl)-N-(4-methyl-3-((4-(pyridin-3-yl)pyrimidin-2-yl)amino)phenyl)benzamide (SIAIS1197001)

Based on the general method of scheme 19 as described herein, compound (SIAIS1197001) was obtained by coupling reaction of demethylated-imatinib analog with HO$_2$C-LIN-ULM analog (SIAIS151001) as a yellow solid (13.3 mg, 38% yield). $^1$H NMR (500 MHz, MeOD) δ 9.43 (d, J=1.7 Hz, 1H), 8.86 (d, J=8.1 Hz, 1H), 8.74 (dd, J=5.2, 1.5 Hz, 1H), 8.52 (d, J=5.3 Hz, 1H), 8.24 (d, J=1.8 Hz, 1H), 7.98 (d, J=8.3 Hz, 2H), 7.77 (dd, J=7.9, 5.3 Hz, 1H), 7.60-7.51 (m, 3H), 7.43 (d, J=5.2 Hz, 1H), 7.36 (dd, J=8.3, 2.1 Hz, 1H), 7.28 (d, J=8.5 Hz, 1H), 7.08 (dd, J=10.5, 7.8 Hz, 2H), 5.04 (dd, J=12.6, 5.5 Hz, 1H), 4.38 (s, 2H), 3.79 (t, J=5.7 Hz, 2H), 3.69 (t, J=5.2 Hz, 2H), 3.48 (t, J=5.0 Hz, 2H), 3.38-3.31 (m, 8H), 2.91-2.84 (m, 2H), 2.78-2.60 (m, 3H), 2.33 (s, 3H), 2.13-2.05 (m, 1H). HRMS (ESI) m/z: calcd $C_{46}H_{47}N_{10}O_7^+$ [M+H]$^+$, 851.3624; found, 851.3165.

Example 67: Preparation of 4-((4-(3-(2-(2-((2-(2,6-dioxopiperidin-3-yl)-1,3-dioxoisoindolin-4-yl)amino)ethoxy)ethoxy)propanoyl)piperazin-1-yl)methyl)-N-(4-methyl-3-((4-(pyridin-3-yl)pyrimidin-2-yl)amino)phenyl)benzamide (SIAIS1197015)

Based on the general method of scheme 19 as described herein, compound (SIAIS1197015) was obtained by coupling reaction of demethylated-imatinib analog with HO$_2$C-LIN-ULM analog (SIAIS151004) as a yellow solid (12.5 mg, 33% yield). $^1$H NMR (500 MHz, MeOD) δ 9.44 (s, 1H), 8.89 (d, J=8.3 Hz, 1H), 8.75 (d, J=4.7 Hz, 1H), 8.52 (d, J=5.1 Hz, 1H), 8.25 (s, 1H), 8.02 (d, J=8.1 Hz, 2H), 7.80 (s, 1H), 7.60 (t, J=8.4 Hz, 2H), 7.50 (t, J=7.5 Hz, 1H), 7.44 (d, J=5.2 Hz, 1H), 7.36 (d, J=8.2 Hz, 1H), 7.28 (d, J=8.4 Hz, 1H), 7.04 (dd, J=24.0, 7.8 Hz, 2H), 5.03 (dd, J=12.6, 5.6 Hz, 1H), 4.39 (s, 2H), 3.78-3.69 (m, 8H), 3.48 (t, J=5.0 Hz, 2H), 3.30-3.16 (m, 8H), 2.87-2.78 (m, 2H), 2.76-2.66 (m, 3H), 2.33 (s, 3H), 2.12-2.04 (m, 1H). HRMS (ESI) m/z: calcd $C_{48}H_{51}N_{10}O_7^+$ [M+H]$^+$, 895.3886; found, 895.4430.

Example 68: Preparation of 4-((4-(3-(2-(2-(2-((2-(2,6-dioxopiperidin-3-yl)-1,3-dioxoisoindolin-4-yl)amino)ethoxy)ethoxy)ethoxy)propanoyl)piperazin-1-yl)methyl)-N-(4-methyl-3-((4-(pyridin-3-yl)pyrimidin-2-yl)amino)phenyl)benzamide (SIAIS1197017)

Based on the general method of scheme 19 as described herein, compound (SIAIS1197017) was obtained by coupling reaction of demethylated-imatinib analog with HO$_2$C-LIN-ULM analog (SIAIS151005) as a yellow solid (16.6 mg, 43% yield). $^1$H NMR (500 MHz, MeOD) δ 9.38 (s, 1H), 8.76 (d, J=8.2 Hz, 1H), 8.69 (d, J=4.8 Hz, 1H), 8.50 (d, J=5.1 Hz, 1H), 8.24 (s, 1H), 8.01 (d, J=7.9 Hz, 2H), 7.69 (dd, J=7.4, 5.9 Hz, 1H), 7.61 (d, J=8.1 Hz, 1H), 7.49 (t, J=7.6 Hz, 1H), 7.40 (d, J=5.2 Hz, 1H), 7.37 (d, J=8.8 Hz, 1H), 7.28 (d, J=7.9 Hz, 1H), 7.04-6.98 (m, 2H), 5.06-5.02 (m, 1H), 4.41 (s, 2H), 3.78-3.61 (m, 19H), 3.43 (t, J=5.0 Hz, 4H), 2.90-2.79 (m, 1H), 2.77-2.64 (m, 3H), 2.52 (t, J=6.0 Hz, 1H), 2.33

(s, 3H), 2.13-2.05 (m, 1H). HRMS (ESI) m/z: calcd $C_{50}H_{55}N_{10}O_7^+$ [M+H]$^+$, 939.4148; found, 939.4696.

Example 69: Preparation of 4-((4-(1-((2-(2,6-dioxopiperidin-3-yl)-1,3-dioxoisoindolin-4-yl)amino)-3,6,9,12-tetraoxapentadecan-15-oyl)piperazin-1-yl)methyl)-N-(4-methyl-3-((4-(pyridin-3-yl)pyrimidin-2-yl)amino)phenyl)benzamide (SIAIS1197019)

Based on the general method of scheme 19 as described herein, compound (SIAIS1197019) was obtained by coupling reaction of demethylated-imatinib analog with HO$_2$C-LIN-ULM analog (SIAIS151006) as a yellow solid (18.4 mg, 45% yield). $^1$H NMR (500 MHz, MeOD) δ 9.44 (s, 1H), 8.90 (d, J=8.2 Hz, 1H), 8.75 (d, J=5.0 Hz, 1H), 8.52 (d, J=4.9 Hz, 1H), 8.25 (s, 1H), 8.03 (d, J=8.0 Hz, 2H), 7.81 (dd, J=8.1, 5.4 Hz, 1H), 7.63 (d, J=8.1 Hz, 2H), 7.48 (t, J=8.0 Hz, 1H), 7.43 (d, J=5.2 Hz, 1H), 7.35 (dd, J=8.0, 1.7 Hz, 1H), 7.28 (d, J=8.4 Hz, 1H), 6.99 (t, J=8.1 Hz, 2H), 5.03 (dd, J=12.9, 5.5 Hz, 1H), 4.43 (s, 2H), 3.83-3.58 (m, 18H), 3.41-3.35 (m, 9H), 2.89-2.78 (m, 1H), 2.78-2.59 (m, 3H), 2.33 (s, 3H), 2.12-2.04 (m, 1H). HRMS (ESI) m/z: calcd $C_{52}H_{59}N_{10}O_7^+$ [M+H]$^+$, 983.4410; found, 983.3912.

Example 70: Preparation of 4-((4-(1-((2-(2,6-dioxopiperidin-3-yl)-1,3-dioxoisoindolin-4-yl)amino)-3,6,9,12,15-pentaoxaoctadecan-18-oyl)piperazin-1-yl)methyl)-N-(4-methyl-3-((4-(pyridin-3-yl)pyrimidin-2-yl)amino)phenyl)benzamide (SIAIS1197021)

Based on the general method of scheme 19 as described herein, compound (SIAIS1197021) was obtained by coupling reaction of demethylated-imatinib analog with HO$_2$C-LIN-ULM analog (SIAIS151007) as a yellow solid (9.5 mg, 21% yield). $^1$H NMR (500 MHz, MeOD) δ 9.44 (s, 1H), 8.88 (d, J=8.3 Hz, 1H), 8.75 (d, J=4.9 Hz, 1H), 8.51 (d, J=5.4 Hz, 1H), 8.26 (s, 1H), 8.06 (d, J=8.1 Hz, 2H), 7.80 (dd, J=8.0, 5.3 Hz, 1H), 7.65 (d, J=8.1 Hz, 2H), 7.53-7.46 (m, 1H), 7.42 (d, J=5.2 Hz, 1H), 7.35 (d, J=7.7 Hz, 1H), 7.27 (d, J=8.3 Hz, 1H), 7.01 (dd, J=7.9, 4.5 Hz, 2H), 5.03 (dd, J=12.7, 5.4 Hz, 2H), 4.45 (s, 2H), 3.77-3.58 (m, 20H), 3.42 (t, J=5.1 Hz, 2H), 3.34-3.31 (m, 8H), 2.88-2.78 (m, 1H), 2.75-2.64 (m, 3H), 2.32 (s, 3H), 2.12-2.04 (m, 1H). HRMS (ESI) m/z: calcd $C_{54}H_{63}N_{10}O_7^+$ [M+H]$^+$, 1027.4672; found, 1027.4310.

Example 71: Preparation of 4-((4-((2-(2,6-dioxopiperidin-3-yl)-1,3-dioxoisoindolin-4-yl)glycyl)piperazin-1-yl)methyl)-N-(4-methyl-3-((4-(pyridin-3-yl)pyrimidin-2-yl)amino)phenyl)benzamide (SIAIS1197003)

Based on the general method of scheme 19 as described herein, compound (SIAIS1197003) was obtained by coupling reaction of demethylated-imatinib analog with HO$_2$C-LIN-ULM analog (SIAIS151025) as a yellow solid (11.1 mg, 33% yield). $^1$H NMR (500 MHz, MeOD) δ 9.46 (d, J=2.0 Hz, 1H), 8.90 (d, J=7.6 Hz, 1H), 8.79-8.72 (m, 1H), 8.52 (d, J=5.3 Hz, 1H), 8.26 (s, 1H), 8.08 (d, J=8.3 Hz, 2H), 7.82 (dd, J=8.1, 5.2 Hz, 1H), 7.68 (d, J=8.3 Hz, 2H), 7.58-7.52 (m, 1H), 7.44 (d, J=5.3 Hz, 1H), 7.36 (dd, J=8.2, 2.1 Hz, 1H), 7.29 (d, J=8.3 Hz, 1H), 7.10 (d, J=7.1 Hz, 1H), 6.99 (d, J=8.4 Hz, 1H), 5.07 (dd, J=12.4, 5.5 Hz, 1H), 4.48 (s, 2H), 4.26 (s, 2H), 3.45-3.32 (m, 8H), 2.92-2.80 (m, 1H), 2.80-2.63 (m, 2H), 2.33 (s, 3H), 2.18-2.06 (m, 1H). HRMS (ESI) m/z: calcd $C_{43}H_{41}N_{10}O_6^+$ [M+H]$^+$, 793.3205; found, 793.2798.

Example 72: Preparation of 4-((4-(3-((2-(2,6-dioxopiperidin-3-yl)-1,3-dioxoisoindolin-4-yl)amino)propanoyl)piperazin-1-yl)methyl)-N-(4-methyl-3-((4-(pyridin-3-yl)pyrimidin-2-yl)amino)phenyl)benzamide (SIAIS1197005)

Based on the general method of scheme 19 as described herein, compound (SIAIS1197005) was obtained by coupling reaction of demethylated-imatinib analog with HO$_2$C-LIN-ULM analog (SIAIS151026) as a yellow solid (16.8 mg, 50% yield). $^1$H NMR (500 MHz, MeOD) δ 9.46 (s, 1H), 8.91 (d, J=8.2 Hz, 1H), 8.76 (d, J=4.5 Hz, 1H), 8.52 (d, J=5.3 Hz, 1H), 8.26 (d, J=1.9 Hz, 1H), 8.06 (d, J=8.3 Hz, 2H), 7.82 (dd, J=8.0, 5.2 Hz, 1H), 7.64 (d, J=8.4 Hz, 2H), 7.57 (dd, J=8.6, 7.1 Hz, 1H), 7.44 (d, J=5.3 Hz, 1H), 7.36 (dd, J=8.2, 2.1 Hz, 1H), 7.28 (d, J=8.3 Hz, 1H), 7.12 (d, J=8.5 Hz, 1H), 7.07 (d, J=6.8 Hz, 1H), 5.06 (dd, J=12.5, 5.5 Hz, 1H), 4.42 (s, 2H), 3.68 (t, J=6.1 Hz, 2H), 3.30-3.15 (m, 8H), 2.93-2.63 (m, 5H), 2.33 (s, 3H), 2.15-2.04 (m, 1H). HRMS (ESI) m/z: calcd $C_{44}H_{43}N_{10}O_6^+$ [M+H]$^+$, 807.3362; found, 807.2928.

Example 73: Preparation of 4-((4-(4-((2-(2,6-dioxopiperidin-3-yl)-1,3-dioxoisoindolin-4-yl)amino)butanoyl)piperazin-1-yl)methyl)-N-(4-methyl-3-((4-(pyridin-3-yl)pyrimidin-2-yl)amino)phenyl)benzamide (SIAIS1197007)

Based on the general method of scheme 19 as described herein, compound (SIAIS1197007) was obtained by coupling reaction of demethylated-imatinib analog with HO$_2$C-LIN-ULM analog (SIAIS151019) as a yellow solid (14 mg, 40% yield). $^1$H NMR (500 MHz, MeOD) δ 9.47 (d, J=1.7 Hz, 1H), 8.91 (d, J=8.1 Hz, 1H), 8.78 (dd, J=5.2, 1.4 Hz, 1H), 8.54 (d, J=5.3 Hz, 1H), 8.28 (d, J=1.8 Hz, 1H), 8.09 (d, J=8.2 Hz, 2H), 7.82 (dd, J=7.9, 5.4 Hz, 1H), 7.66 (d, J=8.3 Hz, 2H), 7.58 (dd, J=8.5, 7.1 Hz, 1H), 7.46 (d, J=5.3 Hz, 1H), 7.39 (dd, J=8.2, 2.1 Hz, 1H), 7.31 (d, J=8.4 Hz, 1H), 7.14 (d, J=8.6 Hz, 1H), 7.09 (d, J=7.0 Hz, 1H), 5.08 (dd, J=12.5, 5.5 Hz, 1H), 4.44 (s, 2H), 3.44 (t, J=6.7 Hz, 2H), 3.41-3.32 (m, 8H), 2.96-2.64 (m, 3H), 2.57 (t, J=6.9 Hz, 2H), 2.35 (s, 3H), 2.17-2.08 (m, 1H), 2.07-1.95 (m, 2H). HRMS (ESI) m/z: calcd $C_{45}H_{45}N_{10}O_6^+$ [M+H]$^+$, 821.3518; found, 821.3642.

Example 74: Preparation of 4-((4-(5-((2-(2,6-dioxopiperidin-3-yl)-1,3-dioxoisoindolin-4-yl)amino)pentanoyl)piperazin-1-yl)methyl)-N-(4-methyl-3-((4-(pyridin-3-yl)pyrimidin-2-yl)amino)phenyl)benzamide (SIAIS1197009)

Based on the general method of scheme 19 as described herein, compound (SIAIS1197009) was obtained by coupling reaction of demethylated-imatinib analog with HO$_2$C-LIN-ULM analog (SIAIS151020) as a yellow solid (14.8 mg, 43% yield). $^1$H NMR (500 MHz, MeOD) δ 9.43 (d, J=2.0 Hz, 1H), 8.83 (d, J=8.4 Hz, 1H), 8.75 (d, J=5.1 Hz, 1H), 8.53 (d, J=5.2 Hz, 1H), 8.27 (s, 1H), 8.10 (d, J=8.2 Hz, 2H), 7.76 (dd, J=8.1, 5.1 Hz, 1H), 7.67 (d, J=8.3 Hz, 2H), 7.58 (dd, J=8.6, 7.1 Hz, 1H), 7.44 (d, J=5.3 Hz, 1H), 7.40 (d, J=10.2 Hz, 1H), 7.31 (d, J=8.3 Hz, 1H), 7.08 (t, J=7.8 Hz, 2H), 5.07 (dd, J=12.4, 5.5 Hz, 1H), 4.46 (s, 2H), 3.45-3.36 (m, 10H), 2.92-2.66 (m, 3H), 2.53 (s, 2H), 2.35 (s, 3H), 2.17-2.07 (m, 1H), 1.76 (s, 4H). HRMS (ESI) m/z: calcd $C_{46}H_{47}N_{10}O_6^+$ [M+H]$^+$, 835.3675; found, 835.3783.

Example 75: Preparation of 4-((4-(6-((2-(2,6-dioxopiperidin-3-yl)-1,3-dioxoisoindolin-4-yl)amino)hexanoyl)piperazin-1-yl)methyl)-N-(4-methyl-3-((4-(pyridin-3-yl)pyrimidin-2-yl)amino)phenyl)benzamide (SIAIS1197011)

Based on the general method of scheme 19 as described herein, compound (SIAIS1197011) was obtained by coupling reaction of demethylated-imatinib analog with HO$_2$C-LIN-ULM analog (SIAIS151027) as yellow solid (15.4 mg, 43% yield). $^1$H NMR (500 MHz, MeOD) δ 9.45 (d, J=1.8 Hz, 1H), 8.88 (d, J=8.2 Hz, 1H), 8.76 (dd, J=5.2, 1.5 Hz, 1H), 8.54 (d, J=5.3 Hz, 1H), 8.27 (s, 1H), 8.10 (d, J=8.3 Hz, 2H), 7.80 (dd, J=8.0, 5.2 Hz, 1H), 7.68 (d, J=8.3 Hz, 2H), 7.57 (dd, J=8.5, 7.1 Hz, 1H), 7.45 (d, J=5.3 Hz, 1H), 7.39 (dd, J=8.1, 2.1 Hz, 1H), 7.31 (d, J=8.5 Hz, 1H), 7.06 (dd, J=7.8, 4.3 Hz, 2H), 5.07 (dd, J=12.5, 5.5 Hz, 1H), 4.47 (s, 2H), 3.43-3.35 (m, 10H), 2.92-2.82 (m, 1H), 2.79-2.66 (m, 2H), 2.48 (t, J=7.5 Hz, 2H), 2.35 (s, 3H), 2.15-2.08 (m, 1H), 1.77-1.65 (m, 4H), 1.54-1.46 (m, 2H). HRMS (ESI) m/z: calcd $C_{47}H_{49}N_{10}O_6^+$ [M+H]$^+$, 849.3831; found, 849.3960.

Example 76: Preparation of 4-((4-(7-((2-(2,6-dioxopiperidin-3-yl)-1,3-dioxoisoindolin-4-yl)amino)heptanoyl)piperazin-1-yl)methyl)-N-(4-methyl-3-((4-(pyridin-3-yl)pyrimidin-2-yl)amino)phenyl)benzamide (SIAIS1197095)

Based on the general method of scheme 19 as described herein, compound (SIAIS1197095) was obtained by coupling reaction of demethylated-imatinib analog with HO$_2$C-LIN-ULM analog (SIAIS151086) as a yellow solid (16.0 mg, 45% yield). $^1$H NMR (500 MHz, MeOD) δ 9.46 (s, 1H), 8.91 (s, 1H), 8.76 (s, 1H), 8.52 (d, J=5.3 Hz, 1H), 8.26 (s, 1H), 8.08 (d, J=8.3 Hz, 2H), 7.82 (s, 1H), 7.66 (d, J=8.4 Hz, 2H), 7.54 (dd, J=8.6, 7.1 Hz, 1H), 7.44 (d, J=5.2 Hz, 1H), 7.36 (d, J=8.0 Hz, 1H), 7.28 (d, J=8.4 Hz, 1H), 7.03 (dd, J=7.8, 4.0 Hz, 2H), 5.04 (dd, J=12.4, 5.5 Hz, 1H), 4.45 (s, 2H), 3.37-3.32 (m, 10H), 2.89-2.80 (m, 1H), 2.77-2.65 (m, 2H), 2.43 (t, J=7.5 Hz, 2H), 2.33 (s, 3H), 2.13-2.06 (m, 1H), 1.73-1.57 (m, 4H), 1.51-1.37 (m, 4H). HRMS (ESI) m/z: calcd $C_{48}H_{51}N_{10}O_6^+$ [M+H]$^+$, 863.3988; found, 863.4003.

Example 77: Preparation of (2S,4R)-1-((S)-3,3-dimethyl-2-(2-(2-(2-(4-(4-((4-methyl-3-((4-(pyridin-3-yl)pyrimidin-2-yl)amino)phenyl)carbamoyl)benzyl)piperazin-1-yl)-2-oxoethoxy)ethoxy)acetamido)butanoyl)-4-hydroxy-N-(4-(4-methylthiazol-5-yl)benzyl)pyrrolidine-2-carboxamide (SIAIS1197043)

Based on the general method of scheme 19 as described herein, compound (SIAIS1197043) was obtained by coupling reaction of demethylated-imatinib analog with HO$_2$C-LIN-ULM analog (SIAIS151010) as a white solid (15.2 mg, 33% yield). $^1$H NMR (500 MHz, MeOD) δ 9.46 (d, J=1.6 Hz, 1H), 8.8 (s, 1H), 8.76 (dd, J=5.3, 1.5 Hz, 1H), 8.52 (t, J=4.5 Hz, 1H), 8.26 (s, 1H), 8.06 (d, J=8.3 Hz, 2H), 7.83 (dd, J=8.0, 5.0 Hz, 1H), 7.65 (d, J=8.4 Hz, 2H), 7.50-7.37 (m, 5H), 7.35 (dd, J=8.1, 2.2 Hz, 1H), 7.28 (d, J=8.1 Hz, 1H), 4.69 (s, 1H), 4.50 (dd, J=16.5, 6.8 Hz, 1H), 4.47-4.39 (m, 3H), 4.30 (d, J=11.6 Hz, 2H), 4.04 (t, J=6.0 Hz, 2H), 3.80 (dd, J=10.9, 3.7 Hz, 3H), 3.77-3.70 (m, 4H), 3.43-3.32 (m, 10H), 2.49-2.42 (m, 3H), 2.32 (s, 3H), 2.28-2.21 (m, 1H), 2.11-2.03 (m, 1H), 1.03 (s, 9H). HRMS (ESI) m/z: calcd $C_{56}H_{66}N_{11}O_8S^+$ [M+H]$^+$, 1052.4811; found, 1052.4419.

Example 78: Preparation of (2S,4R)-1-((S)-3,3-dimethyl-2-(3-(2-(3-(4-(4-((4-methyl-3-((4-(pyridin-3-yl)pyrimidin-2-yl)amino)phenyl)carbamoyl)benzyl)piperazin-1-yl)-3-oxopropoxy)ethoxy)propanamido)butanoyl)-4-hydroxy-N-(4-(4-methylthiazol-5-yl)benzyl)pyrrolidine-2-carboxamide (SIAIS1197029)

Based on the general method of scheme 19 as described herein, compound (SIAIS1197029) was obtained by coupling reaction of demethylated-imatinib analog with HO$_2$C-LIN-ULM analog (SIAIS151002) as a white solid (13.2 mg, 29% yield). $^1$H NMR (500 MHz, MeOD) δ 9.45 (s, 1H), 8.88 (s, 1H), 8.76 (d, J=5.2 Hz, 1H), 8.52 (d, J=5.2 Hz, 1H), 8.26 (s, 1H), 8.08 (d, J=8.1 Hz, 2H), 7.81 (dd, J=7.9, 5.4 Hz, 1H), 7.67 (d, J=8.1 Hz, 2H), 7.50-7.37 (m, 6H), 7.36 (dd, J=8.2, 1.6 Hz, 1H), 7.28 (d, J=8.3 Hz, 1H), 4.63 (s, 1H), 4.54 (dd, J=22.1, 14.0 Hz, 2H), 4.49-4.46 (m, 3H), 4.35 (d, J=15.4 Hz, 1H), 3.82-3.67 (m, 7H), 3.59 (s, 4H), 3.38-3.32 (m, 8H), 2.56-2.51 (m, 1H), 2.50-2.48 (m, 2H), 2.45 (s, 3H), 2.32 (s, 3H), 2.20 (s, 1H), 2.07 (s, 1H), 1.03 (s, 9H). HRMS (ESI) m/z: calcd $C_{58}H_{70}N_{11}O_8S^+$ [M+H]$^+$, 1080.5124; found, 1080.4665.

Example 79: Preparation of (2S,4R)-1-((S)-2-(tert-butyl)-16-(4-(4-((4-methyl-3-((4-(pyridin-3-yl)pyrimidin-2-yl)amino)phenyl)carbamoyl)benzyl)piperazin-1-yl)-4,16-dioxo-7,10,13-trioxa-3-azahexadecanoyl)-4-hydroxy-N-(4-(4-methylthiazol-5-yl)benzyl)pyrrolidine-2-carboxamide (SIAIS1197031)

Based on the general method of scheme 19 as described herein, compound (SIAIS1197031) was obtained by coupling reaction of demethylated-imatinib analog with HO$_2$C-LIN-ULM analog (SIAIS151003) as a white solid (14.5 mg, 31% yield). $^1$H NMR (500 MHz, MeOD) δ 9.53 (s, 1H), 8.91 (s, 1H), 8.81 (t, J=5.7 Hz, 1H), 8.54 (d, J=5.2 Hz, 1H), 8.28 (s, 1H), 8.08 (d, J=8.3 Hz, 2H), 7.93 (dd, J=8.2, 5.0 Hz, 1H), 7.67 (d, J=8.3 Hz, 2H), 7.50-7.36 (m, 6H), 7.34 (dd, J=8.2, 1.9 Hz, 1H), 7.28 (d, J=8.4 Hz, 1H), 4.63 (s, 1H), 4.56 (dd, J=17.0, 8.2 Hz, 1H), 4.49-4.45 (m, 3H), 4.35 (dd, J=15.6, 4.4 Hz, 1H), 3.82-3.66 (m, 8H), 3.64-3.57 (m, 10H), 3.41-3.31 (m, 4H), 2.66 (t, J=13.2 Hz, 1H), 2.55-2.50 (m, 1H), 2.48-2.45 (m, 3H), 2.50-2.40 (m, 2H), 2.32 (s, 3H), 2.22-2.16 (m, 1H), 2.10-2.04 (m, 1H), 1.03 (s, 9H). HRMS (ESI) m/z: calcd $C_{60}H_{74}N_{11}O_9S^+$ [M+H]$^+$, 1124.5386; found, 1124.4786.

Example 80: Preparation of (2S,4R)-1-((S)-2-(tert-butyl)-19-(4-(4-((4-methyl-3-((4-(pyridin-3-yl)pyrimidin-2-yl)amino)phenyl)carbamoyl)benzyl)piperazin-1-yl)-4,19-dioxo-7,10,13,16-tetraoxa-3-azanonadecanoyl)-4-hydroxy-N-(4-(4-methylthiazol-5-yl)benzyl)pyrrolidine-2-carboxamide (SIAIS1197039)

Based on the general method of scheme 19 as described herein, compound (SIAIS1197039) was obtained by coupling reaction of demethylated-imatinib analog with HO$_2$C-LIN-ULM analog (SIAIS151008) as a white solid (16.0 mg, 36% yield). $^1$H NMR (500 MHz, MeOD) δ 9.47 (d, J=1.6 Hz, 1H), 8.90 (s, 1H), 8.78 (dd, J=5.3, 1.5 Hz, 1H), 8.52 (d, J=5.3 Hz, 1H), 8.26 (s, 1H), 8.09 (d, J=8.3 Hz, 2H), 7.85 (dd, J=8.0, 5.3 Hz, 1H), 7.66 (d, J=8.3 Hz, 2H), 7.49-7.37 (m, 6H), 7.35 (dd, J=8.2, 2.2 Hz, 1H), 7.28 (d, J=8.3 Hz, 1H), 4.60 (s, 1H), 4.54 (dd, J=15.0, 6.2 Hz, 2H), 4.50-4.45 (m, 3H), 4.34 (dd, J=15.5, 7.6 Hz, 1H), 3.79-3.66 (m, 7H), 3.63-3.57 (m, 16H), 3.35-3.32 (m, 4H), 2.53 (t, J=6.3 Hz, 1H), 2.49-2.42 (m, 2H), 2.45 (s, 3H), 2.32 (s, 3H), 2.22-2.15 (m, 1H), 2.10-2.03 (m, 1H), 1.03 (s, 9H). HRMS (ESI) m/z: calcd $C_{62}H_{75}N_{11}O_{10}S^+$ [M+H]$^+$, 1168.5648; found, 1168.5174.

Example 81: Preparation of (2S,4R)-1-((S)-2-(tert-butyl)-22-(4-(4-((4-methyl-3-((4-(pyridin-3-yl)pyrimidin-2-yl)amino)phenyl)carbamoyl)benzyl)piperazin-1-yl)-4,22-dioxo-7,10,13,16,19-pentaoxa-3-azadocosanoyl)-4-hydroxy-N-(4-(4-methylthiazol-5-yl)benzyl)pyrrolidine-2-carboxamide (SIAIS1197041)

Based on the general method of scheme 19 as described herein, compound (SIAIS1197041) was obtained by coupling reaction of demethylated-imatinib analog with HO$_2$C-LIN-ULM analog (SIAIS151009) as a white solid (16.4 mg, 33% yield). $^1$H NMR (500 MHz, MeOD) δ 9.52 (d, J=1.6 Hz, 1H), 8.91 (s, 1H), 8.81 (dd, J=5.4, 1.3 Hz, 1H), 8.54 (d, J=5.2 Hz, 1H), 8.28 (s, 1H), 8.08 (d, J=8.2 Hz, 2H), 7.92 (dd, J=8.0, 5.4 Hz, 1H), 7.67 (d, J=8.3 Hz, 2H), 7.50-7.37 (m, 6H), 7.35 (dd, J=8.2, 2.0 Hz, 1H), 7.28 (d, J=8.4 Hz, 1H), 4.61 (s, 1H), 4.55 (dd, J=18.0, 7.0 Hz, 2H), 4.51-4.46 (m, 3H), 4.35 (dd, J=15.7, 7.4 Hz, 1H), 3.82-3.66 (m, 7H), 3.63-3.57 (m, 20H), 3.40-3.34 (m, 4H), 2.56-2.51 (m, 1H), 2.50-2.43 (m, 1H), 2.46 (s, 4H), 2.32 (s, 3H), 2.23-2.16 (m, 1H), 2.09-2.03 (m, 1H), 1.03 (s, 9H). HRMS (ESI) m/z: calcd $C_{64}H_{82}N_{11}O_{11}S^+$ [M+H]$^+$, 1212.5910; found, 1212.5910.

Example 82: Preparation of (2S,4R)-1-((S)-3,3-dimethyl-2-(4-(4-(4-((4-methyl-3-((4-(pyridin-3-yl)pyrimidin-2-yl)amino)phenyl)carbamoyl)benzyl)piperazin-1-yl)-4-oxobutanamido)butanoyl)-4-hydroxy-N-(4-(4-methylthiazol-5-yl)benzyl)pyrrolidine-2-carboxamide (SIAIS074027)

Based on the general method of scheme 19 as described herein, compound (SIAIS074027) was obtained by coupling reaction of demethylated-imatinib analog with HO$_2$C-LIN-ULM analog (SIAIS074011) as a white solid (42.2 mg, 68% yield). $^1$H NMR (500 MHz, MeOD) δ 9.57 (d, J=1.8 Hz, 1H), 9.14-9.07 (m, 1H), 8.96 (s, 1H), 8.85 (dd, J=5.4, 1.3 Hz, 1H), 8.56 (d, J=5.3 Hz, 1H), 8.28 (s, 1H), 8.08 (d, J=8.2 Hz, 2H), 7.99 (dd, J=8.2, 5.2 Hz, 1H), 7.67 (d, J=8.3 Hz, 2H), 7.50-7.41 (m, 5H), 7.35-7.28 (m, 2H), 4.58-4.47 (m, 5H), 4.36 (d, J=15.5 Hz, 1H), 4.23-3.71 (m, 5H), 3.73-3.46 (m, 2H), 3.38 (s, 4H), 2.76-2.52 (m, 4H), 2.53-2.38 (m, 3H), 2.33 (s, 3H), 2.21-2.19 (m, 1H), 2.10-2.05 (m, 1H), 1.03 (s, 9H). HRMS (ESI) m/z: calcd $C_{54}H_{62}N_{11}O_6S^+$ [M+H]$^+$, 992.4600; found, 992.2307.

Example 83: Preparation of (2S,4R)-1-((S)-3,3-dimethyl-2-(5-(4-(4-((4-methyl-3-((4-(pyridin-3-yl)pyrimidin-2-yl)amino)phenyl)carbamoyl)benzyl)piperazin-1-yl)-5-oxopentanamido)butanoyl)-4-hydroxy-N-(4-(4-methylthiazol-5-yl)benzyl)pyrrolidine-2-carboxamide (SIAIS074028)

Based on the general method of scheme 19 as described herein, compound (SIAIS074028) was obtained by coupling reaction of demethylated-imatinib analog with HO$_2$C-LIN-ULM analog (SIAIS074012) as a white solid (40.3 mg, 64% yield). $^1$H NMR (500 MHz, MeOD) δ 9.59 (s, 1H), 9.14 (d, J=8.1 Hz, 1H), 9.04-8.91 (m, 1H), 8.86 (d, J=4.7 Hz, 1H), 8.56 (d, J=5.3 Hz, 1H), 8.29 (s, 1H), 8.13-7.94 (m, 3H), 7.71-7.55 (m, 2H), 7.56-7.36 (m, 5H), 7.34-7.28 (m, 2H), 4.70-4.40 (m, 6H), 4.37 (d, J=15.5 Hz, 1H), 4.02-3.72 (m, 4H), 3.67-3.48 (m, 2H), 3.48-3.32 (m, 4H), 2.51-2.42 (m, 4H), 2.42-2.27 (m, 5H), 2.23-2.18 (m, 1H), 2.15-1.95 (m, 2H), 1.95-1.83 (m, 2H), 1.04 (d, J=14.1 Hz, 9H). HRMS (ESI) m/z: calcd $C_{55}H_{64}N_{11}O_6S^+$ [M+H]$^+$, 1006.4756; found, 1006.4807.

Example 84: Preparation of (2S,4R)-1-((S)-3,3-dimethyl-2-(6-(4-(4-((4-methyl-3-((4-(pyridin-3-yl)pyrimidin-2-yl)amino)phenyl)carbamoyl)benzyl)piperazin-1-yl)-6-oxohexanamido)butanoyl)-4-hydroxy-N-(4-(4-methylthiazol-5-yl)benzyl)pyrrolidine-2-carboxamide (SIAIS074029)

Based on the general method of scheme 19 as described herein, compound (SIAIS074029) was obtained by coupling reaction of demethylated-imatinib analog with HO$_2$C-LIN-ULM analog (SIAIS074013) as a white solid (38.4 mg, 60% yield). $^1$H NMR (500 MHz, MeOD) δ 9.58 (d, J=1.7 Hz, 1H), 9.14 (d, J=8.3 Hz, 1H), 9.04-8.93 (m, 1H), 8.88-8.83 (m, 1H), 8.56 (d, J=5.3 Hz, 1H), 8.29 (s, 1H), 8.09-7.99 (m, 3H), 7.66 (d, J=9.1 Hz, 2H), 7.52-7.37 (m, 5H), 7.35-7.29 (m, 2H), 4.68-4.29 (m, 8H), 3.97-3.72 (m, 4H), 3.68-3.51 (m, 2H), 2.57-2.41 (m, 5H), 2.39-2.24 (m, 5H), 2.24-2.18 (m, 2H), 2.11-2.01 (m, 2H), 1.64-1.63 (m, 5H), 1.02 (s, 9H). HRMS (ESI) m/z: calcd $C_{56}H_{66}N_{11}O_6S^+$ [M+H]$^+$, 1020.4913; found, 1020.4922.

Example 85: Preparation of (2S,4R)-1-((S)-3,3-dimethyl-2-(7-(4-(4-((4-methyl-3-((4-(pyridin-3-yl)pyrimidin-2-yl)amino)phenyl)carbamoyl)benzyl)piperazin-1-yl)-7-oxoheptanamido)butanoyl)-4-hydroxy-N-(4-(4-methylthiazol-5-yl)benzyl)pyrrolidine-2-carboxamide (SIAIS074030)

Based on the general method of scheme 19 as described herein, compound (SIAIS074030) was obtained by coupling reaction of demethylated-imatinib analog with HO$_2$C-LIN-ULM analog (SIAIS074014) as a white solid (40.2 mg, 62% yield). $^1$H NMR (500 MHz, MeOD) δ 9.60 (s, 1H), 9.16 (d, J=8.2 Hz, 1H), 9.07-8.96 (m, 1H), 8.87 (d, J=5.3 Hz, 1H), 8.57 (d, J=5.3 Hz, 1H), 8.30 (s, 1H), 8.09-8.02 (m, 3H), 7.67 (d, J=7.4 Hz, 2H), 7.56-7.38 (m, 5H), 7.34-7.29 (m, 2H), 4.74-4.19 (m, 8H), 4.01-3.73 (m, 4H), 3.69-3.49 (m, 2H), 2.54-2.36 (m, 5H), 2.36-2.15 (m, 6H), 2.13-1.98 (m, 2H), 1.72-1.54 (m, 4H), 1.46-1.31 (m, 4H), 1.02 (s, 9H). HRMS (ESI) m/z: calcd $C_{57}H_{68}N_{11}O_6S^+$ [M+H]$^+$, 1034.5069; found, 1034.5069.

Example 86: Preparation of (2S,4R)-1-((S)-3,3-dimethyl-2-(8-(4-(4-((4-methyl-3-((4-(pyridin-3-yl)pyrimidin-2-yl)amino)phenyl)carbamoyl)benzyl)piperazin-1-yl)-8-oxooctanamido)butanoyl)-4-hydroxy-N-(4-(4-methylthiazol-5-yl)benzyl)pyrrolidine-2-carboxamide (SIAIS074031)

Based on the general method of scheme 19 as described herein, compound (SIAIS074031) was obtained by coupling reaction of demethylated-imatinib analog with HO$_2$C-LIN-ULM analog (SIAIS074015) as a white solid (33.3 mg, 61% yield). $^1$H NMR (500 MHz, MeOD) δ 9.59 (s, 1H), 9.14 (d, J=8.2 Hz, 1H), 9.05-8.94 (m, 1H), 8.86 (d, J=5.3 Hz, 1H), 8.55 (d, 6.9 Hz, 1H), 8.29 (s, 1H), 8.13-7.95 (m, 3H), 7.67 (d, J=8.3 Hz, 2H), 7.59-7.37 (m, 5H), 7.35-7.29 (m, 2H), 4.79-4.21 (m, 8H), 3.99-3.70 (m, 4H), 3.71-3.47 (m, 2H), 2.53-2.36 (m, 5H), 2.36-2.14 (m, 6H), 2.14-1.96 (m, 2H), 1.61 (s, 4H), 1.43-1.30 (m, 6H), 1.03 (s, 9H). HRMS (ESI) m/z: calcd $C_{58}H_{70}N_{11}O_6S^+$ [M+H]$^+$, 1048.5226; found, 1048.5218.

Example 87: Preparation of (2S,4R)-1-((S)-3,3-dimethyl-2-(9-(4-(4-((4-methyl-3-((4-(pyridin-3-yl)pyrimidin-2-yl)amino)phenyl)carbamoyl)benzyl)piperazin-1-yl)-9-oxononanamido)butanoyl)-4-hydroxy-N-(4-(4-methylthiazol-5-yl)benzyl)pyrrolidine-2-carboxamide (SIAIS074032)

Based on the general method of scheme 19 as described herein, compound (SIAIS074032) was obtained by coupling reaction of demethylated-imatinib analog with $HO_2C$-LIN-ULM analog (SIAIS074016) as a white solid (32.1 mg, 58% yield). $^1$H NMR (500 MHz, MeOD) δ 9.62 (s, 1H), 9.20 (d, J=8.2 Hz, 1H), 9.06-8.98 (m, 1H), 8.89 (d, J=5.3 Hz, 1H), 8.58 (d, J=5.3 Hz, 1H), 8.30 (s, 1H), 8.09-8.04 (m, 3H), 7.67 (d, J=8.3 Hz, 2H), 7.60-7.39 (m, 5H), 7.34-7.29 (m, 2H), 4.79-4.25 (m, 8H), 4.10-3.74 (m, 4H), 3.44-3.39 (m, 2H), 2.55-2.14 (m, 11H), 2.14-1.95 (m, 2H), 1.60 (s, 4H), 1.35-1.30 (m, 8H), 1.03 (s, 9H). HRMS (ESI) m/z: calcd $C_{59}H_{72}N_{11}O_6S^+$ [M+H]$^+$, 1062.5382; found, 1062.5299.

Example 88: Preparation of (2S,4R)-1-((S)-3,3-dimethyl-2-(10-(4-(4-((4-methyl-3-((4-(pyridin-3-yl)pyrimidin-2-yl)amino)phenyl)carbamoyl)benzyl)piperazin-1-yl)-10-oxodecanamido)butanoyl)-4-hydroxy-N-(4-(4-methylthiazol-5-yl)benzyl)pyrrolidine-2-carboxamide (SIAIS074033)

Based on the general method of scheme 19 as described herein, compound (SIAIS074033) was obtained by coupling reaction of demethylated-imatinib analog with $HO_2C$-LIN-ULM analog (SIAIS074019) as a white solid (33.6 mg, 60% yield). $^1$H NMR (500 MHz, MeOD) δ 9.57 (s, 1H), 9.11 (d, J=8.1 Hz, 1H), 8.99-8.93 (m, 1H), 8.85 (d, J=5.4 Hz, 1H), 8.56 (d, J=7.7 Hz, 1H), 8.29 (s, 1H), 8.09 (d, J=8.2 Hz, 2H), 7.99 (dd, J=8.1, 5.5 Hz, 1H), 7.67 (d, J=8.3 Hz, 2H), 7.53-7.38 (m, 5H), 7.35-7.29 (m, 2H), 4.70-4.30 (m, 8H), 3.99-3.74 (m, 4H), 3.71-3.52 (m, 2H), 2.53-2.36 (m, 5H), 2.35-2.17 (m, 6H), 2.12-1.99 (m, 2H), 1.60 (s, 4H), 1.34-1.30 (m, 10H), 1.03 (s, 9H). HRMS (ESI) m/z: calcd $C_{60}H_{74}N_{11}O_6S^+$[M+H]$^+$, 1076.5539; found, 1076.5445.

Example 89: Preparation of (2S,4R)-1-((S)-3,3-dimethyl-2-(11-(4-(4-((4-methyl-3-((4-(pyridin-3-yl)pyrimidin-2-yl)amino)phenyl)carbamoyl)benzyl)piperazin-1-yl)-11-oxoundecanamido)butanoyl)-4-hydroxy-N-(4-(4-methylthiazol-5-yl)benzyl)pyrrolidine-2-carboxamide (SIAIS074034)

Based on the general method of scheme 19 as described herein, compound (SIAIS074034) was obtained by coupling reaction of demethylated-imatinib analog with $HO_2C$-LIN-ULM analog (SIAIS074020) as a white solid (32.4 mg, 57% yield). $^1$H NMR (500 MHz, MeOD) δ 9.57 (s, 1H), 9.11 (d, J=8.3 Hz, 1H), 8.97 (d, J=6.7 Hz, 1H), 8.85 (d, J=5.0 Hz, 1H), 8.56 (d, J=4.8 Hz, 1H), 8.29 (s, 1H), 8.08 (d, J=8.2 Hz, 2H), 7.99 (dd, J=8.0, 5.5 Hz, 1H), 7.67 (d, J=8.2 Hz, 2H), 7.53-7.37 (m, 5H), 7.37-7.27 (m, 2H), 4.69-4.28 (m, 8H), 4.02-3.76 (m, 4H), 3.63-3.61 (m, 2H), 2.52-2.37 (m, 5H), 2.34-2.17 (m, 6H), 2.13-1.99 (m, 2H), 1.60 (s, 4H), 1.32-1.30 (m, 12H), 1.03 (s, 9H). HRMS (ESI) m/z: calcd $C_{61}H_{76}N_{11}O_6S^+$[M+H]$^+$, 1090.5695; found, 1090.5593.

Comparative Example 1: Preparation of N-(2-chloro-6-methylphenyl)-2-((6-(4-((S)-3-((2S,4R)-4-hydroxy-2-((4-(4-methylthiazol-5-yl)benzyl)carbamoyl)pyrrolidine-1-carbonyl)-2,2-dimethyl-5-oxo-11,14,17-trioxa-4-azatricosan-23-yl)piperazin-1-yl)-2-methylpyrimidin-4-yl)amino)thiazole-5-carboxamide (SIAIS180138; Dasa-6-2-2-6-VHL)

Scheme 20

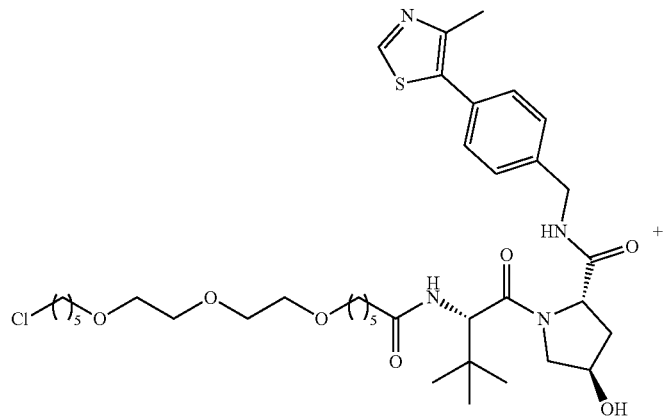

SIAIS180114

-continued

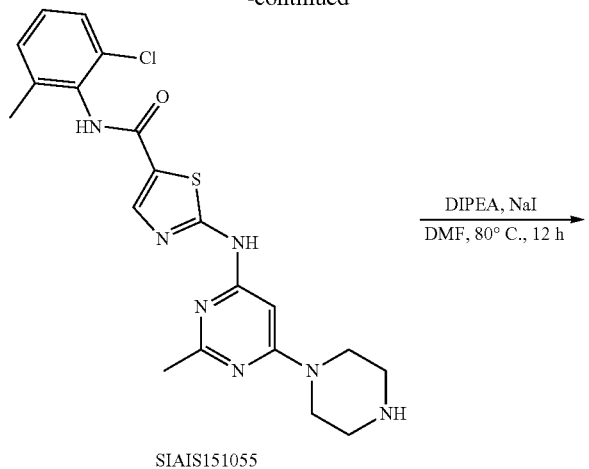

SIAIS151055

$\xrightarrow{\text{DIPEA, NaI}}{\text{DMF, 80° C., 12 h}}$

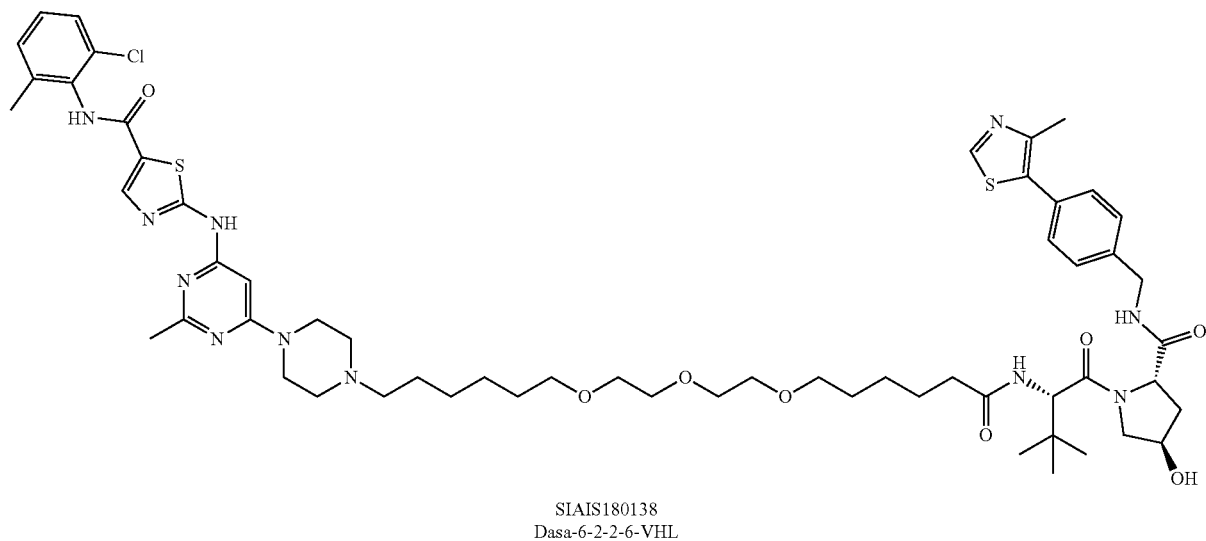

SIAIS180138
Dasa-6-2-2-6-VHL

Based on scheme 20, in a 25 mL of round-bottom flask, to a stirred solution of SIAIS151055 (0.45 mmol, 1 equiv) in anhydrous DMF (2 mL) was added N,N-Diisopropylethylamine (2.25 mmol, 5 equiv), sodium iodide (0.90 mmol, 2 equiv) and SIAIS180114 (0.90 mmol, 2 equiv) at room temperature. After addition, the mixture was stirred overnight at 80° C. LC-MS analysis showed the product peak, The mixture was filtered, the filtrate was purified via C18 reverse phase preparative HPLC column (eluent gradient: acetonitrile/(H$_2$O+0.05% HCl)=10%-100%) to afford desired product (SIAIS180138; Dasa-6-2-2-6-VHL) as a white solid (2.7 mg, 9% yield). $^1$H NMR (500 MHz, MeOD) δ 9.93 (s, 1H), 8.26 (s, 1H), 7.57 (d, J=8.2 Hz, 2H), 7.52 (d, J=8.2 Hz, 2H), 7.37 (dd, J=7.1, 2.2 Hz, 1H), 7.30-7.22 (m, 2H), 6.52 (s, 1H), 4.63 (s, 1H), 4.60-4.53 (m, 2H), 4.52-4.48 (m, 1H), 4.42-4.39 (m, 1H), 3.91 (d, J=11.0 Hz, 1H), 3.80 (dd, J=11.0, 3.9 Hz, 1H), 3.76 (d, J=11.5 Hz, 2H), 3.68-3.60 (m, 6H), 3.59-3.54 (m, 4H), 3.51-3.46 (m, 4H), 3.34-3.31 (m, 2H), 3.30-3.18 (m, 4H), 2.65 (s, 3H), 2.60 (s, 3H), 2.36-2.19 (m, 3H), 2.32 (s, 3H), 2.10-2.04 (m, 1H), 1.88-1.80 (m, 2H), 1.69-1.54 (m, 6H), 1.47-1.37 (m, 6H), 1.04 (s, 9H). HRMS (ESI) m/z: calcd C$_{58}$H$_{81}$ClN$_{11}$O$_8$S$_2^+$ [M+H]$^+$, 1158.5394; found, 1158.3389.

Comparative Example 2: Preparation of N-(2-chloro-6-methylphenyl)-2-((6-(4-(6-(2-(2-((6-((2-(2,6-dioxopiperidin-3-yl)-1,3-dioxoisoindolin-4-yl)amino)-6-oxohexyl)oxy)ethoxy)ethoxy)hexyl)piperazin-1-yl)-2-methylpyrimidin-4-yl)amino)thiazole-5-carboxamide (SIAIS171119; Dasa-6-2-2-6-CRBN)

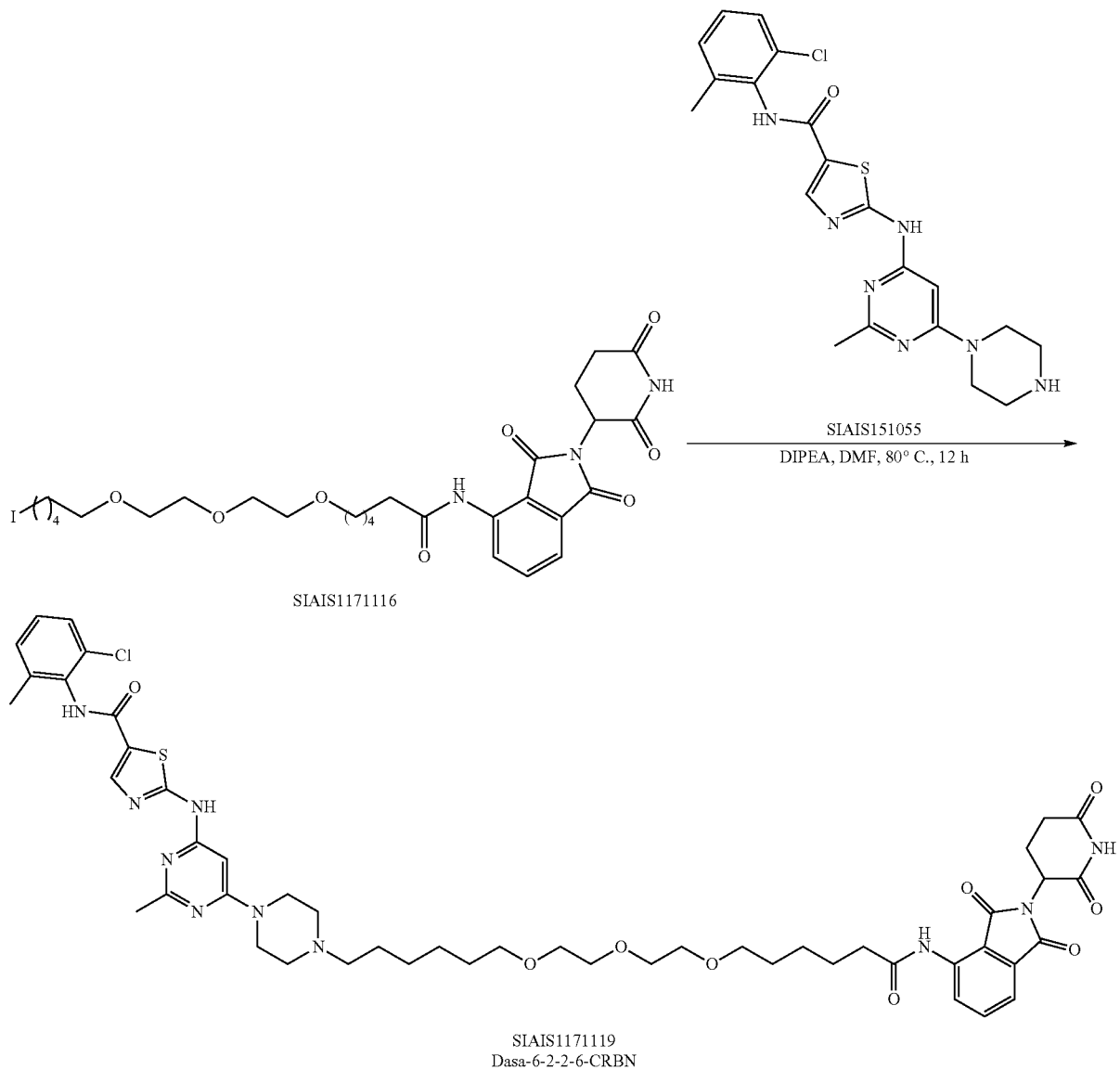

Scheme 21

Based on scheme 21, in a 25 mL of round-bottom flask, to a stirred solution of SIAIS151055 (9.7 mg, 0.022 mmol) in anhydrous DMF (1.5 mL) was added N,N-Diisopropylethylamine (18.8 mg, 0.15 mmol) and SIAIS171116 (10 mg, 0.015 mmol) at room temperature. After addition, the mixture was stirred overnight at 80° C. LC-MS analysis showed the product peak, The mixture was filtered, the filtrate was purified via C18 reverse phase preparative HPLC column (eluent gradient: acetonitrile/(H$_2$O+0.05% HCl)=10%-100%) to afford desired product (SIAIS171119; Dasa-6-2-2-6-CRBN) as a yellow solid (2 mg, 14% yield). $^1$H NMR (500 MHz, MeOD) δ 8.64 (d, J=10.2 Hz, 1H), 8.23 (s, 1H), 7.77 (dd, J=8.4, 7.4 Hz, 1H), 7.57 (d, J=7.0 Hz, 1H), 7.40-7.33 (m, 1H), 7.30-7.20 (m, 2H), 6.47 (s, 1H), 5.13 (dd, J=12.6, 5.5 Hz, 1H), 3.74 (d, J=11.6 Hz, 2H), 3.66-3.44 (m, 14H), 3.31-3.29 (m, 4H), 3.23-3.19 (m, 2H), 2.92-2.83 (m, 1H), 2.78-2.68 (m, 2H), 2.62 (s, 3H), 2.52 (t, J=7.4 Hz, 2H), 2.31 (s, 3H), 2.19-2.12 (m, 1H), 1.90-1.73 (m, 4H), 1.70-1.62 (m, 4H), 1.52-1.36 (m, 6H). HRMS (ESI) m/z: calcd C$_{49}$H$_{62}$ClN$_{10}$O$_9$S$^+$ [M+H]$^+$, 1001.4105; found, 1001.4128.

Biological Activity Detection Assay
Experimental Reagents

| Reagents and Anti-body | Suppliers |
|---|---|
| RPMI1640 | Gibco |
| Fetal bovine serum | Gibco |
| Penicillin-Streptomycin | Gibco |
| DMSO | Sigma-Aldrich |
| Dasatinib | Selleck |
| Cell counting Kit-8 (CCK-8) Cell Proliferation-Toxicity Test Kit | Dojindo |
| MG-132 | Merck Millipore |
| Carfilzomib (PR-171) | Selleck |
| Pierce Detergent Compatible Bradford Assay Kit (#23246) | Thermo Scientific |
| Western Blot Blocking Buffer (Fish Gelatin) | Takara |
| Immobilon western chemilum HRP substrate | Merck Millipore |
| c-Abl (#2862S) | Cell Signaling Technology |
| phospho-c-Abl (Y245) (#2861S) | |
| CRKL (#3182S) | |
| phospho- CRKL(#3181S) | |
| C-Kit(#3074S) | |
| phospho-CRKL (Y207) (#3181S) | |
| STAT5 (#9363S) | |
| phospho-STAT5 (Y694) (#4322S) | |
| β-Actin (13E5) (#5125S) | |
| Anti-rabbit IgG HRP-linked (#7074S) | |

Cell Lines

BCR-ABL (+) k562-cell (human chronic myeloid leukemia cells) purchased from American Type Culture Collection (ATCC);

BCR-ABL (−) cells:

U937 cell (Human monocytic leukemia cell line) purchased from American Type (American Type Culture Collection (ATCC));

HEK293 cell (Human embryonic kidney cell) purchased from American Type Culture Collection (ATCC).

Experimental Method

Cell Culture

Cells were cultured in a 37° C. incubator with 5% $C_{O2}$. The complete medium for cells is RPMI 640, contained 10% fetal bovine serum, and the final concentration of penicillin and streptomycin was 100 u/ml. Before the experiment, all cell lines were examined as negative by the *Mycoplasma* test kit.

I. Evaluation of $IC_{50}$ of PROTAD Compounds on Tumor Cells

Cells were seeded in 100 L RPMI 1640 complete medium with 2000-5000 cells/well. Set 10 concentrations from high to low, three times gradient dilution of the compound to be tested from the highest concentration of 10 μM. Then take 100 μL of diluted PROTAD compound and add it to the inoculated 100 μL cells. After 48 hours of drug treatment, the cell activity is measured based on the reagent operation instructions of CCK-8. The negative control is DMSO, and the positive control is a commercial inhibitor. After 2 hours of treatment with CCK-8, the O.D.450 value was measured using a microplate reader. The calculation formula for the growth inhibition rate of the PROTAD compound of the present disclosure on cells is cell inhibition rate %=(control group O.D.value− experimental group O.D.value)/control group O.D.value*100%, and further the inhibition curve was plotted by Prism Graphpad software and and the $IC_{50}$ values of the compounds were calculated.

Results: the series PROTAD compounds in this disclosure can significantly inhibit the proliferation of BCR-ABL positive K562 cells (as shown in Table 2), and have no significant proliferation inhibition effect on other cell lines not driven by BCR-ABL gene, such as U937 cells or HEK293 cells. It showed that the PROTAD compounds of the present disclosure have significant proliferation inhibition activity and good selectivity. The $IC_{50}$ values of all the compounds are less than 100 nM. It is exciting that the $IC_{50}$ of PROTAD compound designed and synthesized by us is as low as 1.47 nM, while the $IC_{50}$ of Dasatinib is 0.4 nM, and the inhibitory effect on tumor cell growth is very close to that of Dasatinib.

TABLE 2

$IC_{50}$ values of the compounds in the examples of the present disclosure for inhibiting the proliferation of tumor cells were determined by CCK-8.

| | ($IC_{50}$, nM) Proliferative inhibitory activity ($IC_{50}$, nM) | | |
|---|---|---|---|
| Compound | K562 (BCR-ABL+) | U937 (BCR-ABL−) | HEK293 (BCR-ABL−) |
| Dasatinib | 0.47 | NA | NA |
| Bosutinib | 29.63 | NA | |
| Imatinib | 205.5 | NA | NA |
| SIAIS171114 | 2.57 | NA | NA |
| SIAIS151063 | 2.7 | 275.7 | 972.2 |
| SIAIS151064 | 8.054 | NA | NA |
| SIAIS151067 | 14.75 | NA | NA |
| SIAIS151068 | 40.4 | NA | NA |
| SIAIS151069 | 31.9 | NA | NA |
| SIAIS151072 | 1.223 | NA | NA |
| SIAIS172150 | 2.84 | NA | NA |
| SIAIS184128 | 7 | NA | NA |
| SIAIS151074 | 6.8 | NA | NA |
| SIAIS151070 | 5.5 | NA | NA |
| SIAIS151071 | 0.55 | NA | NA |
| SIAIS151075 | 0.03 | NA | NA |
| SIAIS151181 | 1.47 | NA | NA |
| SIAIS184053 | 16.5 | NA | NA |
| SIAIS164108 | 12.25 | NA | NA |
| SIAIS164109 | 7.08 | NA | NA |
| SIAIS164110 | 1.03 | NA | NA |
| SIAIS184052 | 4.2 | NA | NA |
| SIAIS180147 | 14.9 | NA | NA |
| SIAIS151080 | 2240 | NA | NA |
| SIAIS151076 | 670 | NA | NA |
| SIAIS151077 | 3430 | NA | NA |
| SIAIS151078 | 2160 | NA | NA |
| SIAIS151079 | 1610 | NA | NA |
| SIAIS151174 | 78 | NA | NA |
| SIAIS151175 | 87 | NA | 3894 |
| SIAIS151176 | 89 | NA | NA |
| SIAIS151177 | 37.6 | NA | NA |
| SIAIS151178 | 41.3 | NA | NA |
| SIAIS151179 | 22.4 | NA | NA |
| SIAIS151180 | 14.3 | NA | NA |
| SIAIS164193 | 14.4 | NA | NA |
| SIAIS164194 | 32.3 | NA | NA |
| SIAIS184032 | 72 | NA | NA |
| SIAIS164134 | 12 | NA | NA |
| SIAIS164136 | 77.58 | NA | NA |
| SIAIS151158 | 3133 | NA | NA |
| SIAIS151159 | 4258 | NA | NA |
| SIAIS151160 | 4646 | NA | NA |
| SIAIS151161 | 7259 | NA | NA |
| SIAIS151162 | 712.4 | NA | NA |
| SIAIS151163 | 126.2 | NA | NA |
| SIAIS151166 | 894 | NA | NA |
| SIAIS151167 | 3654 | NA | NA |
| SIAIS164136 | 77.58 | NA | NA |
| SIAIS164104 | 811 | NA | NA |
| SIAIS164105 | 459.3 | NA | NA |
| SIAIS164106 | 438.2 | NA | NA |

Note:
NA: means that the highest concentration of 10 μM has no obvious inhibition on proliferation.

II. Determination of the Degradation Concentration ($DC_{50}$) of PROTAD Compounds to the Target Protein Determination of Western Blot Analysis of Protein (Western-Blot)

(1) Cell seed: K562 cells were added to the 24 well plates, with a cell density of $3 \times 10^5$/ml and a total volume of 1.5 ml; Five concentration gradients, 1 nm, 10 nm, 100 nm, 1 μM, and 10 μM, were respectively set for PROTAD series compounds and comparative examples compounds (Dasa-6-2-2-6-VHL, Dasa-6-2-2-6-CRBN). At the same time, DMSO and commercial maternal inhibitors (Dasatinib, Bosutinib, and imatinib) were added as negative and positive controls. At the same time, DMSO and commercial maternal inhibitors (Dasatinib, Bosutinib, and imatinib) were added as negative and positive controls. After 16 hours of drug treatment, the cells were collected in 1.5 ml ep tube, centrifuged at 3000 rpm for 3 minutes, and then added 30 μL PBS and 30 ul 2×SDS to cell precipitated, lysate Heat at 100° C. for 5 minutes, then place on ice for 5 minutes, centrifuged at 10000 rpm for 5 minutes, and take the supernatant as the total protein extracted. The protein concentration was determined by the Bradford method. After each sample was at the same concentration, bromophenol blue was added as the sample indicator.

(2) Electrophoresis: the starting voltage of the BioRad electrophoresis instrument was 80V, and as the dye enters the separation gel, the voltage was adjusted to 120V;

(3) Film transfer: prepare filter paper and nitrocellulose membrane with the corresponding size of the gel, filter paper, and NC film were soaked in transfer electrophoresis buffer. Based on the order of "filter paper gel —NC membrane filter paper", put it into electrophoresis tank, constant pressure 100V, 1.5 h, then the operation of antibody incubation and development was carried out based on the antibody Manual of Cell Signaling Technology.

$DC_{50}$ (concentration required to degrade protein by half) were calculated based on the intensity from western blot, and data were analyzed via Prism GraphPad with non-linear regression.

The results were as shown in Table 3: Western blot was used to detect the expression of BCR-ABL and c-ABL protein in K562 cells treated with PROTAD series compounds of the disclosure after 16 hours. The immunoblotting experiment showed that: (1) The PROTAD series of compounds of the present disclosure (Namely, the degradation agent) can induce the degradation of BCR-ABL and c-ABL proteins, and the degradation was dose-dependent. However, the commercial parent inhibitor only inhibits the activity of tyrosine kinase of BCR-ABL, which is not able to degrade the target protein BCR-ABL as the degradation agent of the present disclosure. (2) The Dasa-Lin-VHL system compound designed and synthesized in this disclosure is the first report that it can effectively degrade BCR-ABL and c-ABL protein, while the Dasa-6-2-2-6-vhl compound of Comparative Example 1 cannot degrade BCR-ABL protein; (3) The degradation activity of the designed and synthesized Dasa-Lin-VHL system compound is more effective than that of the reported comparative compound Dasa-6-2-2-6-crbn. All the original blotting results are shown in FIG. 1.

TABLE 3

Degradation results of PROTAD compound in the examples of the present disclosure on BCR-ABL and c-ABL protein

| Compound | BCR-ABL ($DC_{50}$, nM) | c-ABL ($DC_{50}$, nM) |
|---|---|---|
| Dasatinib | NA | NA |
| Bosutinib | NA | NA |
| Imatinib | NA | NA |
| SIAIS171114 | 10-100 | 10-100 |
| SIAIS151063 | 1-10 | 1-10 |
| SIAIS151064 | 1-10 | 10-100 |
| SIAIS151067 | 1-10 | 10-100 |
| SIAIS151068 | 1-10 | 10-100 |
| SIAIS151069 | 1-10 | 10-100 |
| SIAIS151072 | <1 | 1-10 |
| SIAIS172150 | 10-100 | 10-100 |
| SIAIS184128 | 1-10 | 1-10 |
| SIAIS151070 | 1-10 | 1-10 |
| SIAIS151071 | <1 | 1-10 |
| SIAIS151075 | 1-10 | 1-10 |
| SIAIS151181 | 1-10 | 1-10 |
| SIAIS184053 | 10-100 | 10-100 |
| SIAIS164108 | 10-100 | 10-100 |
| SIAIS164109 | 100-1000 | 100-1000 |
| SIAIS164110 | 10-100 | 10-100 |
| SIAIS184052 | 1-10 | 10-100 |
| SIAIS151078 | 100-1000 | >1000 |
| SIAIS151174 | 100-1000 | 100-1000 |
| SIAIS151175 | 10-100 | 100-1000 |
| SIAIS151176 | 10-100 | 100-1000 |
| SIAIS151177 | 1-10 | 10-100 |
| SIAIS151178 | 1-10 | 10-100 |
| SIAIS151179 | 10-100 | 100-1000 |
| SIAIS151180 | 1-10 | 10-100 |
| SIAIS151158 | 10-100 | 10-100 |
| SIAIS151159 | 10-100 | 10-100 |
| SIAIS151160 | 10-100 | 10-100 |
| SIAIS151161 | 100-1000 | 100-1000 |
| SIAIS151164 | 10-100 | 10-100 |
| SIAIS151162 | 10-100 | 10-100 |
| SIAIS151163 | 10-100 | 10-100 |
| SIAIS151166 | 10-100 | 10-100 |
| SIAIS151167 | 10-100 | 10-100 |
| SIAIS164136 | 1-10 | 1-10 |
| SIAIS164105 | 10-100 | 10-100 |
| SIAIS1197039 | 1000-1000 | 1000-1000 |
| SIAIS074031 | 100-1000 | 100-1000 |

Note:
NA: the highest concentration of 10 μm does not show significant degradation.

III. Degradation Activity of PROTAD Compound SIAIS151178 to BCR-ABL Having Drug Resistance Mutants Acquired drug resistance is a common problem in the use of TKI inhibitors in clinical Ph+ CML patients. A point mutation in BCR-ABL kinase region is the main cause of drug resistance. on this basis, we researched the degradation of PROTAD compounds in the examples of this present disclosure to the mutants of BCR-ABL related to TKI resistance in clinic. Firstly, we used the representative compound SIAIS151178 of Dasa-Lin-VHL system to test its degradation activity to BCR-ABL series mutants.

(1) Establishment of stable BCR-ABL mutant: the target fragment of BCR-ABL was cloned into retroviral vector pmigrl, and then PMIGR1-BCR-ABL-G250E/E255K/V299L/F317L/F317V/T315I/T315A and other mutant forms were obtained by using Stratagene-QuikChange® Site-Directed Mutagenesis Kit. Finally, the cell lines stably expressing BCR-ABL wild type and mutant were established on U937 cells by retrovirus infection system.

Figure 2:
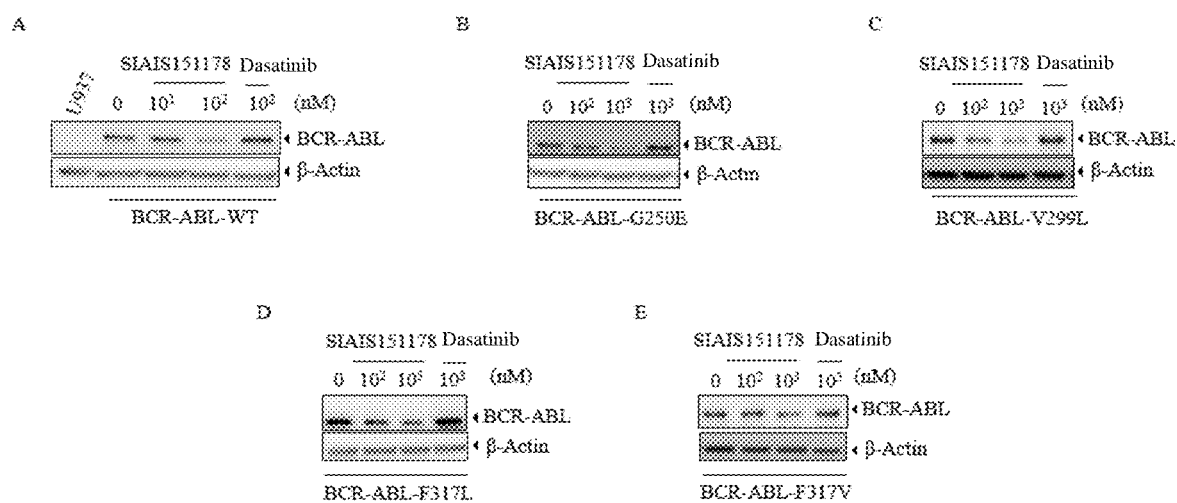
FIG. 2 shows the degradation activity of Dasa-Lin-VHL compound (SIAIS151178) according to an embodiment of the present disclosure against BCR-ABL resistant mutan.

(1) Cell seed: Established cells are added to the 24 well plates, with a cell density of $3 \times 10^5$/ml and a total volume of 1.5 ml; Four concentration gradients, 10 nm, 100 nm, 1 μM, and 10 μM, are respectively set for PROTAD series compounds. At the same time, DMSO and the small molecular inhibitors Dasatinib were added as negative and positive controls, respectively. After 24 hours of drug treatment, the cells were collected in 1.5 ml ep tube, centrifuged at 3000 rpm for 3 minutes, and then added 30 μL PBS and 30 μL 2×SDS to cell precipitated, lysate Heat at 100° C. for 5 minutes, then placed on ice for 5 minutes, centrifuged at 10000 rpm for 5 minutes, and take the supernatant as the total protein extracted. The effect of SIAS151178 on the mutational BCR-ABL protein was detected by Western blotting.

we used U937 cells to detect the degradation of PROTAD small molecule SIAIS151178 in Dasa-Lin-VHL system to various exogenous BCR-ABL mutants related to clinical drug resistance (FIG. 2). The results showed that SIAIS151178, a compound of Dasa-Lin-VHL system designed and synthesized in this disclosure, can significantly degrade the mutant forms of BCR-ABL-G250E/V299L/F317L/F317V in a dose-dependent manner.

IV. Effects of PROTAD Compound on the Transplanted Tumor Model of BCR-ABL+K562 Cell in Mice After preliminary screening of PROTAD series compounds of the disclosure with K562 cell line in vitro, we also used the K562 cell transplantation tumor model to study the antitumor activity of PROTAD compounds of the disclosure in vivo. We also studied the anti BCR-ABL positive leukemia activity in vivo with the representative compound SIAIS151178 of Dasa-Lin-VHL system.

(1) Establishment of K562 Luc cells: the target fragment of luciferase was cloned into lentivirus vector Plenti-IRES-ZSGREEN, and a K562-Luc cell line stably expressing luciferase was established on K562 cells by using lentivirus infection system.

(2) BCR-ABL+K562 cell transplanted mouse model: 5*106 k562 Luc cells were inoculated into the subcutaneous of immunodeficient NOD-SCID mice. After 2 weeks, the tumor volume of mice was nearly 200 mm$^3$. The mice were randomly divided into 5 groups. Vehicle group, the three-dose treatment groups (5, 15, 45 mg/kg) of SIAIS151178 (a compound of Dasa-Lin-VHL system designed and synthesized in this disclosure), and the treatment group of Dasatinib (an inhibitor), were administered for 2 weeks, during which the tumor size and weight change of mice were measured regularly. At the same time, the mice were imaged in vivo to observe the tumor-bearing condition. Then stop the administration and observe the recurrence of the tumor.

Figure 3:
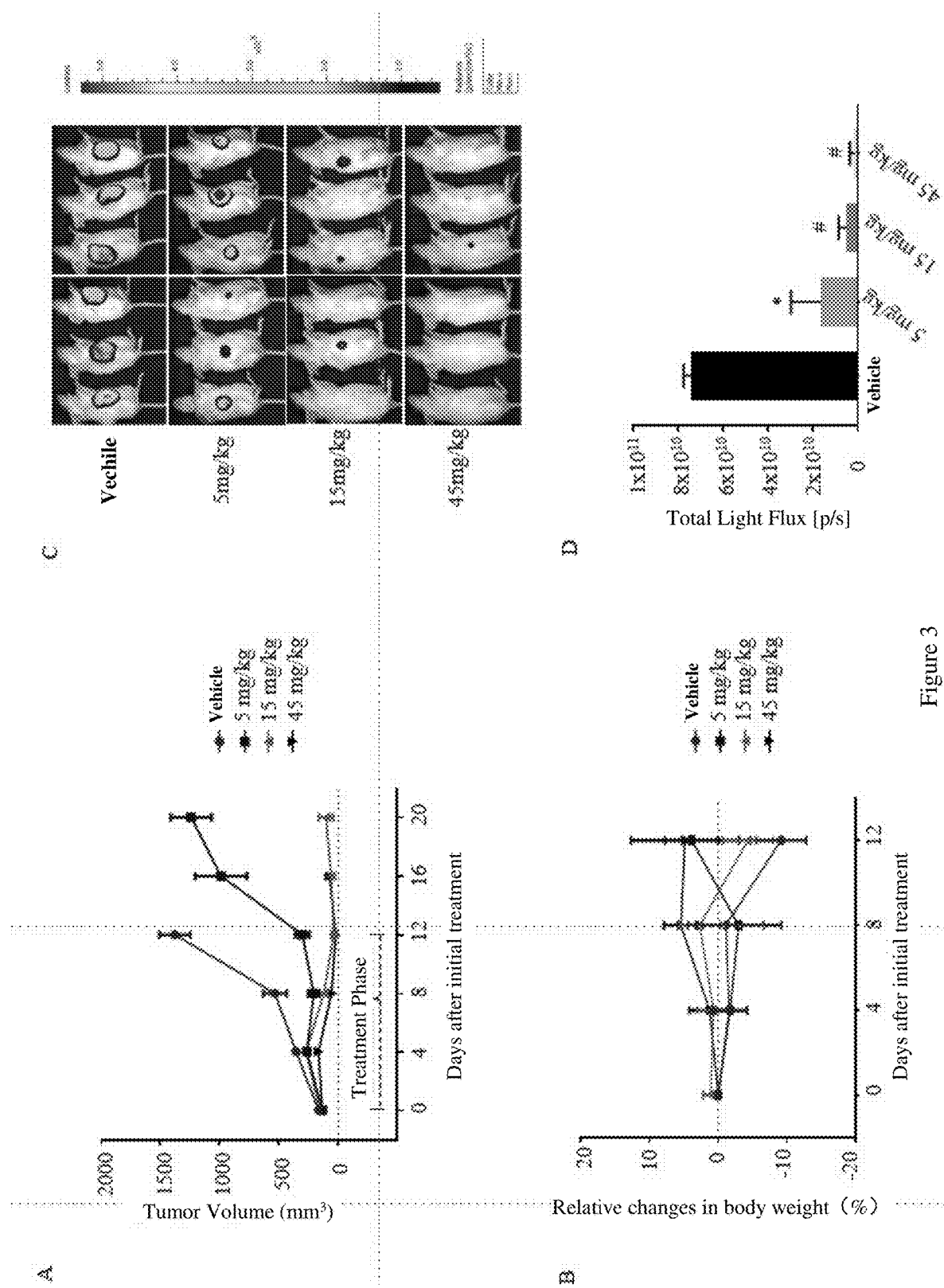
FIG. 3 shows the effect of Dasa-Lin-VHL compound (SIAIS151178) according to an embodiment of the present disclosure on BCR-ABL$^+$ K562 cell transplanted mouse model.

In vivo experiment (FIG. 3) showed that the small molecule SIAIS151178 of PROTAD in Dasa-Lin-VHL system can inhibit the growth of K562 cell transplantation tumor in a dose-dependent manner, and the dose concentration of 15 mg/kg can cause tumor decrease. During the experiment period, SIAIS151178 had no significant effect on the body-weight of mice, and no obvious toxic and side effects were found, indicating that the PROTAD small molecule showed good antitumor activity and safety.

V. Degradation of BCR-ABL Protein by PROTAD Compound In Vivo

Figure 4:
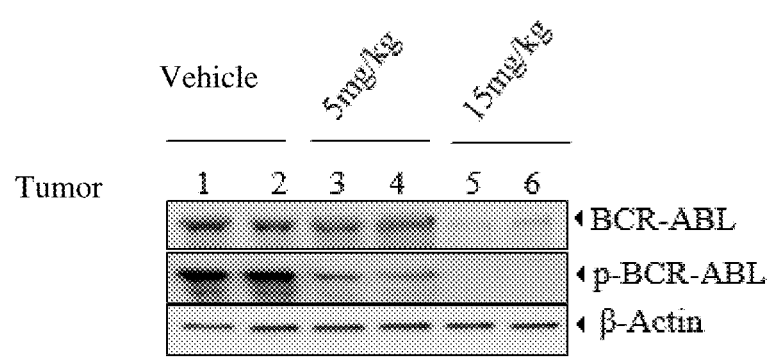
FIG. 4 shows the degradation activity of Dasa-Lin-VHL compound (SIAIS151178) according to an embodiment of the present disclosure on BCR-ABL protein in vivo.

We further study whether PROTAD compound of the disclosure can induce BCR-ABL protein degradation in vivo. We still took the compound SIAIS151178 of Dasa-Lin-VHL system as the representative one. Our research showed that SIAIS151178 can also degrade BCR-ABL and c-ABL protein in a dose-dependent manner in vivo, and significantly inhibit the BCR-ABL signal pathway activity (FIG. 4).

To sum up, the PROTAD series compounds of the present disclosure have been preliminarily screened by using K562 cell line. (1) The PROTAD series compounds of the present disclosure can significantly inhibit the proliferation of BCR-ABL positive cell lines, but have no obvious inhibitory activity on non BCR-ABL driven cell lines, showing excellent cell proliferation inhibitory activity and selectivity. (2) The Dasa-Lin-VHL system compound designed and synthesized in this disclosure is the first report, which can effectively degrade BCR-ABL and c-ABL protein, while the Dasa-6-2-2-6-vhl compound of Comparative Example 1 cannot degrade BCR-ABL protein; And taking SIAIS151178 (a Dasa-Lin-VHL system compound designed and synthesized in this present disclosure) as an Example, SIAIS151178 can degrade wild-type BCR-ABL and some clinically relevant mutant proteins in vitro. In vivo, it can degrade BCR-ABL, inhibit the BCR-ABL signal pathway, and significantly inhibit the growth of tumor. (3) In terms of BCR-ABL degradation activity, the Dasa-Lin-CRBN system compound designed and synthesized in this disclosure is superior to the compound Dasa-6-2-2-6-CRBN in the Comparative example. (4) Taking the Dasa-Lin-VHL system compound SIAIS151178 designed and synthesized in this present disclosure as an example, SIAIS151178 can also degrade other tyrosine kinase receptors, such as Src protein kinase, kit, PDGFR, and so on, which also has potential value for the treatment of these related tumors.

Although the clinical application of BCR-ABL inhibitors has greatly improved the prognosis of Ph$^+$ CML patients, patients still face two main problems: they need to take medicine for a long time, which brings a great economic burden but also faces the problem of acquired drug resistance. Although TKI can induce apoptosis of CML leukemic cells, it fail to kill CML leukemic progenitor cells. In addition to the kinase function, BCR-ABL can also be used as a scaffold protein to recruit protein complexes. Therefore, knockdown of BCR-ABL protein has therapeutic significance. In theory, the PROTAD compound of this disclosure can degrade BCR-ABL protein, to some extent, it may clear leukemic stem cells, delay the occurrence of drug resistance, and can also degrade the mutant forms related to drug resistance, which is of great significance to solve the problem of drug withdrawal and recurrence and drug resistance of TKI in the clinic. This study provides a new treatment strategy for Philadelphia chromosome-positive leukemia and other solid tumor patients.

The basic principles, main features and advantages of the present disclosure are shown and described above. Those skilled in the art should understand that the present disclosure is not limited by the foregoing embodiments, and they can make various changes, substitutions and alterations herein without departing from the spirit and scope of the present disclosure. These changes, substitutions and alterations fall within the scope of the present disclosure. The claimed scope of the present disclosure is defined by the appended claims and their equivalents.

REFERENCES

1. Nowell, P. C., *The minute chromosome (Phl) in chronic granulocytic leukemia*. Blut, 1962. 8: p. 65-6.
2. Rowley, J. D., *Letter: A new consistent chromosomal abnormality in chronic myelogenous leukaemia identified by quinacrine fluorescence and Giemsa staining*. Nature, 1973. 243 (5405): p. 290-3.
3. Kurzrock, R., et al., *Philadelphia chromosome-positive leukemias: from basic mechanisms to molecular therapeutics*. Ann Intern Med, 2003. 138(10): p. 819-30.
4. Kantarjian, H., et al., *Hematologic and cytogenetic responses to imatinib mesylate in chronic myelogenous leukemia*. N Engl J Med, 2002. 346(9): p. 645-52.
5. Mauro, M. J. and B. J. Druker, *STI571: targeting BCR-ABL as therapy for CML*. Oncologist, 2001. 6(3): p. 233-8.
6. Leoni, V. and A. Biondi, *Tyrosine kinase inhibitors in BCR-ABL positive acute lymphoblastic leukemia*. Haematologica, 2015. 100(3): p. 295-9.
7. Buchdunger, E., A. Matter, and B. J. Druker, *Bcr-Abl inhibition as a modality of CML therapeutics*. Biochim Biophys Acta, 2001. 1551(1): p. M11-8.
8. O'Hare, T., C. A. Eide, and M. W. Deininger, *Bcr-Abl kinase domain mutations, drug resistance, and the road to a cure for chronic myeloid leukemia*. Blood, 2007. 110(7): p. 2242-9.
9. Quintas-Cardama, A., et al., *Dasatinib (BMS-354825) is active in Philadelphia chromosome-positive chronic myelogenous leukemia after imatinib and nilotinib (AMN107) therapy failure*. Blood, 2007. 109(2): p. 497-9.
10. Kantarjian, H. M., et al., *Nilotinib (formerly AMN107), a highly selective BCR-ABL tyrosine kinase inhibitor, is effective in patients with Philadelphia chromosome-positive chronic myelogenous leukemia in chronic phase following imatinib resistance and intolerance*. Blood, 2007. 110(10): p. 3540-6.
11. Cortes, J., *Bosutinib in the treatment of chronic myelogenous leukemia*. Clin Adv Hematol Oncol, 2012. 10(11): p. 736-7.
12. Li, S., *Src-family kinases in the development and therapy of Philadelphia chromosome-positive chronic myeloid leukemia and acute lymphoblastic leukemia*. Leuk Lymphoma, 2008. 49(1): p. 19-26.
13. Araujo, J. and C. Logothetis, *Dasatinib: a potent SRC inhibitor in clinical development for the treatment of solid tumors*. Cancer Treat Rev, 2010. 36(6): p. 492-500.
14. Daud, A. I., et al., *Phase I study of bosutinib, a src/abl tyrosine kinase inhibitor, administered to patients with advanced solid tumors*. Clin Cancer Res, 2012. 18(4): p. 1092-100.
15. Poch Martell, M., et al., *Ponatinib in the therapy of chronic myeloid leukemia*. Expert Rev Hematol, 2016. 9(10): p. 923-32.
16. Konig, H., et al., *Enhanced BCR-ABL kinase inhibition does not result in increased inhibition of downstream signaling pathways or increased growth suppression in CML progenitors*. Leukemia, 2008. 22(4): p. 748-55.
17. Ichim, C. V., *Kinase-independent mechanisms of resistance of leukemia stem cells to tyrosine kinase inhibitors*. Stem Cells Transl Med, 2014. 3(4): p. 405-15.
18. Komander, D. and M. Rape, *The ubiquitin code*. Annu Rev Biochem, 2012. 81: p. 203-29.
19. Sakamoto, K. M., *Protacs for treatment of cancer*. Pediatr Res, 2010. 67(5): p. 505-8.
20. Lu, J., et al., *Hijacking the E3 Ubiquitin Ligase Cereblon to Efficiently Target BRD4*. Chem Biol, 2015. 22(6): p. 755-63.
21. Bondeson, D. P., et al., *Catalytic in vivo protein knockdown by small-molecule PROTACs*. Nat Chem Biol, 2015. 11(8): p. 611-7.
22. Itoh, Y., et al., *Development of target protein-selective degradation inducer for protein knockdown*. Bioorg Med Chem, 2011. 19(10): p. 3229-41.
23. Lai, A. C., et al., *Modular PROTAC Design for the Degradation of Oncogenic BCR-ABL*. Angew Chem Int Ed Engl, 2016. 55(2): p. 807-10.

The invention claimed is:
1. A compound of formula (I):

Formula (I)

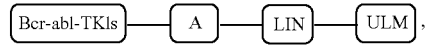

or a salt, or enantiomer thereof, in which:
the BCR-ABL-TKIs is covalently bonded to LIN via group A, and ULM covalently binds to the LIN;
wherein the BCR-ABL-TKIs is a Bcr-abl tyrosine kinase inhibitor and represents the moiety of following formula (Ia), (Ib), or (Ic):

Formula (Ia)

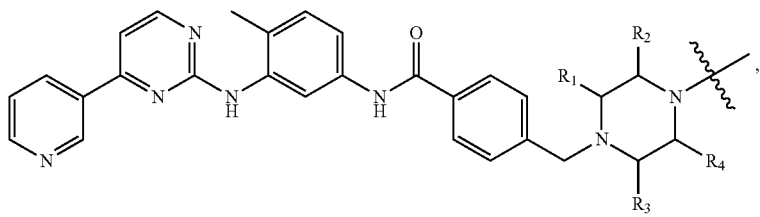

Formula (Ib)

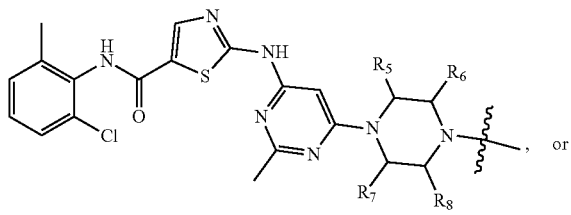

Formula (Ic)

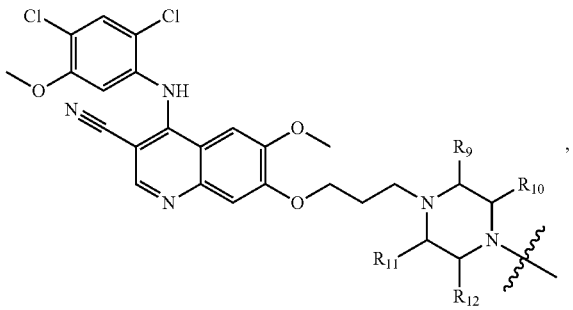

wherein $R_1$, $R_2$, $R_3$, $R_4$, $R_5$, $R_6$, $R_7$, $R_8$, $R_9$, $R_{10}$, $R_{11}$, and $R_{12}$ each independently represent $C_{1-10}$alkyl or H;

the LIN is a linker, which represents:

a linear or branched $C_1$-$C_{30}$ alkylene chain optionally substituted by one or more substituents selected from the group consisting of hydroxyl, amino, mercapto, halogen or any combination thereof, or —$(CH_2)_{n1}$—$(O(CH_2)_{n2})_{m1}$—, —$(CH_2)_{n1}$—$(O(CH_2)_{n2})_{m1}$—$O$—$(CH_2)_{n3}$—, —$(CR_{13}R_{14})_{n1}$—$(O(CR_{15}R_{16})_{n2})_{m1}$—, —$(CR_{17}R_{18})_{n1}$—$(O(CR_{19}R_{20})_{n2})_{m1}$—$O$—$(CR_{21}R_{22})_{n3}$—, —$(CH_2)_{n1}$—$(CONH$—$(CH_2)_{n2})_{m1}$—, —$(CH_2)_{n1}$—$(CONH$—$(CH_2)_{n2})_{m1}$—$O$—$(CH_2)_{n3}$—, —$(CH_2)_{n1}$—$(O(CH_2)_{n2})_{m1}$—$O$—$(CH_2)_{n3}$—$CONH$—$(CH_2)_{n4}$—$(O(CH_2)_{n5})_{m2}$—$O$—$(CH_2)_{n6}$—, —$(CR_{23}R_{24})_{n1}$—$(O(CR_{25}R_{26})_{n2})_{m1}$—$O$—$(CR_{27}R_{28})_{n3}$—$CONH$—$(CR_{29}R_{30})_{n4}$—$(O(CR_{31}R_{32})_{n5})_{m2}$—$O$—$(CR_{33}R_{34})_{n6}$—, —$(CR_{35}R_{36})_{n1}$—$CONH$—$(O(CR_{37}R_{38})_{n2})_{m1}$—, —$(CH_2)_{n1}$—$NHCO$—$(CH_2)_{n2}$—, —$(CH_2)_{n1}$—$(NHCO$—$(CH_2)_{n2})_{m1}$—, —$(CH_2)_{n1}$—$(NHCO$—$(CH_2)_{n2})_{m1}$—$O$—$(CH_2)_{n3}$—, or —$(CH_2)_{n1}$-triazolylene—$(CH_2)_{n2}$—, wherein $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{33}$, $R_{34}$, $R_{35}$, $R_{36}$, $R_{37}$, and $R_{38}$ each independently represent H, a linear or branched $C_1$-$C_{10}$ alkyl or $C_3$-$C_{10}$ cycloalkyl, wherein $R_{13}$, $R_{14}$, $R_{15}$, and $R_{16}$ are not H at the same time, $R_{17}$, $R_{18}$, $R_{19}$, $R_{20}$, $R_{21}$, and $R_{22}$ are not H at the same time, $R_{23}$, $R_{24}$, $R_{25}$, $R_{26}$, $R_{27}$, $R_{28}$, $R_{29}$, $R_{30}$, $R_{31}$, $R_{32}$, $R_{33}$, and $R_{34}$ are not H at the same time, or $R_{35}$, $R_{36}$, $R_{37}$, and $R_{38}$ are not H at the same time; and n1, n2, n3, n4, n5, n6, m1, and m2 are each independently an integer of 1, 2, 3, 4, 5, 6, 7, 8, 9, 10, 11, 12, 13, 14, 15, 16, 17, 18, 19, or 20;

ULM is a small molecule ligand with a ubiquitination function on VHL or CRBN protease and represents the structure of formula (II) or (III):

Formula (II)

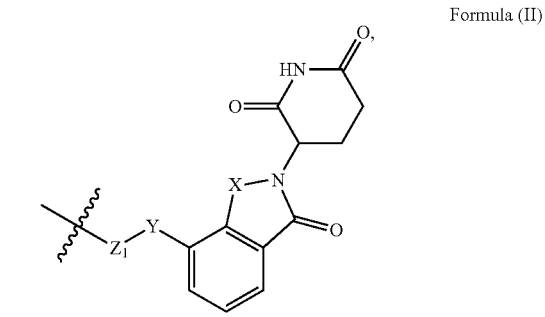

wherein X represents —$CH_2$— or —$CO$—, Y represents —$CH_2$—, —$NH$—, or —$O$—, and $Z_1$ represents carbonyl or $Z_1$ is absent;

Formula (III)

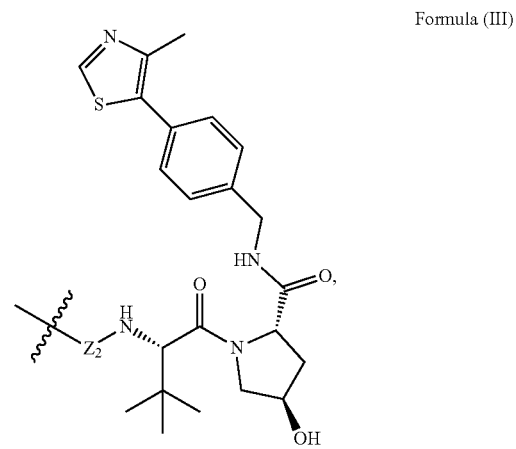

wherein Z2 represents carbonyl or Z2 is absent; and the group A is carbonyl (—CO—).

2. The compound of formula (I), or a salt, or enantiomer thereof as recited in claim 1, wherein the $R_1$, $R_2$, $R_3$, $R_4$, $R_5$, $R_6$, $R_7$, $R_8$, $R_9$, $R_{10}$, $R_{11}$, and $R_{12}$ each independently represent a linear or branched $C_{1-6}$ alkyl or H.

3. The compound of formula (I), or a salt, or enantiomer thereof as recited in claim 1, wherein the compound of formula (I) is also a compound of formula (IV):

Formula (IV)

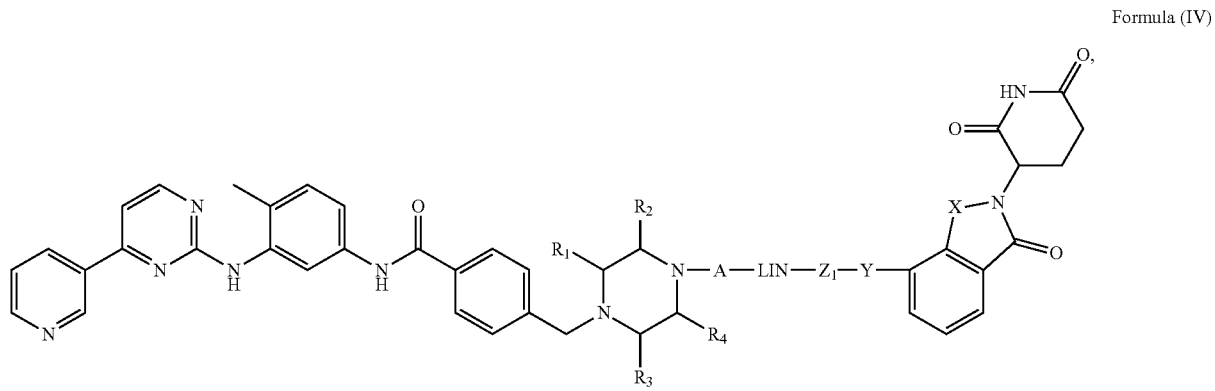

wherein group A, LIN, X, Y, $Z_1$, $R_1$, $R_2$, $R_3$, and $R_4$ are as defined in claim 1.

4. The compound of formula (I), or a salt, or enantiomer thereof as recited in claim 1, wherein the compound of formula (I) is also a compound of formula (V):

Formula (V)

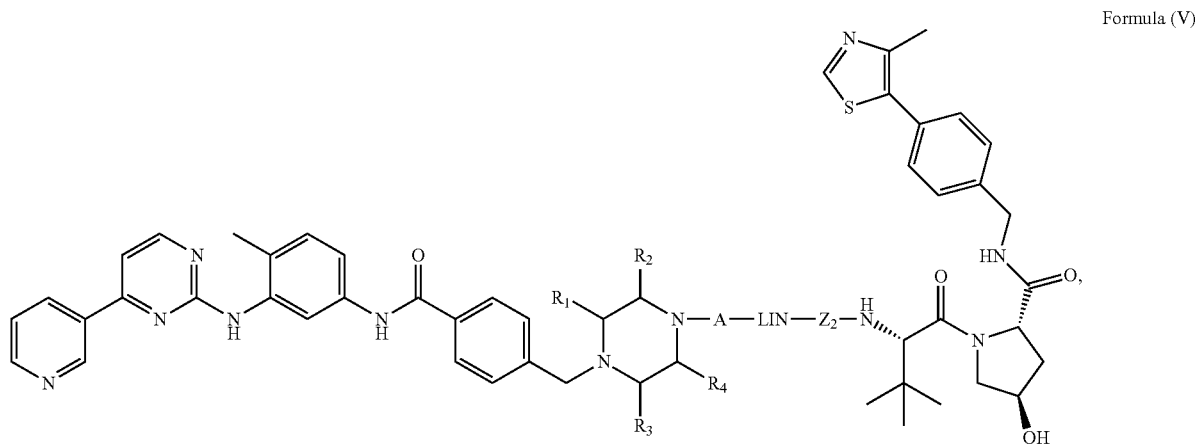

wherein group A, LIN, $Z_2$, $R_1$, $R_2$, $R_3$, and $R_4$ are as defined in claim 1.

5. The compound of formula (I), or a salt, or enantiomer thereof as recited in claim 1, wherein the compound of formula (I) is also a compound of formula (VI):

Formula (VI)

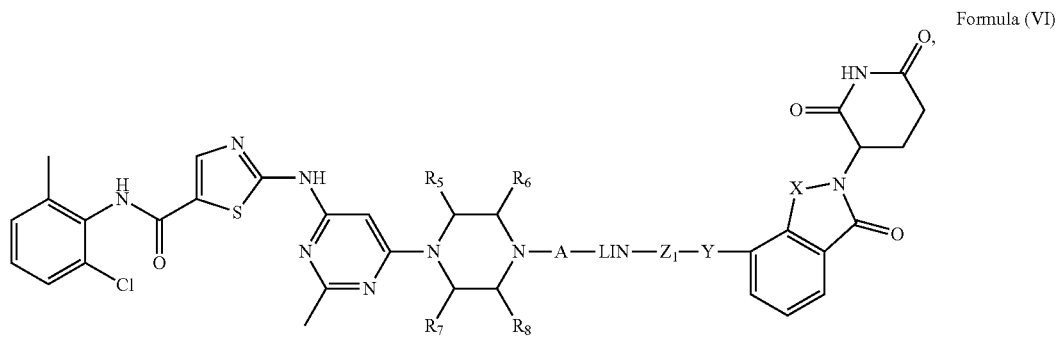

wherein group A, LIN, X, Y, $Z_1$, $R_5$, $R_6$, $R_7$, and $R_8$ are as defined in claim 1.

6. The compound of formula (I), or a salt, or enantiomer thereof as recited in claim 1, wherein the compound of formula (I) is also a compound of formula (VII):

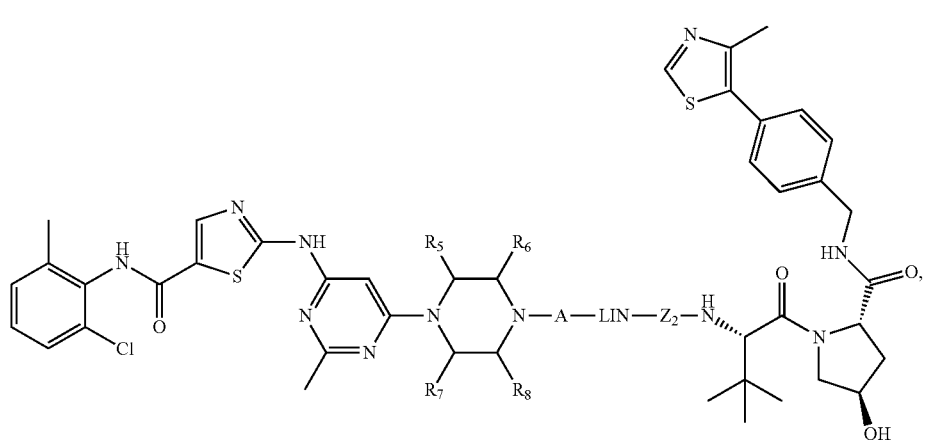

Formula (VII)

wherein group A, LIN, $Z_2$, $R_5$, $R_6$, $R_7$, and $R_8$ are as defined in claim 1.

7. The compound of formula (I), or a salt, or enantiomer thereof as recited in claim 1, wherein the compound of formula (I) is also a compound of formula (VIII):

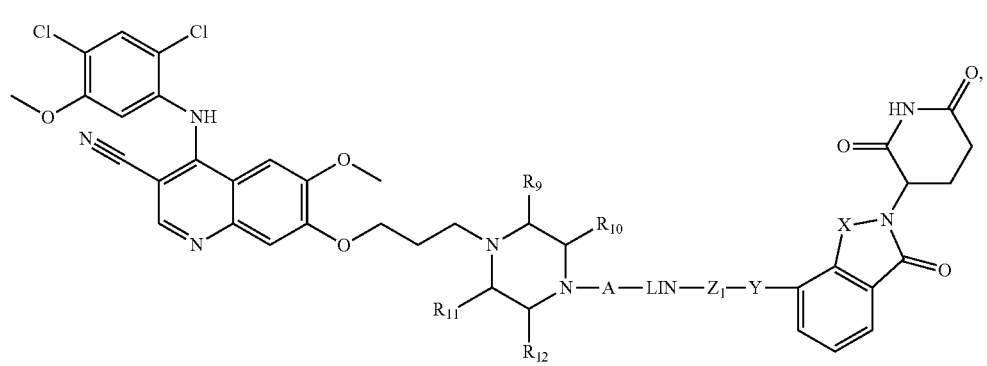

Formula (VIII)

wherein group A, LIN, X, Y, $Z_1$, $R_9$, $R_{10}$, $R_{11}$, and $R_{12}$ are as defined in claim 1.

8. The compound of formula (I), or a salt, or enantiomer thereof as recited in claim 1, wherein the compound of formula (I) is also a compound of formula (IX):

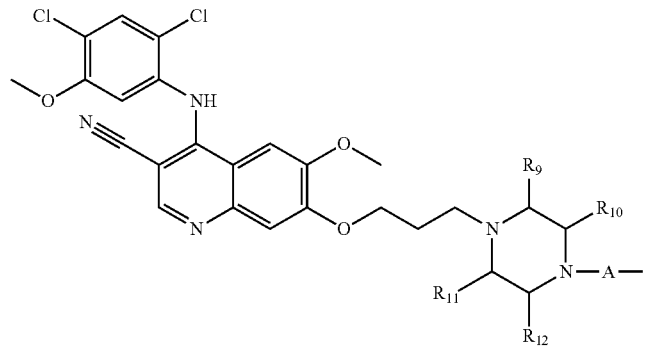

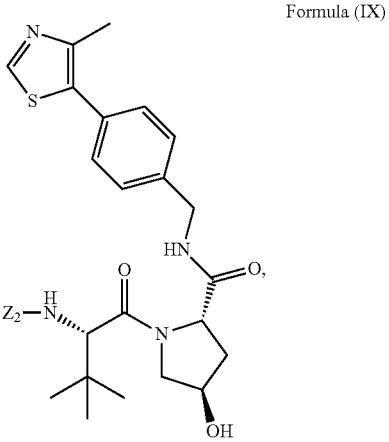

Formula (IX)

wherein group A, LIN, $Z_2$, $R_9$, $R_{10}$, $R_{11}$, and $R_{12}$ are as defined in claim 1.

9. The compound of formula (I), or a salt, or enantiomer thereof as recited in claim 1, wherein the LIN represents:

—CH$_2$O(CH$_2$)$_2$OCH$_2$—;
—CH$_2$O(CH$_2$)$_2$O(CH$_2$)$_2$—;
—(CH$_2$)$_3$O(CH$_2$)$_2$—;
—(CH$_2$)$_3$O(CH$_2$)$_2$O(CH$_2$)$_2$—;
—(CH$_2$)$_3$O(CH$_2$)$_3$—;
—(CH$_2$)$_2$O(CH$_2$)$_2$—;
—(CH$_2$)$_2$O(CH$_2$)$_2$OCH$_2$—;
—(CH$_2$)$_2$O(CH$_2$)$_2$O(CH$_2$)$_2$—;
—(CH$_2$)$_2$O(CH$_2$)$_2$O(CH$_2$)$_3$—;
—(CH$_2$)$_2$O(CH$_2$)$_2$O(CH$_2$)$_2$O(CH$_2$)$_2$—;
—(CH$_2$)$_2$O(CH$_2$)$_2$O(CH$_2$)$_2$O(CH$_2$)$_3$—;
—(CH$_2$)$_5$O(CH$_2$)$_2$O(CH$_2$)$_2$O(CH$_2$)$_5$—;
—(CH$_2$)$_5$O(CH$_2$)$_2$O(CH$_2$)$_2$O(CH$_2$)$_6$—;
—(CH$_2$)$_2$O(CH$_2$)$_2$O(CH$_2$)$_2$O(CH$_2$)$_2$O(CH$_2$)$_2$—;
—(CH$_2$)$_2$O(CH$_2$)$_2$O(CH$_2$)$_2$O(CH$_2$)$_2$O(CH$_2$)$_3$—;
—(CH$_2$)$_2$O(CH$_2$)$_2$O(CH$_2$)$_2$O(CH$_2$)$_2$O(CH$_2$)$_2$O(CH$_2$)$_2$—;
—(CH$_2$)$_3$O(CH$_2$)$_2$O(CH$_2$)$_2$O(CH$_2$)$_2$O(CH$_2$)$_2$O(CH$_2$)$_2$—; or
—(CH$_2$)$_3$O(CH$_2$)$_2$O(CH$_2$)$_2$O(CH$_2$)$_2$O(CH$_2$)$_2$O(CH$_2$)$_3$—.

10. The compound of formula (I), or a salt, or enantiomer thereof as recited in claim 1, wherein the LIN represents:

—CH$_2$—; —(CH$_2$)$_2$—; —(CH$_2$)$_3$—; —(CH$_2$)$_4$—;
—(CH$_2$)$_5$—; —(CH$_2$)$_6$—; —(CH$_2$)$_7$—; —(CH$_2$)$_8$—;
—(CH$_2$)$_9$—; —(CH$_2$)$_{10}$—; —(CH$_2$)$_{11}$—;
—(CH$_2$)$_{12}$—; —(CH$_2$)$_{13}$—; —(CH$_2$)$_{14}$—;
—(CH$_2$)$_{15}$—; —(CH$_2$)$_{16}$—; —(CH$_2$)$_{17}$—;
—(CH$_2$)$_{18}$—; —(CH$_2$)$_{19}$—; or —(CH$_2$)$_{20}$—.

11. The compound of formula (I), or a salt, or enantiomer thereof as recited in claim 1, wherein the substituent is selected from the group consisting of hydroxyl, amino, mercapto and halogen.

12. The compound of formula (I), or a salt, or enantiomer thereof as recited in claim 11, wherein the LIN is a linear or branched $C_1$-$C_{20}$ alkylene chain substituted with one or more substituents selected from the group consisting of hydroxyl, amino, mercapto, halogen or any combination thereof.

13. The compound of formula (I), or a salt, or enantiomer thereof as recited in claim 1, wherein the LIN represents:

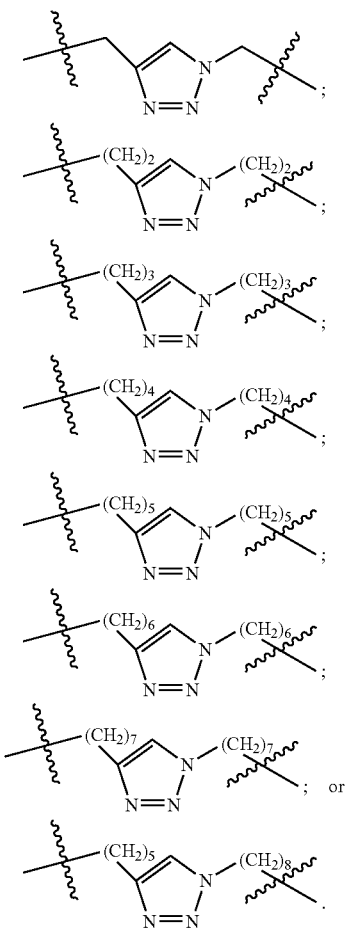

14. The compound of formula (I), or a salt, or enantiomer thereof as recited in claim 1, wherein the LIN represents:

—CH$_2$CONHCH$_2$—; —(CH$_2$)$_2$CONH(CH$_2$)$_2$—;
—(CH$_2$)$_3$CONH(CH$_2$)$_3$—;
(CH$_2$)$_3$CONH(CH$_2$)$_4$—; —(CH$_2$)$_4$CONH(CH$_2$)$_4$—;
—(CH$_2$)$_5$CONH(CH$_2$)$_5$—;

—(CH₂)₆CONH(CH₂)₇—;  —(CH₂)₆CONH(CH₂)₆—;
—(CH₂)₇CONH(CH₂)₇—;
—(CH₂)₈CONH(CH₂)₈—;  —(CH₂)₉CONH(CH₂)₉—;
—(CH₂)₁₀CONH(CH₂)₁₀—; or
—(CH₂)₂CONH(CH₂)₂—O—(CH₂)₂—.

15. The compound of formula (I), or a salt, or enantiomer thereof as recited in claim 1, wherein the LIN represents —(CH₂)$_{n1}$—NHCO—(CH₂)$_{n2}$—, wherein n1 and n2 each independently represent an integer of 1, 2, 3, 4, 5, 6, 7, 8, 9, 10, 11, 12, 13, 14, 15, 16, 17, 18, 19, or 20.

16. The compound of formula (I), or a salt, or enantiomer thereof as recited in claim 15, wherein the LIN represents —(CH₂)₄NHCO(CH₂)₈—.

17. The compound of formula (I), or a salt, or enantiomer thereof as recited in claim 1, wherein the LIN represents —(CH₂)$_{n1}$—CH=CH—(CH₂)$_{n2}$—, wherein n1 and n2 each independently represent an integer of 1, 2, 3, 4, 5, 6, 7, 8, 9, 10, 11, 12, 13, 14, 15, 16, 17, 18, 19, or 20.

18. The compound of formula (I), or a salt, or enantiomer thereof as recited in claim 1, wherein the LIN represents —(CH₂)$_{n1}$—C≡C—(CH₂)$_{n2}$— or —(CH₂)$_{n1}$—C≡C—C≡C—(CH₂)$_{n2}$—, wherein n1 and n2 each independently represent an integer of 1, 2, 3, 4, 5, 6, 7, 8, 9, 10, 11, 12, 13, 14, 15, 16, 17, 18, 19, or 20.

19. The compound of formula (I), or a salt, or enantiomer thereof as recited in claim 1, which is selected from the group consisting of:

N-(2-chloro-6-methylphenyl)-2-((6-(4-(6-(2-(2-((6-((2-(2,6-dioxopiperidin-3-yl)-1,3-dioxoisoindolin-4-yl)amino)-6-oxohexyl)oxy)ethoxy)ethoxy)hexanoyl)piperazin-1-yl)-2-methylpyrimidin-4-yl)amino)thiazole-5-carboxamide;

N-(2-chloro-6-methylphenyl)-2-((6-(4-(6-(2-(2-((6-((2-(2,6-dioxopiperidin-3-yl)-1,3-dioxoisoindolin-4-yl)amino)hexyl)oxy)ethoxy)ethoxy)hexanoyl)piperazin-1-yl)-2-methylpyrimidin-4-yl)amino)thiazole-5-carboxamide;

N-(2-chloro-6-methylphenyl)-2-((6-(4-(3-(2-((2-(2,6-dioxopiperidin-3-yl)-1,3-dioxoisoindolin-4-yl)amino)ethoxy)propanoyl)piperazin-1-yl)-2-methylpyrimidin-4-yl)amino)thiazole-5-carboxamide;

N-(2-chloro-6-methylphenyl)-2-((6-(4-(3-(3-(2-(2,6-dioxopiperidin-3-yl)-1,3-dioxoisoindolin-4-yl)propoxy)propanoyl)piperazin-1-yl)-2-methylpyrimidin-4-yl)amino)thiazole-5-carboxamide;

N-(2-chloro-6-methylphenyl)-2-((6-(4-(3-(2-((2-(2,6-dioxopiperidin-3-yl)-1,3-dioxoisoindolin-4-yl)oxy)ethoxy)propanoyl)piperazin-1-yl)-2-methylpyrimidin-4-yl)amino)thiazole-5-carboxamide;

N-(2-chloro-6-methylphenyl)-2-((6-(4-(3-(2-(2-((2-(2,6-dioxopiperidin-3-yl)-1,3-dioxoisoindolin-4-yl)amino)ethoxy)ethoxy)propanoyl)piperazin-1-yl)-2-methylpyrimidin-4-yl)amino)thiazole-5-carboxamide;

N-(2-chloro-6-methylphenyl)-2-((6-(4-(3-(2-(3-(2-(2,6-dioxopiperidin-3-yl)-1,3-dioxoisoindolin-4-yl)propoxy)ethoxy)propanoyl)piperazin-1-yl)-2-methylpyrimidin-4-yl)amino)thiazole-5-carboxamide;

N-(2-chloro-6-methylphenyl)-2-((6-(4-(3-(2-(2-((2-(2,6-dioxopiperidin-3-yl)-1,3-dioxoisoindolin-4-yl)oxy)ethoxy)ethoxy)propanoyl)piperazin-1-yl)-2-methylpyrimidin-4-yl)amino)thiazole-5-carboxamide;

N-(2-chloro-6-methylphenyl)-2-((6-(4-(3-(2-(2-(2-((2-(2,6-dioxopiperidin-3-yl)-1,3-dioxoisoindolin-4-yl)amino)ethoxy)ethoxy)ethoxy)propanoyl)piperazin-1-yl)-2-methylpyrimidin-4-yl)amino)thiazole-5-carboxamide;

N-(2-chloro-6-methylphenyl)-2-((6-(4-(1-((2-(2,6-dioxopiperidin-3-yl)-1,3-dioxoisoindolin-4-yl)amino)-3,6,9,12-tetraoxapentadecan-15-oyl)piperazin-1-yl)-2-methylpyrimidin-4-yl)amino)thiazole-5-carboxamide;

N-(2-chloro-6-methylphenyl)-2-((6-(4-(16-(2-(2,6-dioxopiperidin-3-yl)-1,3-dioxoisoindolin-4-yl)-4,7,10,13-tetraoxahexadecanoyl)piperazin-1-yl)-2-methylpyrimidin-4-yl)amino)thiazole-5-carboxamide;

N-(2-chloro-6-methylphenyl)-2-((6-(4-(1-((2-(2,6-dioxopiperidin-3-yl)-1,3-dioxoisoindolin-4-yl)oxy)-3,6,9,12-tetraoxapentadecan-15-oyl)piperazin-1-yl)-2-methylpyrimidin-4-yl)amino)thiazole-5-carboxamide;

N-(2-chloro-6-methylphenyl)-2-((6-(4-(1-((2-(2,6-dioxopiperidin-3-yl)-1,3-dioxoisoindolin-4-yl)amino)-3,6,9,12,15-pentaoxaoctadecan-18-oyl)piperazin-1-yl)-2-methylpyrimidin-4-yl)amino)thiazole-5-carboxamide;

N-(2-chloro-6-methylphenyl)-2-((6-(4-((2-(2,6-dioxopiperidin-3-yl)-1,3-dioxoisoindolin-4-yl)glycyl)piperazin-1-yl)-2-methylpyrimidin-4-yl)amino)thiazole-5-carboxamide;

N-(2-chloro-6-methylphenyl)-2-((6-(4-(3-(2-(2,6-dioxopiperidin-3-yl)-1,3-dioxoisoindolin-4-yl)propanoyl)piperazin-1-yl)-2-methylpyrimidin-4-yl)amino)thiazole-5-carboxamide;

N-(2-chloro-6-methylphenyl)-2-((6-(4-(2-((2-(2,6-dioxopiperidin-3-yl)-1,3-dioxoisoindolin-4-yl)oxy)acetyl)piperazin-1-yl)-2-methylpyrimidin-4-yl)amino)thiazole-5-carboxamide;

N-(2-chloro-6-methylphenyl)-2-((6-(4-(3-((2-(2,6-dioxopiperidin-3-yl)-1,3-dioxoisoindolin-4-yl)amino)propanoyl)piperazin-1-yl)-2-methylpyrimidin-4-yl)amino)thiazole-5-carboxamide;

N-(2-chloro-6-methylphenyl)-2-((6-(4-(4-((2-(2,6-dioxopiperidin-3-yl)-1,3-dioxoisoindolin-4-yl)amino)butanoyl)piperazin-1-yl)-2-methylpyrimidin-4-yl)amino)thiazole-5-carboxamide;

N-(2-chloro-6-methylphenyl)-2-((6-(4-(5-(2-(2,6-dioxopiperidin-3-yl)-1,3-dioxoisoindolin-4-yl)pentanoyl)piperazin-1-yl)-2-methylpyrimidin-4-yl)amino)thiazole-5-carboxamide;

N-(2-chloro-6-methylphenyl)-2-((6-(4-(4-((2-(2,6-dioxopiperidin-3-yl)-1,3-dioxoisoindolin-4-yl)oxy)butanoyl)piperazin-1-yl)-2-methylpyrimidin-4-yl)amino)thiazole-5-carboxamide;

N-(2-chloro-6-methylphenyl)-2-((6-(4-(5-((2-(2,6-dioxopiperidin-3-yl)-1,3-dioxoisoindolin-4-yl)amino)pentanoyl)piperazin-1-yl)-2-methylpyrimidin-4-yl)amino)thiazole-5-carboxamide;

N-(2-chloro-6-methylphenyl)-2-((6-(4-(6-((2-(2,6-dioxopiperidin-3-yl)-1,3-dioxoisoindolin-4-yl)amino)hexanoyl)piperazin-1-yl)-2-methylpyrimidin-4-yl)amino)thiazole-5-carboxamide;

N-(2-chloro-6-methylphenyl)-2-((6-(4-(7-(2-(2,6-dioxopiperidin-3-yl)-1,3-dioxoisoindolin-4-yl)heptanoyl)piperazin-1-yl)-2-methylpyrimidin-4-yl)amino)thiazole-5-carboxamide;

N-(2-chloro-6-methylphenyl)-2-((6-(4-(6-((2-(2,6-dioxopiperidin-3-yl)-1,3-dioxoisoindolin-4-yl)oxy)hexanoyl)piperazin-1-yl)-2-methylpyrimidin-4-yl)amino)thiazole-5-carboxamide;

N-(2-chloro-6-methylphenyl)-2-((6-(4-(7-((2-(2,6-dioxopiperidin-3-yl)-1,3-dioxoisoindolin-4-yl)amino)heptanoyl)piperazin-1-yl)-2-methylpyrimidin-4-yl)amino)thiazole-5-carboxamide;

N-(2-chloro-6-methylphenyl)-2-((6-(4-(8-((2-(2,6-dioxopiperidin-3-yl)-1,3-dioxoisoindolin-4-yl)amino)octanoyl)piperazin-1-yl)-2-methylpyrimidin-4-yl)amino)thiazole-5-carboxamide;

N-(2-chloro-6-methylphenyl)-2-((6-(4-(9-(2-(2,6-dioxopiperidin-3-yl)-1,3-dioxoisoindolin-4-yl)nonanoyl)piperazin-1-yl)-2-methylpyrimidin-4-yl)amino)thiazole-5-carboxamide;

N-(2-chloro-6-methylphenyl)-2-((6-(4-(8-((2-(2,6-dioxopiperidin-3-yl)-1,3-dioxoisoindolin-4-yl)oxy)octanoyl)piperazin-1-yl)-2-methylpyrimidin-4-yl)amino)thiazole-5-carboxamide;

N-(2-chloro-6-methylphenyl)-2-((6-(4-(5-((2-(2,6-dioxopiperidin-3-yl)-1,3-dioxoisoindolin-4-yl)amino)-5-oxopentanoyl)piperazin-1-yl)-2-methylpyrimidin-4-yl)amino)thiazole-5-carboxamide;

N-(2-chloro-6-methylphenyl)-2-((6-(4-(6-((2-(2,6-dioxopiperidin-3-yl)-1,3-dioxoisoindolin-4-yl)amino)-6-oxohexanoyl)piperazin-1-yl)-2-methylpyrimidin-4-yl)amino)thiazole-5-carboxamide;

N-(2-chloro-6-methylphenyl)-2-((6-(4-(7-((2-(2,6-dioxopiperidin-3-yl)-1,3-dioxoisoindolin-4-yl)amino)-7-oxoheptanoyl)piperazin-1-yl)-2-methylpyrimidin-4-yl)amino)thiazole-5-carboxamide;

N-(2-chloro-6-methylphenyl)-2-((6-(4-(8-((2-(2,6-dioxopiperidin-3-yl)-1,3-dioxoisoindolin-4-yl)amino)-8-oxooctanoyl)piperazin-1-yl)-2-methylpyrimidin-4-yl)amino)thiazole-5-carboxamide;

N-(2-chloro-6-methylphenyl)-2-((6-(4-(4-((2-((2-(2,6-dioxopiperidin-3-yl)-1,3-dioxoisoindolin-4-yl)amino)ethyl)amino)-4-oxobutanoyl)piperazin-1-yl)-2-methylpyrimidin-4-yl)amino)thiazole-5-carboxamide;

N-(2-chloro-6-methylphenyl)-2-((6-(4-(4-((2-(2-((2-(2,6-dioxopiperidin-3-yl)-1,3-dioxoisoindolin-4-yl)amino)ethoxy)ethyl)amino)-4-oxobutanoyl)piperazin-1-yl)-2-methylpyrimidin-4-yl)amino)thiazole-5-carboxamide;

N-(2-chloro-6-methylphenyl)-2-((6-(4-(3-((2-(2,6-dioxopiperidin-3-yl)-1-oxoisoindolin-4-yl)amino)-3-oxopropanoyl)piperazin-1-yl)-2-methylpyrimidin-4-yl)amino)thiazole-5-carboxamide;

N-(2-chloro-6-methylphenyl)-2-((6-(4-(4-((2-(2,6-dioxopiperidin-3-yl)-1-oxoisoindolin-4-yl)amino)-4-oxobutanoyl)piperazin-1-yl)-2-methylpyrimidin-4-yl)amino)thiazole-5-carboxamide;

N-(2-chloro-6-methylphenyl)-2-((6-(4-(5-((2-(2,6-dioxopiperidin-3-yl)-1-oxoisoindolin-4-yl)amino)-5-oxopentanoyl)piperazin-1-yl)-2-methylpyrimidin-4-yl)amino)thiazole-5-carboxamide;

N-(2-chloro-6-methylphenyl)-2-((6-(4-(6-((2-(2,6-dioxopiperidin-3-yl)-1-oxoisoindolin-4-yl)amino)-6-oxohexanoyl)piperazin-1-yl)-2-methylpyrimidin-4-yl)amino)thiazole-5-carboxamide;

N-(2-chloro-6-methylphenyl)-2-((6-(4-(7-((2-(2,6-dioxopiperidin-3-yl)-1-oxoisoindolin-4-yl)amino)-7-oxoheptanoyl)piperazin-1-yl)-2-methylpyrimidin-4-yl)amino)thiazole-5-carboxamide;

N-(2-chloro-6-methylphenyl)-2-((6-(4-(8-((2-(2,6-dioxopiperidin-3-yl)-1-oxoisoindolin-4-yl)amino)-8-oxooctanoyl)piperazin-1-yl)-2-methylpyrimidin-4-yl)amino)thiazole-5-carboxamide;

N-(2-chloro-6-methylphenyl)-2-((6-(4-(9-((2-(2,6-dioxopiperidin-3-yl)-1-oxoisoindolin-4-yl)amino)-9-oxononanoyl)piperazin-1-yl)-2-methylpyrimidin-4-yl)amino)thiazole-5-carboxamide;

N-(2-chloro-6-methylphenyl)-2-((6-(4-(10-((2-(2,6-dioxopiperidin-3-yl)-1-oxoisoindolin-4-yl)amino)-10-oxodecanoyl)piperazin-1-yl)-2-methylpyrimidin-4-yl)amino)thiazole-5-carboxamide;

N-(2-chloro-6-methylphenyl)-2-((6-(4-(11-((2-(2,6-dioxopiperidin-3-yl)-1-oxoisoindolin-4-yl)amino)-11-oxoundecanoyl)piperazin-1-yl)-2-methylpyrimidin-4-yl)amino)thiazole-5-carboxamide;

N-(2-chloro-6-methylphenyl)-2-((6-(4-(3-((2-(2,6-dioxopiperidin-3-yl)-1-oxoisoindolin-4-yl)amino)propanoyl)piperazin-1-yl)-2-methylpyrimidin-4-yl)amino)thiazole-5-carboxamide;

N-(2-chloro-6-methylphenyl)-2-((6-(4-(4-(2-(2,6-dioxopiperidin-3-yl)-1-oxoisoindolin-4-yl)butanoyl)piperazin-1-yl)-2-methylpyrimidin-4-yl)amino)thiazole-5-carboxamide;

N-(2-chloro-6-methylphenyl)-2-((6-(4-(3-((2-(2,6-dioxopiperidin-3-yl)-1-oxoisoindolin-4-yl)oxy)propanoyl)piperazin-1-yl)-2-methylpyrimidin-4-yl)amino)thiazole-5-carboxamide;

N-(2-chloro-6-methylphenyl)-2-((6-(4-(4-((2-(2,6-dioxopiperidin-3-yl)-1-oxoisoindolin-4-yl)amino)butanoyl)piperazin-1-yl)-2-methylpyrimidin-4-yl)amino)thiazole-5-carboxamide;

N-(2-chloro-6-methylphenyl)-2-((6-(4-(5-(2-(2,6-dioxopiperidin-3-yl)-1-oxoisoindolin-4-yl)pentanoyl)piperazin-1-yl)-2-methylpyrimidin-4-yl)amino)thiazole-5-carboxamide;

N-(2-chloro-6-methylphenyl)-2-((6-(4-(4-((2-(2,6-dioxopiperidin-3-yl)-1-oxoisoindolin-4-yl)oxy)butanoyl)piperazin-1-yl)-2-methylpyrimidin-4-yl)amino)thiazole-5-carboxamide;

N-(2-chloro-6-methylphenyl)-2-((6-(4-(5-((2-(2,6-dioxopiperidin-3-yl)-1-oxoisoindolin-4-yl)amino)pentanoyl)piperazin-1-yl)-2-methylpyrimidin-4-yl)amino)thiazole-5-carboxamide;

N-(2-chloro-6-methylphenyl)-2-((6-(4-(6-(2-(2,6-dioxopiperidin-3-yl)-1-oxoisoindolin-4-yl)hexanoyl)piperazin-1-yl)-2-methylpyrimidin-4-yl)amino)thiazole-5-carboxamide;

N-(2-chloro-6-methylphenyl)-2-((6-(4-(5-((2-(2,6-dioxopiperidin-3-yl)-1-oxoisoindolin-4-yl)oxy)pentanoyl)piperazin-1-yl)-2-methylpyrimidin-4-yl)amino)thiazole-5-carboxamide;

N-(2-chloro-6-methylphenyl)-2-((6-(4-(6-((2-(2,6-dioxopiperidin-3-yl)-1-oxoisoindolin-4-yl)amino)hexanoyl)piperazin-1-yl)-2-methylpyrimidin-4-yl)amino)thiazole-5-carboxamide;

N-(2-chloro-6-methylphenyl)-2-((6-(4-(7-((2-(2,6-dioxopiperidin-3-yl)-1-oxoisoindolin-4-yl)amino)heptanoyl)piperazin-1-yl)-2-methylpyrimidin-4-yl)amino)thiazole-5-carboxamide;

N-(2-chloro-6-methylphenyl)-2-((6-(4-(8-(2-(2,6-dioxopiperidin-3-yl)-1-oxoisoindolin-4-yl)octanoyl)piperazin-1-yl)-2-methylpyrimidin-4-yl)amino)thiazole-5-carboxamide;

N-(2-chloro-6-methylphenyl)-2-((6-(4-(7-((2-(2,6-dioxopiperidin-3-yl)-1-oxoisoindolin-4-yl)oxy)heptanoyl)piperazin-1-yl)-2-methylpyrimidin-4-yl)amino)thiazole-5-carboxamide;

N-(2-chloro-6-methylphenyl)-2-((6-(4-((S)-3-((2S,4R)-4-hydroxy-2-((4-(4-methylthiazol-5-yl)benzyl)carbamoyl)pyrrolidine-1-carbonyl)-2,2-dimethyl-5-oxo-11,14,17-trioxa-4-azatricosan-23-oyl)piperazin-1-yl)-2-methylpyrimidin-4-yl)amino)thiazole-5-carboxamide;

N-(2-chloro-6-methylphenyl)-2-((6-(4-((S)-3-((2S,4R)-4-hydroxy-2-((4-(4-methylthiazol-5-yl)benzyl)carbamoyl)pyrrolidine-1-carbonyl)-2,2-dimethyl-11,14,17-trioxa-4-azatricosan-23-oyl)piperazin-1-yl)-2-
methylpyrimidin-4-yl)amino)thiazole-5-carboxamide;
N-(2-chloro-6-methylphenyl)-2-((6-(4-(2-(2-(2-(((S)-1-
((2S,4R)-4-hydroxy-2-((4-(4-methylthiazol-5-yl)ben-
zyl)carbamoyl)pyrrolidin-1-yl)-3,3-dimethyl-1-oxobu-
tan-2-yl)amino)-2-oxoethoxy)ethoxy)acetyl)piperazin-
1-yl)-2-methylpyrimidin-4-yl)amino)thiazole-5-
carboxamide;
N-(2-chloro-6-methylphenyl)-2-((6-(4-(2-(2-(2-(((S)-1-
((2S,4R)-4-hydroxy-2-((4-(4-methylthiazol-5-yl)ben-
zyl)carbamoyl)pyrrolidin-1-yl)-3,3-dimethyl-1-oxobu-
tan-2-yl)amino)-2-oxoethoxy)ethoxy)acetyl)piperazin-
1-yl)-2-methylpyrimidin-4-yl)amino)thiazole-5-
carboxamide;
N-(2-chloro-6-methylphenyl)-2-((6-(4-((S)-15-((2S,4R)-
4-hydroxy-2-((4-(4-methylthiazol-5-yl)benzyl)car-
bamoyl)pyrrolidine-1-carbonyl)-16,16-dimethyl-13-
oxo-4,7,10-trioxa-14-azaheptadecanoyl)piperazin-1-
yl)-2-methylpyrimidin-4-yl)amino)thiazole-5-
carboxamide;
N-(2-chloro-6-methylphenyl)-2-((6-(4-((S)-18-((2S,4R)-
4-hydroxy-2-((4-(4-methylthiazol-5-yl)benzyl)car-
bamoyl)pyrrolidine-1-carbonyl)-19,19-dimethyl-16-
oxo-4,7,10,13-tetraoxa-17-azaicosanoyl)piperazin-1-
yl)-2-methylpyrimidin-4-yl)amino)thiazole-5-
carboxamide;
N-(2-chloro-6-methylphenyl)-2-((6-(4-((S)-21-((2S,4R)-
4-hydroxy-2-((4-(4-methylthiazol-5-yl)benzyl)car-
bamoyl)pyrrolidine-1-carbonyl)-22,22-dimethyl-19-
oxo-4,7,10,13,16-pentaoxa-20-azatricosanoyl)
piperazin-1-yl)-2-methylpyrimidin-4-yl)amino)
thiazole-5-carboxamide;
N-(2-chloro-6-methylphenyl)-2-((6-(4-(2-(2-(2-(((S)-1-
((2S,4R)-4-hydroxy-2-((4-(4-methylthiazol-5-yl)ben-
zyl)carbamoyl)pyrrolidin-1-yl)-3,3-dimethyl-1-oxobu-
tan-2-yl)amino)ethoxy)ethoxy)acetyl)piperazin-1-yl)-
2-methylpyrimidin-4-yl)amino)thiazole-5-
carboxamide;
N-(2-chloro-6-methylphenyl)-2-((6-(4-(3-(2-(3-(((S)-1-
((2S,4R)-4-hydroxy-2-((4-(4-methylthiazol-5-yl)ben-
zyl)carbamoyl)pyrrolidin-1-yl)-3,3-dimethyl-1-oxobu-
tan-2-yl)amino)propoxy)ethoxy)propanoyl)piperazin-
1-yl)-2-methylpyrimidin-4-yl)amino)thiazole-5-
carboxamide;
N-(2-chloro-6-methylphenyl)-2-((6-(4-((S)-15-((2S,4R)-
4-hydroxy-2-((4-(4-methylthiazol-5-yl)benzyl)car-
bamoyl)pyrrolidine-1-carbonyl)-16,16-dimethyl-4,7,
10-trioxa-14-azaheptadecanoyl)piperazin-1-yl)-2-
methylpyrimidin-4-yl)amino)thiazole-5-carboxamide;
N-(2-chloro-6-methylphenyl)-2-((6-(4-((S)-18-((2S,4R)-
4-hydroxy-2-((4-(4-methylthiazol-5-yl)benzyl)car-
bamoyl)pyrrolidine-1-carbonyl)-19,19-dimethyl-4,7,
10,13-tetraoxa-17-azaicosanoyl)piperazin-1-yl)-2-
methylpyrimidin-4-yl)amino)thiazole-5-carboxamide;
N-(2-chloro-6-methylphenyl)-2-((6-(4-(4-(((S)-1-((2S,
4R)-4-hydroxy-2-((4-(4-methylthiazol-5-yl)benzyl)
carbamoyl)pyrrolidin-1-yl)-3,3-dimethyl-1-oxobutan-
2-yl)amino)-4-oxobutanoyl)piperazin-1-yl)-2-
methylpyrimidin-4-yl)amino)thiazole-5-carboxamide;
N-(2-chloro-6-methylphenyl)-2-((6-(4-(5-(((S)-1-((2S,
4R)-4-hydroxy-2-((4-(4-methylthiazol-5-yl)benzyl)
carbamoyl)pyrrolidin-1-yl)-3,3-dimethyl-1-oxobutan-
2-yl)amino)-5-oxopentanoyl)piperazin-1-yl)-2-
methylpyrimidin-4-yl)amino)thiazole-5-carboxamide;
N-(2-chloro-6-methylphenyl)-2-((6-(4-(6-(((S)-1-((2S,
4R)-4-hydroxy-2-((4-(4-methylthiazol-5-yl)benzyl)
carbamoyl)pyrrolidin-1-yl)-3,3-dimethyl-1-oxobutan-
2-yl)amino)-6-oxohexanoyl)piperazin-1-yl)-2-
methylpyrimidin-4-yl)amino)thiazole-5-carboxamide;
N-(2-chloro-6-methylphenyl)-2-((6-(4-(6-(((S)-1-((2S,
4R)-4-hydroxy-2-((4-(4-methylthiazol-5-yl)benzyl)
carbamoyl)pyrrolidin-1-yl)-3,3-dimethyl-1-oxobutan-
2-yl)amino)hexanoyl)piperazin-1-yl)-2-
methylpyrimidin-4-yl)amino)thiazole-5-carboxamide;
N-(2-chloro-6-methylphenyl)-2-((6-(4-(7-(((S)-1-((2S,
4R)-4-hydroxy-2-((4-(4-methylthiazol-5-yl)benzyl)
carbamoyl)pyrrolidin-1-yl)-3,3-dimethyl-1-oxobutan-
2-yl)amino)-7-oxoheptanoyl)piperazin-1-yl)-2-
methylpyrimidin-4-yl)amino)thiazole-5-carboxamide;
N-(2-chloro-6-methylphenyl)-2-((6-(4-(7-(((S)-1-((2S,
4R)-4-hydroxy-2-((4-(4-methylthiazol-5-yl)benzyl)
carbamoyl)pyrrolidin-1-yl)-3,3-dimethyl-1-oxobutan-
2-yl)amino)heptanoyl)piperazin-1-yl)-2-
methylpyrimidin-4-yl)amino)thiazole-5-carboxamide;
N-(2-chloro-6-methylphenyl)-2-((6-(4-(8-(((S)-1-((2S,
4R)-4-hydroxy-2-((4-(4-methylthiazol-5-yl)benzyl)
carbamoyl)pyrrolidin-1-yl)-3,3-dimethyl-1-oxobutan-
2-yl)amino)-8-oxooctanoyl)piperazin-1-yl)-2-
methylpyrimidin-4-yl)amino)thiazole-5-carboxamide;
N-(2-chloro-6-methylphenyl)-2-((6-(4-(8-(((S)-1-((2S,
4R)-4-hydroxy-2-((4-(4-methylthiazol-5-yl)benzyl)
carbamoyl)pyrrolidin-1-yl)-3,3-dimethyl-1-oxobutan-
2-yl)amino)octanoyl)piperazin-1-yl)-2-
methylpyrimidin-4-yl)amino)thiazole-5-carboxamide;
N-(2-chloro-6-methylphenyl)-2-((6-(4-(9-(((S)-1-((2S,
4R)-4-hydroxy-2-((4-(4-methylthiazol-5-yl)benzyl)
carbamoyl)pyrrolidin-1-yl)-3,3-dimethyl-1-oxobutan-
2-yl)amino)-9-oxononanoyl)piperazin-1-yl)-2-
methylpyrimidin-4-yl)amino)thiazole-5-carboxamide;
N-(2-chloro-6-methylphenyl)-2-((6-(4-(9-(((S)-1-((2S,
4R)-4-hydroxy-2-((4-(4-methylthiazol-5-yl)benzyl)
carbamoyl)pyrrolidin-1-yl)-3,3-dimethyl-1-oxobutan-
2-yl)amino)nonanoyl)piperazin-1-yl)-2-
methylpyrimidin-4-yl)amino)thiazole-5-carboxamide;
N-(2-chloro-6-methylphenyl)-2-((6-(4-(10-(((S)-1-((2S,
4R)-4-hydroxy-2-((4-(4-methylthiazol-5-yl)benzyl)
carbamoyl)pyrrolidin-1-yl)-3,3-dimethyl-1-oxobutan-
2-yl)amino)-10-oxodecanoyl)piperazin-1-yl)-2-
methylpyrimidin-4-yl)amino)thiazole-5-carboxamide;
N-(2-chloro-6-methylphenyl)-2-((6-(4-(11-(((S)-1-((2S,
4R)-4-hydroxy-2-((4-(4-methylthiazol-5-yl)benzyl)
carbamoyl)pyrrolidin-1-yl)-3,3-dimethyl-1-oxobutan-
2-yl)amino)-11-oxoundecanoyl)piperazin-1-yl)-2-
methylpyrimidin-4-yl)amino)thiazole-5-carboxamide;
N-(2-chloro-6-methylphenyl)-2-((6-(4-(12-(((S)-1-((2S,
4R)-4-hydroxy-2-((4-(4-methylthiazol-5-yl)benzyl)
carbamoyl)pyrrolidin-1-yl)-3,3-dimethyl-1-oxobutan-
2-yl)amino)-12-oxododecanoyl)piperazin-1-yl)-2-
methylpyrimidin-4-yl)amino)thiazole-5-carboxamide;
N-(2-chloro-6-methylphenyl)-2-((6-(4-(13-(((S)-1-((2S,
4R)-4-hydroxy-2-((4-(4-methylthiazol-5-yl)benzyl)
carbamoyl)pyrrolidin-1-yl)-3,3-dimethyl-1-oxobutan-
2-yl)amino)-13-oxotridecanoyl)piperazin-1-yl)-2-
methylpyrimidin-4-yl)amino)thiazole-5-carboxamide;
N-(2-chloro-6-methylphenyl)-2-((6-(4-(14-(((S)-1-((2S,
4R)-4-hydroxy-2-((4-(4-methylthiazol-5-yl)benzyl)
carbamoyl)pyrrolidin-1-yl)-3,3-dimethyl-1-oxobutan-
2-yl)amino)-14-oxotetradecanoyl)piperazin-1-yl)-2-
methylpyrimidin-4-yl)amino)thiazole-5-carboxamide;
N-(2-chloro-6-methylphenyl)-2-((6-(4-(15-(((S)-1-((2S,
4R)-4-hydroxy-2-((4-(4-methylthiazol-5-yl)benzyl)
carbamoyl)pyrrolidin-1-yl)-3,3-dimethyl-1-oxobutan-
2-yl)amino)-15-oxopentadecanoyl)piperazin-1-yl)-2-
methylpyrimidin-4-yl)amino)thiazole-5-carboxamide;

N-(2-chloro-6-methylphenyl)-2-((6-(4-(15-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)pentadecanoyl)piperazin-1-yl)-2-methylpyrimidin-4-yl)amino)thiazole-5-carboxamide;

N-(2-chloro-6-methylphenyl)-2-((6-(4-(16-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-16-oxohexadecanoyl)piperazin-1-yl)-2-methylpyrimidin-4-yl)amino)thiazole-5-carboxamide;

N1-(5-(4-(6-((5-((2-chloro-6-methylphenyl)carbamoyl)thiazol-2-yl)amino)-2-methylpyrimidin-4-yl)piperazin-1-yl)-5-oxopentyl)-N10-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)decanediamide;

N-(2-chloro-6-methylphenyl)-2-((6-(4-(4-(1-(4-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-4-oxobutyl)-1H-1,2,3-triazol-4-yl)butanoyl)piperazin-1-yl)-2-methylpyrimidin-4-yl)amino)thiazole-5-carboxamide;

6-(2-(2-((6-(4-(3-((3-cyano-4-((2,4-dichloro-5-methoxyphenyl)amino)-6-methoxyquinolin-7-yl)oxy)propyl)piperazin-1-yl)-6-oxohexyl)oxy)ethoxy)ethoxy)-N-(2-(2,6-dioxopiperidin-3-yl)-1,3-dioxoisoindolin-4-yl)hexanamide;

4-((2,4-dichloro-5-methoxyphenyl)amino)-7-(3-(4-(6-(2-(2-((6-((2-(2,6-dioxopiperidin-3-yl)-1,3-dioxoisoindolin-4-yl)amino)hexyl)oxy)ethoxy)ethoxy)hexanoyl)piperazin-1-yl)propoxy)-6-methoxyquinoline-3-carbonitrile;

4-((2,4-dichloro-5-methoxyphenyl)amino)-7-(3-(4-(3-(2-((2-(2,6-dioxopiperidin-3-yl)-1,3-dioxoisoindolin-4-yl)amino)ethoxy)propanoyl)piperazin-1-yl)propoxy)-6-methoxyquinoline-3-carbonitrile;

4-((2,4-dichloro-5-methoxyphenyl)amino)-7-(3-(4-(3-(2-((2-(2,6-dioxopiperidin-3-yl)-1,3-dioxoisoindolin-4-yl)oxy)ethoxy)propanoyl)piperazin-1-yl)propoxy)-6-methoxyquinoline-3-carbonitrile;

4-((2,4-dichloro-5-methoxyphenyl)amino)-7-(3-(4-(3-(3-(2-(2,6-dioxopiperidin-3-yl)-1,3-dioxoisoindolin-4-yl)propoxy)propanoyl)piperazin-1-yl)propoxy)-6-methoxyquinoline-3-carbonitrile;

4-((2,4-dichloro-5-methoxyphenyl)amino)-7-(3-(4-(3-(2-(2-((2-(2,6-dioxopiperidin-3-yl)-1,3-dioxoisoindolin-4-yl)amino)ethoxy)ethoxy)propanoyl)piperazin-1-yl)propoxy)-6-methoxyquinoline-3-carbonitrile;

4-((2,4-dichloro-5-methoxyphenyl)amino)-7-(3-(4-(3-(2-(3-(2-(2,6-dioxopiperidin-3-yl)-1,3-dioxoisoindolin-4-yl)propoxy)ethoxy)propanoyl)piperazin-1-yl)propoxy)-6-methoxyquinoline-3-carbonitrile;

4-((2,4-dichloro-5-methoxyphenyl)amino)-7-(3-(4-(3-(2-((2-(2,6-dioxopiperidin-3-yl)-1,3-dioxoisoindolin-4-yl)oxy)ethoxy)ethoxy)propanoyl)piperazin-1-yl)propoxy)-6-methoxyquinoline-3-carbonitrile;

4-((2,4-dichloro-5-methoxyphenyl)amino)-7-(3-(4-(3-(2-(2-((2-(2,6-dioxopiperidin-3-yl)-1,3-dioxoisoindolin-4-yl)amino)ethoxy)ethoxy)ethoxy)propanoyl)piperazin-1-yl)propoxy)-6-methoxyquinoline-3-carbonitrile;

4-((2,4-dichloro-5-methoxyphenyl)amino)-7-(3-(4-(3-(2-(2-(3-(2-(2,6-dioxopiperidin-3-yl)-1,3-dioxoisoindolin-4-yl)propoxy)ethoxy)ethoxy)propanoyl)piperazin-1-yl)propoxy)-6-methoxyquinoline-3-carbonitrile;

4-((2,4-dichloro-5-methoxyphenyl)amino)-7-(3-(4-(3-(2-(2-(2-((2-(2,6-dioxopiperidin-3-yl)-1,3-dioxoisoindolin-4-yl)oxy)ethoxy)ethoxy)ethoxy)propanoyl)piperazin-1-yl)propoxy)-6-methoxyquinoline-3-carbonitrile;

4-((2,4-dichloro-5-methoxyphenyl)amino)-7-(3-(4-(1-((2-(2,6-dioxopiperidin-3-yl)-1,3-dioxoisoindolin-4-yl)amino)-3,6,9,12-tetraoxapentadecan-15-oyl)piperazin-1-yl)propoxy)-6-methoxyquinoline-3-carbonitrile;

4-((2,4-dichloro-5-methoxyphenyl)amino)-7-(3-(4-(16-(2-(2,6-dioxopiperidin-3-yl)-1,3-dioxoisoindolin-4-yl)-4,7,10,13-tetraoxahexadecanoyl)piperazin-1-yl)propoxy)-6-methoxyquinoline-3-carbonitrile;

4-((2,4-dichloro-5-methoxyphenyl)amino)-7-(3-(4-(1-((2-(2,6-dioxopiperidin-3-yl)-1,3-dioxoisoindolin-4-yl)oxy)-3,6,9,12-tetraoxapentadecan-15-oyl)piperazin-1-yl)propoxy)-6-methoxyquinoline-3-carbonitrile;

4-((2,4-dichloro-5-methoxyphenyl)amino)-7-(3-(4-(1-((2-(2,6-dioxopiperidin-3-yl)-1,3-dioxoisoindolin-4-yl)amino)-3,6,9,12,15-pentaoxaoctadecan-18-oyl)piperazin-1-yl)propoxy)-6-methoxyquinoline-3-carbonitrile;

4-((2,4-dichloro-5-methoxyphenyl)amino)-7-(3-(4-((2-(2,6-dioxopiperidin-3-yl)-1,3-dioxoisoindolin-4-yl)glycyl)piperazin-1-yl)propoxy)-6-methoxyquinoline-3-carbonitrile;

4-((2,4-dichloro-5-methoxyphenyl)amino)-7-(3-(4-(2-((2-(2,6-dioxopiperidin-3-yl)-1,3-dioxoisoindolin-4-yl)oxy)acetyl)piperazin-1-yl)propoxy)-6-methoxyquinoline-3-carbonitrile;

4-((2,4-dichloro-5-methoxyphenyl)amino)-7-(3-(4-(3-(2-(2,6-dioxopiperidin-3-yl)-1,3-dioxoisoindolin-4-yl)propanoyl)piperazin-1-yl)propoxy)-6-methoxyquinoline-3-carbonitrile;

4-((2,4-dichloro-5-methoxyphenyl)amino)-7-(3-(4-(3-((2-(2,6-dioxopiperidin-3-yl)-1,3-dioxoisoindolin-4-yl)amino)propanoyl)piperazin-1-yl)propoxy)-6-methoxyquinoline-3-carbonitrile;

4-((2,4-dichloro-5-methoxyphenyl)amino)-7-(3-(4-(4-((2-(2,6-dioxopiperidin-3-yl)-1,3-dioxoisoindolin-4-yl)amino)butanoyl)piperazin-1-yl)propoxy)-6-methoxyquinoline-3-carbonitrile;

4-((2,4-dichloro-5-methoxyphenyl)amino)-7-(3-(4-(4-((2-(2,6-dioxopiperidin-3-yl)-1,3-dioxoisoindolin-4-yl)oxy)butanoyl)piperazin-1-yl)propoxy)-6-methoxyquinoline-3-carbonitrile;

4-((2,4-dichloro-5-methoxyphenyl)amino)-7-(3-(4-(5-(2-(2,6-dioxopiperidin-3-yl)-1,3-dioxoisoindolin-4-yl)pentanoyl)piperazin-1-yl)propoxy)-6-methoxyquinoline-3-carbonitrile, 4-((2,4-dichloro-5-methoxyphenyl)amino)-7-(3-(4-(5-((2-(2,6-dioxopiperidin-3-yl)-1,3-dioxoisoindolin-4-yl)amino)pentanoyl)piperazin-1-yl)propoxy)-6-methoxyquinoline-3-carbonitrile;

4-((2,4-dichloro-5-methoxyphenyl)amino)-7-(3-(4-(5-((2-(2,6-dioxopiperidin-3-yl)-1,3-dioxoisoindolin-4-yl)oxy)pentanoyl)piperazin-1-yl)propoxy)-6-methoxyquinoline-3-carbonitrile;

4-((2,4-dichloro-5-methoxyphenyl)amino)-7-(3-(4-(6-(2-(2,6-dioxopiperidin-3-yl)-1,3-dioxoisoindolin-4-yl)hexanoyl)piperazin-1-yl)propoxy)-6-methoxyquinoline-3-carbonitrile;

4-((2,4-dichloro-5-methoxyphenyl)amino)-7-(3-(4-(6-((2-(2,6-dioxopiperidin-3-yl)-1,3-dioxoisoindolin-4-yl)amino)hexanoyl)piperazin-1-yl)propoxy)-6-methoxyquinoline-3-carbonitrile;

4-((2,4-dichloro-5-methoxyphenyl)amino)-7-(3-(4-(7-((2-(2,6-dioxopiperidin-3-yl)-1,3-dioxoisoindolin-4- yl)amino)heptanoyl)piperazin-1-yl)propoxy)-6-methoxyquinoline-3-carbonitrile;
4-((2,4-dichloro-5-methoxyphenyl)amino)-7-(3-(4-(8-((2-(2,6-dioxopiperidin-3-yl)-1,3-dioxoisoindolin-4-yl)amino)octanoyl)piperazin-1-yl)propoxy)-6-methoxyquinoline-3-carbonitrile;
4-((2,4-dichloro-5-methoxyphenyl)amino)-7-(3-(4-(9-(2-(2,6-dioxopiperidin-3-yl)-1,3-dioxoisoindolin-4-yl)nonanoyl)piperazin-1-yl)propoxy)-6-methoxyquinoline-3-carbonitrile;
4-((2,4-dichloro-5-methoxyphenyl)amino)-7-(3-(4-(8-((2-(2,6-dioxopiperidin-3-yl)-1,3-dioxoisoindolin-4-yl)oxy)octanoyl)piperazin-1-yl)propoxy)-6-methoxyquinoline-3-carbonitrile;
4-(4-(3-((3-cyano-4-((2,4-dichloro-5-methoxyphenyl)amino)-6-methoxyquinolin-7-yl)oxy)propyl)piperazin-1-yl)-N-(2-((2-(2,6-dioxopiperidin-3-yl)-1,3-dioxoisoindolin-4-yl)amino)ethyl)-4-oxobutanamide;
3-(4-(3-((3-cyano-4-((2,4-dichloro-5-methoxyphenyl)amino)-6-methoxyquinolin-7-yl)oxy)propyl)piperazin-1-yl)-N-(2-(2,6-dioxopiperidin-3-yl)-1-oxoisoindolin-4-yl)-3-oxopropanamide;
4-(4-(3-((3-cyano-4-((2,4-dichloro-5-methoxyphenyl)amino)-6-methoxyquinolin-7-yl)oxy)propyl)piperazin-1-yl)-N-(2-(2,6-dioxopiperidin-3-yl)-1-oxoisoindolin-4-yl)-4-oxobutanamide;
5-(4-(3-((3-cyano-4-((2,4-dichloro-5-methoxyphenyl)amino)-6-methoxyquinolin-7-yl)oxy)propyl)piperazin-1-yl)-N-(2-(2,6-dioxopiperidin-3-yl)-1-oxoisoindolin-4-yl)-5-oxopentanamide;
6-(4-(3-((3-cyano-4-((2,4-dichloro-5-methoxyphenyl)amino)-6-methoxyquinolin-7-yl)oxy)propyl)piperazin-1-yl)-N-(2-(2,6-dioxopiperidin-3-yl)-1-oxoisoindolin-4-yl)-6-oxohexanamide;
7-(4-(3-((3-cyano-4-((2,4-dichloro-5-methoxyphenyl)amino)-6-methoxyquinolin-7-yl)oxy)propyl)piperazin-1-yl)-N-(2-(2,6-dioxopiperidin-3-yl)-1-oxoisoindolin-4-yl)-7-oxoheptanamide;
8-(4-(3-((3-cyano-4-((2,4-dichloro-5-methoxyphenyl)amino)-6-methoxyquinolin-7-yl)oxy)propyl)piperazin-1-yl)-N-(2-(2,6-dioxopiperidin-3-yl)-1-oxoisoindolin-4-yl)-8-oxooctanamide;
9-(4-(3-((3-cyano-4-((2,4-dichloro-5-methoxyphenyl)amino)-6-methoxyquinolin-7-yl)oxy)propyl)piperazin-1-yl)-N-(2-(2,6-dioxopiperidin-3-yl)-1-oxoisoindolin-4-yl)-9-oxononanamide;
10-(4-(3-((3-cyano-4-((2,4-dichloro-5-methoxyphenyl)amino)-6-methoxyquinolin-7-yl)oxy)propyl)piperazin-1-yl)-N-(2-(2,6-dioxopiperidin-3-yl)-1-oxoisoindolin-4-yl)-10-oxodecanamide;
11-(4-(3-((3-cyano-4-((2,4-dichloro-5-methoxyphenyl)amino)-6-methoxyquinolin-7-yl)oxy)propyl)piperazin-1-yl)-N-(2-(2,6-dioxopiperidin-3-yl)-1-oxoisoindolin-4-yl)-11-oxoundecanamide;
4-((2,4-dichloro-5-methoxyphenyl)amino)-7-(3-(4-(3-((2-(2,6-dioxopiperidin-3-yl)-1-oxoisoindolin-4-yl)amino)propanoyl)piperazin-1-yl)propoxy)-6-methoxyquinoline-3-carbonitrile;
4-((2,4-dichloro-5-methoxyphenyl)amino)-7-(3-(4-(4-((2-(2,6-dioxopiperidin-3-yl)-1-oxoisoindolin-4-yl)amino)butanoyl)piperazin-1-yl)propoxy)-6-methoxyquinoline-3-carbonitrile;
4-((2,4-dichloro-5-methoxyphenyl)amino)-7-(3-(4-(5-((2-(2,6-dioxopiperidin-3-yl)-1-oxoisoindolin-4-yl)amino)pentanoyl)piperazin-1-yl)propoxy)-6-methoxyquinoline-3-carbonitrile;
4-((2,4-dichloro-5-methoxyphenyl)amino)-7-(3-(4-(6-((2-(2,6-dioxopiperidin-3-yl)-1-oxoisoindolin-4-yl)amino)hexanoyl)piperazin-1-yl)propoxy)-6-methoxyquinoline-3-carbonitrile;
4-((2,4-dichloro-5-methoxyphenyl)amino)-7-(3-(4-(7-((2-(2,6-dioxopiperidin-3-yl)-1-oxoisoindolin-4-yl)amino)heptanoyl)piperazin-1-yl)propoxy)-6-methoxyquinoline-3-carbonitrile;
4-((2,4-dichloro-5-methoxyphenyl)amino)-7-(3-(4-(8-((2-(2,6-dioxopiperidin-3-yl)-1-oxoisoindolin-4-yl)amino)octanoyl)piperazin-1-yl)propoxy)-6-methoxyquinoline-3-carbonitrile;
4-((2,4-dichloro-5-methoxyphenyl)amino)-7-(3-(4-(9-((2-(2,6-dioxopiperidin-3-yl)-1-oxoisoindolin-4-yl)amino)nonanoyl)piperazin-1-yl)propoxy)-6-methoxyquinoline-3-carbonitrile;
4-((2,4-dichloro-5-methoxyphenyl)amino)-7-(3-(4-(3-((2-(2,6-dioxopiperidin-3-yl)-1-oxoisoindolin-4-yl)oxy)propanoyl)piperazin-1-yl)propoxy)-6-methoxyquinoline-3-carbonitrile;
4-((2,4-dichloro-5-methoxyphenyl)amino)-7-(3-(4-(4-((2-(2,6-dioxopiperidin-3-yl)-1-oxoisoindolin-4-yl)oxy)butanoyl)piperazin-1-yl)propoxy)-6-methoxyquinoline-3-carbonitrile;
4-((2,4-dichloro-5-methoxyphenyl)amino)-7-(3-(4-(5-((2-(2,6-dioxopiperidin-3-yl)-1-oxoisoindolin-4-yl)oxy)pentanoyl)piperazin-1-yl)propoxy)-6-methoxyquinoline-3-carbonitrile;
4-((2,4-dichloro-5-methoxyphenyl)amino)-7-(3-(4-(6-((2-(2,6-dioxopiperidin-3-yl)-1-oxoisoindolin-4-yl)oxy)hexanoyl)piperazin-1-yl)propoxy)-6-methoxyquinoline-3-carbonitrile;
4-((2,4-dichloro-5-methoxyphenyl)amino)-7-(3-(4-(7-((2-(2,6-dioxopiperidin-3-yl)-1-oxoisoindolin-4-yl)oxy)heptanoyl)piperazin-1-yl)propoxy)-6-methoxyquinoline-3-carbonitrile;
4-((2,4-dichloro-5-methoxyphenyl)amino)-7-(3-(4-(8-((2-(2,6-dioxopiperidin-3-yl)-1-oxoisoindolin-4-yl)oxy)octanoyl)piperazin-1-yl)propoxy)-6-methoxyquinoline-3-carbonitrile;
4-((2,4-dichloro-5-methoxyphenyl)amino)-7-(3-(4-(9-((2-(2,6-dioxopiperidin-3-yl)-1-oxoisoindolin-4-yl)oxy)nonanoyl)piperazin-1-yl)propoxy)-6-methoxyquinoline-3-carbonitrile;
4-((2,4-dichloro-5-methoxyphenyl)amino)-7-(3-(4-(8-(2-(2,6-dioxopiperidin-3-yl)-1-oxoisoindolin-4-yl)octanoyl)piperazin-1-yl)propoxy)-6-methoxyquinoline-3-carbonitrile;
4-((2,4-dichloro-5-methoxyphenyl)amino)-7-(3-(4-(9-(2-(2,6-dioxopiperidin-3-yl)-1-oxoisoindolin-4-yl)nonanoyl)piperazin-1-yl)propoxy)-6-methoxyquinoline-3-carbonitrile;
4-((2,4-dichloro-5-methoxyphenyl)amino)-7-(3-(4-(3-(2-((2-(2,6-dioxopiperidin-3-yl)-1-oxoisoindolin-4-yl)amino)ethoxy)propanoyl)piperazin-1-yl)propoxy)-6-methoxyquinoline-3-carbonitrile;
4-((2,4-dichloro-5-methoxyphenyl)amino)-7-(3-(4-(4-(2-((2-(2,6-dioxopiperidin-3-yl)-1-oxoisoindolin-4-yl)amino)ethoxy)butanoyl)piperazin-1-yl)propoxy)-6-methoxyquinoline-3-carbonitrile;
4-((2,4-dichloro-5-methoxyphenyl)amino)-7-(3-(4-(2-(2-(2-((2-(2,6-dioxopiperidin-3-yl)-1-oxoisoindolin-4-yl)amino)ethoxy)ethoxy)acetyl)piperazin-1-yl)propoxy)-6-methoxyquinoline-3-carbonitrile;
4-((2,4-dichloro-5-methoxyphenyl)amino)-7-(3-(4-(3-(2-(2-((2-(2,6-dioxopiperidin-3-yl)-1-oxoisoindolin-4-yl)

amino)ethoxy)ethoxy)propanoyl)piperazin-1-yl) propoxy)-6-methoxyquinoline-3-carbonitrile;

4-((2,4-dichloro-5-methoxyphenyl)amino)-7-(3-(4-(4-(3-(2-(2,6-dioxopiperidin-3-yl)-1-oxoisoindolin-4-yl) propoxy)butanoyl)piperazin-1-yl)propoxy)-6-methoxyquinoline-3-carbonitrile;

4-((2,4-dichloro-5-methoxyphenyl)amino)-7-(3-(4-(2-(2-(3-(2-(2,6-dioxopiperidin-3-yl)-1-oxoisoindolin-4-yl) propoxy)ethoxy)acetyl)piperazin-1-yl)propoxy)-6-methoxyquinoline-3-carbonitrile;

(2S,4R)-1-((S)-2-(tert-butyl)-22-(4-(3-((3-cyano-4-((2,4-dichloro-5-methoxyphenyl)amino)-6-methoxyquinolin-7-yl)oxy)propyl)piperazin-1-yl)-4,22-dioxo-10,13,16-trioxa-3-azadocosanoyl)-4-hydroxy-N-(4-(4-methylthiazol-5-yl)benzyl)pyrrolidine-2-carboxamide;

(2S,4R)-1-((S)-2-(tert-butyl)-22-(4-(3-((3-cyano-4-((2,4-dichloro-5-methoxyphenyl)amino)-6-methoxyquinolin-7-yl)oxy)propyl)piperazin-1-yl)-22-oxo-10,13,16-trioxa-3-azadocosanoyl)-4-hydroxy-N-(4-(4-methylthiazol-5-yl)benzyl)pyrrolidine-2-carboxamide;

(2S,4R)-1-((S)-2-(2-(2-(2-(4-(3-((3-cyano-4-((2,4-dichloro-5-methoxyphenyl)amino)-6-methoxyquinolin-7-yl)oxy)propyl)piperazin-1-yl)-2-oxoethoxy)ethoxy) acetamido)-3,3-dimethylbutanoyl)-4-hydroxy-N-(4-(4-methylthiazol-5-yl)benzyl)pyrrolidine-2-carboxamide;

(2S,4R)-1-((S)-2-(2-(2-(3-(4-(3-((3-cyano-4-((2,4-dichloro-5-methoxyphenyl)amino)-6-methoxyquinolin-7-yl)oxy)propyl)piperazin-1-yl)-3-oxopropoxy) ethoxy)propanamido)-3,3-dimethylbutanoyl)-4-hydroxy-N-(4-(4-methylthiazol-5-yl)benzyl) pyrrolidine-2-carboxamide;

(2S,4R)-1-((S)-2-((3-(2-(3-(4-(3-((3-cyano-4-((2,4-dichloro-5-methoxyphenyl)amino)-6-methoxyquinolin-7-yl)oxy)propyl)piperazin-1-yl)-3-oxopropoxy) ethoxy)propyl)amino)-3,3-dimethylbutanoyl)-4-hydroxy-N-(4-(4-methylthiazol-5-yl)benzyl) pyrrolidine-2-carboxamide;

(2S,4R)-1-((S)-2-(tert-butyl)-16-(4-(3-((3-cyano-4-((2,4-dichloro-5-methoxyphenyl)amino)-6-methoxyquinolin-7-yl)oxy)propyl)piperazin-1-yl)-4,16-dioxo-7,10,13-trioxa-3-azahexadecanoyl)-4-hydroxy-N-(4-(4-methylthiazol-5-yl)benzyl)pyrrolidine-2-carboxamide;

(2S,4R)-1-((S)-2-(tert-butyl)-16-(4-(3-((3-cyano-4-((2,4-dichloro-5-methoxyphenyl)amino)-6-methoxyquinolin-7-yl)oxy)propyl)piperazin-1-yl)-16-oxo-7,10,13-trioxa-3-azahexadecanoyl)-4-hydroxy-N-(4-(4-methylthiazol-5-yl)benzyl)pyrrolidine-2-carboxamide;

(2S,4R)-1-((S)-2-(tert-butyl)-19-(4-(3-((3-cyano-4-((2,4-dichloro-5-methoxyphenyl)amino)-6-methoxyquinolin-7-yl)oxy)propyl)piperazin-1-yl)-4,19-dioxo-7,10,13,16-tetraoxa-3-azanonadecanoyl)-4-hydroxy-N-(4-(4-methylthiazol-5-yl)benzyl)pyrrolidine-2-carboxamide;

(2S,4R)-1-((S)-2-(tert-butyl)-22-(4-(3-((3-cyano-4-((2,4-dichloro-5-methoxyphenyl)amino)-6-methoxyquinolin-7-yl)oxy)propyl)piperazin-1-yl)-4,22-dioxo-7,10,13,16,19-pentaoxa-3-azadocosanoyl)-4-hydroxy-N-(4-(4-methylthiazol-5-yl)benzyl)pyrrolidine-2-carboxamide;

(2S,4R)-1-((S)-2-(4-(4-(3-((3-cyano-4-((2,4-dichloro-5-methoxyphenyl)amino)-6-methoxyquinolin-7-yl)oxy) propyl)piperazin-1-yl)-4-oxobutanamido)-3,3-dimethylbutanoyl)-4-hydroxy-N-(4-(4-methylthiazol-5-yl) benzyl)pyrrolidine-2-carboxamide;

(2S,4R)-1-((S)-2-(5-(4-(3-((3-cyano-4-((2,4-dichloro-5-methoxyphenyl)amino)-6-methoxyquinolin-7-yl)oxy) propyl)piperazin-1-yl)-5-oxopentanamido)-3,3-dimethylbutanoyl)-4-hydroxy-N-(4-(4-methylthiazol-5-yl) benzyl)pyrrolidine-2-carboxamide;

(2S,4R)-1-((S)-2-(6-(4-(3-((3-cyano-4-((2,4-dichloro-5-methoxyphenyl)amino)-6-methoxyquinolin-7-yl)oxy) propyl)piperazin-1-yl)-6-oxohexanamido)-3,3-dimethylbutanoyl)-4-hydroxy-N-(4-(4-methylthiazol-5-yl) benzyl)pyrrolidine-2-carboxamide;

(2S,4R)-1-((S)-2-((6-(4-(3-((3-cyano-4-((2,4-dichloro-5-methoxyphenyl)amino)-6-methoxyquinolin-7-yl)oxy) propyl)piperazin-1-yl)-6-oxohexyl)amino)-3,3-dimethylbutanoyl)-4-hydroxy-N-(4-(4-methylthiazol-5-yl) benzyl)pyrrolidine-2-carboxamide;

(2S,4R)-1-((S)-2-(7-(4-(3-((3-cyano-4-((2,4-dichloro-5-methoxyphenyl)amino)-6-methoxyquinolin-7-yl)oxy) propyl)piperazin-1-yl)-7-oxoheptanamido)-3,3-dimethylbutanoyl)-4-hydroxy-N-(4-(4-methylthiazol-5-yl) benzyl)pyrrolidine-2-carboxamide;

(2S,4R)-1-((S)-2-((7-(4-(3-((3-cyano-4-((2,4-dichloro-5-methoxyphenyl)amino)-6-methoxyquinolin-7-yl)oxy) propyl)piperazin-1-yl)-7-oxoheptyl)amino)-3,3-dimethylbutanoyl)-4-hydroxy-N-(4-(4-methylthiazol-5-yl) benzyl)pyrrolidine-2-carboxamide;

(2S,4R)-1-((S)-2-(8-(4-(3-((3-cyano-4-((2,4-dichloro-5-methoxyphenyl)amino)-6-methoxyquinolin-7-yl)oxy) propyl)piperazin-1-yl)-8-oxooctanamido)-3,3-dimethylbutanoyl)-4-hydroxy-N-(4-(4-methylthiazol-5-yl) benzyl)pyrrolidine-2-carboxamide;

(2S,4R)-1-((S)-2-((8-(4-(3-((3-cyano-4-((2,4-dichloro-5-methoxyphenyl)amino)-6-methoxyquinolin-7-yl)oxy) propyl)piperazin-1-yl)-8-oxooctyl)amino)-3,3-dimethylbutanoyl)-4-hydroxy-N-(4-(4-methylthiazol-5-yl) benzyl)pyrrolidine-2-carboxamide;

(2S,4R)-1-((S)-2-(9-(4-(3-((3-cyano-4-((2,4-dichloro-5-methoxyphenyl)amino)-6-methoxyquinolin-7-yl)oxy) propyl)piperazin-1-yl)-9-oxononanamido)-3,3-dimethylbutanoyl)-4-hydroxy-N-(4-(4-methylthiazol-5-yl) benzyl)pyrrolidine-2-carboxamide;

(2S,4R)-1-((S)-2-(10-(4-(3-((3-cyano-4-((2,4-dichloro-5-methoxyphenyl)amino)-6-methoxyquinolin-7-yl)oxy) propyl)piperazin-1-yl)-10-oxodecanamido)-3,3-dimethylbutanoyl)-4-hydroxy-N-(4-(4-methylthiazol-5-yl) benzyl)pyrrolidine-2-carboxamide;

(2S,4R)-1-((S)-2-(11-(4-(3-((3-cyano-4-((2,4-dichloro-5-methoxyphenyl)amino)-6-methoxyquinolin-7-yl)oxy) propyl)piperazin-1-yl)-11-oxoundecanamido)-3,3-dimethylbutanoyl)-4-hydroxy-N-(4-(4-methylthiazol-5-yl)benzyl)pyrrolidine-2-carboxamide;

(2S,4R)-1-((S)-2-((11-(4-(3-((3-cyano-4-((2,4-dichloro-5-methoxyphenyl)amino)-6-methoxyquinolin-7-yl) oxy)propyl)piperazin-1-yl)-11-oxoundecyl)amino)-3,3-dimethylbutanoyl)-4-hydroxy-N-(4-(4-methylthiazol-5-yl)benzyl)pyrrolidine-2-carboxamide;

(2S,4R)-1-((S)-2-(14-(4-(3-((3-cyano-4-((2,4-dichloro-5-methoxyphenyl)amino)-6-methoxyquinolin-7-yl)oxy) propyl)piperazin-1-yl)-14-oxotetradecanamido)-3,3-dimethylbutanoyl)-4-hydroxy-N-(4-(4-methylthiazol-5-yl)benzyl)pyrrolidine-2-carboxamide;

(2S,4R)-1-((S)-2-(16-(4-(3-((3-cyano-4-((2,4-dichloro-5-methoxyphenyl)amino)-6-methoxyquinolin-7-yl)oxy) propyl)piperazin-1-yl)-16-oxohexadecanamido)-3,3-dimethylbutanoyl)-4-hydroxy-N-(4-(4-methylthiazol-5-yl)benzyl)pyrrolidine-2-carboxamide;

4-((4-(6-(2-(2-((6-((2-(2,6-dioxopiperidin-3-yl)-1,3-dioxoisoindolin-4-yl)amino)-6-oxohexyl)oxy)ethoxy) ethoxy)hexanoyl)piperazin-1-yl)methyl)-N-(4-methyl-3-((4-(pyridin-3-yl)pyrimidin-2-yl)amino)phenyl) benzamide;

4-((4-(6-(2-(2-((6-((2-(2,6-dioxopiperidin-3-yl)-1,3-dioxoisoindolin-4-yl)amino)hexyl)oxy)ethoxy)ethoxy)hexanoyl)piperazin-1-yl)methyl)-N-(4-methyl-3-((4-(pyridin-3-yl)pyrimidin-2-yl)amino)phenyl)benzamide;

4-((4-(3-(2-((2-(2,6-dioxopiperidin-3-yl)-1,3-dioxoisoindolin-4-yl)amino)ethoxy)propanoyl)piperazin-1-yl)methyl)-N-(4-methyl-3-((4-(pyridin-3-yl)pyrimidin-2-yl)amino)phenyl)benzamide;

4-((4-(3-(2-(2-((2-(2,6-dioxopiperidin-3-yl)-1,3-dioxoisoindolin-4-yl)amino)ethoxy)ethoxy)propanoyl)piperazin-1-yl)methyl)-N-(4-methyl-3-((4-(pyridin-3-yl)pyrimidin-2-yl)amino)phenyl)benzamide;

4-((4-(3-(2-(2-(2-((2-(2,6-dioxopiperidin-3-yl)-1,3-dioxoisoindolin-4-yl)amino)ethoxy)ethoxy)ethoxy)propanoyl)piperazin-1-yl)methyl)-N-(4-methyl-3-((4-(pyridin-3-yl)pyrimidin-2-yl)amino)phenyl)benzamide;

4-((4-(1-((2-(2,6-dioxopiperidin-3-yl)-1,3-dioxoisoindolin-4-yl)amino)-3,6,9,12-tetraoxapentadecan-15-oyl)piperazin-1-yl)methyl)-N-(4-methyl-3-((4-(pyridin-3-yl)pyrimidin-2-yl)amino)phenyl)benzamide;

4-((4-(1-((2-(2,6-dioxopiperidin-3-yl)-1,3-dioxoisoindolin-4-yl)amino)-3,6,9,12,15-pentaoxaoctadecan-18-oyl)piperazin-1-yl)methyl)-N-(4-methyl-3-((4-(pyridin-3-yl)pyrimidin-2-yl)amino)phenyl)benzamide;

4-((4-(3-(3-(2-(2,6-dioxopiperidin-3-yl)-1,3-dioxoisoindolin-4-yl)propoxy)propanoyl)piperazin-1-yl)methyl)-N-(4-methyl-3-((4-(pyridin-3-yl)pyrimidin-2-yl)amino)phenyl)benzamide;

4-((4-(3-(2-(3-(2-(2,6-dioxopiperidin-3-yl)-1,3-dioxoisoindolin-4-yl)propoxy)ethoxy)propanoyl)piperazin-1-yl)methyl)-N-(4-methyl-3-((4-(pyridin-3-yl)pyrimidin-2-yl)amino)phenyl)benzamide;

4-((4-(3-(2-(2-(3-(2-(2,6-dioxopiperidin-3-yl)-1,3-dioxoisoindolin-4-yl)propoxy)ethoxy)ethoxy)propanoyl)piperazin-1-yl)methyl)-N-(4-methyl-3-((4-(pyridin-3-yl)pyrimidin-2-yl)amino)phenyl)benzamide;

4-((4-((2-(2,6-dioxopiperidin-3-yl)-1,3-dioxoisoindolin-4-yl)glycyl)piperazin-1-yl)methyl)-N-(4-methyl-3-((4-(pyridin-3-yl)pyrimidin-2-yl)amino)phenyl)benzamide;

4-((4-(3-((2-(2,6-dioxopiperidin-3-yl)-1,3-dioxoisoindolin-4-yl)amino)propanoyl)piperazin-1-yl)methyl)-N-(4-methyl-3-((4-(pyridin-3-yl)pyrimidin-2-yl)amino)phenyl)benzamide;

4-((4-(4-((2-(2,6-dioxopiperidin-3-yl)-1,3-dioxoisoindolin-4-yl)amino)butanoyl)piperazin-1-yl)methyl)-N-(4-methyl-3-((4-(pyridin-3-yl)pyrimidin-2-yl)amino)phenyl)benzamide;

4-((4-(5-((2-(2,6-dioxopiperidin-3-yl)-1,3-dioxoisoindolin-4-yl)amino)pentanoyl)piperazin-1-yl)methyl)-N-(4-methyl-3-((4-(pyridin-3-yl)pyrimidin-2-yl)amino)phenyl)benzamide;

4-((4-(6-((2-(2,6-dioxopiperidin-3-yl)-1,3-dioxoisoindolin-4-yl)amino)hexanoyl)piperazin-1-yl)methyl)-N-(4-methyl-3-((4-(pyridin-3-yl)pyrimidin-2-yl)amino)phenyl)benzamide;

4-((4-(7-((2-(2,6-dioxopiperidin-3-yl)-1,3-dioxoisoindolin-4-yl)amino)heptanoyl)piperazin-1-yl)methyl)-N-(4-methyl-3-((4-(pyridin-3-yl)pyrimidin-2-yl)amino)phenyl)benzamide;

4-((4-(8-((2-(2,6-dioxopiperidin-3-yl)-1,3-dioxoisoindolin-4-yl)amino)octanoyl)piperazin-1-yl)methyl)-N-(4-methyl-3-((4-(pyridin-3-yl)pyrimidin-2-yl)amino)phenyl)benzamide;

4-((4-(5-(2-(2,6-dioxopiperidin-3-yl)-1,3-dioxoisoindolin-4-yl)pentanoyl)piperazin-1-yl)methyl)-N-(4-methyl-3-((4-(pyridin-3-yl)pyrimidin-2-yl)amino)phenyl)benzamide;

4-((4-(6-(2-(2,6-dioxopiperidin-3-yl)-1,3-dioxoisoindolin-4-yl)hexanoyl)piperazin-1-yl)methyl)-N-(4-methyl-3-((4-(pyridin-3-yl)pyrimidin-2-yl)amino)phenyl)benzamide;

4-((4-(7-(2-(2,6-dioxopiperidin-3-yl)-1,3-dioxoisoindolin-4-yl)heptanoyl)piperazin-1-yl)methyl)-N-(4-methyl-3-((4-(pyridin-3-yl)pyrimidin-2-yl)amino)phenyl)benzamide;

4-((4-(8-(2-(2,6-dioxopiperidin-3-yl)-1,3-dioxoisoindolin-4-yl)octanoyl)piperazin-1-yl)methyl)-N-(4-methyl-3-((4-(pyridin-3-yl)pyrimidin-2-yl)amino)phenyl)benzamide;

4-((4-(9-(2-(2,6-dioxopiperidin-3-yl)-1,3-dioxoisoindolin-4-yl)nonanoyl)piperazin-1-yl)methyl)-N-(4-methyl-3-((4-(pyridin-3-yl)pyrimidin-2-yl)amino)phenyl)benzamide;

4-((4-(4-((2-(2,6-dioxopiperidin-3-yl)-1-oxoisoindolin-4-yl)amino)-4-oxobutanoyl)piperazin-1-yl)methyl)-N-(4-methyl-3-((4-(pyridin-3-yl)pyrimidin-2-yl)amino)phenyl)benzamide;

4-((4-(5-((2-(2,6-dioxopiperidin-3-yl)-1-oxoisoindolin-4-yl)amino)-5-oxopentanoyl)piperazin-1-yl)methyl)-N-(4-methyl-3-((4-(pyridin-3-yl)pyrimidin-2-yl)amino)phenyl)benzamide;

4-((4-(6-((2-(2,6-dioxopiperidin-3-yl)-1-oxoisoindolin-4-yl)amino)-6-oxohexanoyl)piperazin-1-yl)methyl)-N-(4-methyl-3-((4-(pyridin-3-yl)pyrimidin-2-yl)amino)phenyl)benzamide;

4-((4-(7-((2-(2,6-dioxopiperidin-3-yl)-1-oxoisoindolin-4-yl)amino)-7-oxoheptanoyl)piperazin-1-yl)methyl)-N-(4-methyl-3-((4-(pyridin-3-yl)pyrimidin-2-yl)amino)phenyl)benzamide;

4-((4-(8-((2-(2,6-dioxopiperidin-3-yl)-1-oxoisoindolin-4-yl)amino)-8-oxooctanoyl)piperazin-1-yl)methyl)-N-(4-methyl-3-((4-(pyridin-3-yl)pyrimidin-2-yl)amino)phenyl)benzamide;

4-((4-(9-((2-(2,6-dioxopiperidin-3-yl)-1-oxoisoindolin-4-yl)amino)-9-oxononanoyl)piperazin-1-yl)methyl)-N-(4-methyl-3-((4-(pyridin-3-yl)pyrimidin-2-yl)amino)phenyl)benzamide;

4-((4-(10-((2-(2,6-dioxopiperidin-3-yl)-1-oxoisoindolin-4-yl)amino)-10-oxodecanoyl)piperazin-1-yl)methyl)-N-(4-methyl-3-((4-(pyridin-3-yl)pyrimidin-2-yl)amino)phenyl)benzamide;

(2S,4R)-14(S)-2-(tert-butyl)-22-(4-(4-((4-methyl-3-((4-(pyridin-3-yl)pyrimidin-2-yl)amino)phenyl)carbamoyl)benzyl)piperazin-1-yl)-4,22-dioxo-10,13,16-trioxa-3-azadocosanoyl)-4-hydroxy-N-(4-(4-methylthiazol-5-yl)benzyl)pyrrolidine-2-carboxamide;

(2S,4R)-1-((S)-2-(tert-butyl)-22-(4-(4-((4-methyl-3-((4-(pyridin-3-yl)pyrimidin-2-yl)amino)phenyl)carbamoyl)benzyl)piperazin-1-yl)-22-oxo-10,13,16-trioxa-3-azadocosanoyl)-4-hydroxy-N-(4-(4-methylthiazol-5-yl)benzyl)pyrrolidine-2-carboxamide;

(2S,4R)-1-((S)-3,3-dimethyl-2-(2-(2-(2-(4-(4-((4-methyl-3-((4-(pyridin-3-yl)pyrimidin-2-yl)amino)phenyl)carbamoyl)benzyl)piperazin-1-yl)-2-oxoethoxy)ethoxy)acetamido)butanoyl)-4-hydroxy-N-(4-(4-methylthiazol-5-yl)benzyl)pyrrolidine-2-carboxamide;

(2S,4R)-1-((S)-3,3-dimethyl-2-(3-(2-(3-(4-(4-((4-methyl-3-((4-(pyridin-3-yl)pyrimidin-2-yl)amino)phenyl)carbamoyl)benzyl)piperazin-1-yl)-3-oxopropoxy)ethoxy)

propanamido)butanoyl)-4-hydroxy-N-(4-(4-methylthiazol-5-yl)benzyl)pyrrolidine-2-carboxamide;
(2S,4R)-1-((S)-3,3-dimethyl-2-((3-(2-(3-(4-(4-(((4-methyl-3-((4-(pyridin-3-yl)pyrimidin-2-yl)amino)phenyl)carbamoyl)benzyl)piperazin-1-yl)-3-oxopropoxy)ethoxy)propyl)amino)butanoyl)-4-hydroxy-N-(4-(4-methylthiazol-5-yl)benzyl)pyrrolidine-2-carboxamide;
(2S,4R)-1-((S)-2-(tert-butyl)-16-(4-(44(4-methyl-34(4-(pyridin-3-yl)pyrimidin-2-yl)amino)phenyl)carbamoyl)benzyl)piperazin-1-yl)-4,16-dioxo-7,10,13-trioxa-3-azahexadecanoyl)-4-hydroxy-N-(4-(4-methylthiazol-5-yl)benzyl)pyrrolidine-2-carboxamide;
(2S,4R)-1-((S)-2-(tert-butyl)-19-(4-(4-(((4-methyl-3-((4-(pyridin-3-yl)pyrimidin-2-yl)amino)phenyl)carbamoyl)benzyl)piperazin-1-yl)-4,19-dioxo-7,10,13,16-tetraoxa-3-azanonadecanoyl)-4-hydroxy-N-(4-(4-methylthiazol-5-yl)benzyl)pyrrolidine-2-carboxamide;
(2S,4R)-1-((S)-2-(tert-butyl)-22-(4-(44(4-methyl-34(4-(pyridin-3-yl)pyrimidin-2-yl)amino)phenyl)carbamoyl)benzyl)piperazin-1-yl)-4,22-dioxo-7,10,13,16,19-pentaoxa-3-azadocosanoyl)-4-hydroxy-N-(4-(4-methylthiazol-5-yl)benzyl)pyrrolidine-2-carboxamide;
(2S,4R)-1-((S)-3,3-dimethyl-2-(4-(4-(4-((4-methyl-3-((4-(pyridin-3-yl)pyrimidin-2-yl)amino)phenyl)carbamoyl)benzyl)piperazin-1-yl)-4-oxobutanamido)butanoyl)-4-hydroxy-N-(4-(4-methylthiazol-5-yl)benzyl)pyrrolidine-2-carboxamide;
(2S,4R)-1-((S)-3,3-dimethyl-2-(5-(4-(4-((4-methyl-3-((4-(pyridin-3-yl)pyrimidin-2-yl)amino)phenyl)carbamoyl)benzyl)piperazin-1-yl)-5-oxopentanamido)butanoyl)-4-hydroxy-N-(4-(4-methylthiazol-5-yl)benzyl)pyrrolidine-2-carboxamide;
(2S,4R)-1-((S)-3,3-dimethyl-2-(6-(4-(4-((4-methyl-3-((4-(pyridin-3-yl)pyrimidin-2-yl)amino)phenyl)carbamoyl)benzyl)piperazin-1-yl)-6-oxohexanamido)butanoyl)-4-hydroxy-N-(4-(4-methylthiazol-5-yl)benzyl)pyrrolidine-2-carboxamide;
(2S,4R)-1-((S)-3,3-dimethyl-2-(7-(4-(4-((4-methyl-3-((4-(pyridin-3-yl)pyrimidin-2-yl)amino)phenyl)carbamoyl)benzyl)piperazin-1-yl)-7-oxoheptanamido)butanoyl)-4-hydroxy-N-(4-(4-methylthiazol-5-yl)benzyl)pyrrolidine-2-carboxamide;
(2S,4R)-1-((S)-3,3-dimethyl-2-(8-(4-(4-((4-methyl-3-((4-(pyridin-3-yl)pyrimidin-2-yl)amino)phenyl)carbamoyl)benzyl)piperazin-1-yl)-8-oxooctanamido)butanoyl)-4-hydroxy-N-(4-(4-methylthiazol-5-yl)benzyl)pyrrolidine-2-carboxamide;
(2S,4R)-1-((S)-3,3-dimethyl-2-(9-(4-(4-((4-methyl-3-((4-(pyridin-3-yl)pyrimidin-2-yl)amino)phenyl)carbamoyl)benzyl)piperazin-1-yl)-9-oxononanamido)butanoyl)-4-hydroxy-N-(4-(4-methylthiazol-5-yl)benzyl)pyrrolidine-2-carboxamide;
(2S,4R)-1-((S)-3,3-dimethyl-2-(10-(4-(4-((4-methyl-3-((4-(pyridin-3-yl)pyrimidin-2-yl)amino)phenyl)carbamoyl)benzyl)piperazin-1-yl)-10-oxodecanamido)butanoyl)-4-hydroxy-N-(4-(4-methylthiazol-5-yl)benzyl)pyrrolidine-2-carboxamide;
(2S,4R)-1-((S)-3,3-dimethyl-2-(11-(4-(4-((4-methyl-3-((4-(pyridin-3-yl)pyrimidin-2-yl)amino)phenyl)carbamoyl)benzyl)piperazin-1-yl)-11-oxoundecanamido)butanoyl)-4-hydroxy-N-(4-(4-methylthiazol-5-yl)benzyl)pyrrolidine-2-carboxamide;
(2S,4R)-1-((S)-3,3-dimethyl-2-(14-(4-(4-((4-methyl-3-((4-(pyridin-3-yl)pyrimidin-2-yl)amino)phenyl)carbamoyl)benzyl)piperazin-1-yl)-14-oxotetradecanamido)butanoyl)-4-hydroxy-N-(4-(4-methylthiazol-5-yl)benzyl)pyrrolidine-2-carboxamide;
(2S,4R)-1-((S)-3,3-dimethyl-2-(16-(4-(4-((4-methyl-3-((4-(pyridin-3-yl)pyrimidin-2-yl)amino)phenyl)carbamoyl)benzyl)piperazin-1-yl)-16-oxohexadecanamido)butanoyl)-4-hydroxy-N-(4-(4-methylthiazol-5-yl)benzyl)pyrrolidine-2-carboxamide;
(2S,4R)-1-((S)-3,3-dimethyl-2-((7-(4-(4-((4-methyl-3-((4-(pyridin-3-yl)pyrimidin-2-yl)amino)phenyl)carbamoyl)benzyl)piperazin-1-yl)-7-oxoheptyl)amino)butanoyl)-4-hydroxy-N-(4-(4-methylthiazol-5-yl)benzyl)pyrrolidine-2-carboxamide;
(2S,4R)-1-((S)-3,3-dimethyl-24(8-(4-(44(4-methyl-34(4-(pyridin-3-yl)pyrimidin-2-yl)amino)phenyl)carbamoyl)benzyl)piperazin-1-yl)-8-oxooctyl)amino)butanoyl)-4-hydroxy-N-(4-(4-methylthiazol-5-yl)benzyl)pyrrolidine-2-carboxamide; and
(2S,4R)-1-((S)-3,3-dimethyl-24(9-(4-(44(4-methyl-34(4-(pyridin-3-yl)pyrimidin-2-yl)amino)phenyl)carbamoyl)benzyl)piperazin-1-yl)-9-oxononyl)amino)butanoyl)-4-hydroxy-N-(4-(4-methylthiazol-5-yl)benzyl)pyrrolidine-2-carboxamide.

20. A pharmaceutical composition, comprising the compound of formula (I) as recited in claim 1 or a pharmaceutically acceptable salt thereof, and at least one pharmaceutically acceptable carrier.

21. The pharmaceutical composition as recited in claim 20, further comprising at least one additional agent for treating a cancer.

22. A compound of formula (I) as recited in claim 1, or a pharmaceutically acceptable salt thereof, for use as a medicament.

23. The compound of formula (I) as recited in claim 1, or a pharmaceutically acceptable salt thereof, for use in treating a cancer associated with BCR-ABL, phosphorylated BCR-ABL, C-ABL, phosphorylated CRKL, phosphorylated STAT5, Src, phosphorylated Src, C-Kit protein kinases and/or PDGFR.

24. The compound of formula (I) as recited in claim 23, or a pharmaceutically acceptable salt, wherein the cancer is selected from the group consisting of: $Ph^+$ chronic myeloid leukemia (CML); $Ph^+$ acute lymphoblastic leukemia (ALL); PDGFR (platelet-derived growth factor receptor) gene rearrangement-related myelodysplastic/myeloproliferative diseases (MDS/MPD); aggressive systemic mastocytosis (ASM); Hypereosinophilic Syndrome (HES); Chronic Eosinophilic Leukemia (CEL); Dermatofibrosarcoma protuberans (DFSP); and $Kit^+$ gastrointestinal stromal tumor (GIST).

25. The compound of formula (I) as recited in claim 24, or a pharmaceutically acceptable salt, wherein the $Ph^+$ chronic myeloid leukemia is in a phase of chronic, accelerated, or acute.

26. A method for treating a cancer in a subject, comprising administering to the subject in need a therapeutically effective amount of the compound of formula (I) as recited in claim 1, or a pharmaceutically acceptable salt thereof, wherein the cancer is associated with BCR-ABL, phosphorylated BCR-ABL, C-ABL, phosphorylated CRKL, phosphorylated STAT5, Src, phosphorylated Src, C-Kit protein kinases and/or PDGFR.

27. The method as recited in claim 26, wherein the cancer is selected from the group consisting of: $Ph^+$ chronic myeloid leukemia (CML) (the CML relating to chronic phase (CP), accelerated phase (AP) and acute blast crisis (BC) patient); $Ph^+$ acute lymphoblastic leukemia (ALL); PDGFR (platelet-derived growth factor receptor) gene rearrangement-related myelodysplastic/myeloproliferative diseases (MDS/MPD); aggressive systemic mastocytosis (ASM); Hypereosinophilic Syndrome (HES); Chronic Eosinophilic Leukemia (CEL); Dermatofibrosarcoma protuberans (DFSP); and Kit$^+$ gastrointestinal stromal tumor (GIST).

28. The method as recited in claim 27, wherein the Ph$^+$ chronic myeloid leukemia is in a phase of chronic, accelerated, or acute.

29. The method as recited in claim 26, wherein the administering to the subject is through at least one mode of administration selected from the group consisting of nasal administration, inhalation administration, topical administration, oral administration, oral mucosal administration, rectal administration, pleural cavity administration, peritoneal administration, vaginal administration, intramuscular administration, subcutaneous, transdermal, epidural, intrathecal, and intravenous administration.

* * * * *